US012378207B2

(12) United States Patent
Liu et al.

(10) Patent No.: US 12,378,207 B2
(45) Date of Patent: *Aug. 5, 2025

(54) HETEROCYCLIC COMPOUND AND ORGANIC ELECTROLUMINESCENT DEVICE COMPRISING SAME

(71) Applicant: Changchun Hyperions Technology Co., Ltd., Changchun (CN)

(72) Inventors: Hui Liu, Changchun (CN); Qiu Lu, Changchun (CN); Yue Sun, Changchun (CN); Jing Sun, Changchun (CN)

(73) Assignee: Changchun Hyperions Technology Co., Ltd., Changchun (CN)

( * ) Notice: Subject to any disclaimer, the term of this patent is extended or adjusted under 35 U.S.C. 154(b) by 852 days.

This patent is subject to a terminal disclaimer.

(21) Appl. No.: 17/557,595

(22) Filed: Dec. 21, 2021

(65) Prior Publication Data

US 2022/0209132 A1  Jun. 30, 2022

(30) Foreign Application Priority Data

Dec. 22, 2020 (CN) .......................... 202011535037.6

(51) Int. Cl.
| | | |
|---|---|---|
| H10K 85/60 | (2023.01) | |
| C07D 263/57 | (2006.01) | |
| C07D 263/64 | (2006.01) | |
| C07D 277/66 | (2006.01) | |
| C07D 413/14 | (2006.01) | |
| C09K 11/06 | (2006.01) | |
| H10K 50/16 | (2023.01) | |
| H10K 50/18 | (2023.01) | |

(52) U.S. Cl.
CPC ......... *C07D 263/64* (2013.01); *C07D 263/57* (2013.01); *C07D 277/66* (2013.01); *C07D 413/14* (2013.01); *C09K 11/06* (2013.01); *H10K 85/615* (2023.02); *H10K 85/622* (2023.02); *H10K 85/624* (2023.02); *H10K 85/654* (2023.02); *H10K 85/657* (2023.02); *H10K 85/6574* (2023.02); *C09K 2211/1018* (2013.01); *H10K 50/16* (2023.02); *H10K 50/18* (2023.02)

(58) Field of Classification Search
None
See application file for complete search history.

(56) References Cited

U.S. PATENT DOCUMENTS

| | | |
|---|---|---|
| 6,171,715 B1 | 1/2001 | Sato et al. |
| 9,266,851 B2 | 2/2016 | Yoshida et al. |
| 10,903,430 B2 | 1/2021 | Jatsch et al. |
| 2015/0318487 A1 | 11/2015 | Ito et al. |
| 2015/0318510 A1 | 11/2015 | Ito et al. |
| 2019/0027695 A1 | 1/2019 | Zhang et al. |
| 2022/0173333 A1* | 6/2022 | Zhao .................... C07D 417/10 |

FOREIGN PATENT DOCUMENTS

| | | |
|---|---|---|
| CN | 104193738 A | 12/2014 |
| CN | 106536485 | 3/2017 |
| CN | 106753340 A | 5/2017 |
| CN | 108997322 A | 12/2018 |
| CN | 109206420 | 1/2019 |
| CN | 109879812 A | 6/2019 |
| CN | 110229145 A | 9/2019 |
| CN | 111253332 | 6/2020 |
| CN | 111943902 A | 11/2020 |
| CN | 112442023 | 3/2021 |
| EP | 4006025 | 6/2022 |
| JP | 2017524699 | 8/2017 |
| JP | 2022-087059 A | 6/2022 |
| JP | 7262138 | 4/2023 |
| KR | 20170032414 | 3/2017 |
| WO | WO 2011046182 | 4/2011 |
| WO | WO 2016/012075 | 1/2016 |
| WO | WO 2019114478 | 6/2019 |
| WO | WO-2019166206 A1 * | 9/2019 ........... C07D 239/26 |

OTHER PUBLICATIONS

Machine translation of CN-109879812, translation generated Oct. 2024, 15 pages. (Year: 2024).*
Office Action dated Feb. 20, 2024 in JP Patent Application No. 2021-206236, pp. 1-6.
Office Action undated in CN Patent Application No. 2020115350376, pp. 1-11.
Search Report undated in CN Patent Application No. 2020115350376, pp. 1 (translation only).
European Search Report dated Apr. 25, 2022 in EP Patent Application No. 21214051, pp. 1-12.
Negi, S., et al., "Impact of Different Layers on Performance of OLED", in Microsystem Technologies, vol. 24, No. 12, Berlin, DE, May 4, 2018, pp. 4981-4989.
Office Action dated Dec. 14, 2022 in JP Patent Application No. 2021-206236, pp. 1-14.

(Continued)

*Primary Examiner* — Robert S Loewe
(74) *Attorney, Agent, or Firm* — Byrne Poh LLP; Nina R. Horan

(57) ABSTRACT

Provided are a heterocyclic compound and an organic electroluminescent device comprising the same, which relate to the field of organic electroluminescent technologies. The heterocyclic compound has advantages of good film-forming property, good thermal stability, and relatively high glass-transition temperature, and the service life of the device can be prolonged when the heterocyclic compound is applied to an organic layer of the organic electroluminescent device; meanwhile, the structure has a deep HOMO energy level so that holes can be effectively prevented from diffusing from the emissive layer to the electron transport layer and the recombination probability of the holes and electrons in the emissive layer can be effectively improved; and when the heterocyclic compound is applied to the electron transport layer or hole blocking layer, the luminous efficiency of the device can be effectively improved.

7 Claims, 6 Drawing Sheets

(56) References Cited

OTHER PUBLICATIONS

European Search Report dated Aug. 1, 2022 in EP Patent Application No. 21214051.1, pp. 1-11.
Office Action dated Jun. 16, 2023 in JP Patent Application No. 2021-206236, pp. 1-13.
Extended European Search Report dated Apr. 25, 2022 in EP Patent Application No. 21208948.6, pp. 1-7.
First Search Report in CN Patent Application No. 202011377608.8, Date: Unknown, pp. 1.
Notice of Allowance dated Mar. 12, 2025 in U.S. Appl. No. 17/535,110, pp. 1-5.
Office Action dated Jan. 12, 2024 in KR Patent Application No. 10-2021-0167964, pp. 1-15.
Office Action dated Apr. 20, 2021 in CN Patent Application No. 202011377608.8, pp. 1-8.
Office Action dated Nov. 4, 2022 in JP Patent Application No. 2021-192199, pp. 1-5.
Office Action dated Nov. 6, 2024 in U.S. Appl. No. 17/535,110, pp. 1-32.

* cited by examiner

HETEROCYCLIC COMPOUND AND ORGANIC ELECTROLUMINESCENT DEVICE COMPRISING SAME

CROSS-REFERENCE TO RELATED APPLICATION(S)

This application claims priority to Chinese Patent Application No. 202011535037.6 filed on Dec. 22, 2020, the disclosure of which is incorporated herein by reference in its entirety.

TECHNICAL FIELD

The present disclosure relates to the field of organic electroluminescent technologies and specifically, relates to a heterocyclic compound and an organic electroluminescent device comprising the same.

BACKGROUND

An electroluminescent device (EL device) is a type of self-luminous device and has high research and development value and extensive application prospects due to its advantages of a wide viewing angle, a large contrast ratio, and fast response time.

An organic EL device (OLED) converts electric energy into light by applying electric power to organic light-emitting material and generally includes an anode, a cathode, and an organic layer formed between these two electrodes. The organic layer of an OLED may include a hole injection layer, a hole transport layer, an electron blocking layer, an emissive layer (including a host material and a dopant material), an electron buffer layer, a hole blocking layer, an electron transport layer, an electron injection layer, etc. The materials used in the organic layer can be divided into hole injection materials, hole transport materials, electron blocking materials, light-emitting materials, electron buffer materials, hole blocking materials, electron transport materials, electron injection materials, etc., according to their functions. In the OLED, holes from the anode and electrons from the cathode are injected into the emissive layer by applying a voltage, and the holes and electrons are recombined to generate excitons with high energy. The organic light-emitting compound moves to the excited state through energy and emits light depending on the energy generated when the organic light-emitting compound returns from the excited state to the ground state.

The organic electroluminescent device are mainly used in panel and illumination fields, which require the devices to meet the characteristics of high luminous efficiency, low drive voltage, and long service life. Therefore, the main content of OLED research is to improve the efficiency of the device, reduce the drive voltage, prolong the service life, etc. Specifically, in one aspect, the manufacturing process of the device is required to be optimized to improve the efficiency of the device by adding a variety of functional auxiliary layers and adopting doping methods, and in another aspect, organic electroluminescent materials with excellent properties need to be developed since the properties of the materials directly affect the efficiency, lifetime, and stability of devices.

One of the manners to improve the luminous efficiency of OLED devices is to improve the recombination probability of electrons and holes in the emissive layer. Since the hole mobility of hole transport materials is two orders of magnitude higher than the electron mobility of electron transport materials, the effective transport balance between holes and electrons cannot be reached, and some holes easily pass through the emissive layer and recombine with electrons at the interface between the emissive layer and the electron transport layer or in the electron transport layer, resulting in the obvious reduction of the efficiency of devices. In order to make electrons and holes recombine well in the emissive layer to form excitons and emit light, a material having a hole blocking ability is often introduced to block holes within the emissive layer. The materials commonly used to block holes can be selected from BCP. The BCP has a work function of 6.7 eV and a great hole blocking ability. However, The BCP has a low glass-transition temperature ($T_g$) which is only 83° C. and poor film stability, which leads to the decline of efficiency and lifetime of devices. Therefore, it is urgent to introduce a material that can effectively control electrons and holes within the area of the emissive layer, has a high glass-transition temperature, and can effectively improve the luminous efficiency and service life of devices.

SUMMARY

In order to solve the problems of the reduction of luminous efficiency and the shortening of service life of the device caused by the fact that some holes easily pass through the emissive layer and recombine with electrons because the hole mobility of hole transport materials is higher than the electron mobility of electron transport materials at present, the present disclosure provides a heterocyclic compound and an organic electroluminescent device containing the heterocyclic compound. When the heterocyclic compound is applied to the hole blocking layer, holes can be effectively blocked within the emissive layer and the recombination probability of the holes and electrons in the emissive layer can be improved, thereby improving the luminous efficiency of the organic electroluminescent device and prolonging the service life of the device.

The present disclosure provides a heterocyclic compound which has a structure as shown in Formula I:

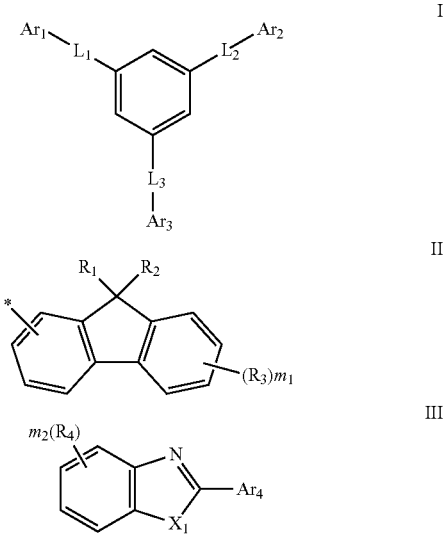

wherein, in the structure as shown in Formula I, $Ar_1$ is selected from a structure as shown in Formula II, and $Ar_2$ and $Ar_3$ are identical to each other or different from each other and independently selected from a structure as shown in Formula III;

$L_1$ to $L_3$ are identical to each other or different from each other and independently selected from any one of a single bond, substituted or unsubstituted C6 to C30 arylene or substituted or unsubstituted C3 to C30 heteroarylene;

* is the attachment site between $L_1$ and $Ar_1$, the attachment site between $L_2$ and $Ar_2$ is any position on the structure as shown in Formula III, and the attachment site between $L_3$ and $Ar_3$ is any position on the structure as shown in Formula III;

in the structure as shown in Formula II, $R_1$ and $R_2$ are identical to each other or different from each other and independently selected from any one of hydrogen, C1 to C12 alkyl, substituted or unsubstituted phenyl, or $R_1$ and $R_2$ are joined to form a substituted or unsubstituted ring, wherein "substituted" refers to mono- or multi-substitution with any of the following groups: deuterium, methyl, ethyl, tert-butyl, phenyl, biphenyl or naphthyl, or $R_1$ and $R_2$ are joined to form a ring;

$R_3$ is selected from any one of hydrogen, deuterium, halogen, cyano, hydroxyl, amino, sulfanyl, adamantyl, norcamphanyl, substituted or unsubstituted C1 to C12 alkyl, substituted or unsubstituted C2 to C12 alkenyl or substituted or unsubstituted C6 to C30 aryl;

$m_1$ is an integer selected from 0 to 4, and when $m_1$ is greater than 1, two or more $R_3$ are identical to each other or different from each other, or two adjacent $R_3$ are joined to form a ring;

in the structure as shown in Formula III, $X_1$ is independently selected from any one of O, S or N—$Ar_5$;

$R_4$ is selected from any one of hydrogen, deuterium, halogen, cyano, hydroxyl, substituted or unsubstituted C1 to C12 alkyl, substituted or unsubstituted C2 to C12 alkenyl or substituted or unsubstituted C6 to C30 aryl;

$m_2$ is an integer selected from 0 to 4, and when $m_2$ is greater than 1, two or more $R_4$ are identical to each other or different from each other, or two adjacent $R_4$ are joined to form a ring; and $Ar_4$ and $Ar_5$ are independently selected from any one of hydrogen, deuterium, halogen, cyano, substituted or unsubstituted C1 to C12 alkyl, substituted or unsubstituted C6 to C30 aryl or substituted or unsubstituted C3 to C30 heteroaryl.

The present disclosure further provides an organic electroluminescent device which includes an anode, a cathode, and an organic layer disposed between the anode and the cathode, wherein the organic layer includes the heterocyclic compound described above.

Beneficial Effect

The heterocyclic compound provided by the present disclosure has a rigid structure so that the structure of the heterocyclic compound has a high glass-transition temperature, and meanwhile, the heterocyclic compound provided by the present disclosure has molecular asymmetry so that the aggregation manner of molecules can be changed and molecules can be effectively prevented from crystallization, thereby improving the film-forming property and thermal stability of the compound and effectively prolonging the service life of the organic electroluminescent device.

In another aspect, the heterocyclic compound provided by the present disclosure has high electron mobility so that the transport balance between holes and electrons can be effectively improved, thereby reducing the drive voltage of the organic electroluminescent device and improving the luminous efficiency of the device; and meanwhile, the heterocyclic compound provided by the present disclosure has a deep HOMO energy level so that holes can be prevented from diffusing from the emissive layer to the electron transport layer, holes can be effectively limited within the emissive layer, and the recombination probability of the holes and electrons in the emissive layer can be improved, thereby improving the luminous efficiency of the organic electroluminescent device.

DETAILED DESCRIPTION

Figure 1:
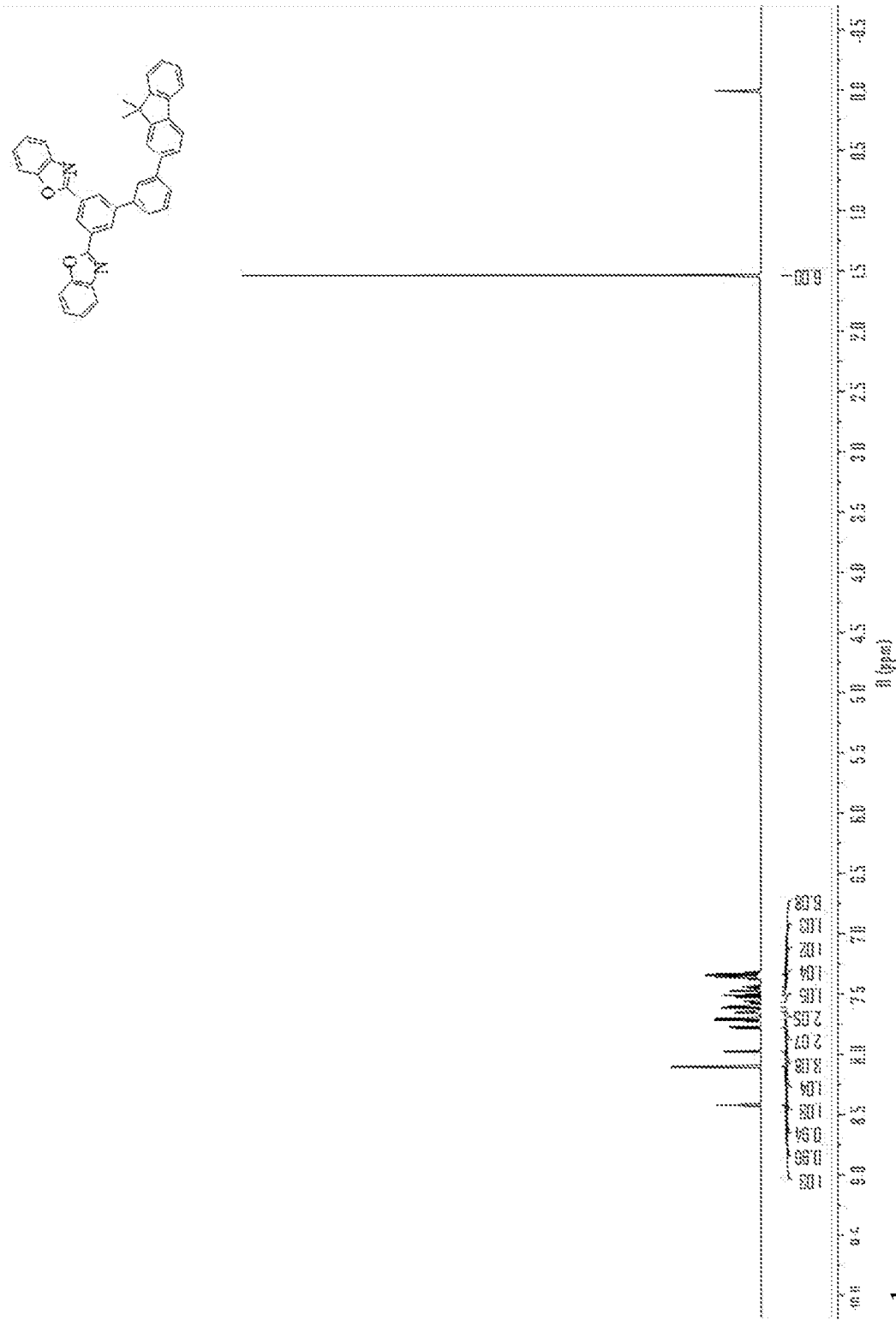
FIG. 1 is a $^1$H NMR graph of Compound 1 of the present disclosure.
Figure 2:
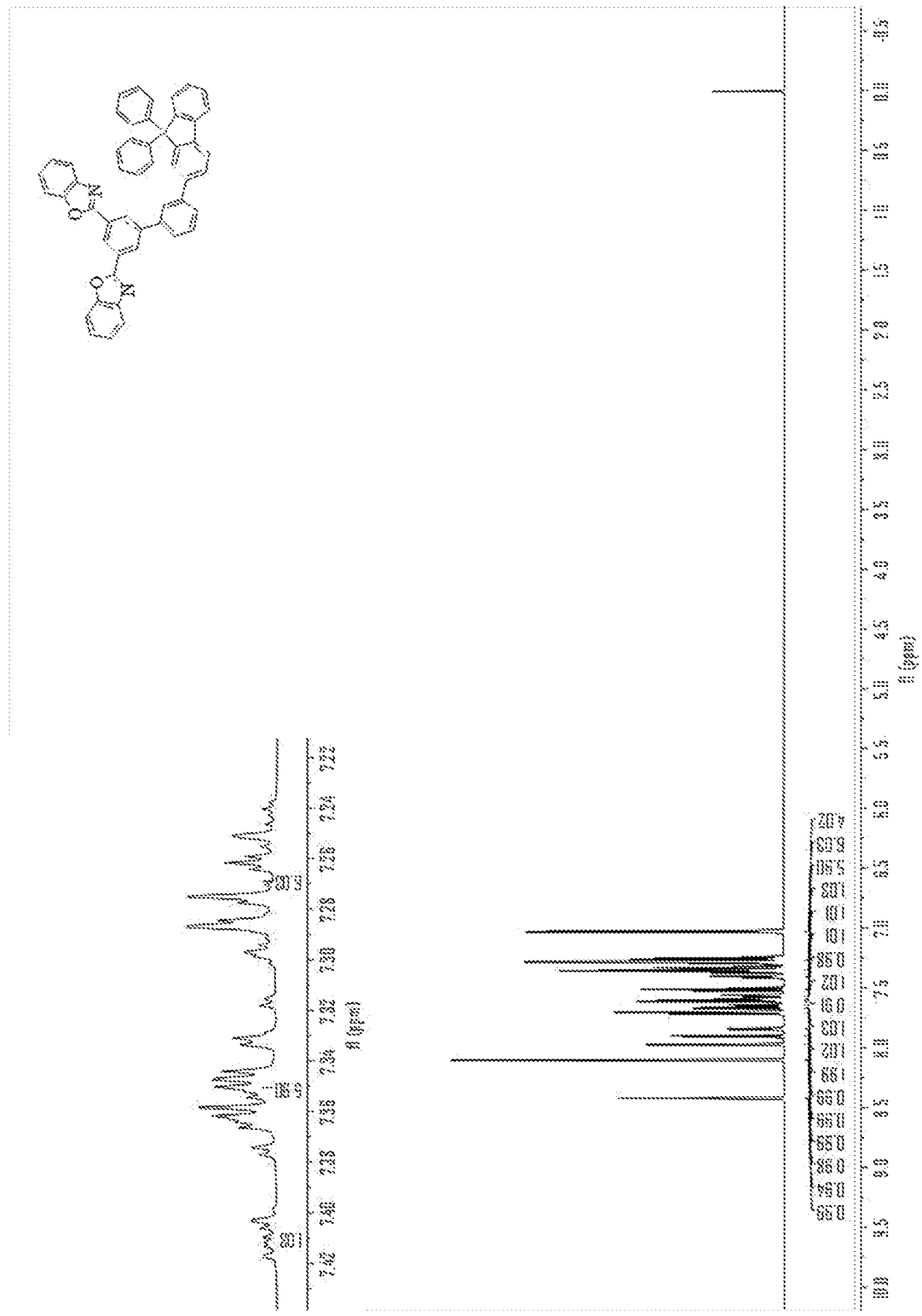
FIG. 2 is a $^1$H NMR graph of Compound 4 of the present disclosure.
Figure 3:
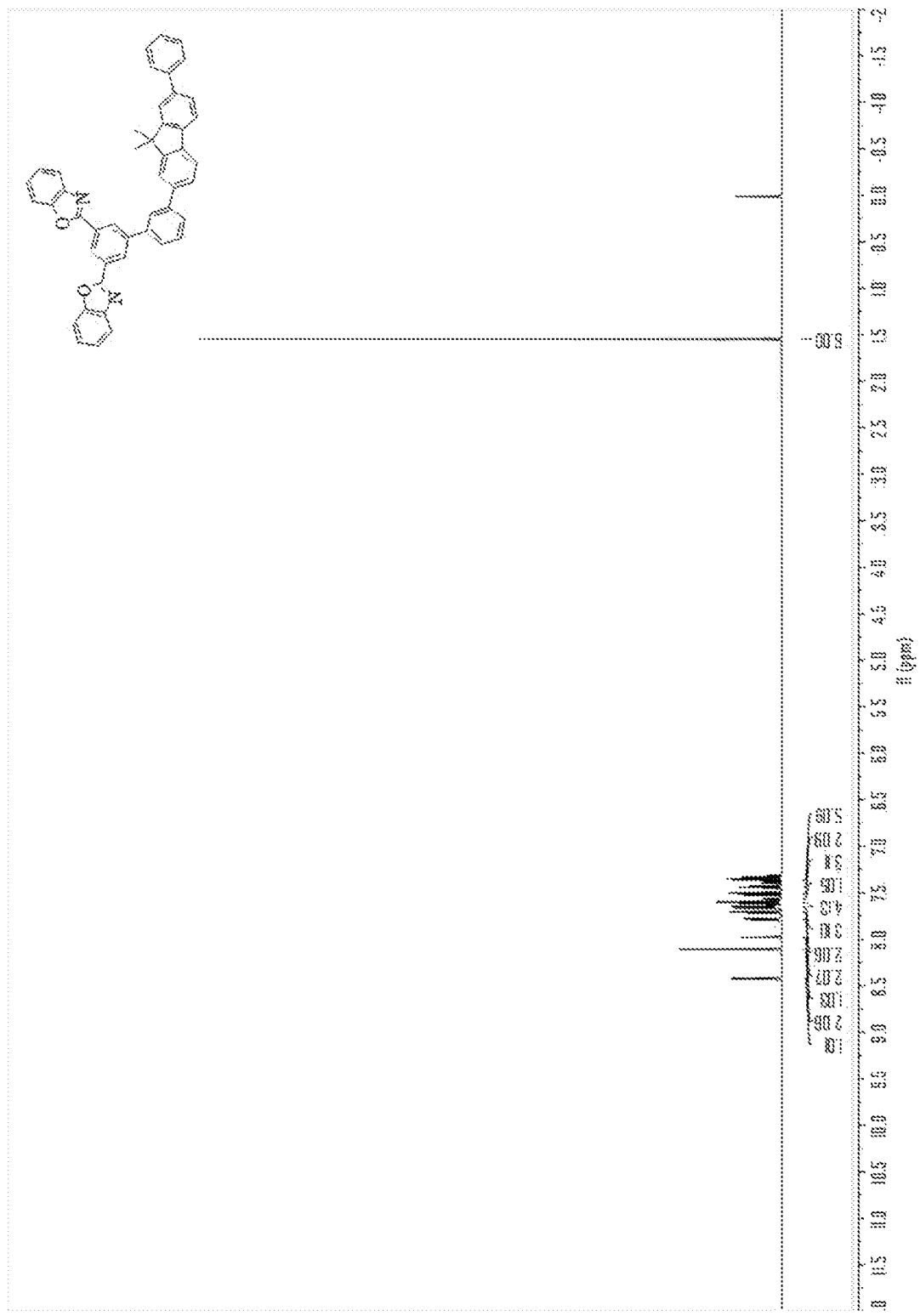
FIG. 3 is a $^1$H NMR graph of Compound 5 of the present disclosure.
Figure 4:
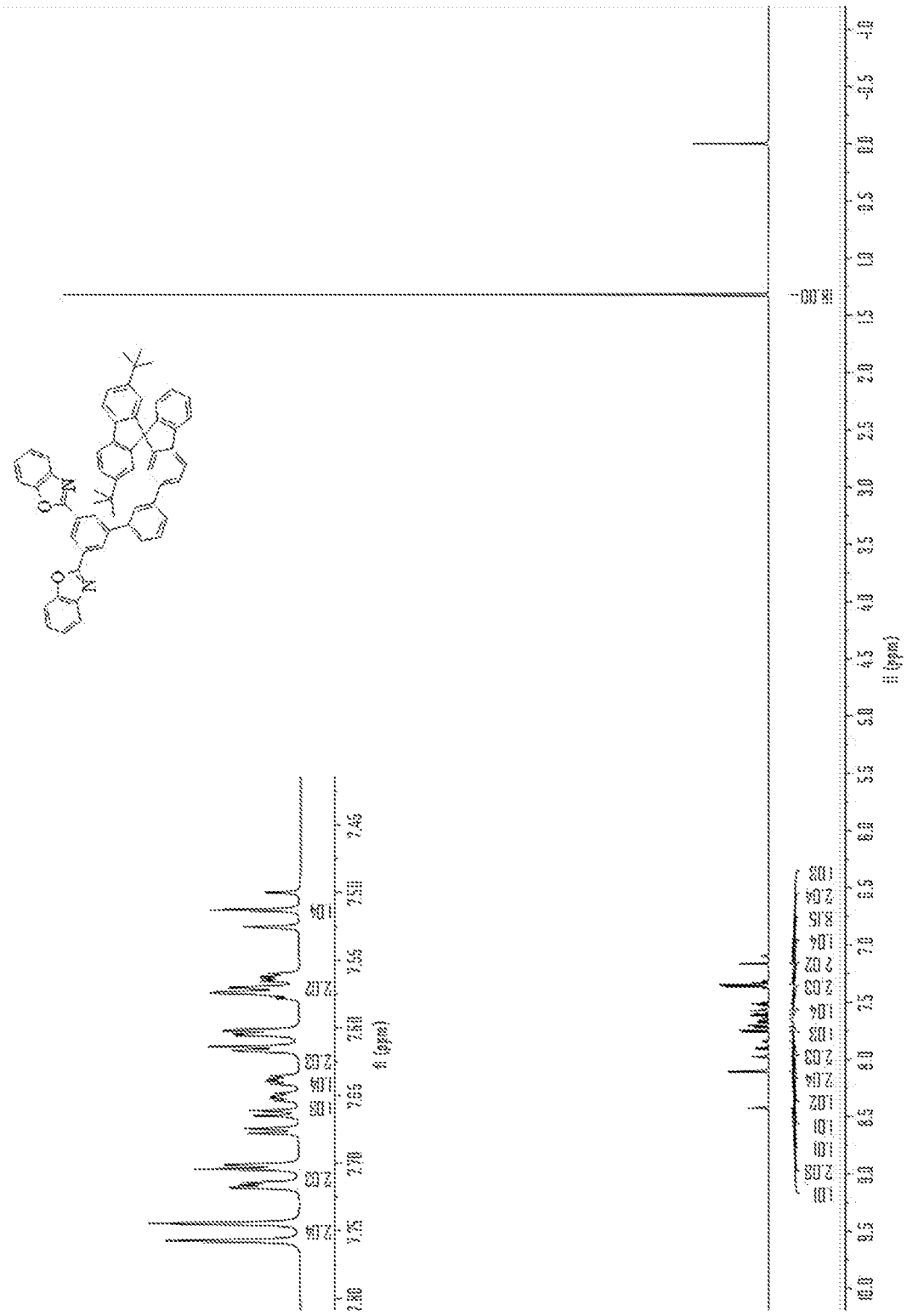
FIG. 4 is a $^1$H NMR graph of Compound 10 of the present disclosure.
Figure 5:
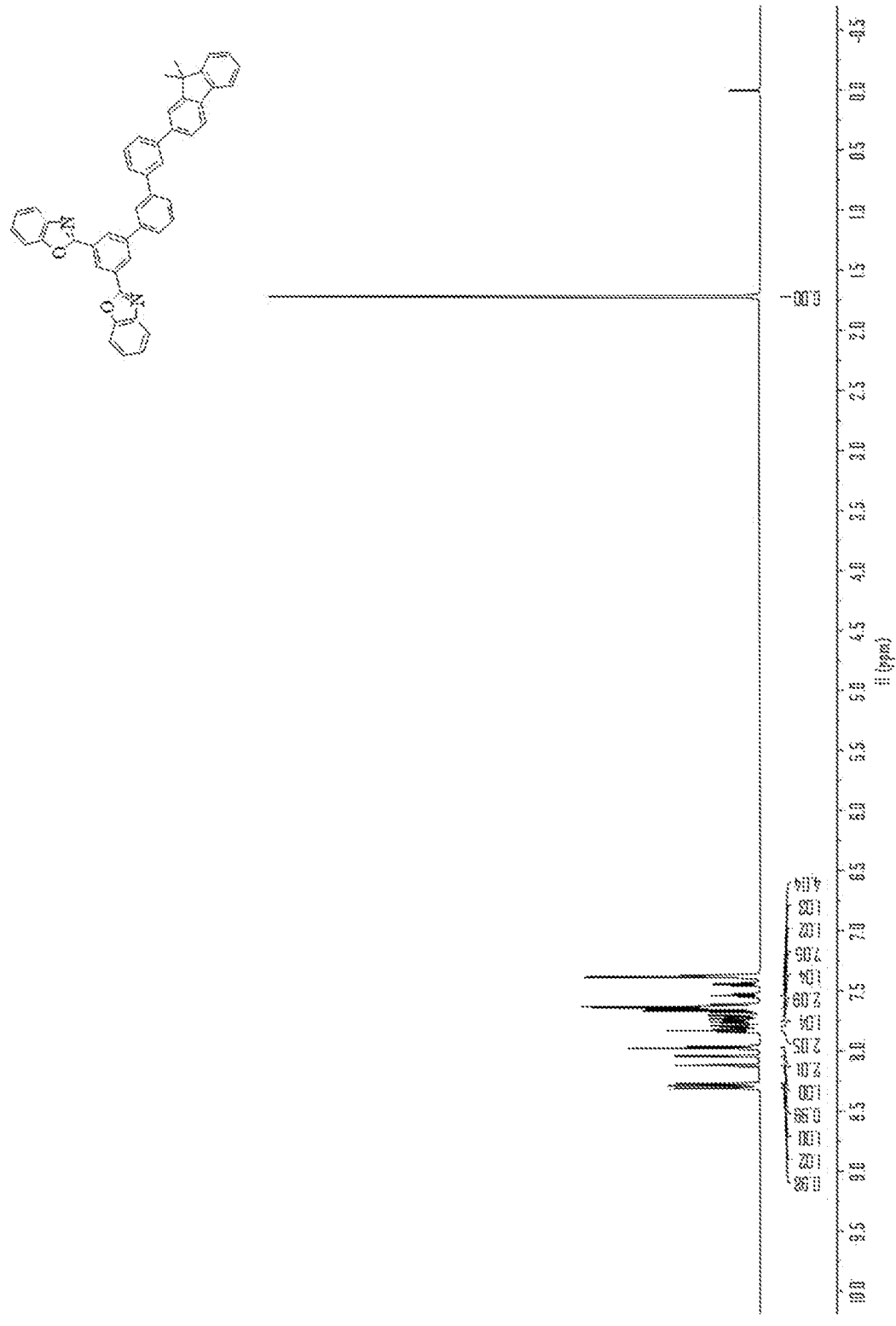
FIG. 5 is a $^1$H NMR graph of Compound 82 of the present disclosure.
Figure 6:
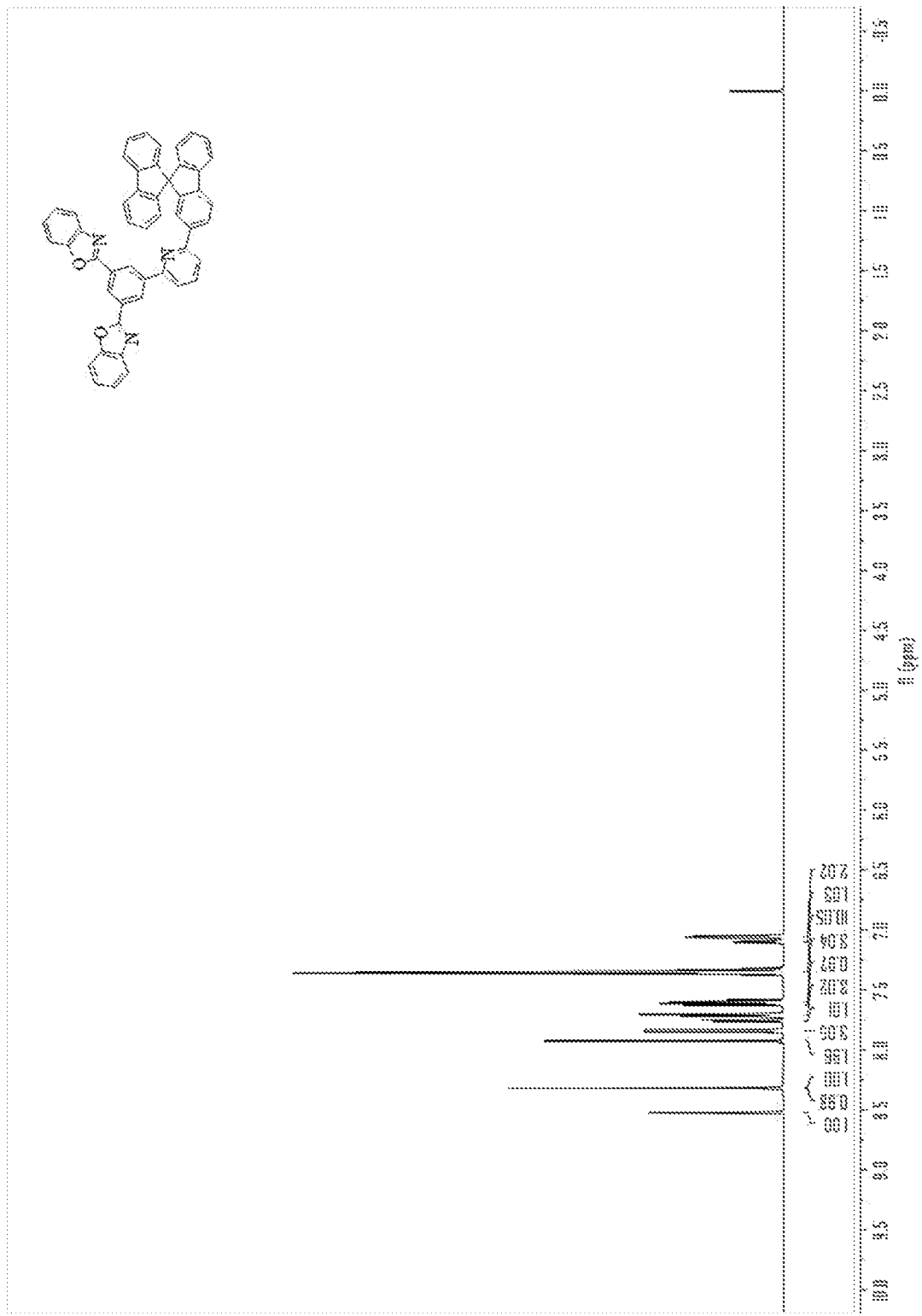
FIG. 6 is a $^1$H NMR graph of Compound 292 of the present disclosure.

The present disclosure will be described clearly and completely in conjunction with technical solutions in the specific embodiments of the present disclosure. Apparently, the embodiments described are part, not all, of the embodiments of the present disclosure. Based on the embodiments of the present disclosure, all other embodiments obtained by those skilled in the art are within the scope of the present disclosure on the premise that no creative work is done.

Definition

In the specification, "*" means a part attached with another substituent.

In the present disclosure, examples of the halogen include fluorine, chlorine, bromine, and iodine.

In the present disclosure, the alkyl may be linear or branched alkyl which is not particularly limited in the number of carbon atoms it has, preferably, having 1 to 12 carbon atoms, more preferably, having 1 to 8 carbon atoms, and particularly preferably, having 1 to 6 carbon atoms. Specific examples may include methyl, ethyl, n-propyl, isopropyl, n-butyl, isobutyl, tert-butyl, sec-butyl, n-pentyl, isopentyl, neopentyl, tert-pentyl, 1-methylpenty, 4-methyl-2-pentyl, 3,3-dimethylbutyl, and heptyl, but not limited thereto.

In the present disclosure, the alkenyl may be linear or branched alkenyl which is not particularly limited in the number of carbon atoms it has, preferably, having 2 to 12 carbon atoms, more preferably, having 2 to 8 carbon atoms, and particularly preferably, having 2 to 6 carbon atoms. Specific examples may include vinyl, 1-propenyl, isopropenyl, 1-butenyl, 3-butenyl, 1-pentenyl, 2-pentenyl, allyl, 1,3-butadienyl, 1-phenylvinyl-1-yl, diphenylvinyl, and styryl, but not limited thereto.

In the present disclosure, the aryl may be monocyclic aryl, polycyclic aryl or fused ring aryl which is not particularly limited in the number of carbon atoms it has, preferably, having 6 to 30 carbon atoms, more preferably, having 6 to 18 carbon atoms, particularly preferably, having 6 to 14 carbon atoms, and most preferably, having 6 to 12 carbon atoms. Specific examples may include phenyl, biphenyl, triprenyl, naphthyl, anthryl, phenanthryl, triphenylene, pyrenl, fluorenyl, perylenyl, and fluoranthenyl, but not limited thereto.

In the present disclosure, the heteroaryl may contain one or more of N, O, P, S, Si, and Se as heteroatoms, and may be monocyclic heteroaryl, polycyclic heteroaryl or fused ring heteroaryl which is not particularly limited in the number of carbon atoms it has, preferably, having 2 to 30 carbon atoms, more preferably, having 2 to 20 carbon atoms, particularly preferably, having 3 to 12 carbon atoms, and most preferably, having 3 to 8 carbon atoms. Examples may include thienyl, pyrrolyl, furanyl, imidazolyl, thiazolyl, oxazolyl, oxadiazolyl, thiadiazolyl, triazolyl, pyridyl, bipyridyl, pyrazinyl, pyridazinyl, pyrimidinyl, triazinyl, quinolinyl, isoquinolinyl, quinoxalinyl, quinazolinyl, phenothiazinyl, phenoxazinyl, indolyl, carbazolyl, benzoxazolyl, benzothiophenyl, benzimidazolyl, benzothiophenyl, benzofuranyl, benzothiazolyl, dibenzofuranyl, dibenzothiophenyl, etc., but not limited thereto.

In the present disclosure, the arylene may be monocyclic arylene, polycyclic arylene or fused ring arylene which is not particularly limited in the number of carbon atoms it has, preferably, having 6 to 30 carbon atoms, more preferably, having 6 to 18 carbon atoms, particularly preferably, having 6 to 14 carbon atoms, and most preferably, having 6 to 12 carbon atoms. Specific examples may include phenylene, biphenylene, terphenylene, naphthylene, anthrylene, phenanthrylene, triphenylenylene, pyrenylene, fluorenylene, perylenylene, and fluoranthenylene, but not limited thereto.

In the present disclosure, the heteroarylene may contain one or more of N, O, P, S, Si, and Se as heteroatoms, and may be monocyclic heteroarylene, polycyclic heteroarylene or fused ring heteroarylene which is not particularly limited in the number of carbon atoms it has, preferably, having 2 to 30 carbon atoms, more preferably, having 2 to 20 carbon atoms, particularly preferably, having 3 to 12 carbon atoms, and most preferably, having 3 to 8 carbon atoms. Examples may include thienylene, pyrrolylene, furanylene, imidazolylene, thiazolylene, oxazolylene, oxadiazolylene, thiadiazolylene, triazolylene, pyridinylene, bipyridylene, pyrazinylene, pyridazinylene, pyrimidinylene, triazinylene, quinolinylene, isoquinolinylene, quinoxalinylene, quinazolinylene, phenothiazinylene, phenoxazinylene, indolylene, carbazolylene, benzothiazolylene, benzothienylene, benzimidazolylene, benzothienylene, benzofuranylene, benzothiazolylene, dibenzofuranylene, dibenzothienylene, etc., but not limited thereto.

When a definition is not otherwise provided, "substituted" refers to substitution of at least one hydrogen in a compound with deuterium, halogen, hydroxyl, amino, nitryl, cyano, C1 to C30 alkyl, C6 to C30 aryl, C6 to C30 arylamine, C2 to C30 heteroaryl or combinations thereof, preferably deuterium, a halogen atom, cyano, C1 to C12 alkyl, C6 to C30 aryl or C2 to C30 heteroaryl. Specific examples may include deuterium, fluorine, chlorine, bromine, iodine, cyano, methyl, ethyl, isopropyl, t-butyl, phenyl, naphthyl, anthryl, phenanthrenyl, pyrenyl, chrysenyl, perylenyl, fluoranthenyl, benzyl, 9,9-dimethylfluorenyl, 9,9-diphenylfluorenyl, 9,9-spirodifluorenyl, dimethylamino, diphenylamino, carbazolyl, 9-phenylcarbazolyl, pyrrolyl, furanyl, thienyl, benzoxazoly, benzothiazolyl, benzofuranyl, benzothiophenyl, dibenzofuranyl, dibenzothiophenyl, dibenzothienyl, phenothiazinyl, phenoxazinyl, acridyl, biphenyl, triphenyl, etc., but not limited thereto.

In the present disclosure, the "integer selected from 0 to M" means that the value is selected from any one of integers from 0 to M, including 0, 1, 2 . . . , M−2, M−1, and M. For example, the expression that mi is an integer selected from 0 to 4 means that $m_1$ is selected from 0, 1, 2, 3, or 4; the expression that $m_2$ is an integer selected from 0 to 4 means that $m_2$ is selected from 0, 1, 2, 3, or 4; the expression that $m_3$ is an integer selected from 0 to 4 means that $m_3$ is selected from 0, 1, 2, 3, or 4.

The expression of joined to form a ring in the present disclosure means that two groups are joined to each other via chemical bonds and are optionally aromatized, which can be exemplified by the following formulas:

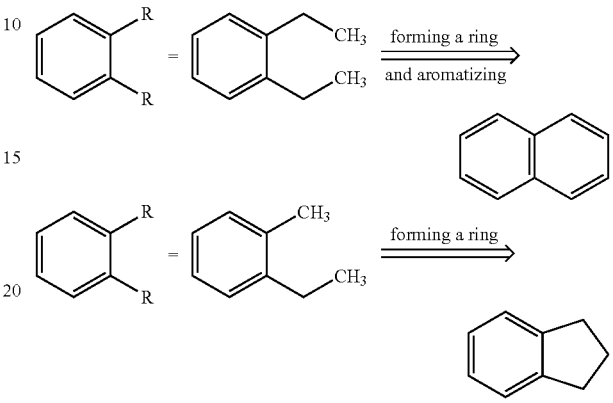

In the present disclosure, the ring formed through joining may be a five-membered ring, a six-membered ring or a fused ring, for example, phenyl, naphthyl, cyclopentenyl, cyclopentyl, cyclohexanophenyl, quinolinyl, isoquinolinyl, dibenzothiophenyl, phenanthryl or pyrenyl.

The present disclosure provides a heterocyclic compound which has a structure as shown in Formula I:

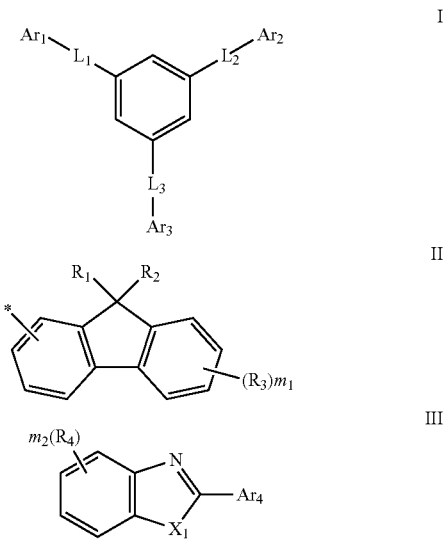

wherein, in the structure as shown in Formula I, $Ar_1$ is selected from a structure as shown in Formula II, and $Ar_2$ and $Ar_3$ are identical to each other or different from each other and independently selected from a structure as shown in Formula III;

$L_1$ to $L_3$ are identical to each other or different from each other and independently selected from any one of a single bond, substituted or unsubstituted C6 to C30 arylene or substituted or unsubstituted C3 to C30 heteroarylene;

* is the attachment site between $L_1$ and $Ar_1$, the attachment site between $L_2$ and $Ar_2$ is any position on the structure as shown in Formula III, and the attachment site between $L_3$ and $Ar_3$ is any position on the structure as shown in Formula III;

in the structure as shown in Formula II, $R_1$ and $R_2$ are identical to each other or different from each other and independently selected from any one of hydrogen, C1 to C12 alkyl, substituted or unsubstituted phenyl, or $R_1$ and $R_2$ are joined to form a substituted or unsubstituted ring, wherein "substituted" refers to mono- or multi-substitution with any of the following groups: deuterium, methyl, ethyl, t-butyl, phenyl, biphenyl or naphthyl, or $R_1$ and $R_2$ are joined to form a ring;

$R_3$ is selected from any one of hydrogen, deuterium, halogen, cyano, hydroxyl, amino, sulfanyl, adamantyl, norcamphanyl, substituted or unsubstituted C1 to C12 alkyl, substituted or unsubstituted C2 to C12 alkenyl or substituted or unsubstituted C6 to C30 aryl;

$m_1$ is an integer selected from 0 to 4, and when $m_1$ is greater than 1, two or more $R_3$ are identical to each other or different from each other, or two adjacent $R_3$ are joined to form a ring; in the structure as shown in Formula III, $X_1$ is independently selected from any one of O, S or N—$Ar_5$;

$R_4$ is selected from any one of hydrogen, deuterium, halogen, cyano, hydroxyl, substituted or unsubstituted C1 to C12 alkyl, substituted or unsubstituted C2 to C12 alkenyl or substituted or unsubstituted C6 to C30 aryl;

$m_2$ is an integer selected from 0 to 4, and when $m_2$ is greater than 1, two or more $R_4$ are identical to each other or different from each other, or two adjacent $R_4$ are joined to form a ring; and $Ar_4$ and $Ar_5$ are independently selected from any one of hydrogen, deuterium, halogen, cyano, substituted or unsubstituted C1 to C12 alkyl, substituted or unsubstituted C6 to C30 aryl or substituted or unsubstituted C3 to C30 heteroaryl. Preferably, the structure as shown in Formula II is selected from any one of structures as shown in Formula II-1 to Formula II-4:

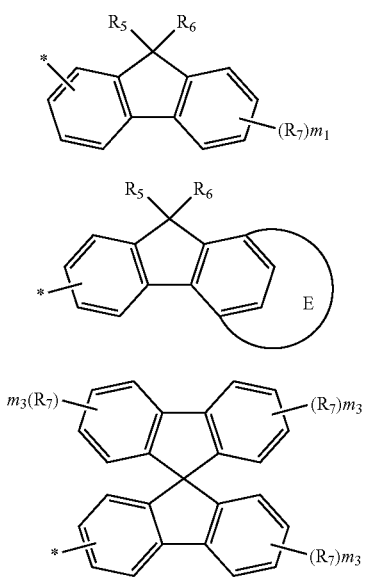

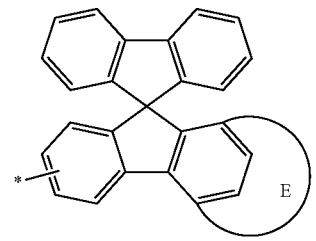

wherein, * represents an attachment site to $L_1$;

$R_5$ and $R_6$ are identical to each other or different from each other and independently selected from any one of hydrogen, methyl, ethyl or phenyl;

$R_7$ is selected from any one of hydrogen, deuterium, cyano, adamantyl, norcamphanyl, substituted or unsubstituted C1 to C6 alkyl or substituted or unsubstituted C6 to C18 aryl;

$m_3$ is an integer selected from 0 to 4, and when $m_3$ is greater than 1, two or more $R_7$ are identical to each other or different from each other;

ring E is selected from any one of the following structures:

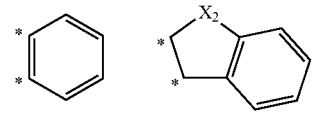

wherein, * represents a fusion site; and $X_2$ is selected from any one of C—$R_8R_9$, N—$R_{10}$, O or S;

$R_8$ and $R_9$ are identical to each other or different from each other and independently selected from any one of hydrogen, substituted or unsubstituted C1 to C12 alkyl or substituted or unsubstituted C6 to C30 aryl; and $R_{10}$ is selected from any one of substituted or unsubstituted C1 to C12 alkyl, substituted or unsubstituted C6 to C30 aryl or substituted or unsubstituted C3 to C30 heteroaryl.

Further preferably, the structure as shown in Formula II is selected from any one of the following groups:

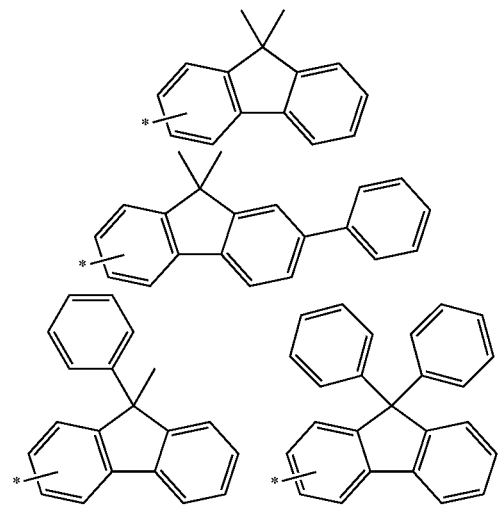

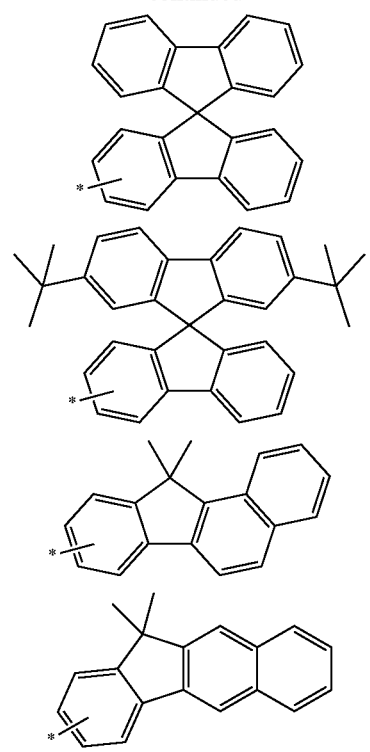
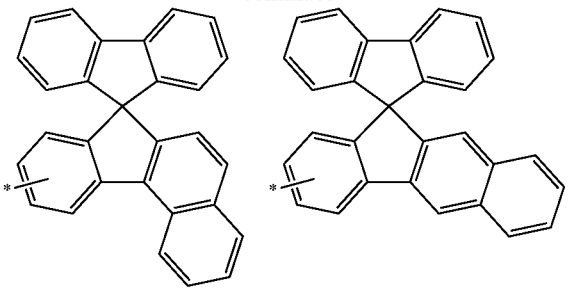
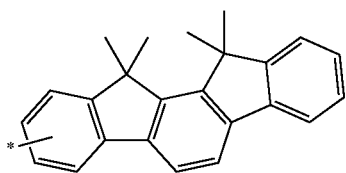
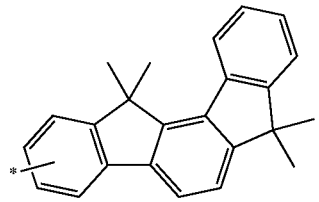
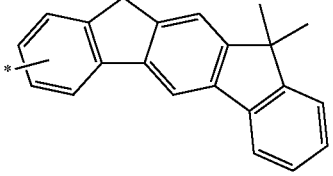
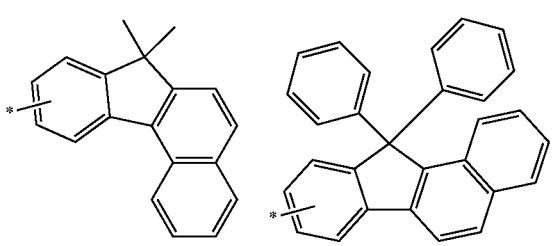
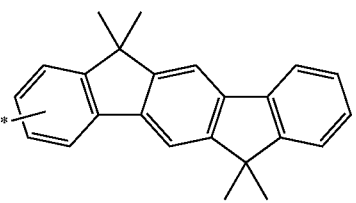
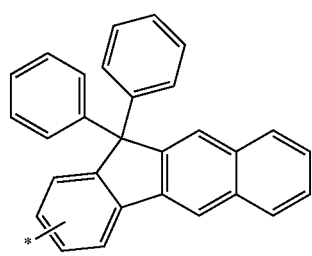
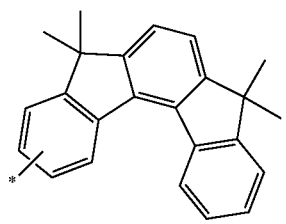
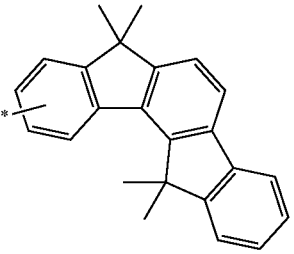
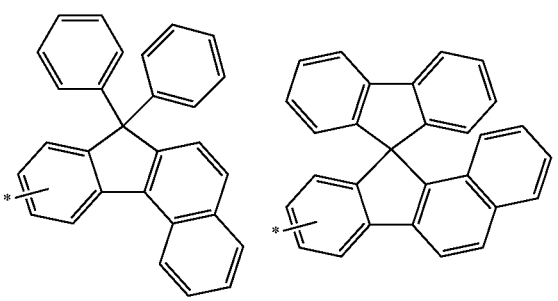
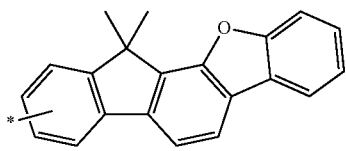

11
-continued
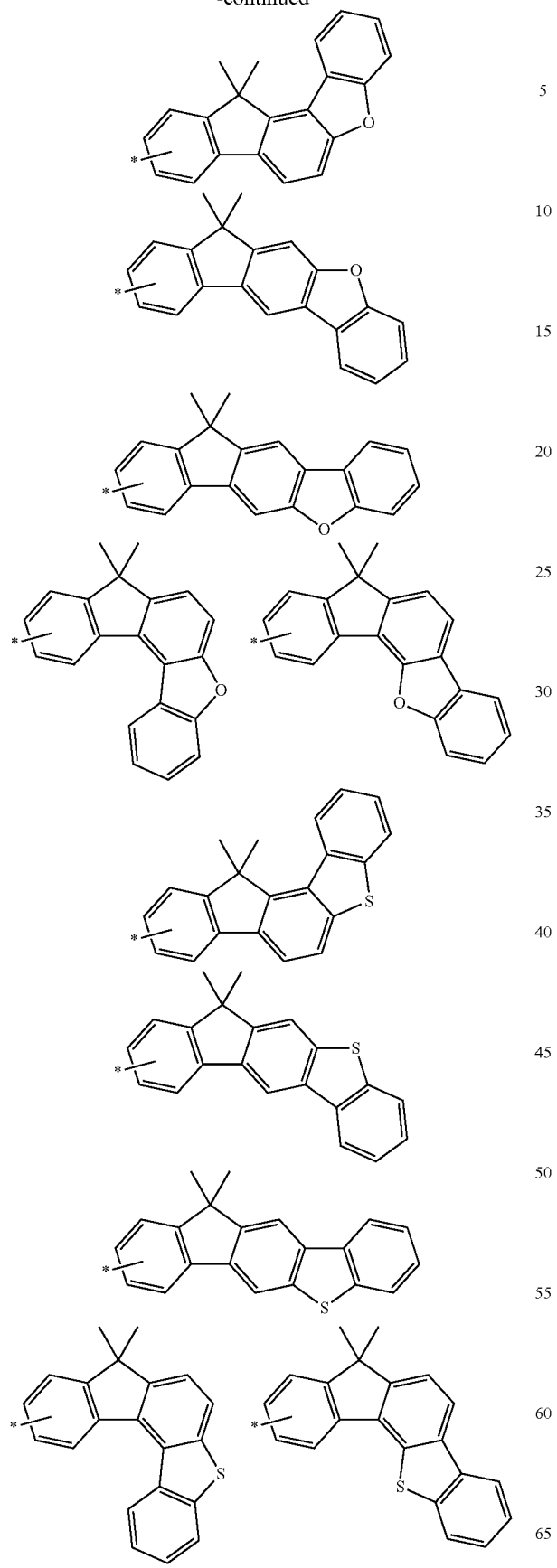
12
-continued
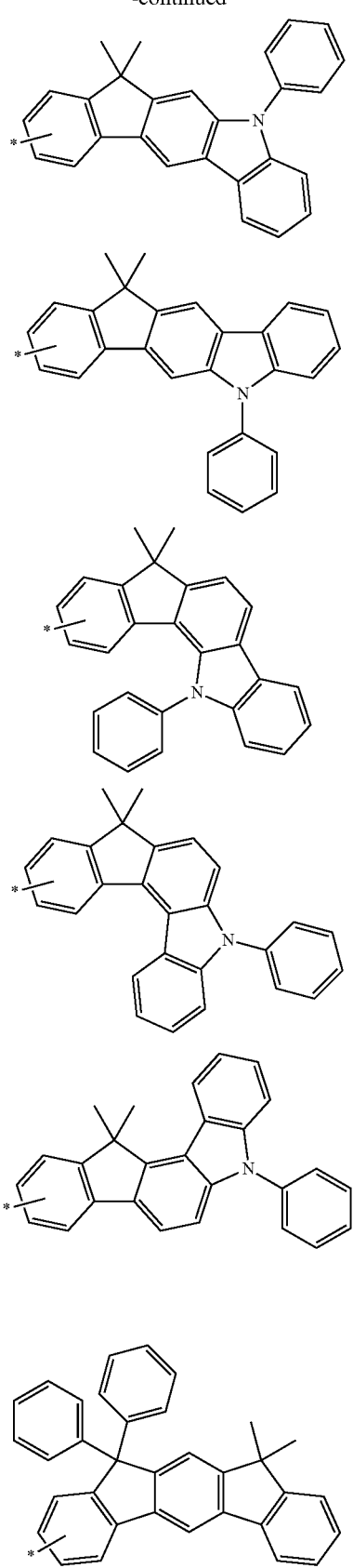

-continued
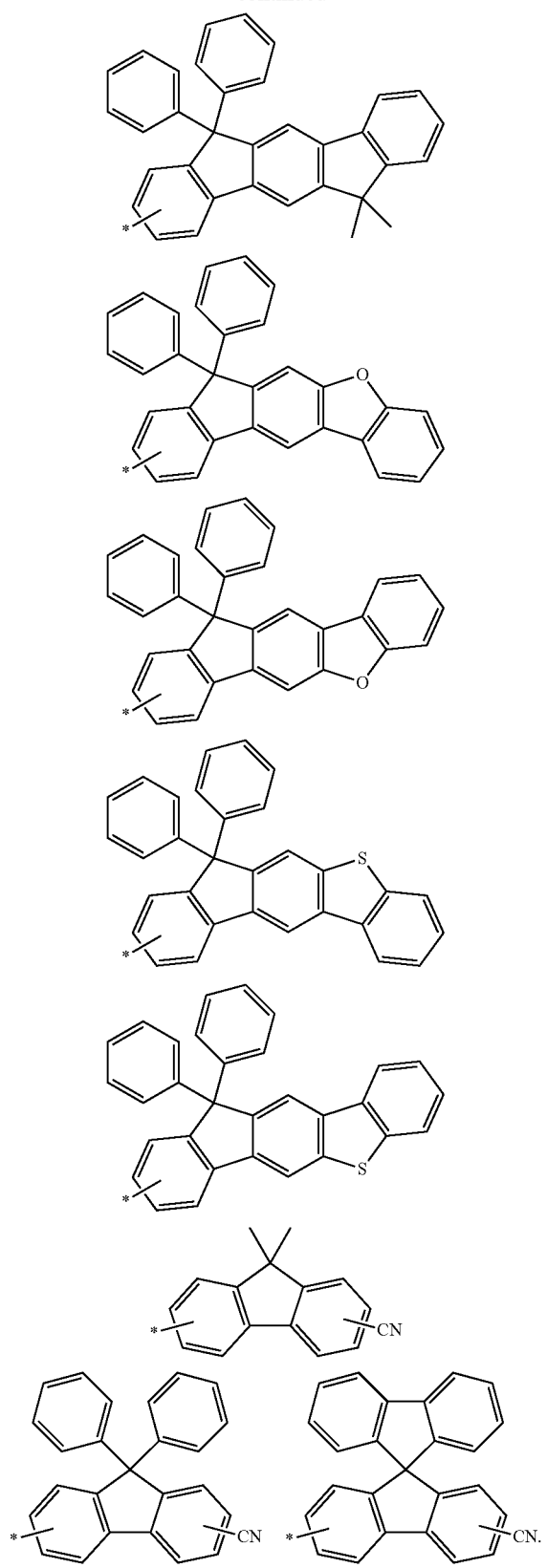
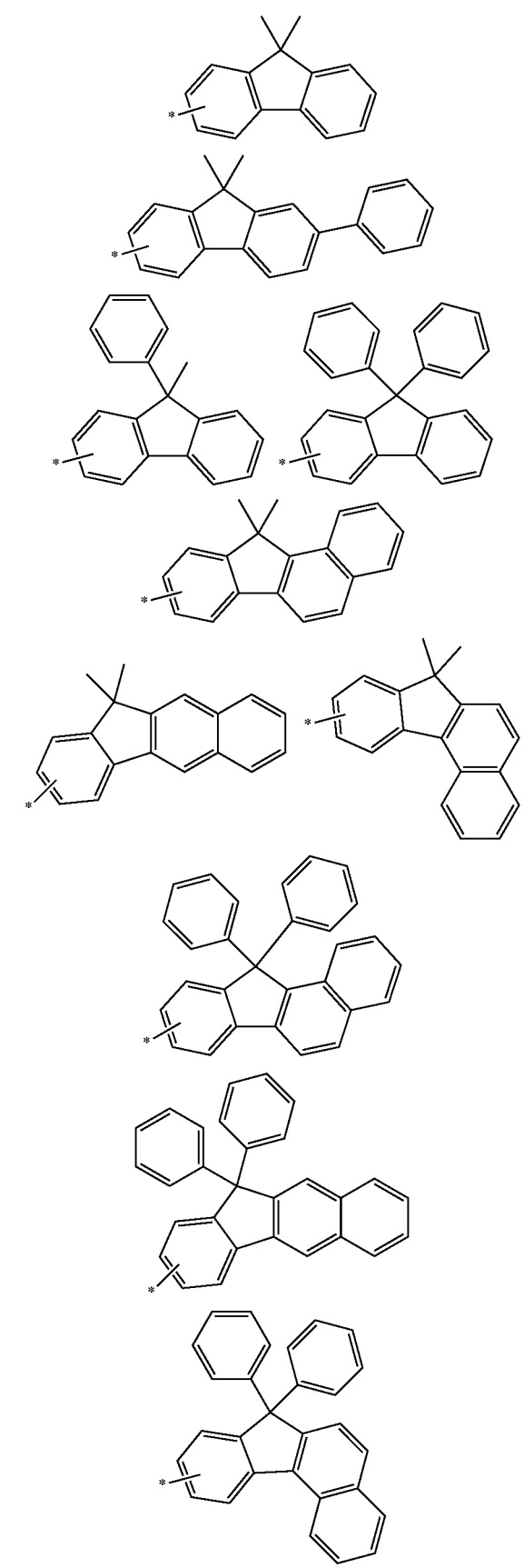
Further preferably, the structure as shown in Formula II is selected from any one of the following groups:

-continued
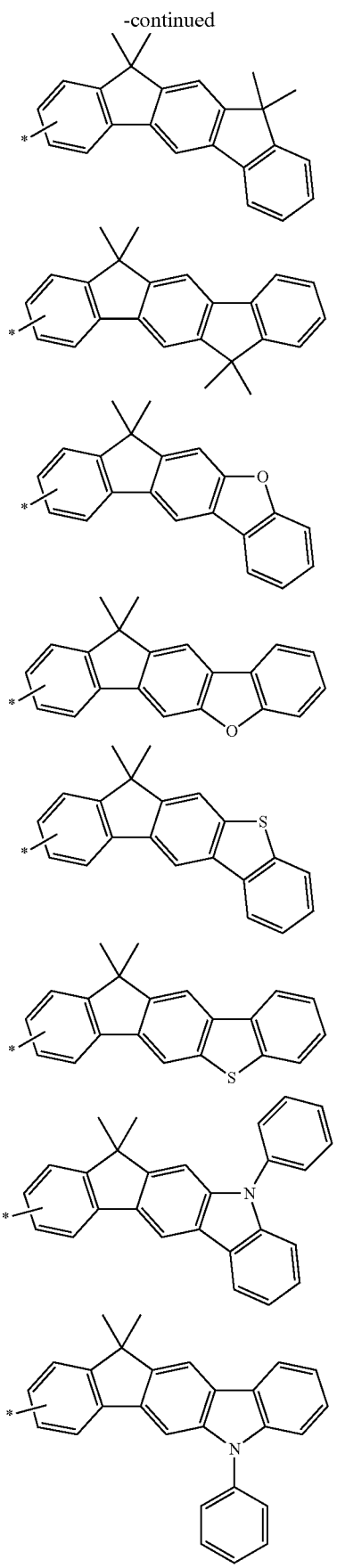
-continued
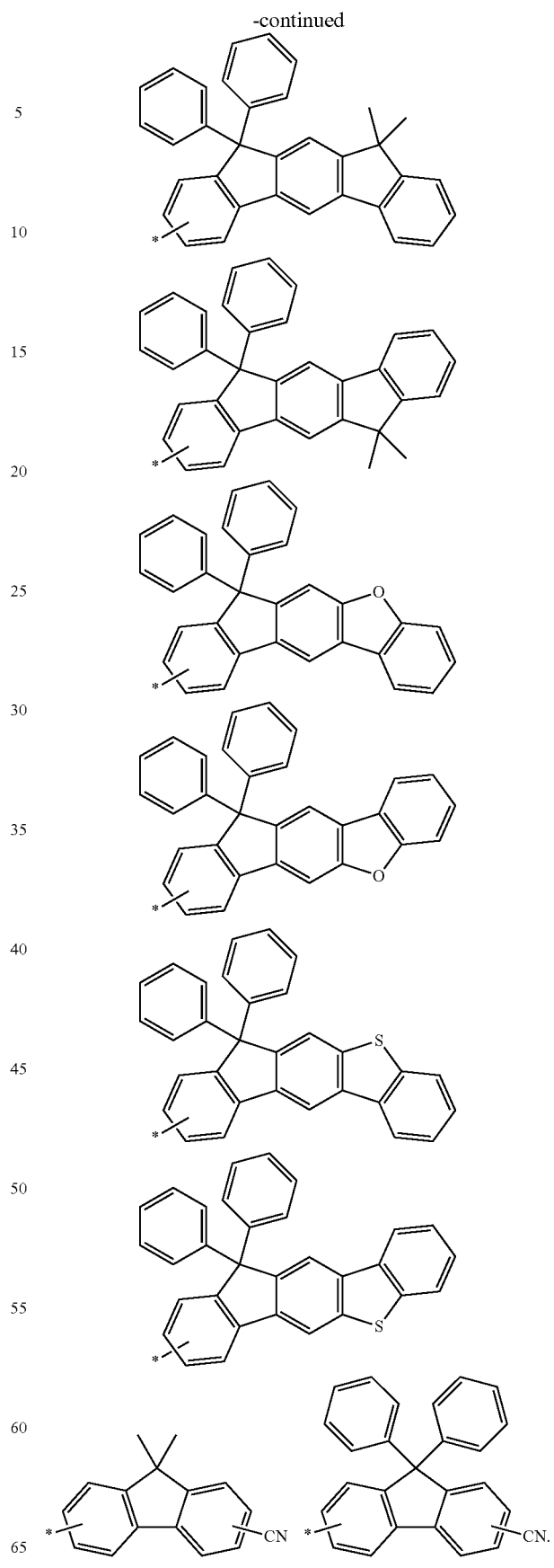

More preferably, the structure as shown in Formula II is selected from any one of the following groups:

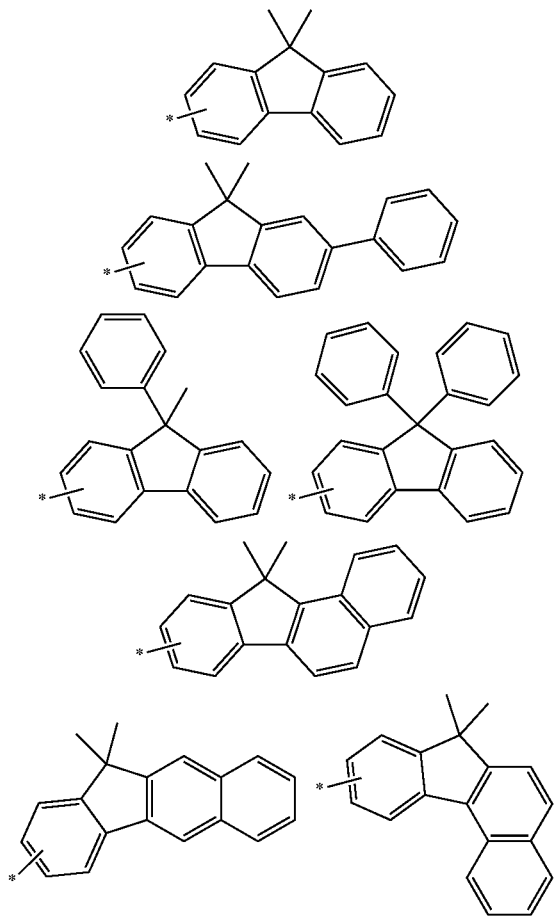

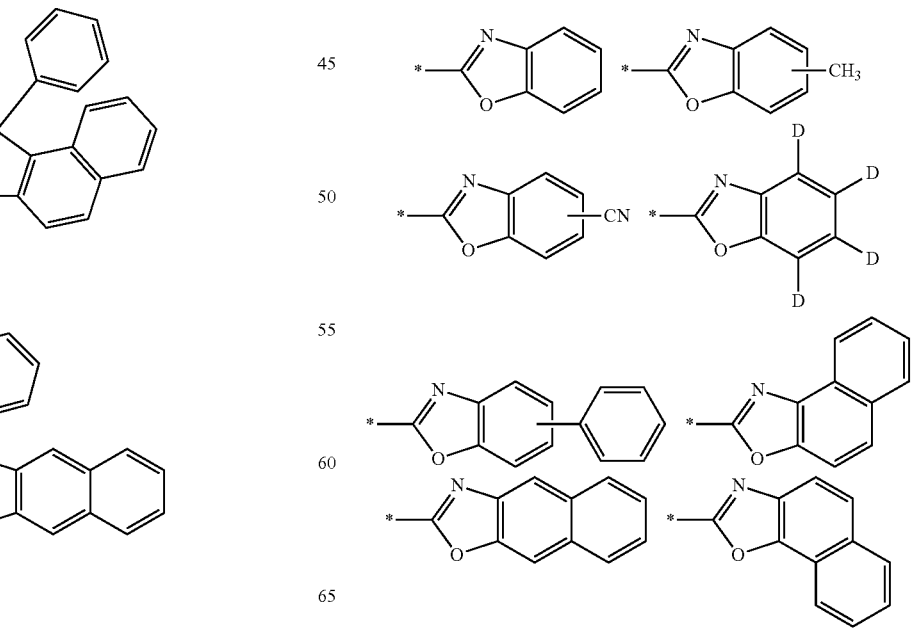

Preferably, the structure as shown in Formula III is selected from any one of the structures as shown in Formula III-1 and Formula III-2:

wherein, * represents an attachment site between $L_2$ and $L_3$; and ring A is selected from any one of hydrogen or substituted or unsubstituted C6 to C10 aryl.

Further preferably, the structure as shown in Formula III is selected from any one of the following groups:

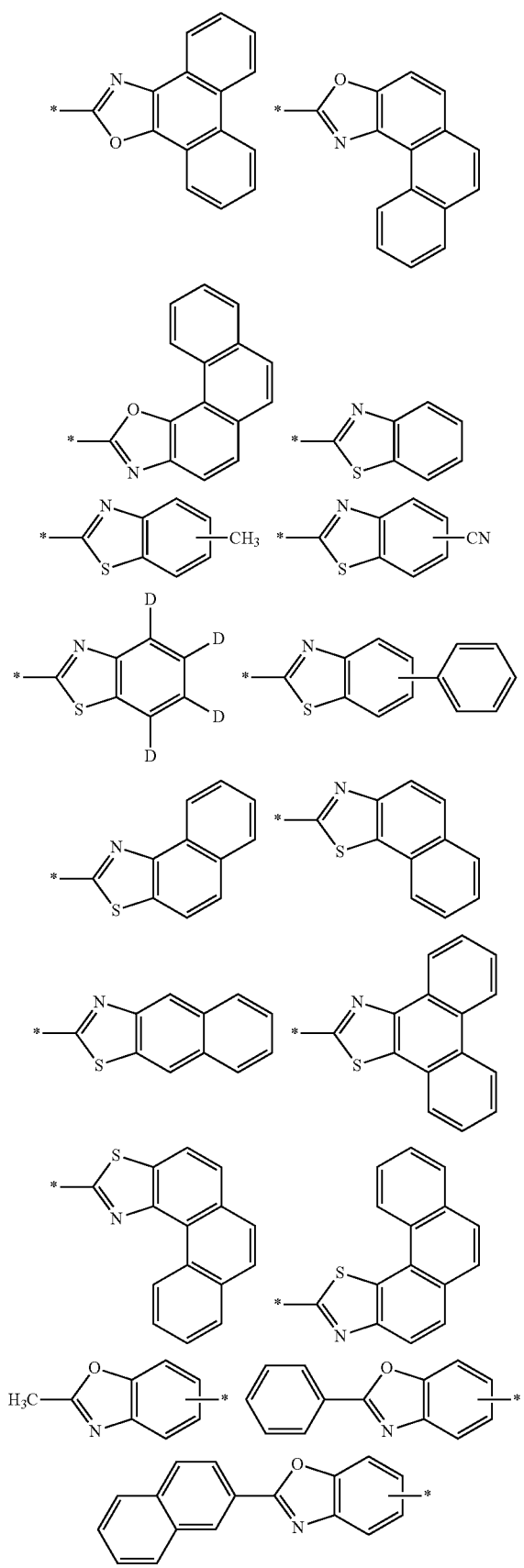
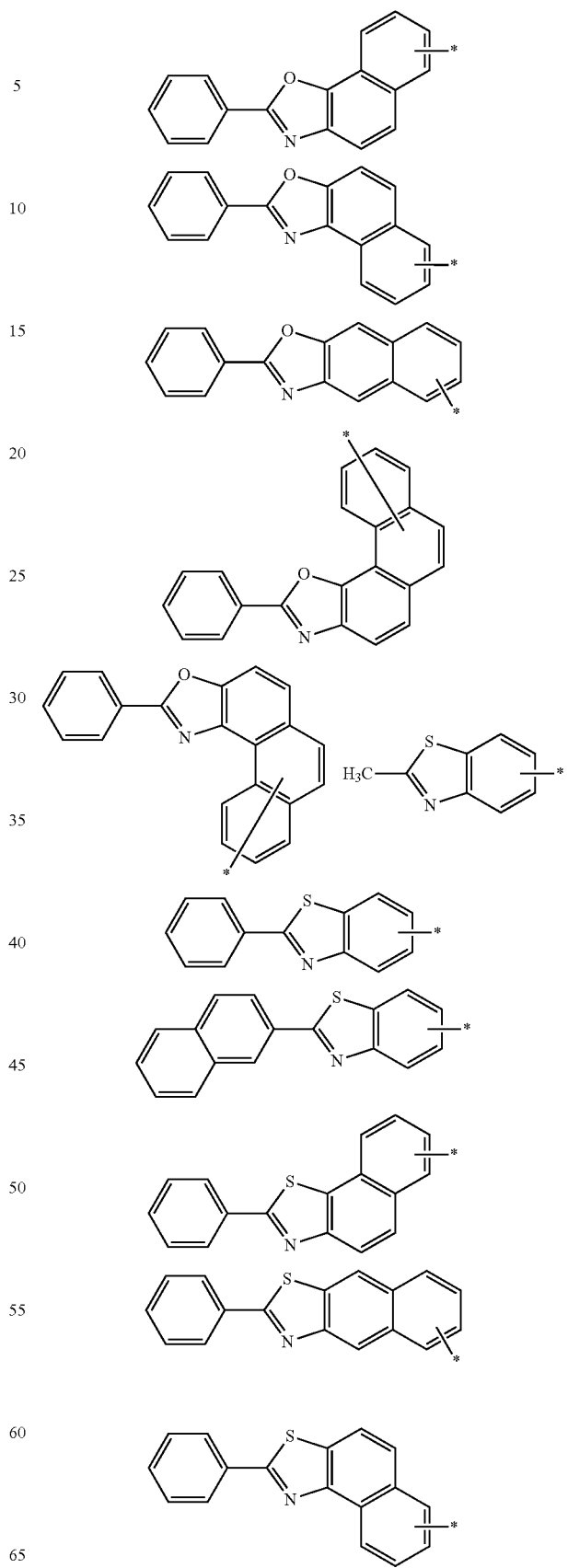

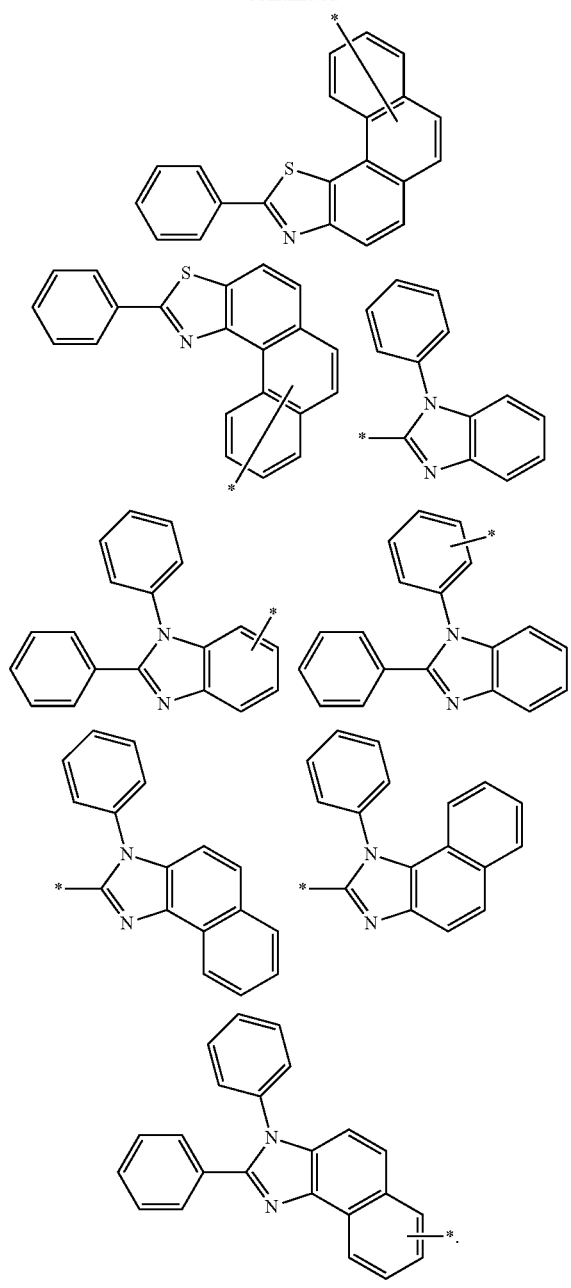
Further preferably, X₁ is selected from O or S.
More preferably, the structure as shown in Formula III is selected from any one of the following groups:
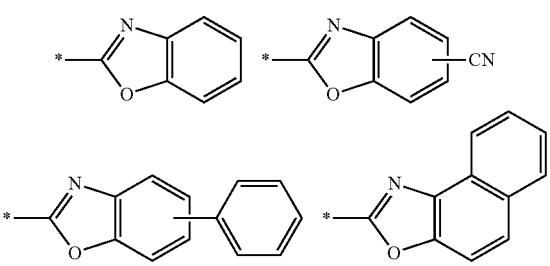
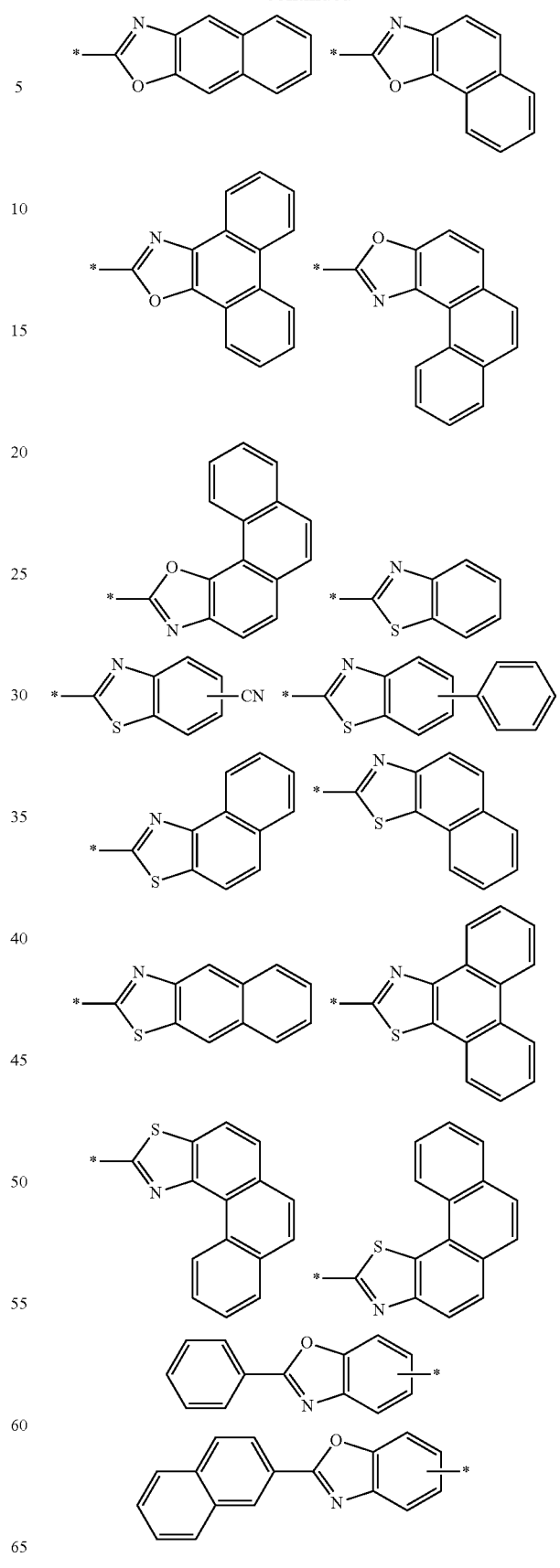

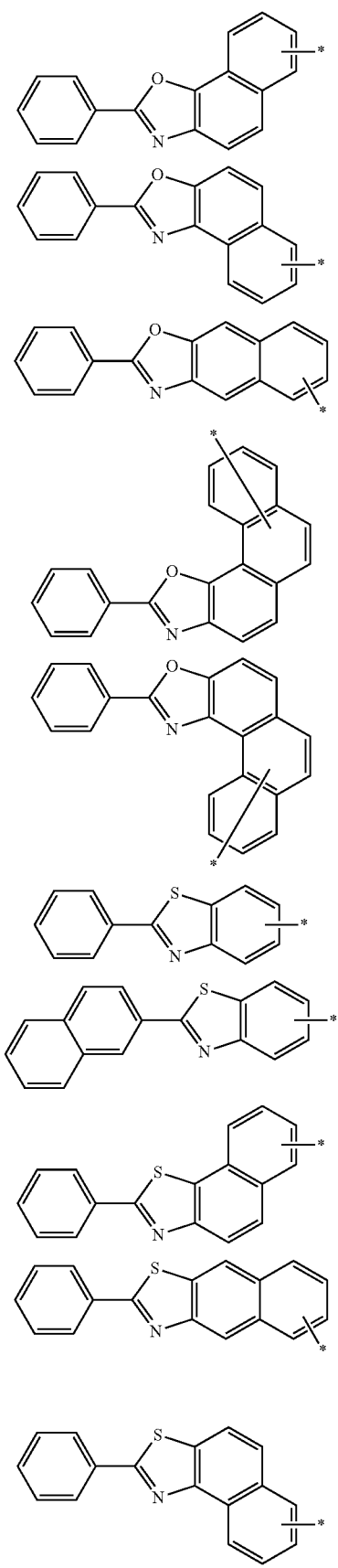
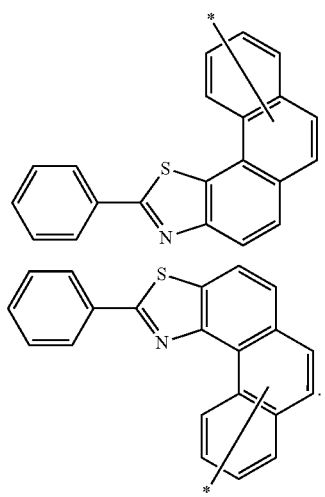
Further preferably, $X_1$ is selected from O.
More preferably, the structure as shown in Formula III is selected from any one of the following groups:
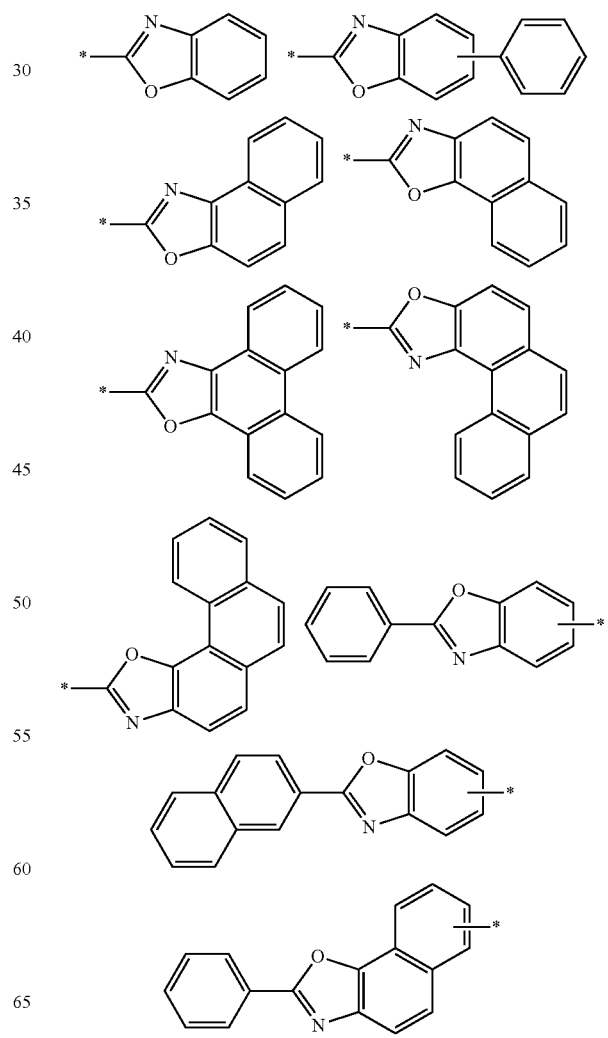

-continued

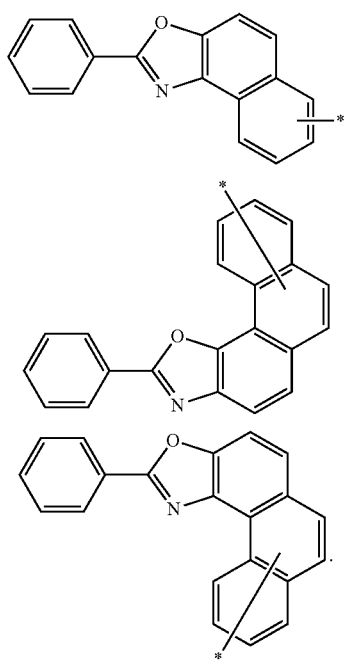

Preferably, $L_1$ is independently selected from a single bond or any one of the following groups:

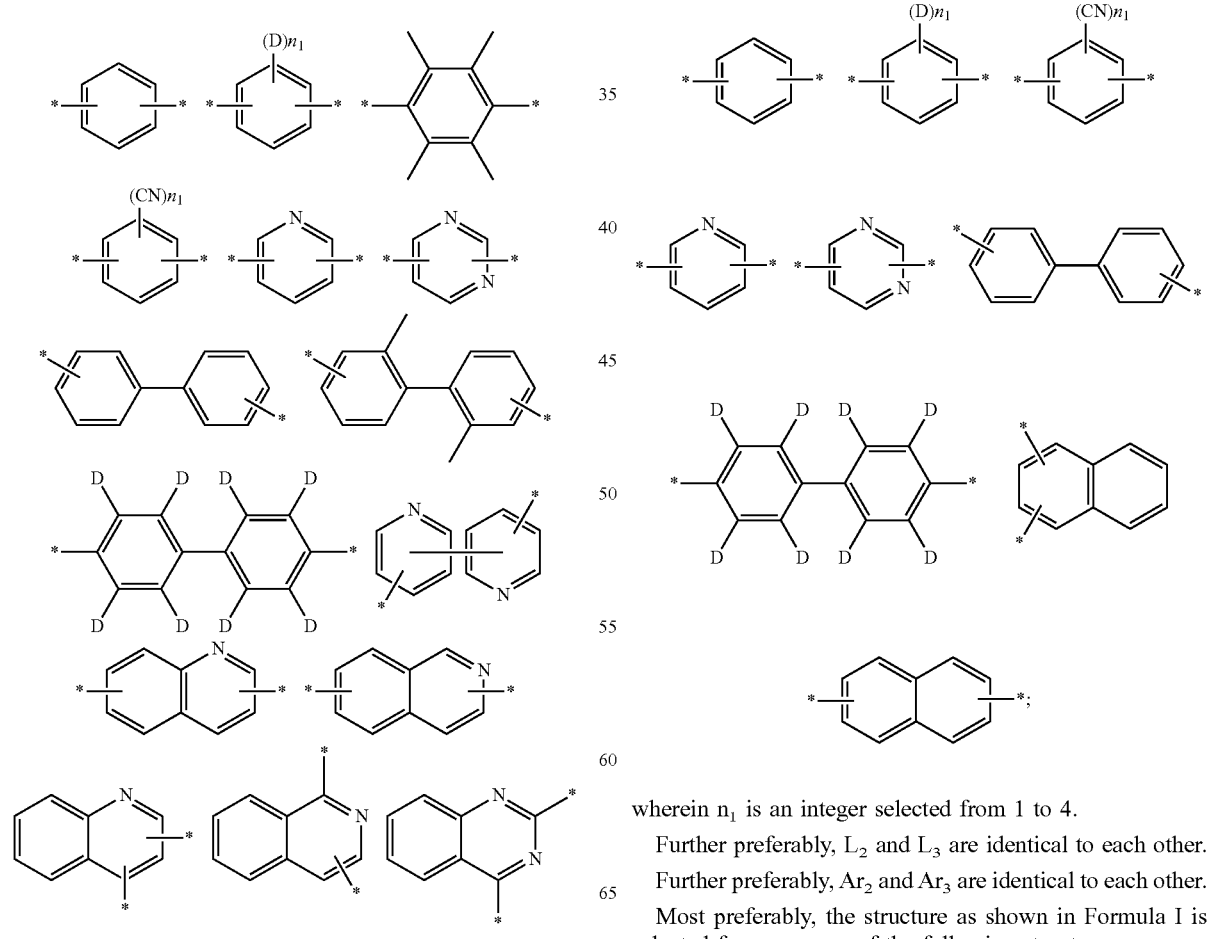

-continued

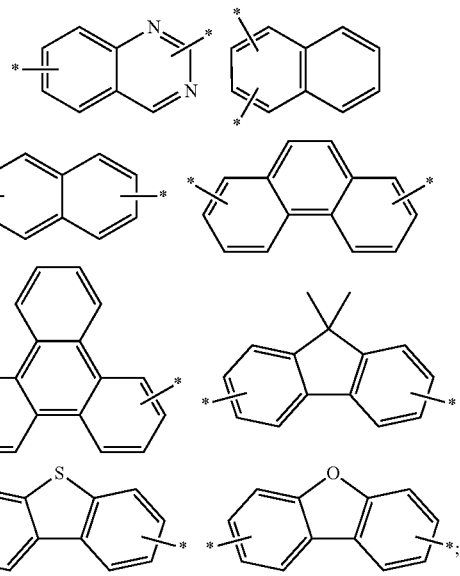

wherein $n_1$ is an integer selected from 1 to 4.

Preferably, $L_2$ and $L_3$ are identical to each other or different from each other and independently selected from a single bond or any one of the following groups:

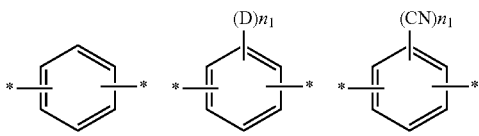

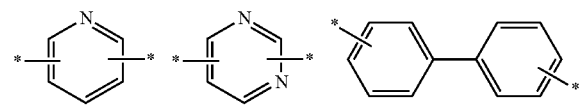

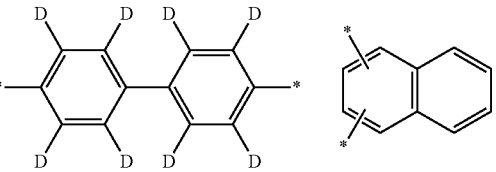

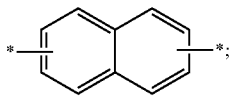

wherein $n_1$ is an integer selected from 1 to 4.

Further preferably, $L_2$ and $L_3$ are identical to each other.

Further preferably, $Ar_2$ and $Ar_3$ are identical to each other.

Most preferably, the structure as shown in Formula I is selected from any one of the following structures:

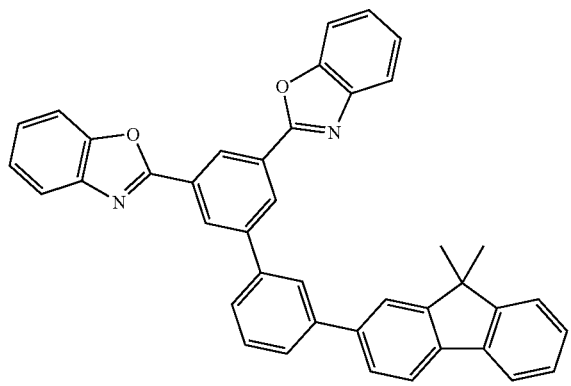
1
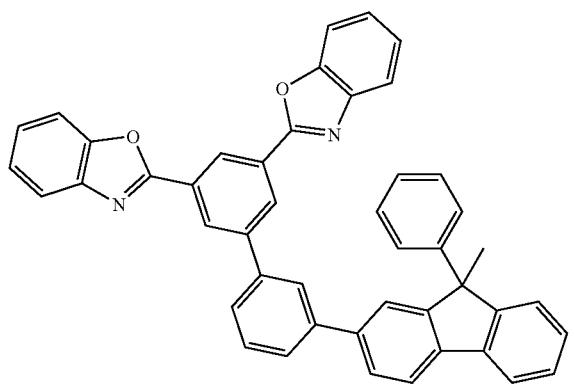
2
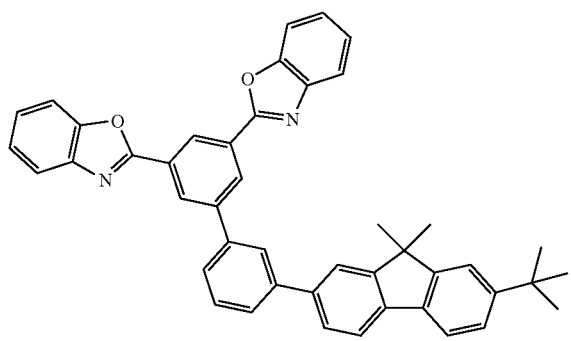
3
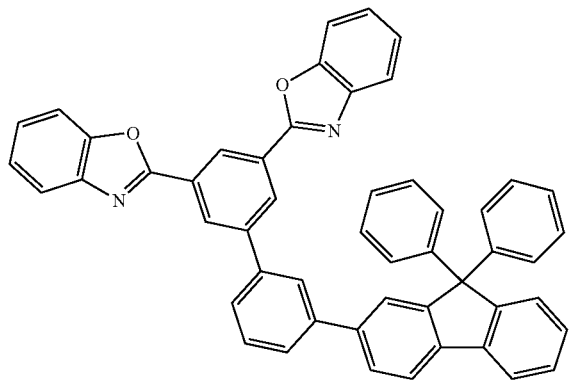
4
-continued
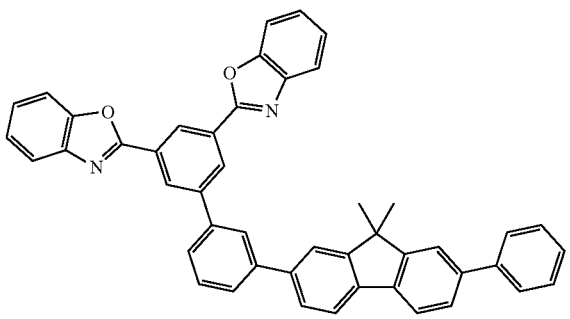
5
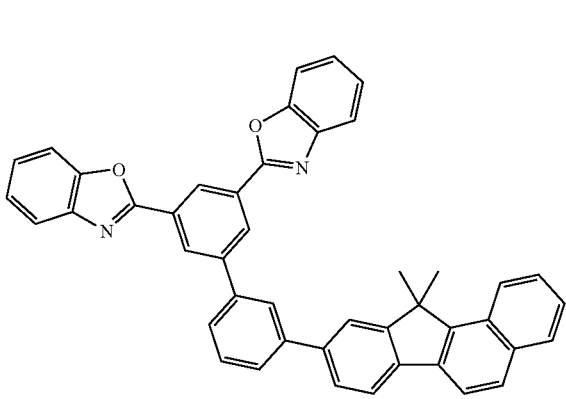
6
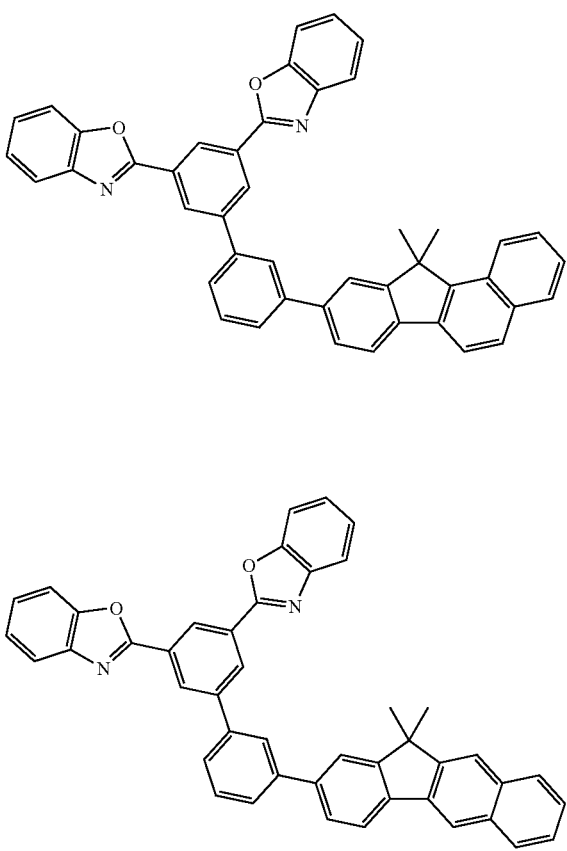

9
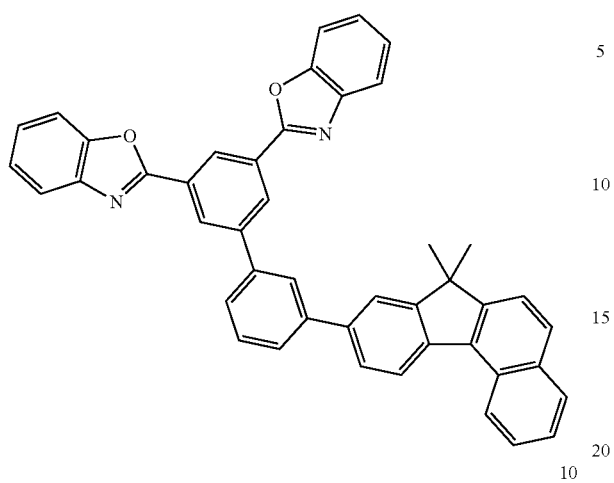
10
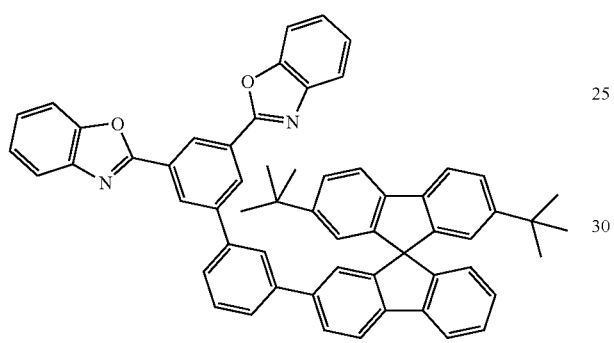
11
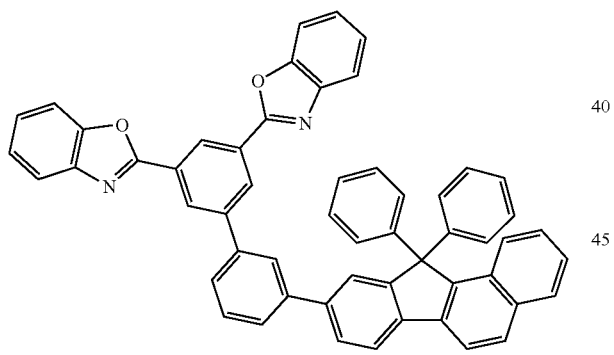
12
13
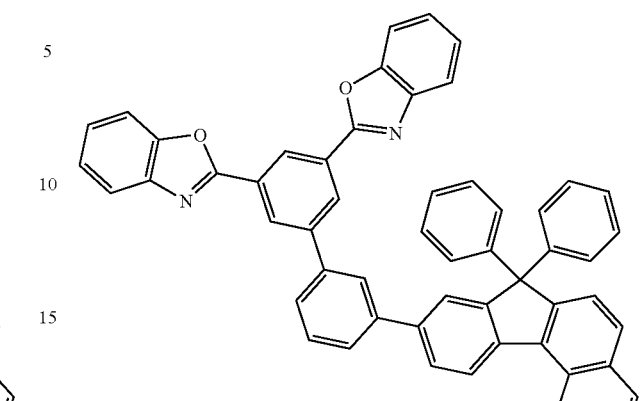
14
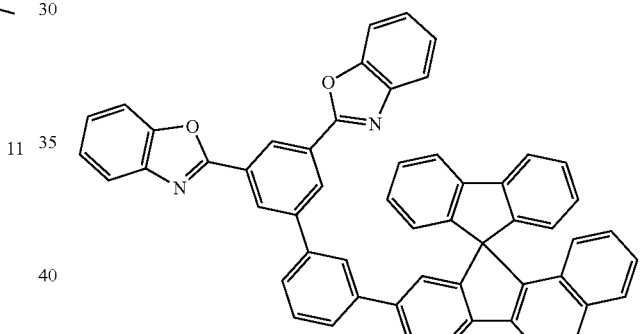
15
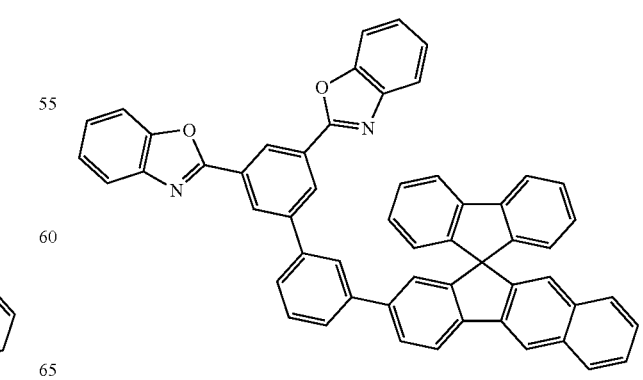

16
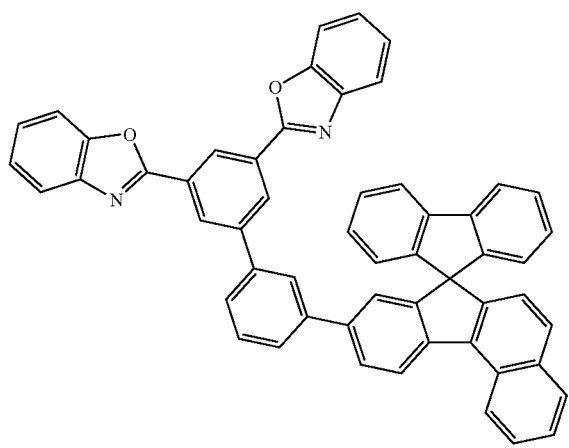
19
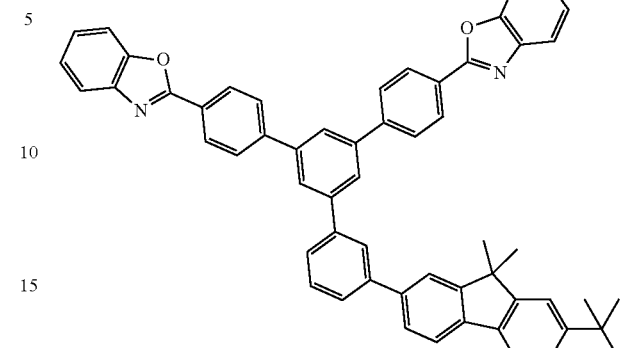
17
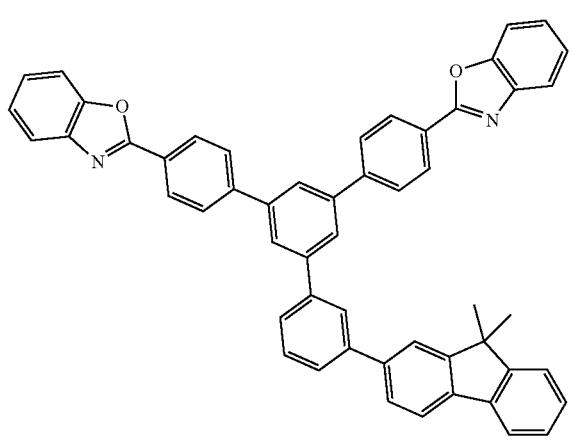
20
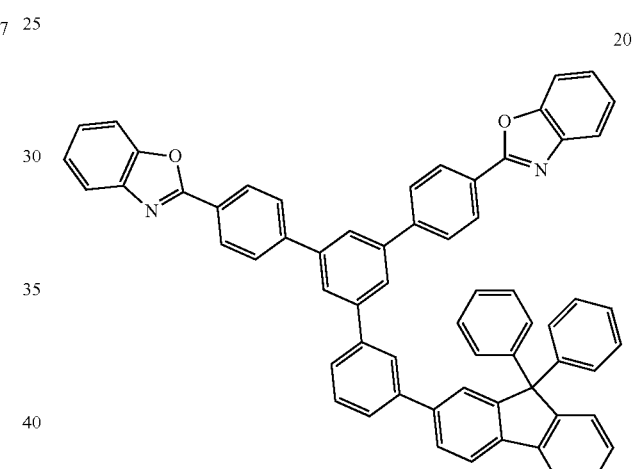
18
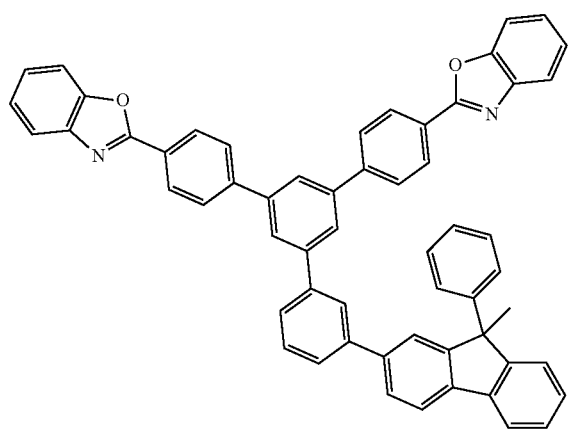
21
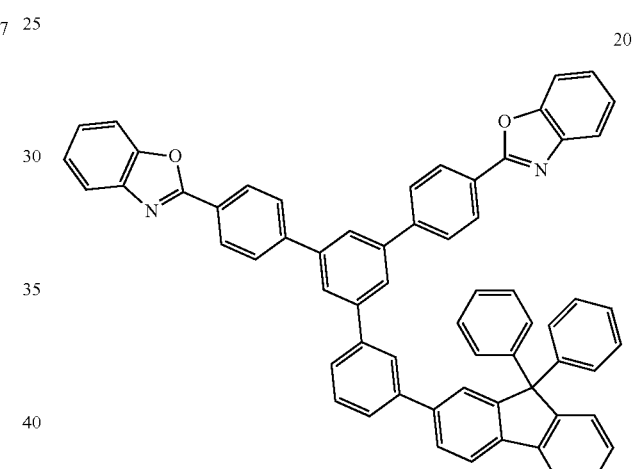

22
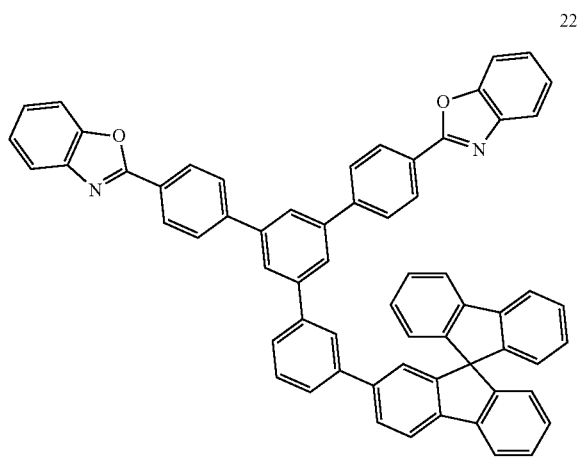
23
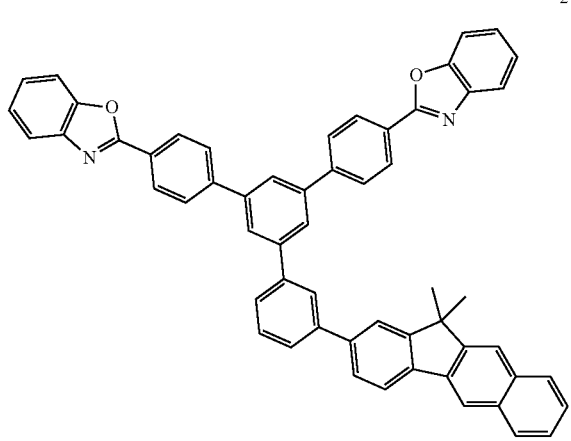
24
25
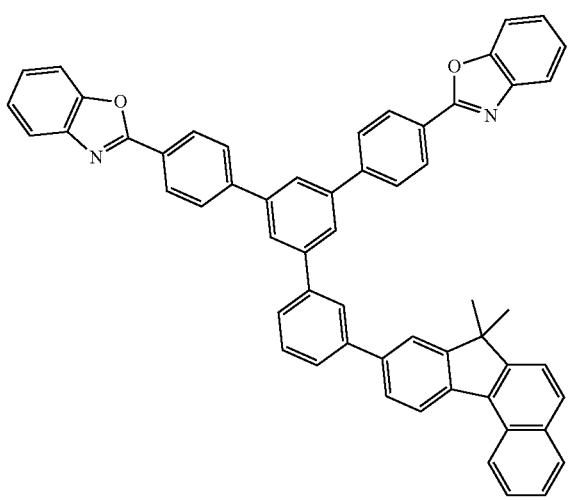
26
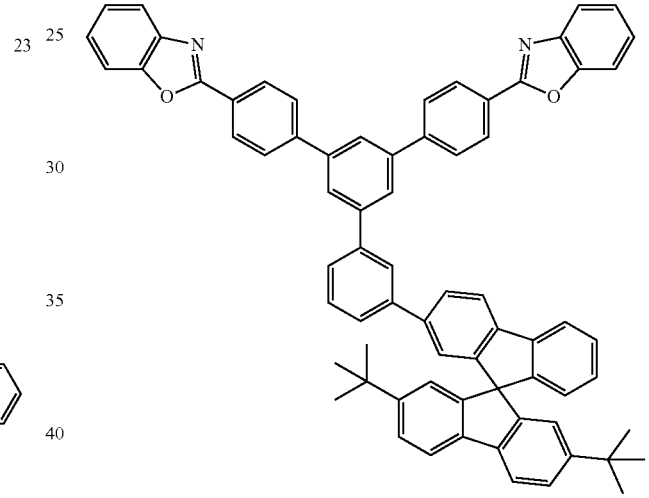
27
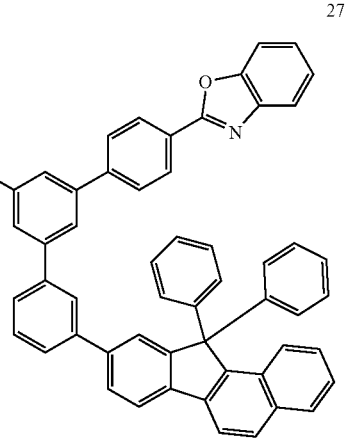

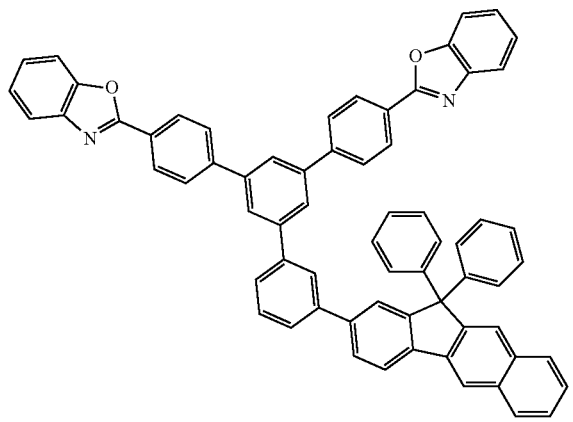
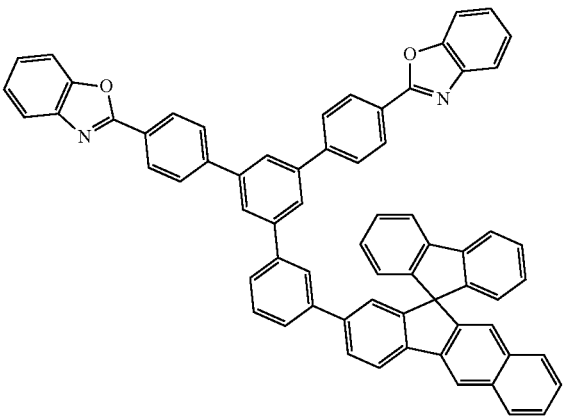
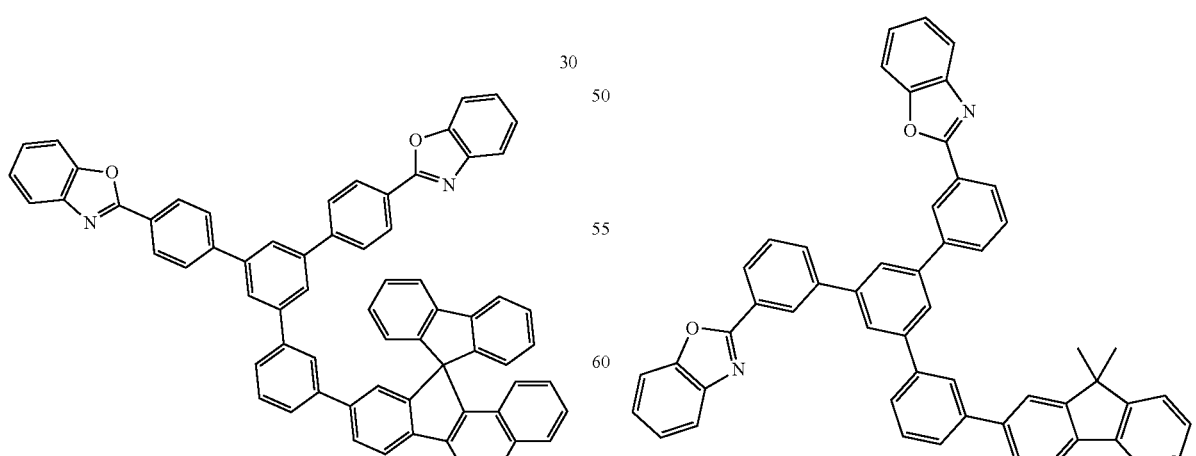

34
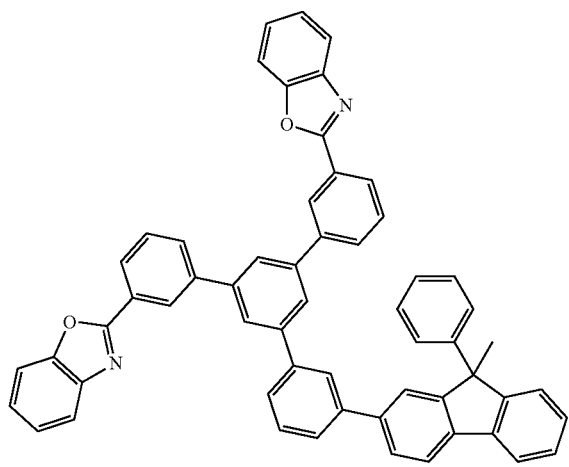
35
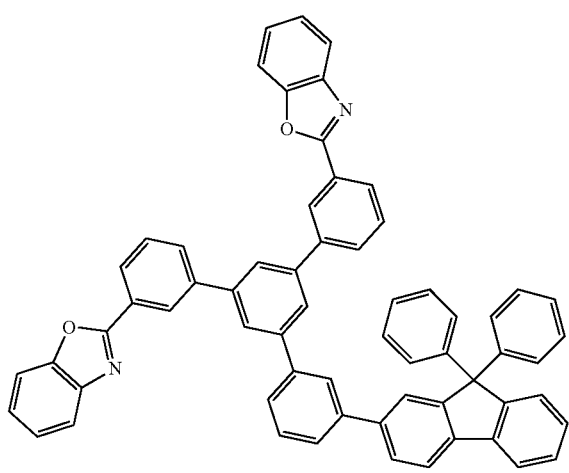
36
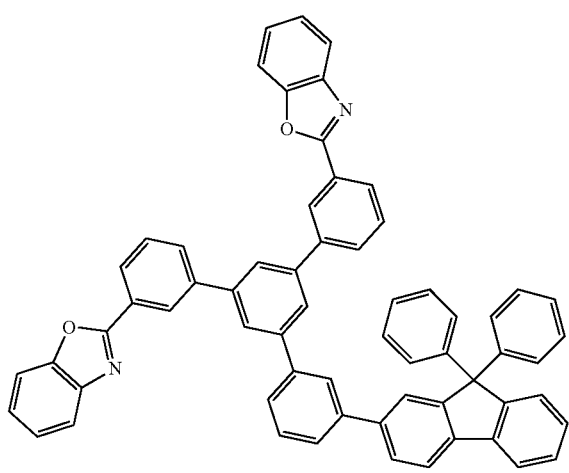
37
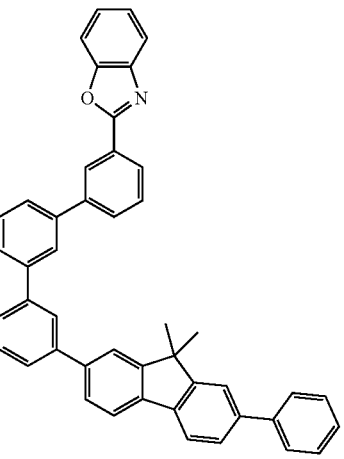
38
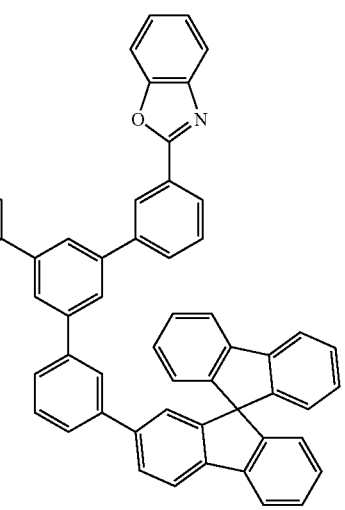
39
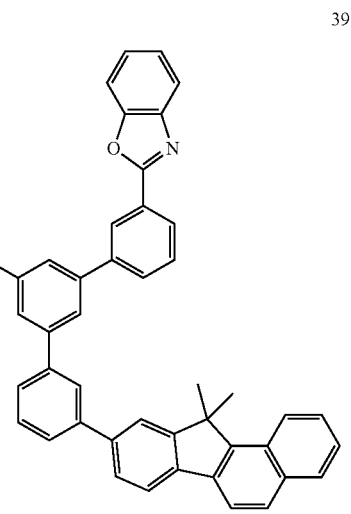

40
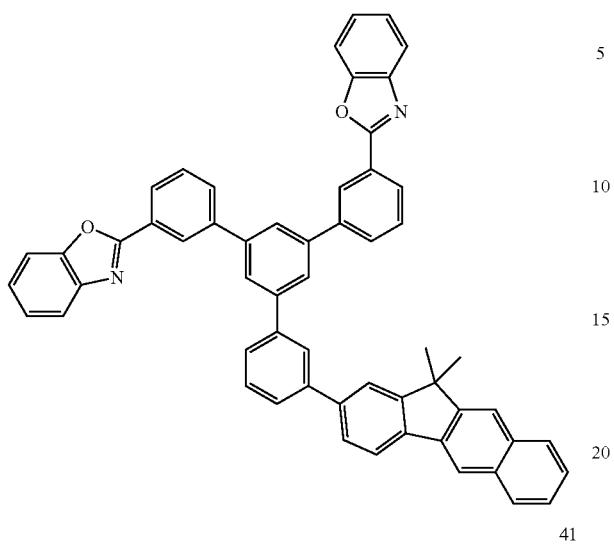
41
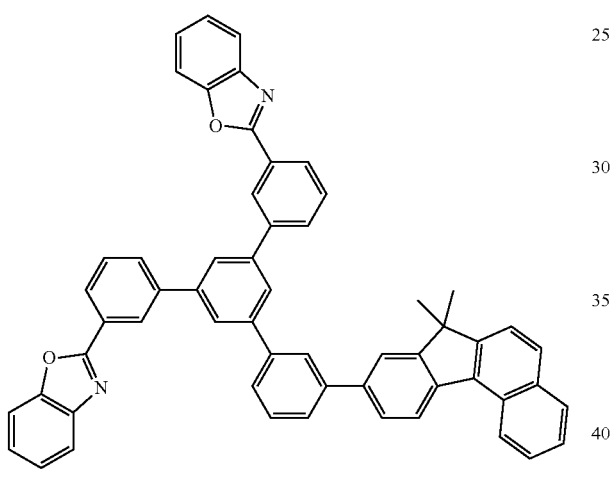
42
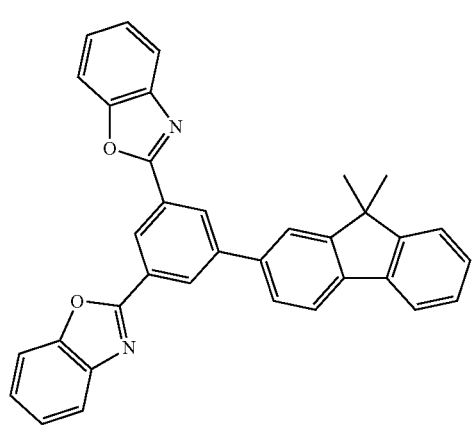
43
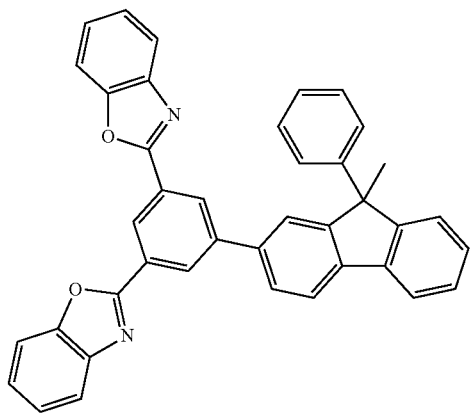
44
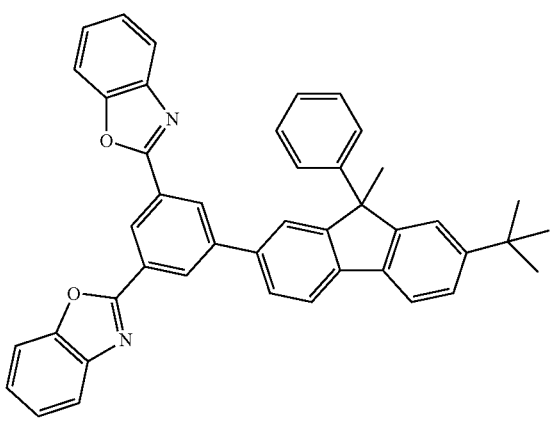
45
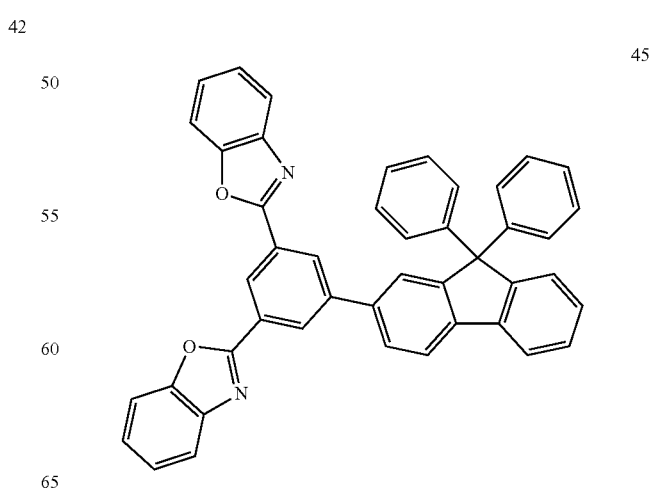

46
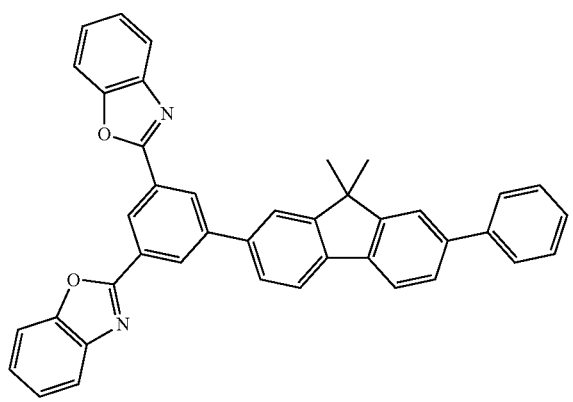
47
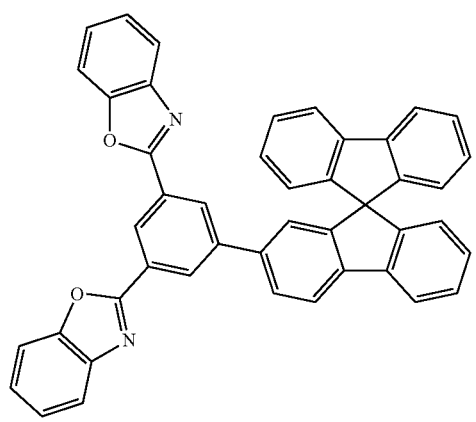
48
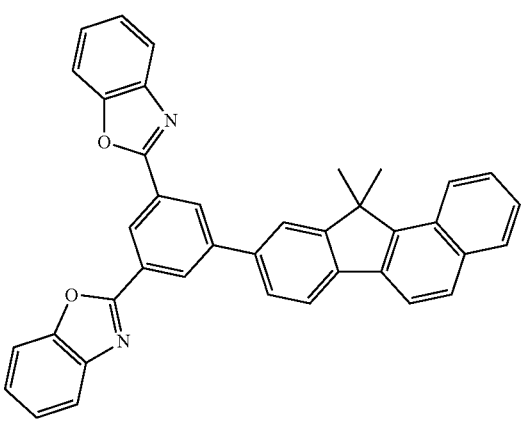
49
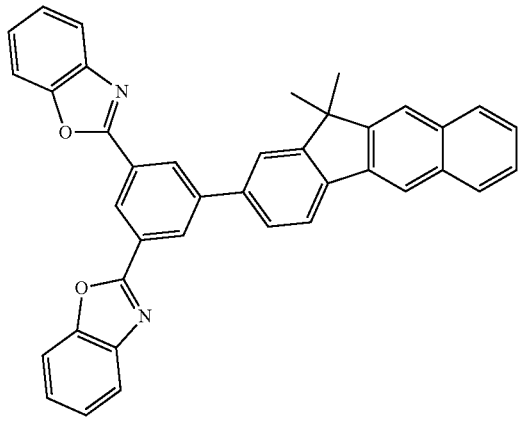
50
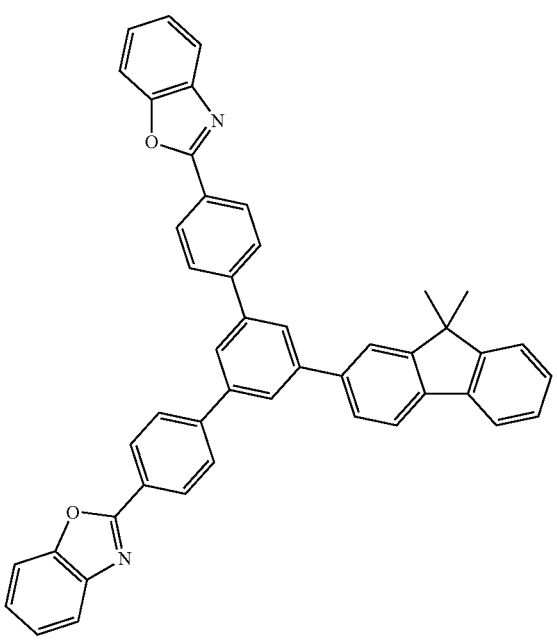
51

52
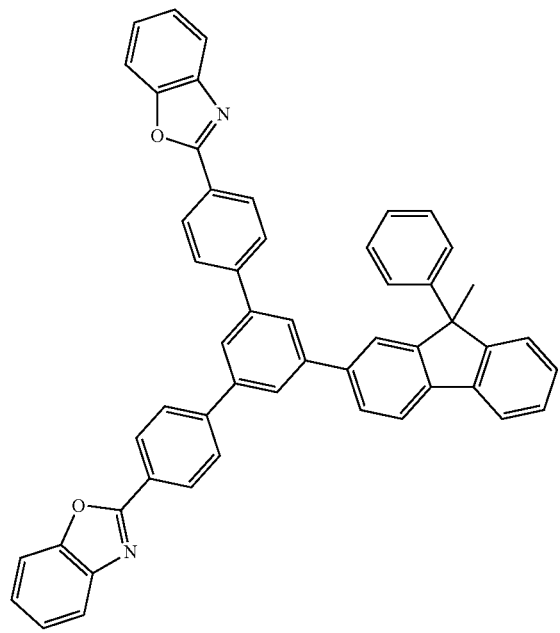
53
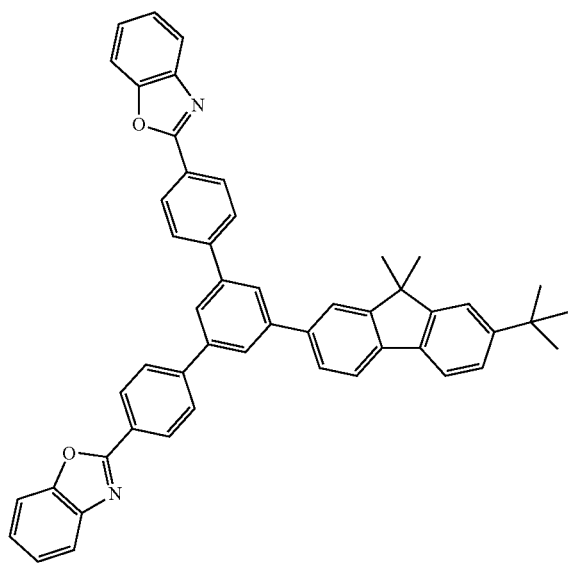
54
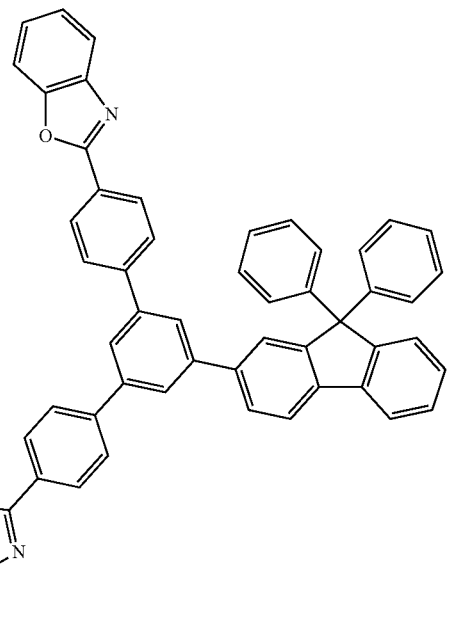
55
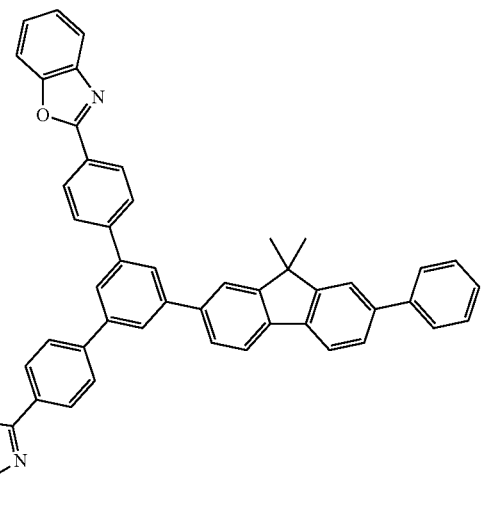

56
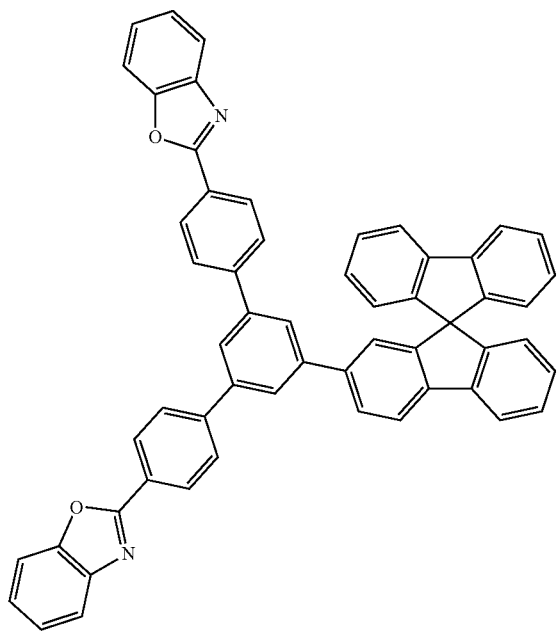
57
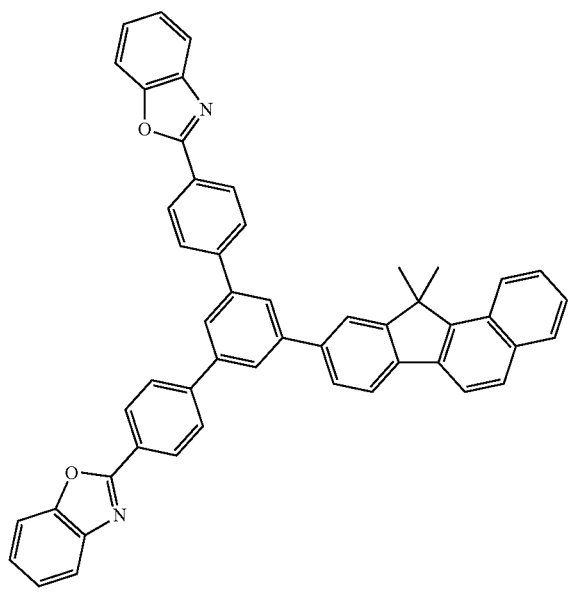
58
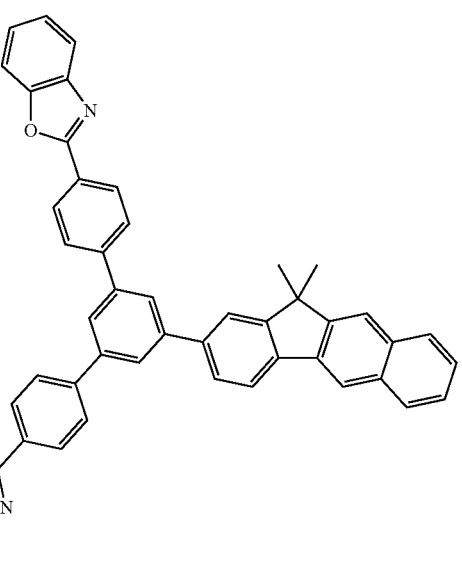
59
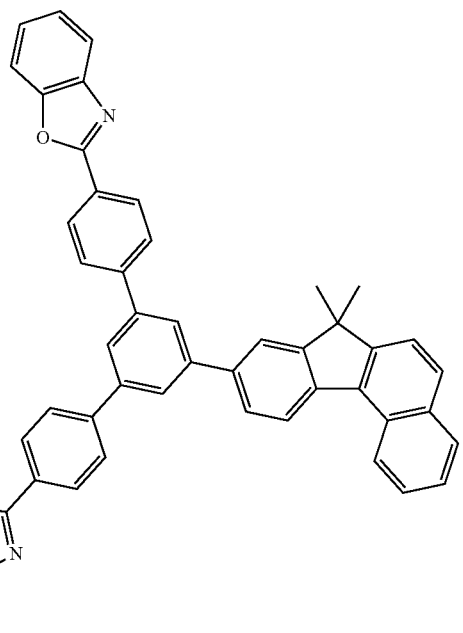

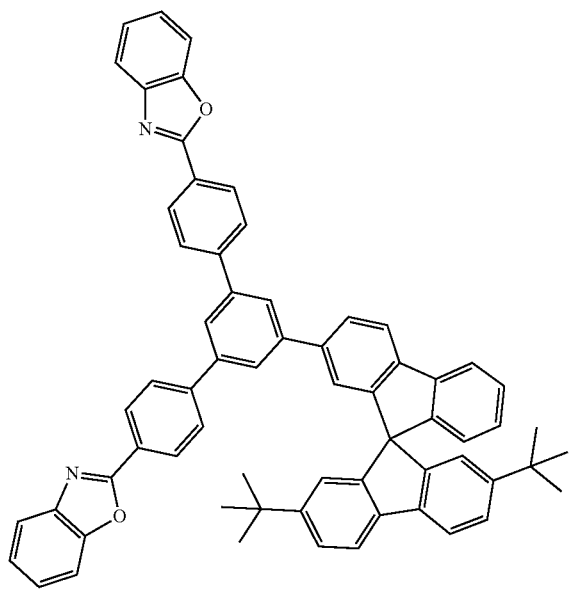
60
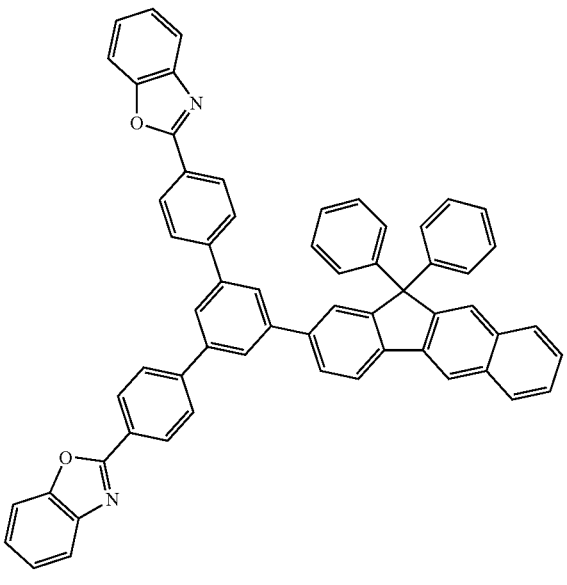
62
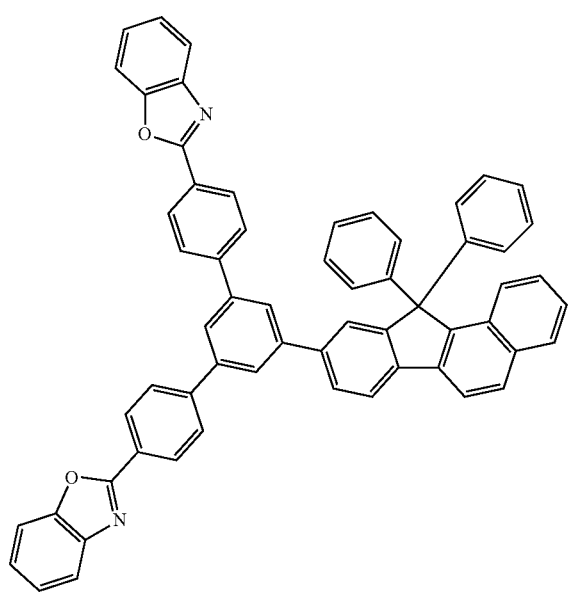
61
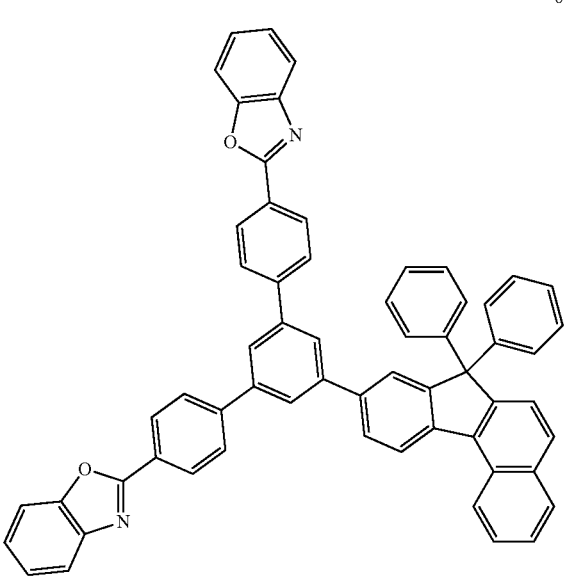
63

-continued
64
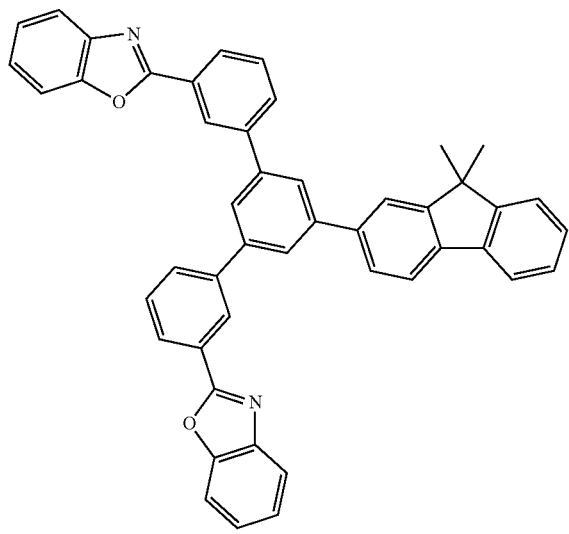
65
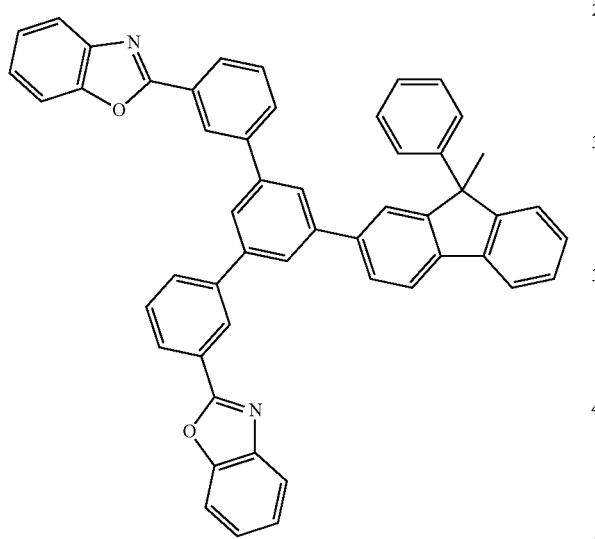
66
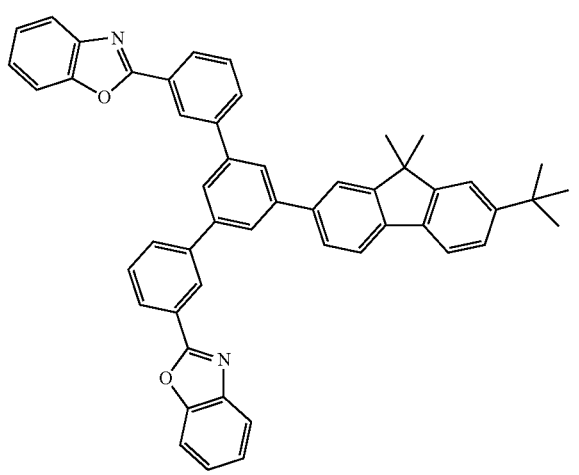
67
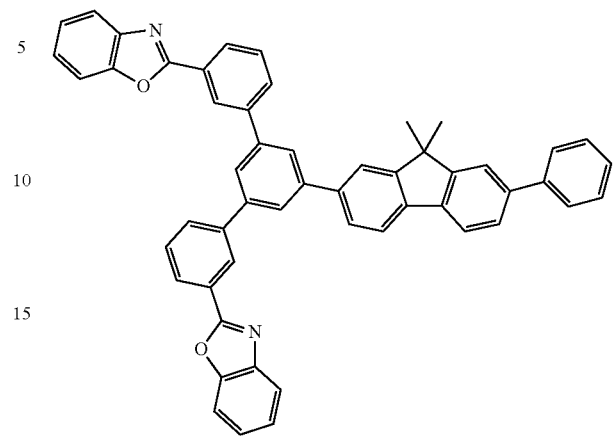
68
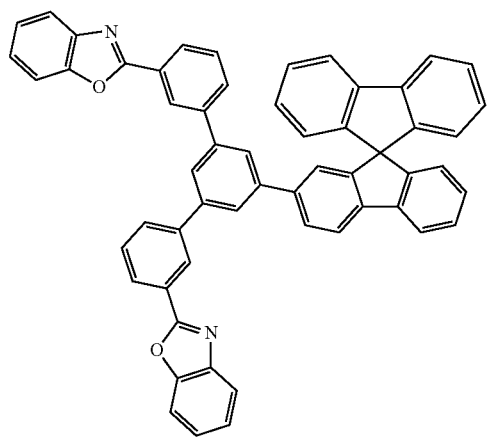
69
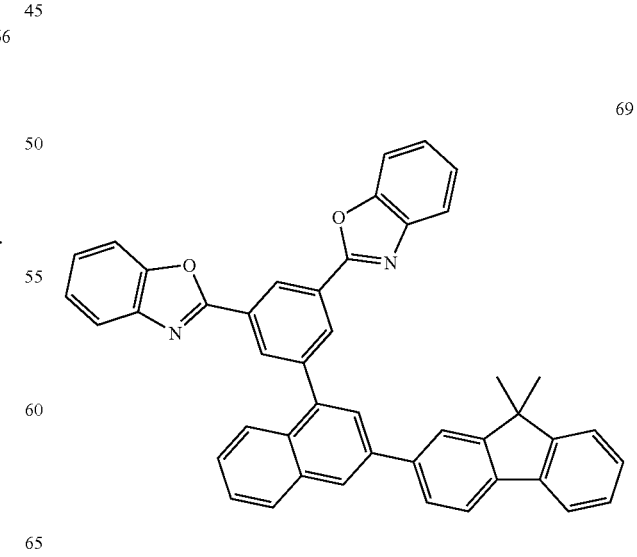

70
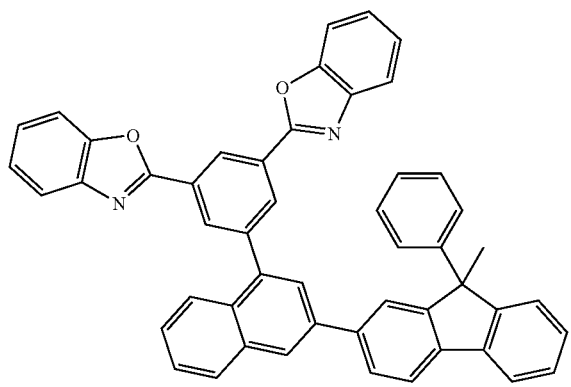
71
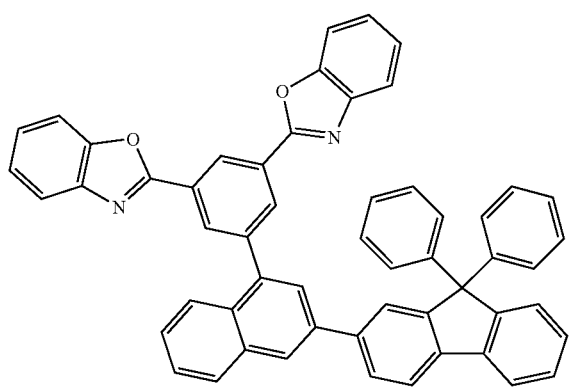
72
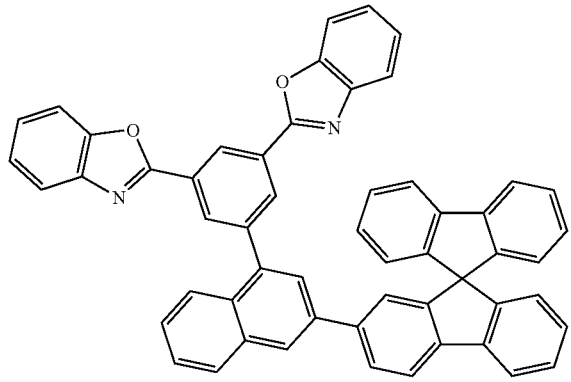
73
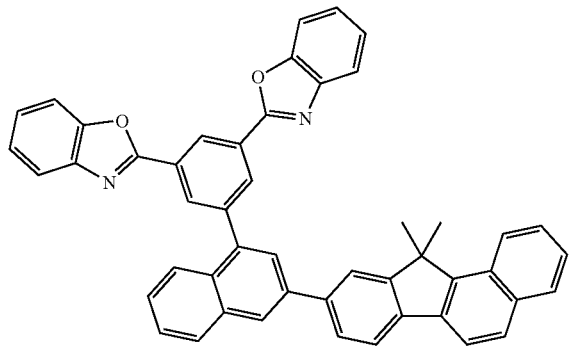
74
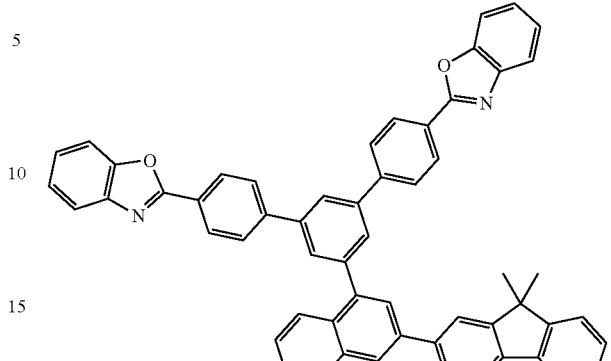
75
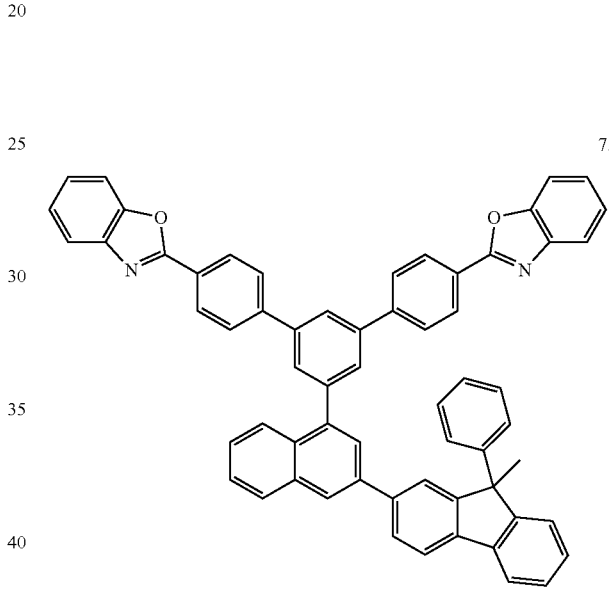
76
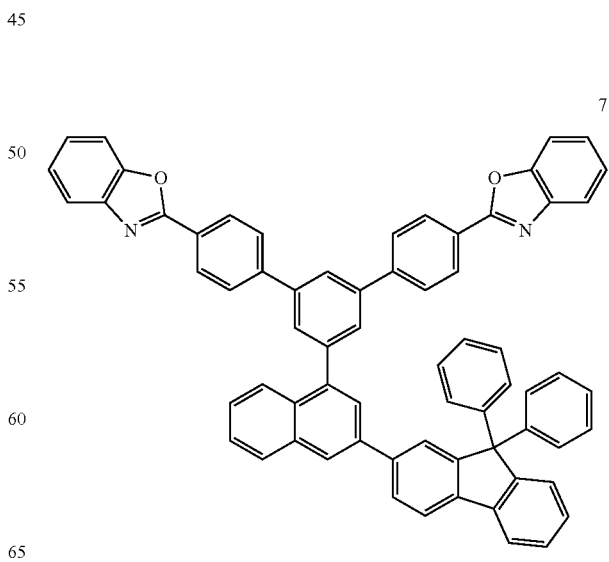

77
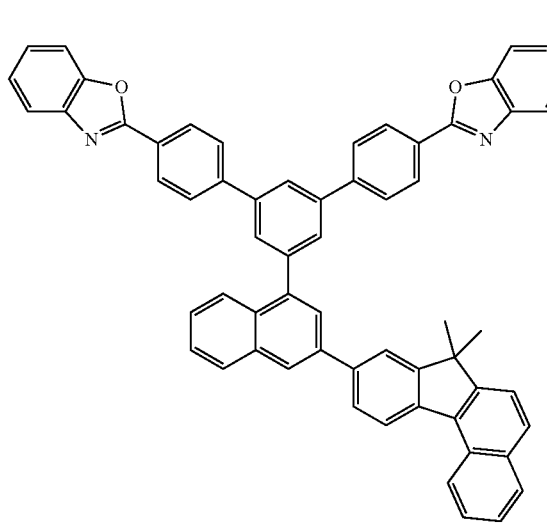
80
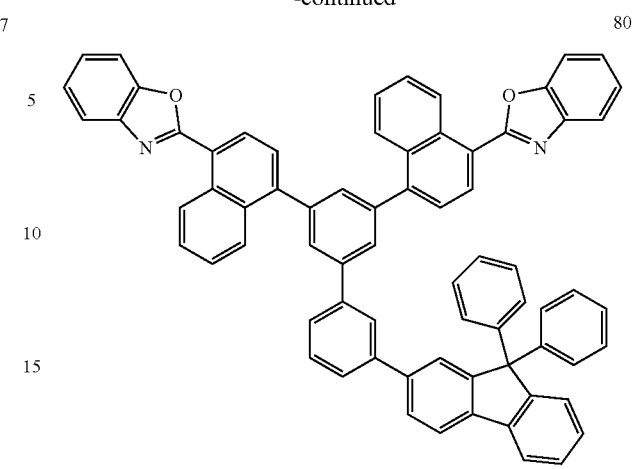
78
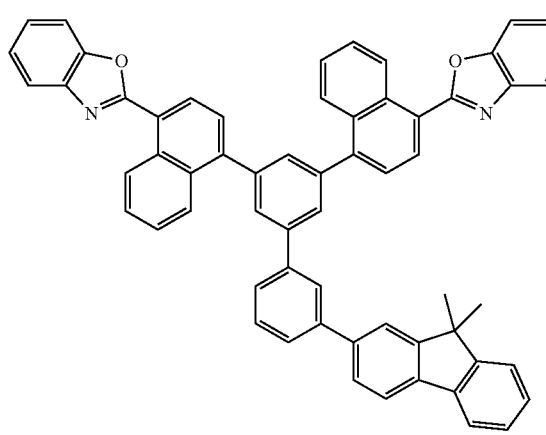
81
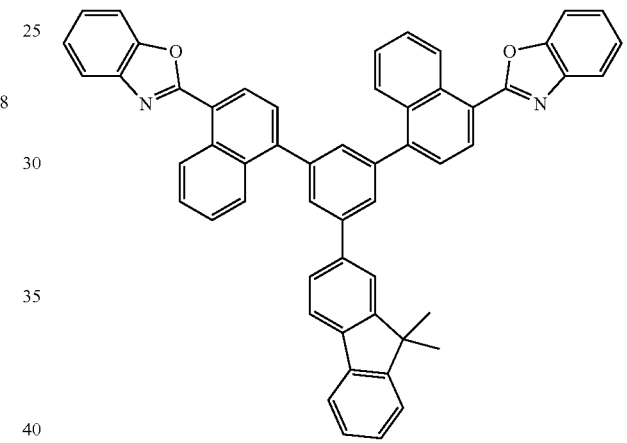
79
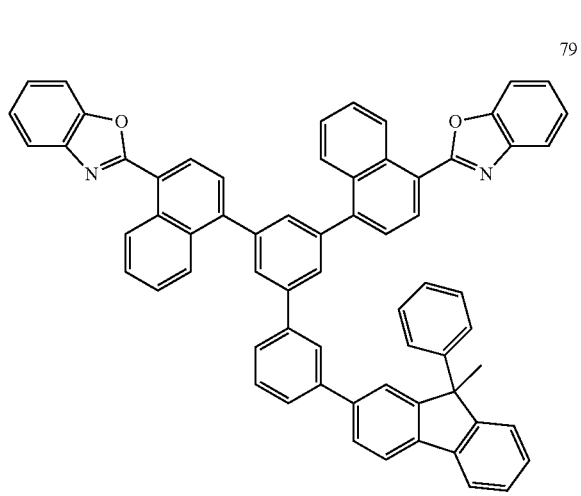
82
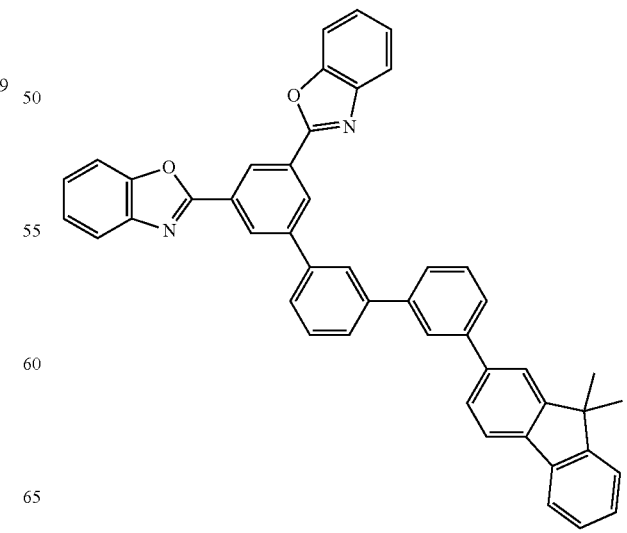

83
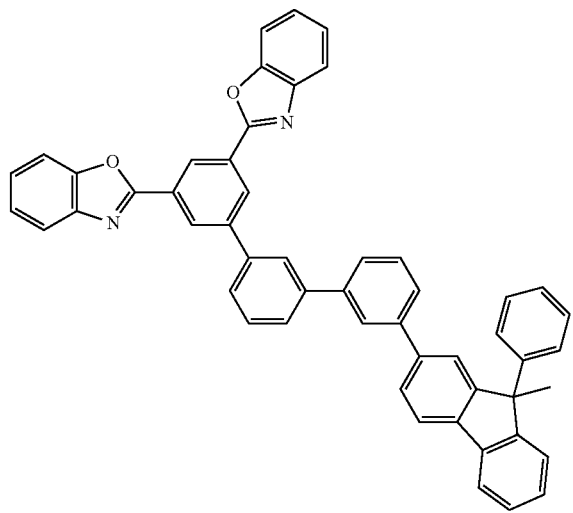
84
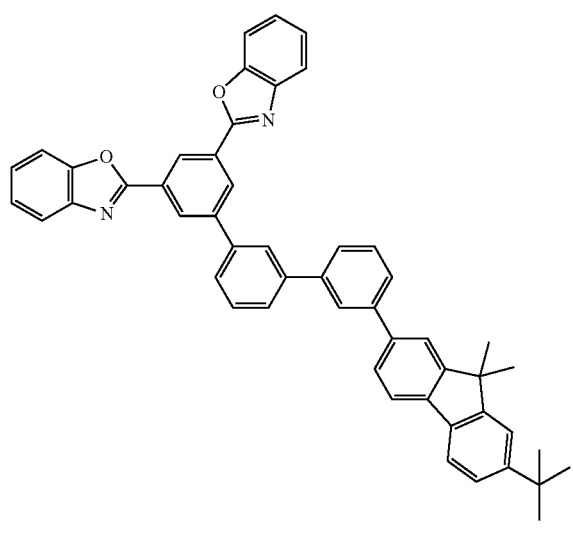
85
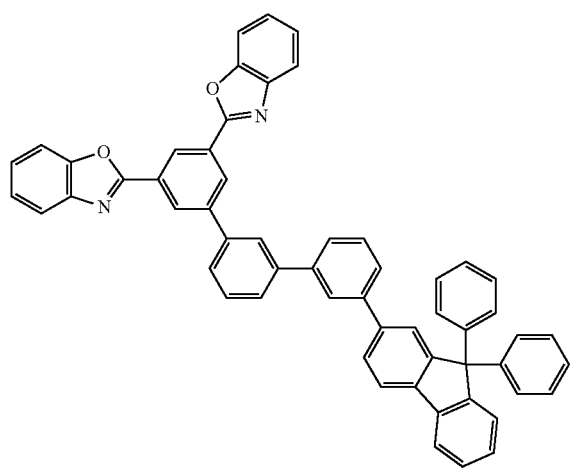
86
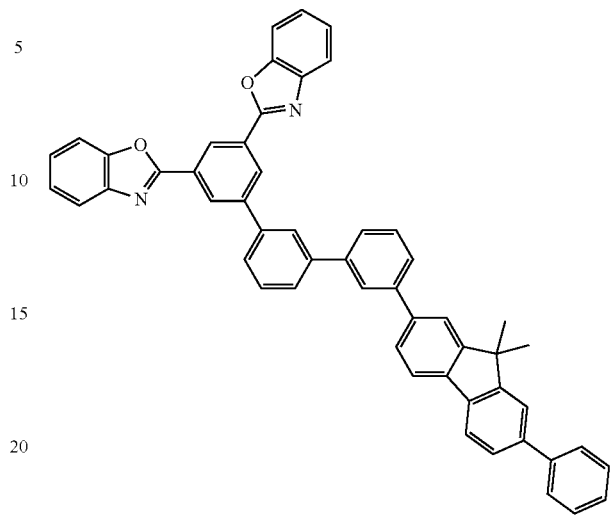
87
88

-continued
89
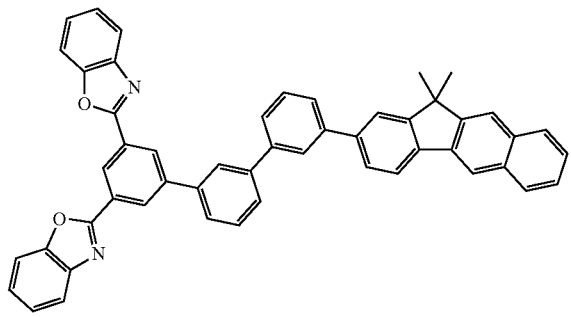
90
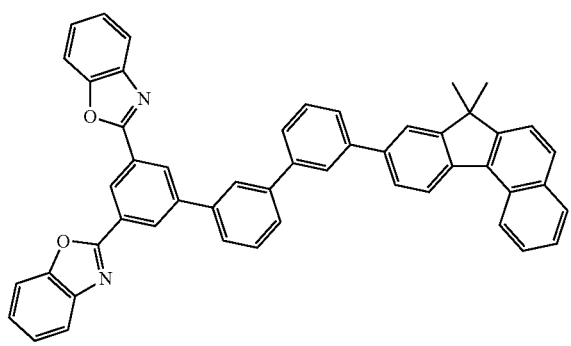
91
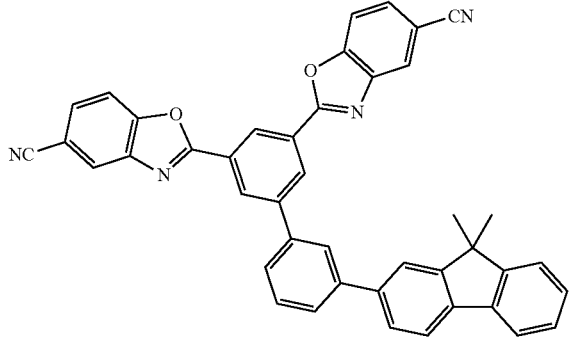
92
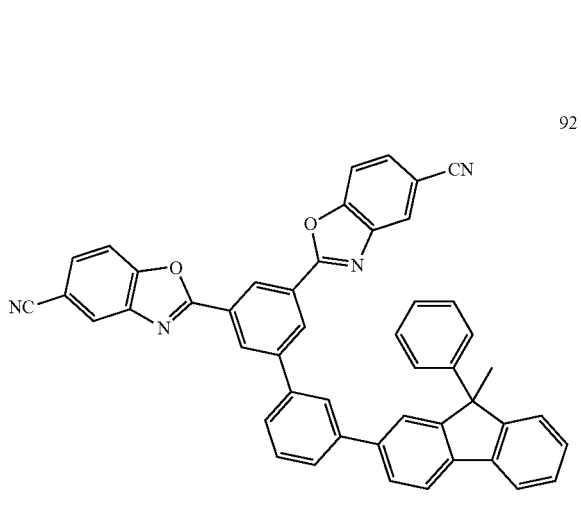
-continued
93
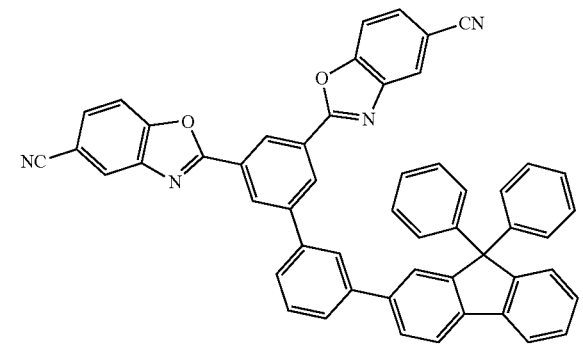
94
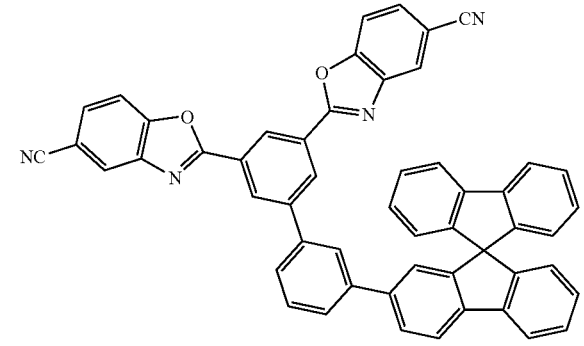
95
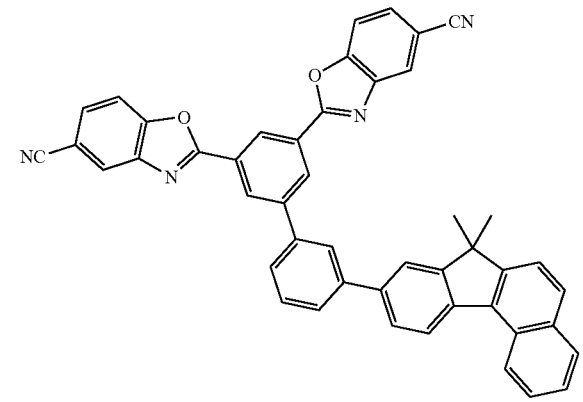
96
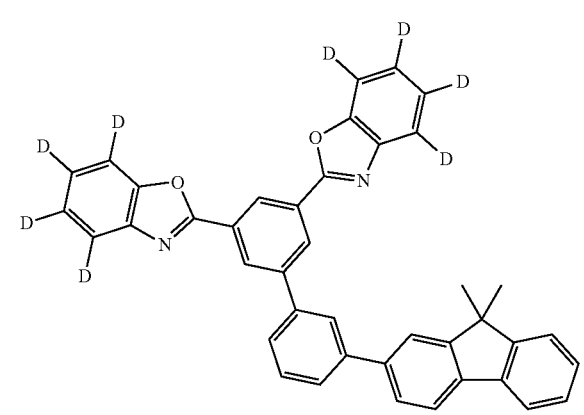

97
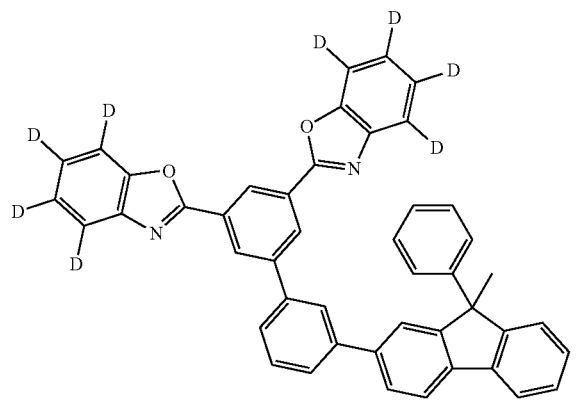
98
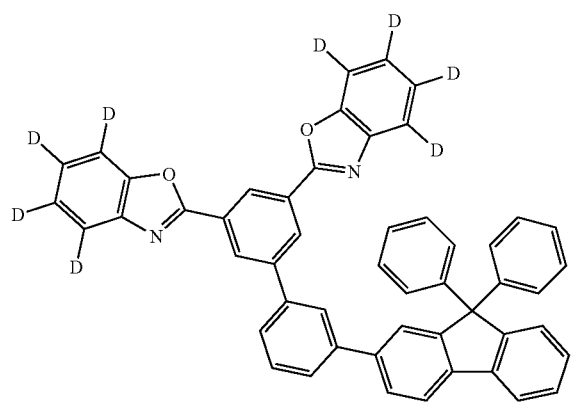
99
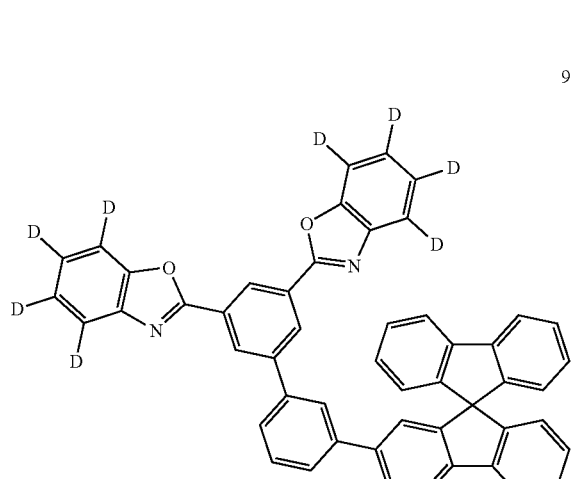
100
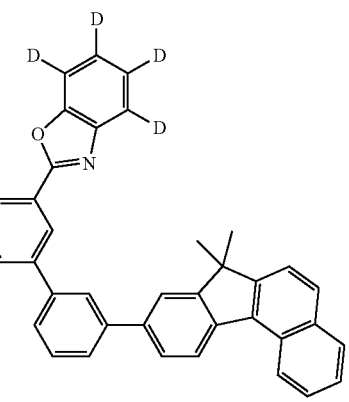
101
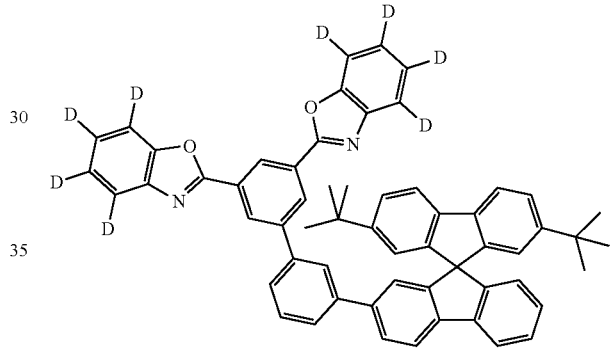
102
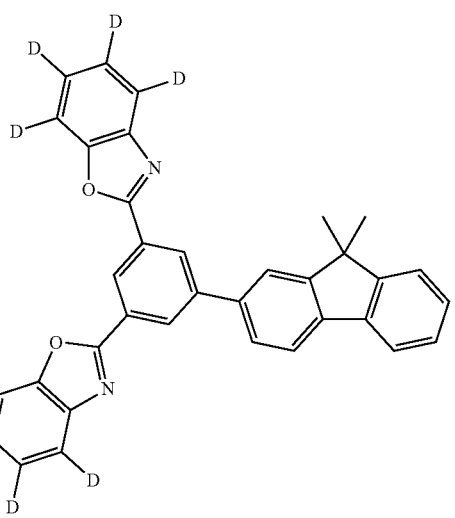

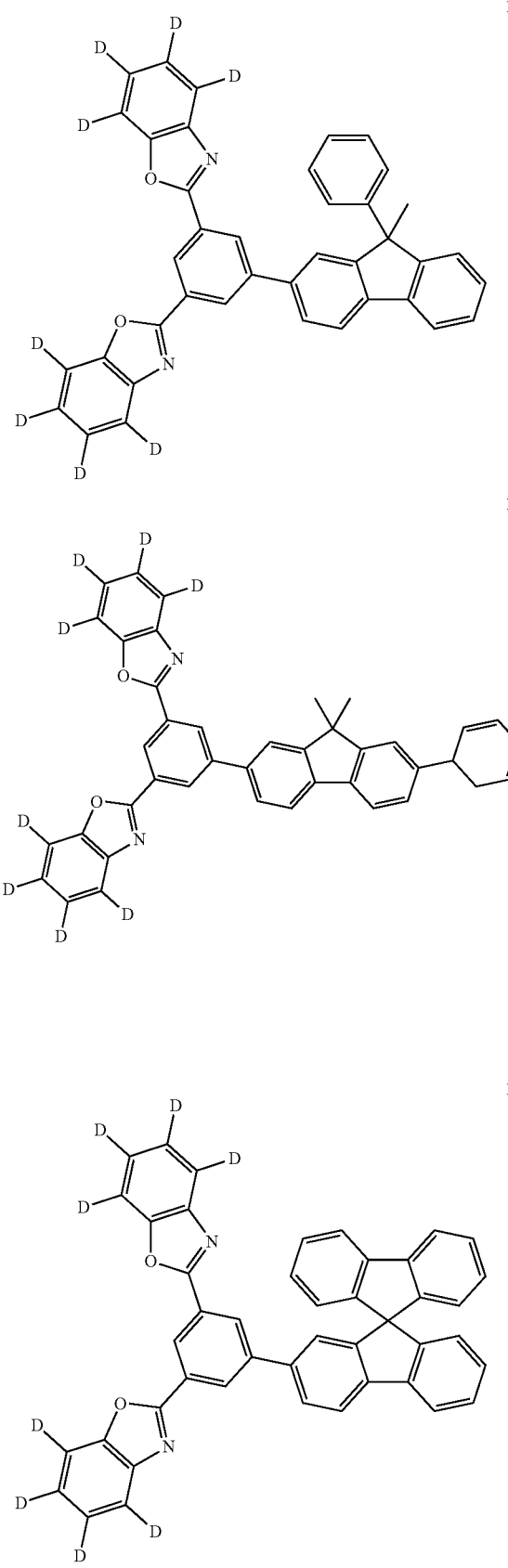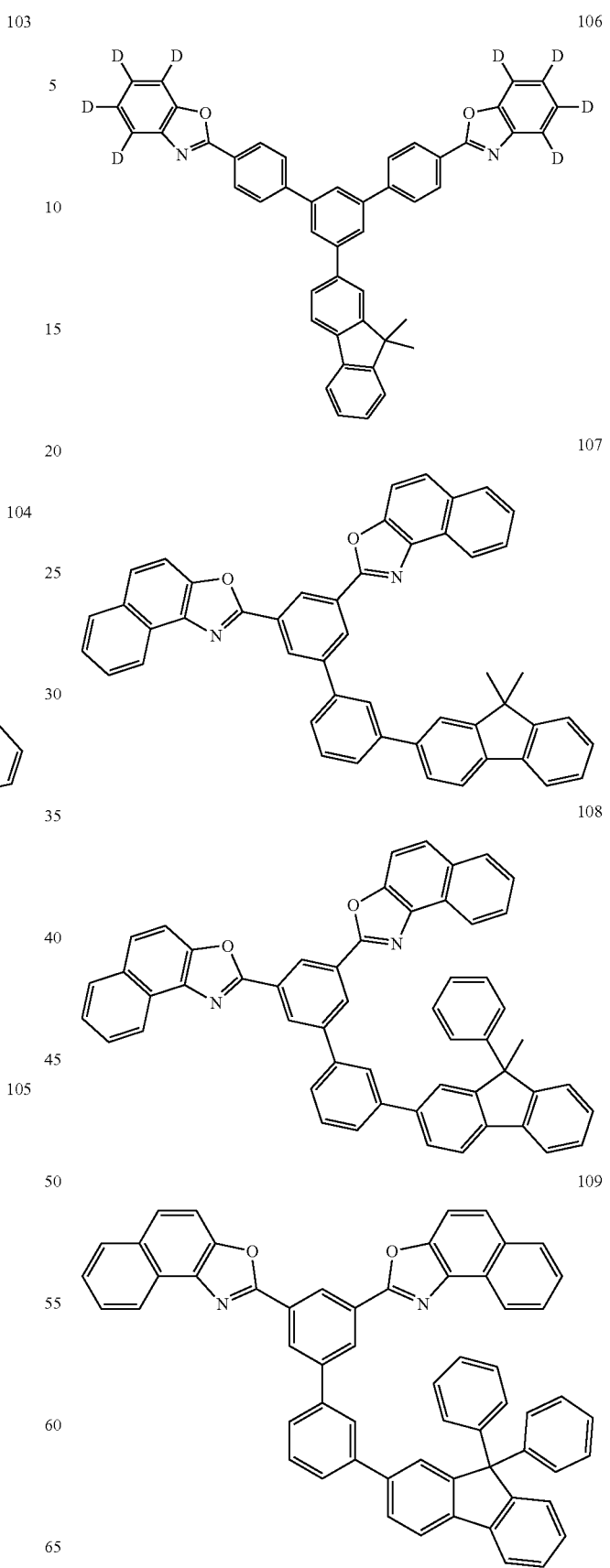

110
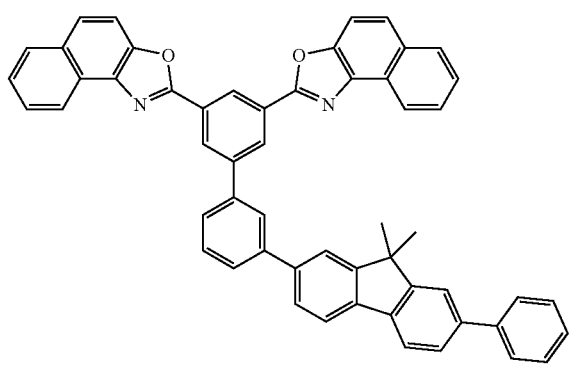
111
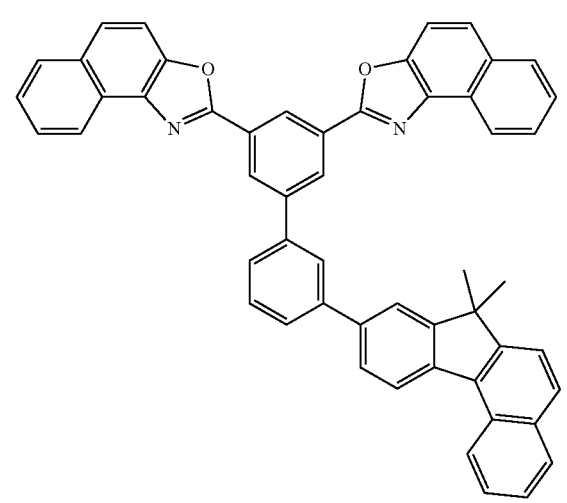
112
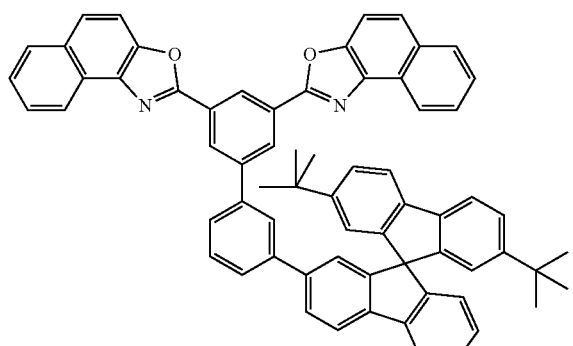
113
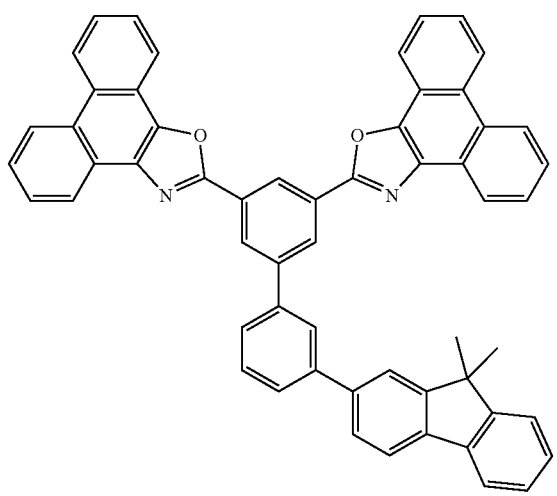
114
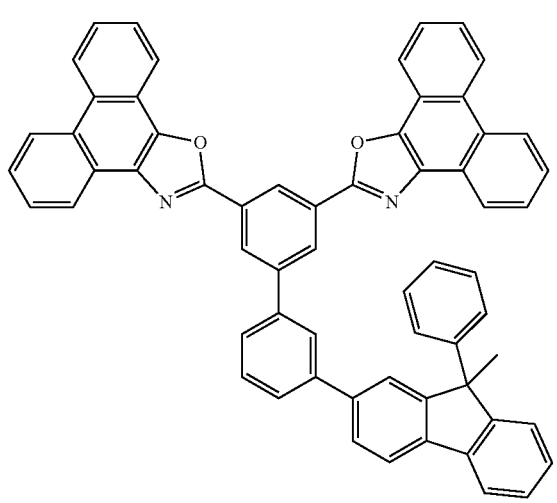
115
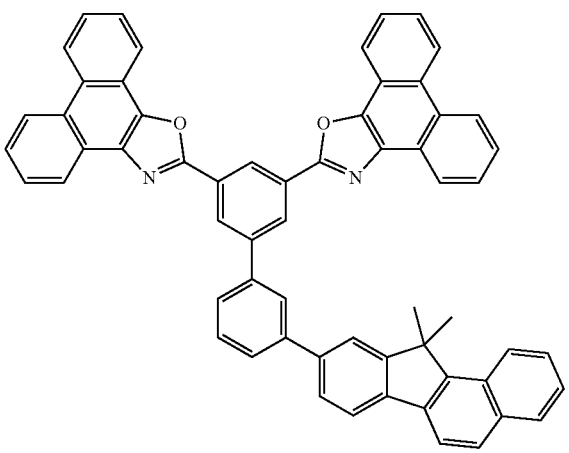

116
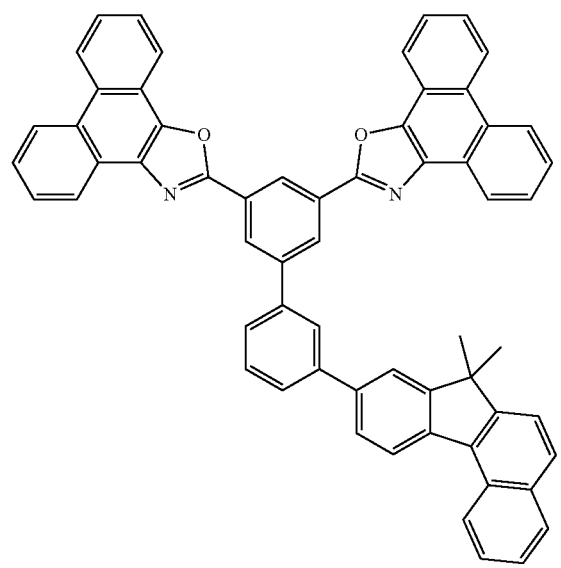
117
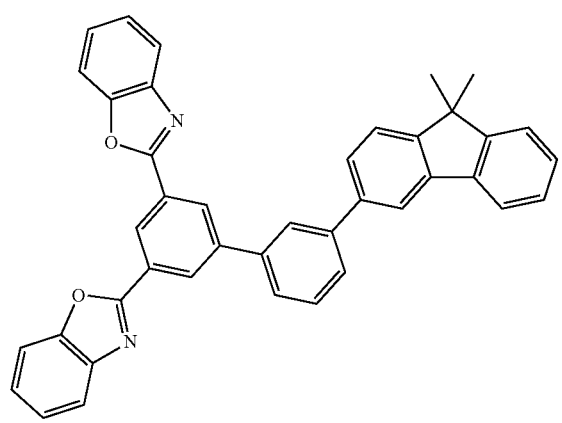
118
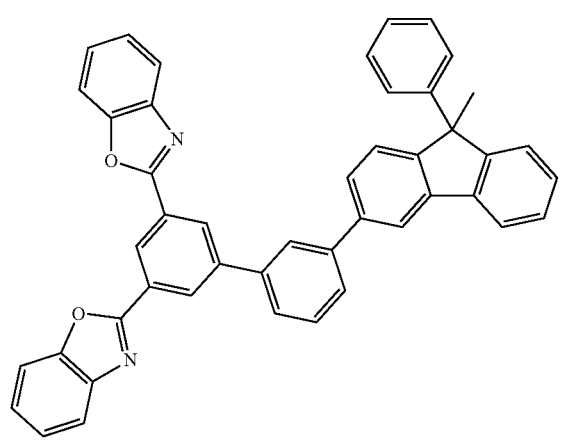
119
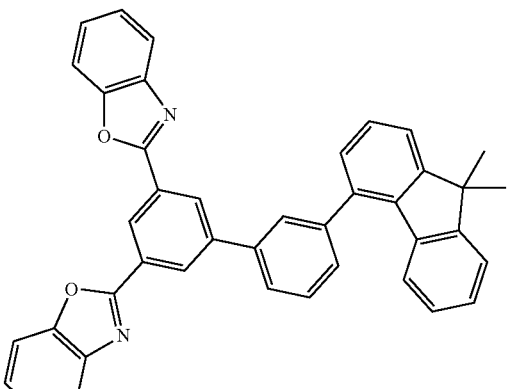
120
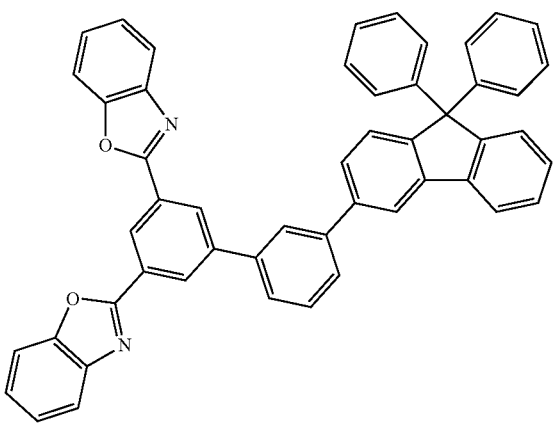
121

122
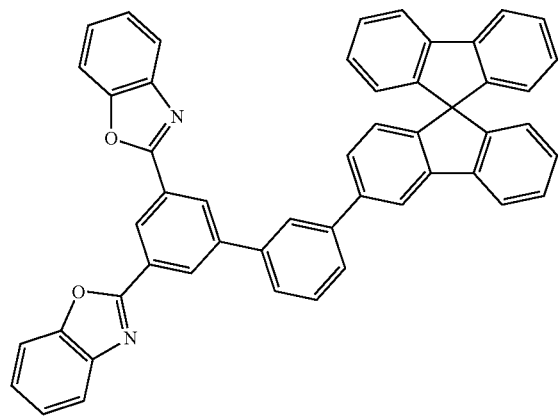
123
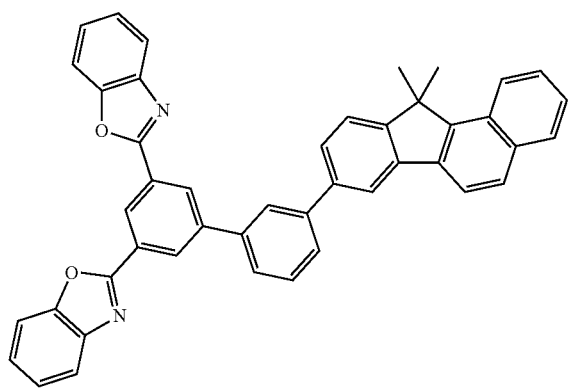
124
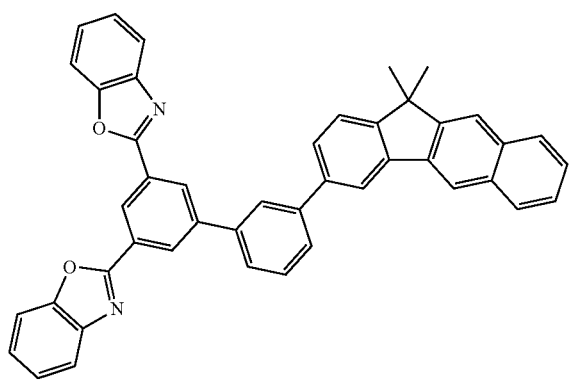
125
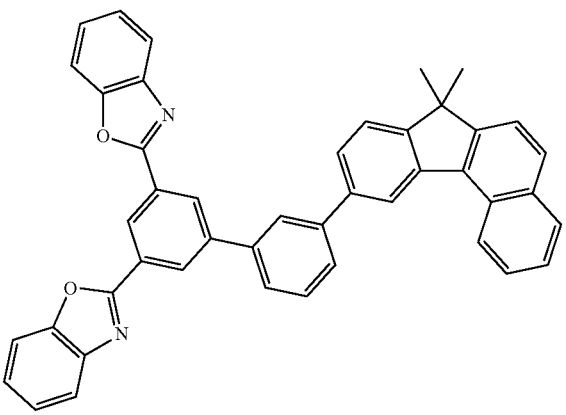
126
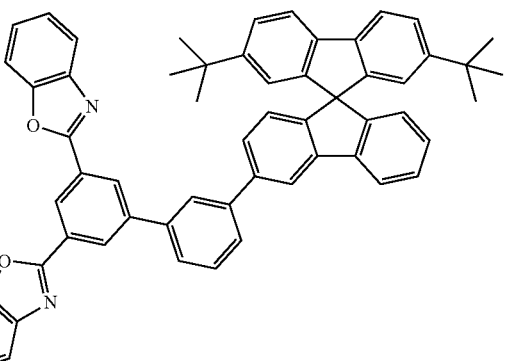
127
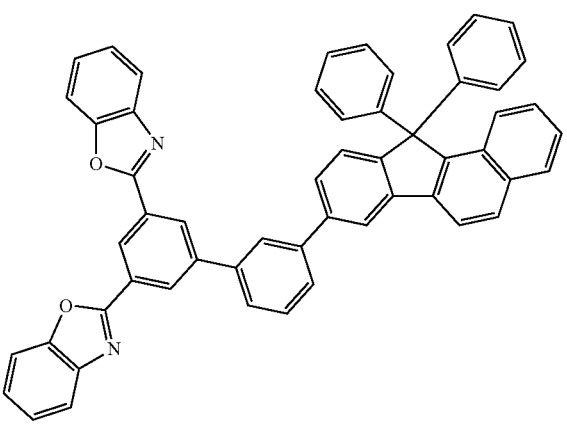

128
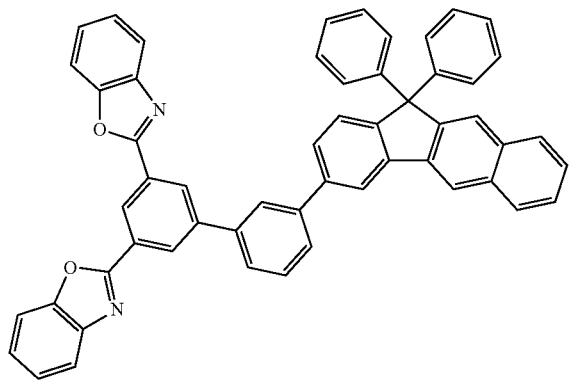
129
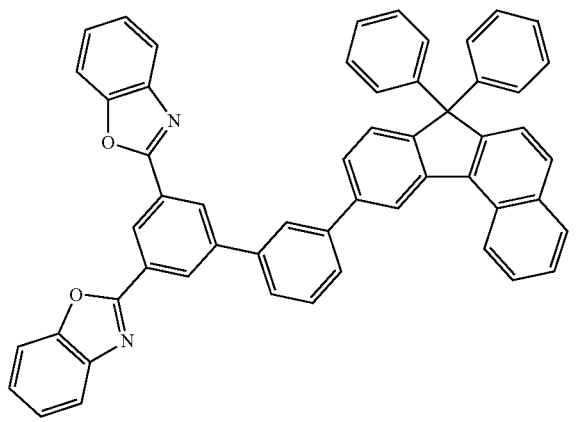
130
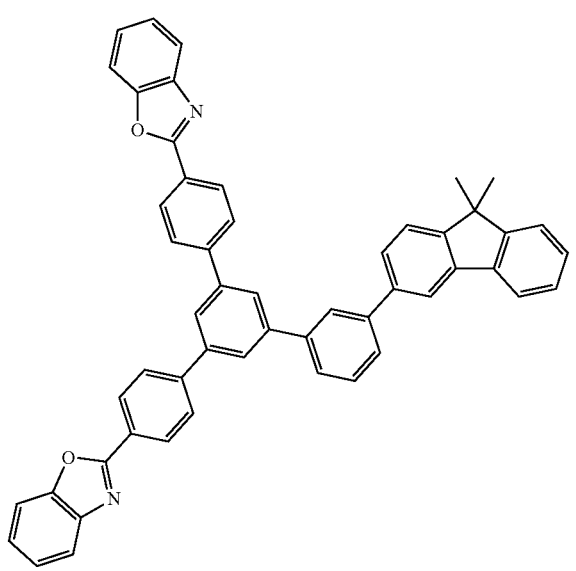
131
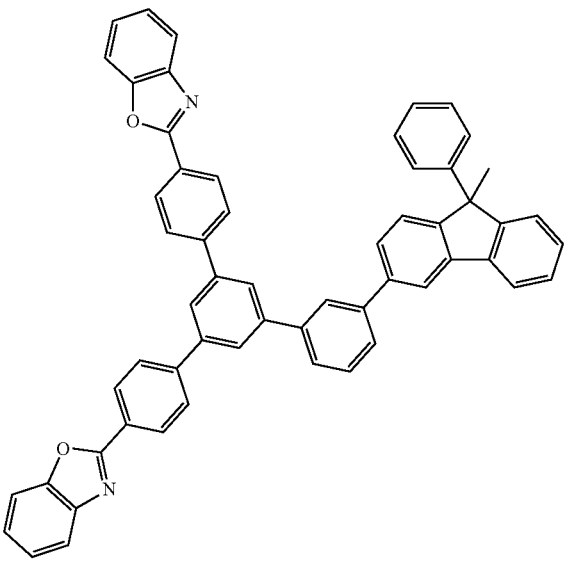
132
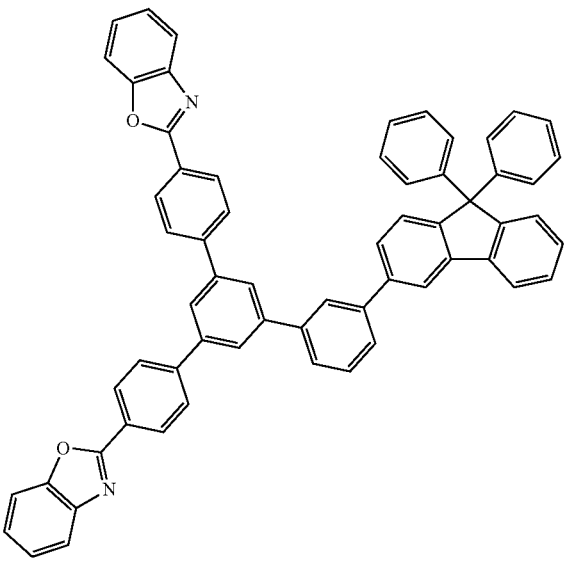

133
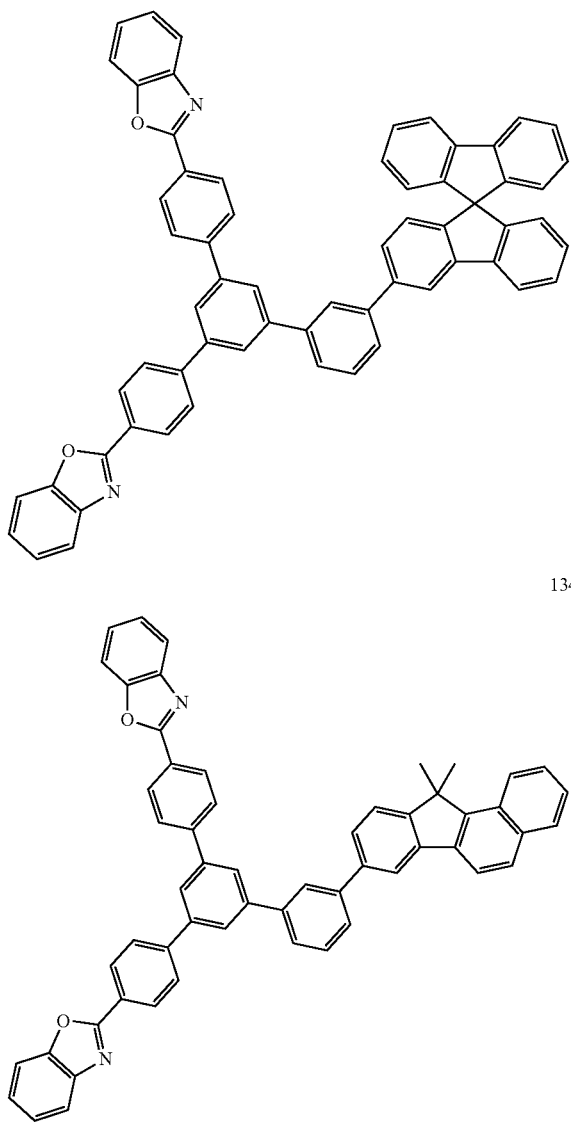
134
135
136
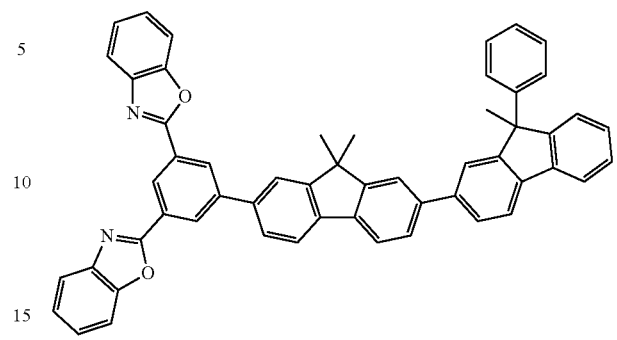
137
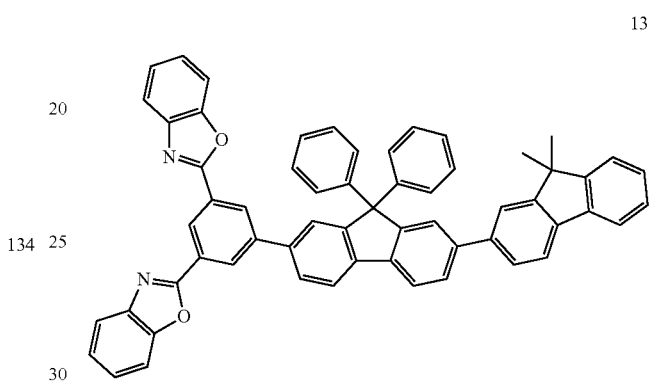
138
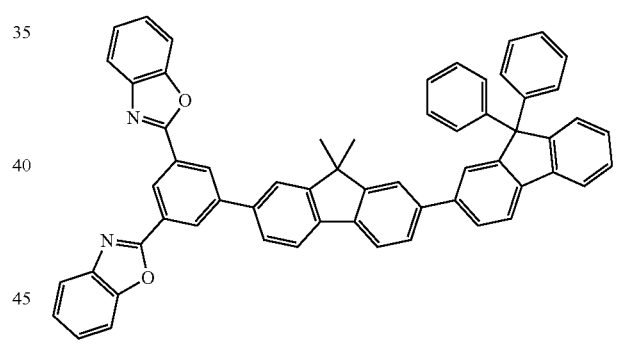
139
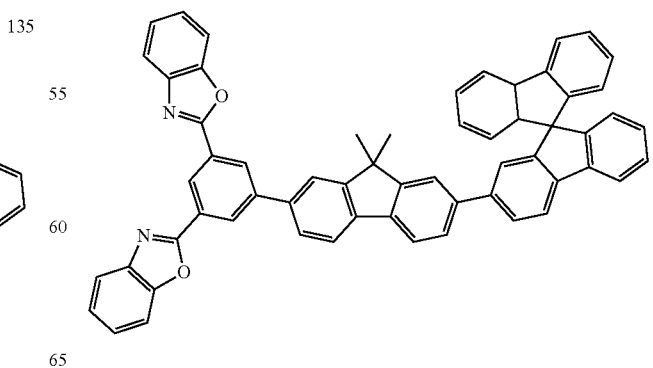

140
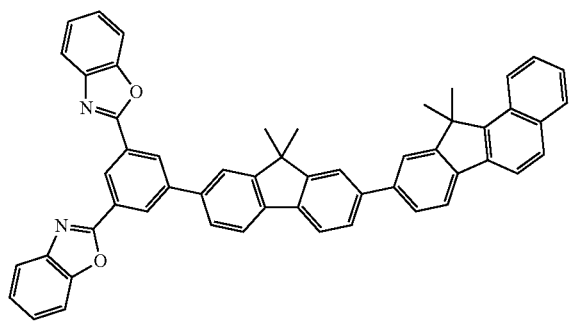
141
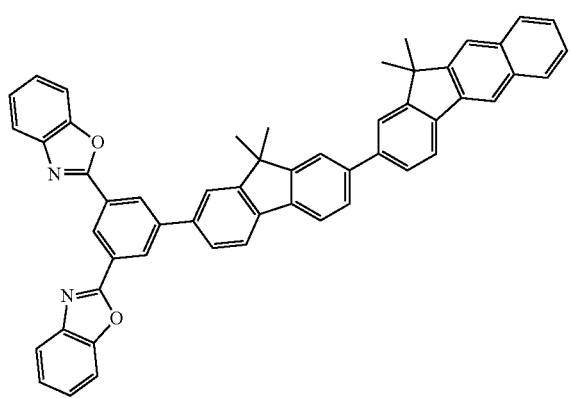
142
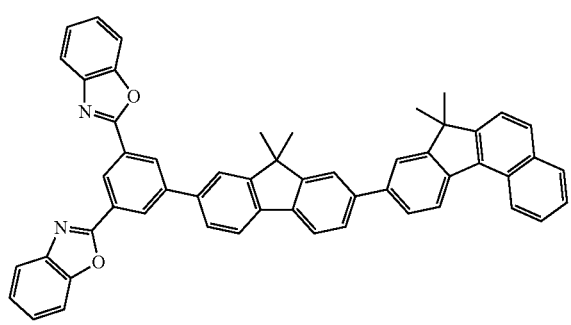
143
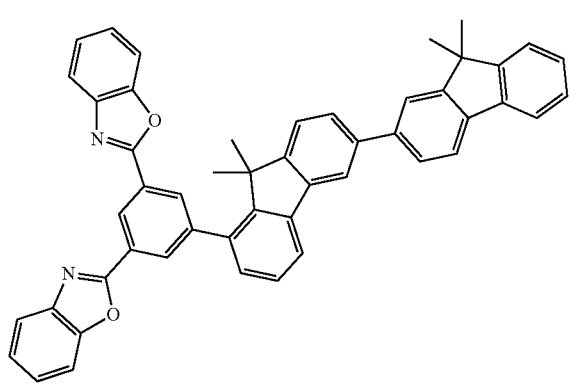
144
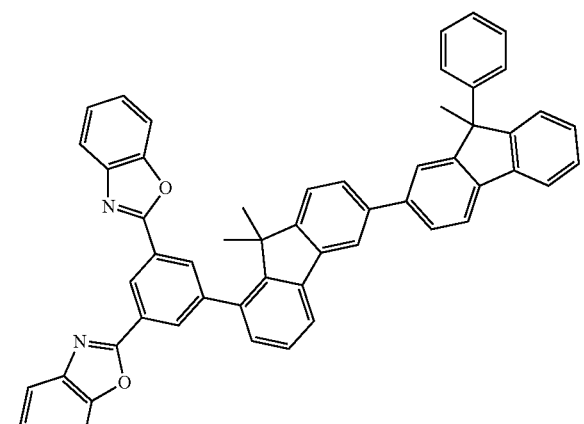
145
146
147
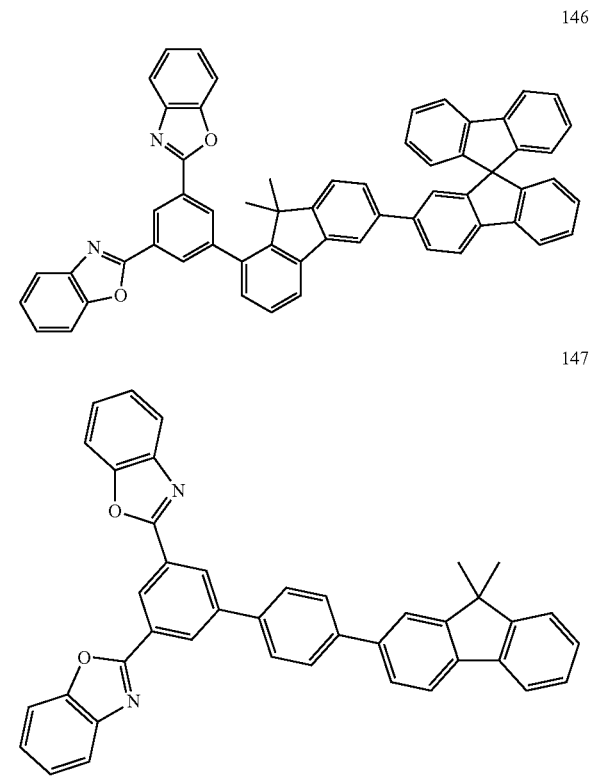

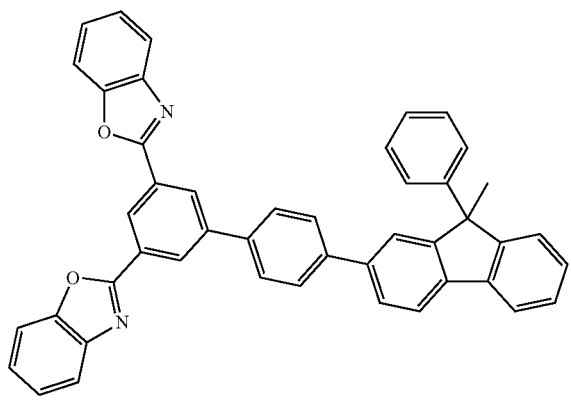
148
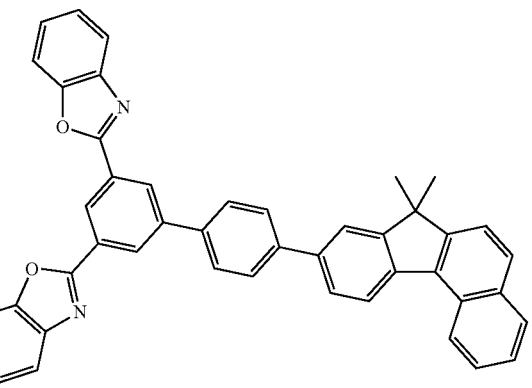
152
149
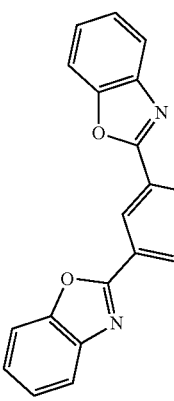
153
150
154
151
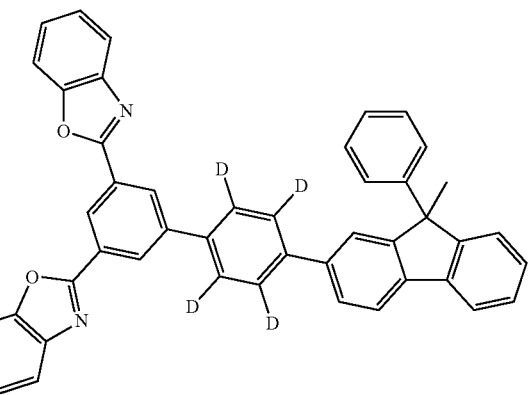
155
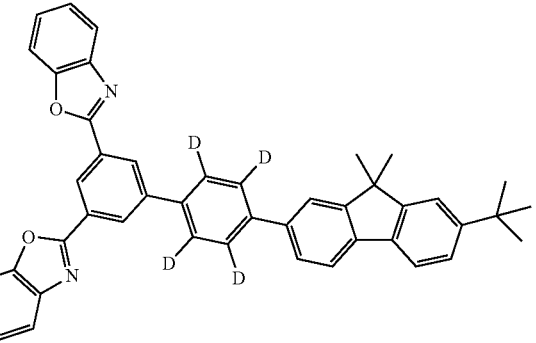

156
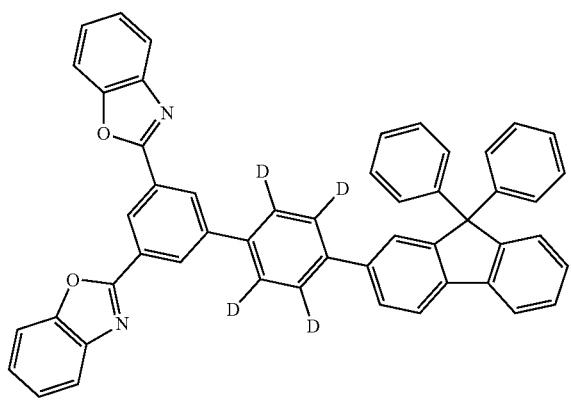
157
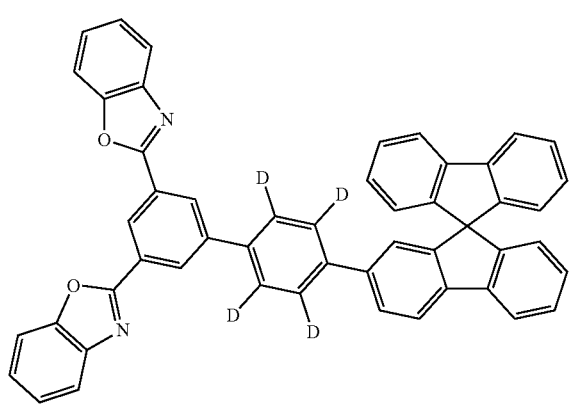
158
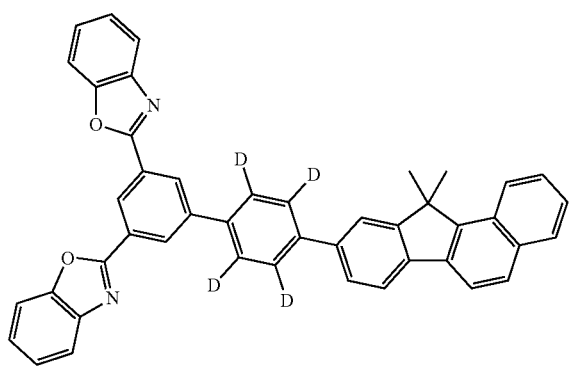
159
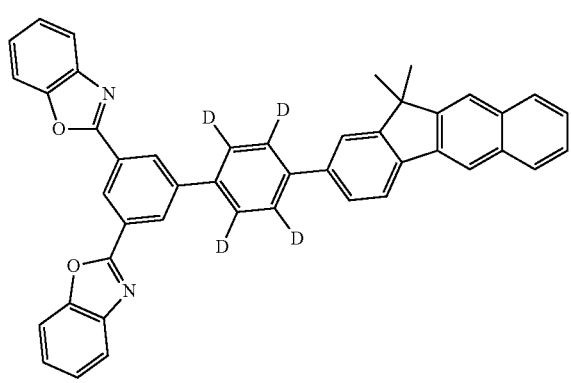
160
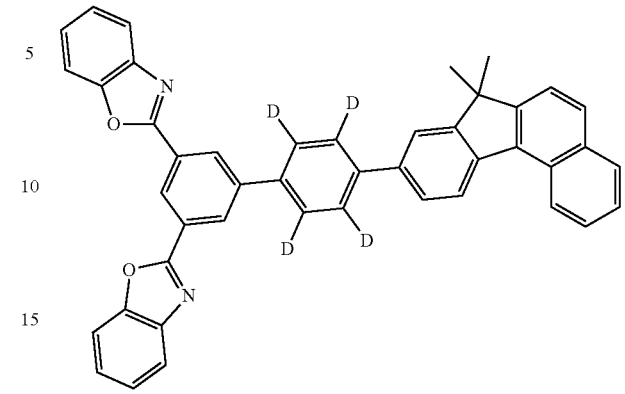
161
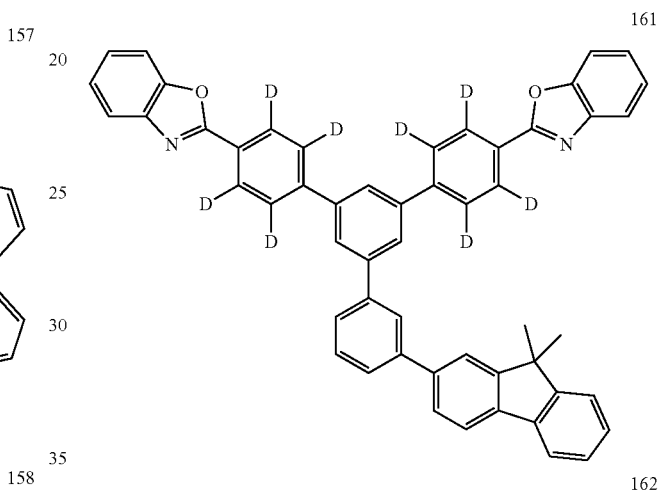
162
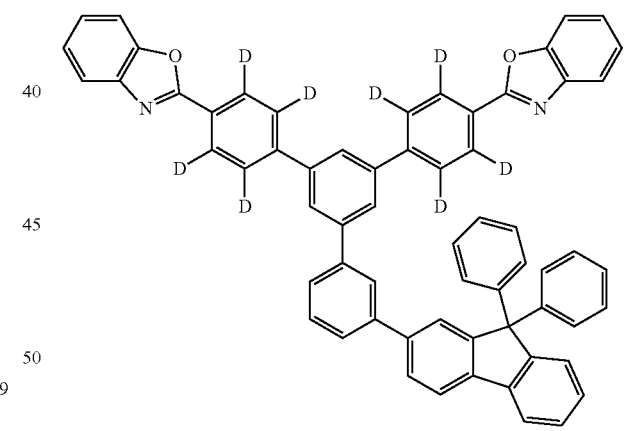
163
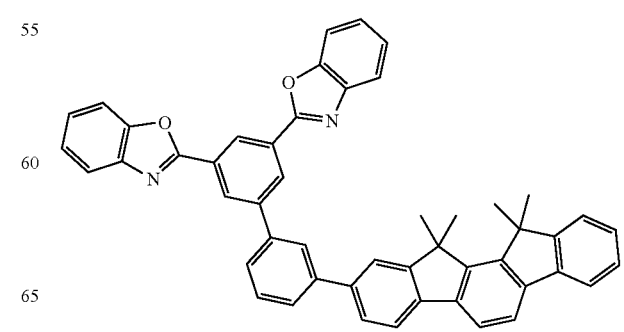

164
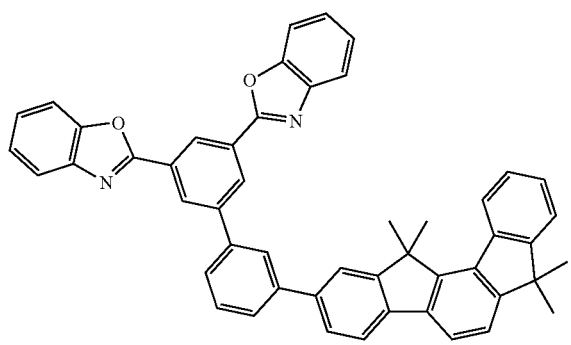
165
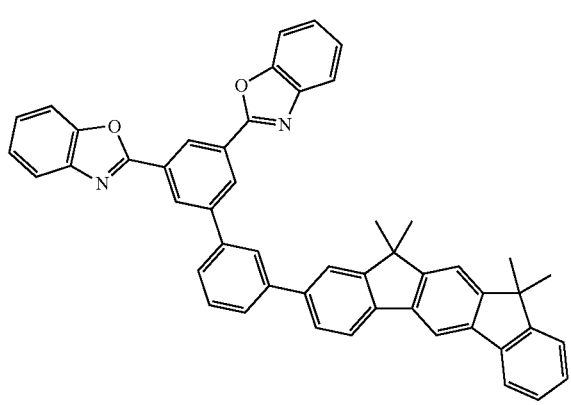
166
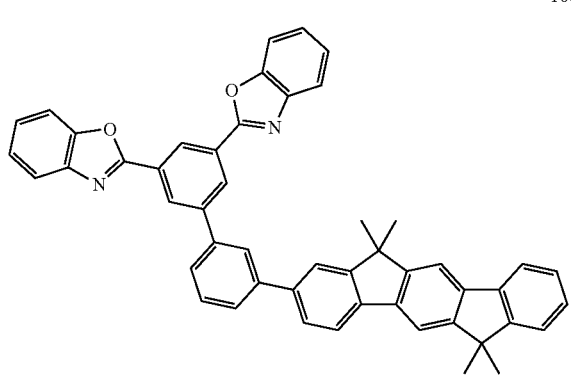
167
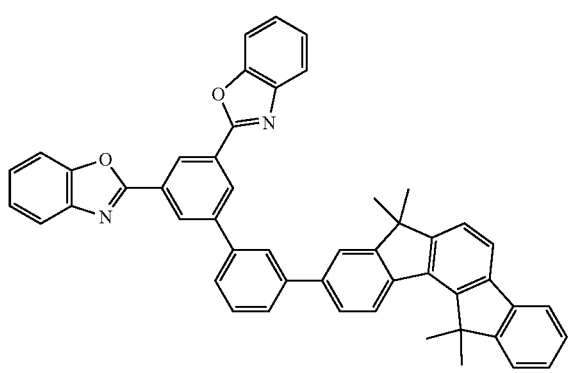
168
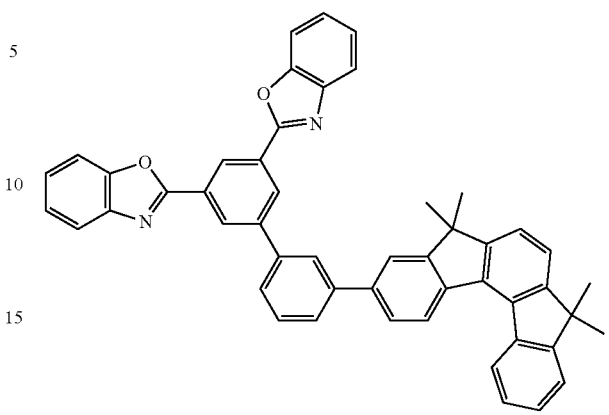
169
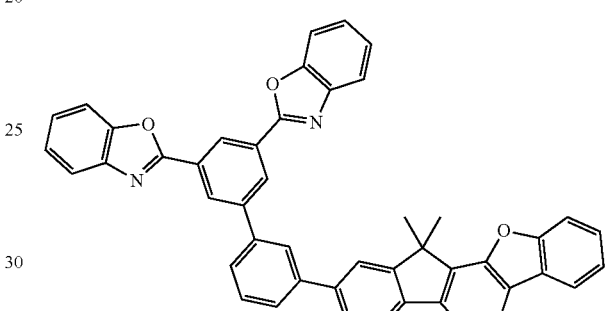
170
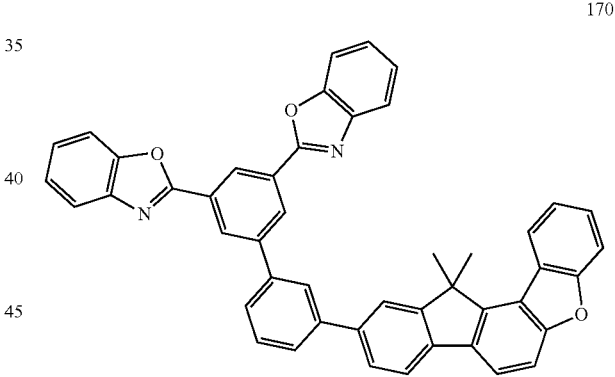
171
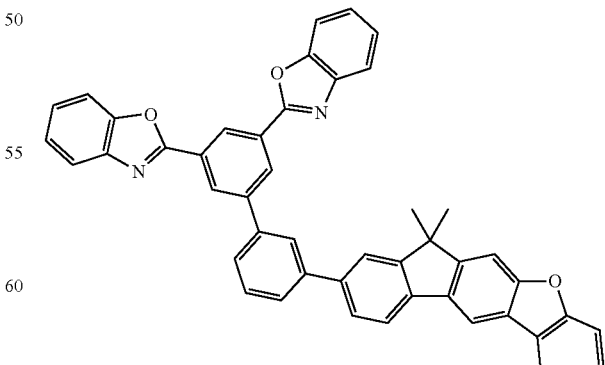

172
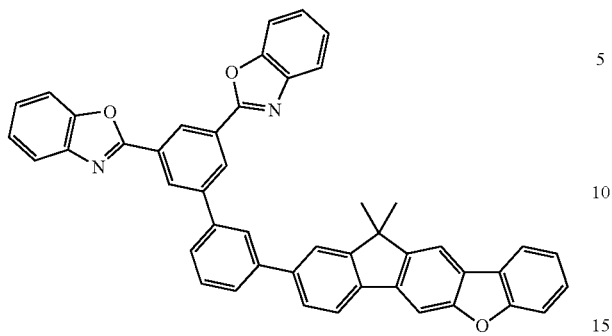
173
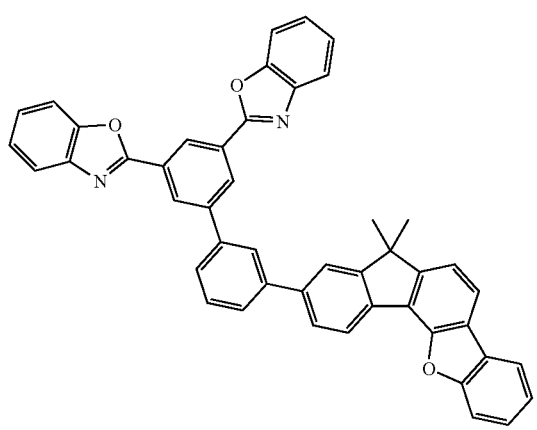
174
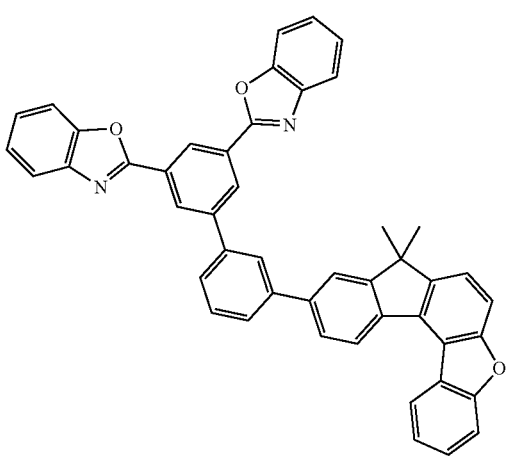
175
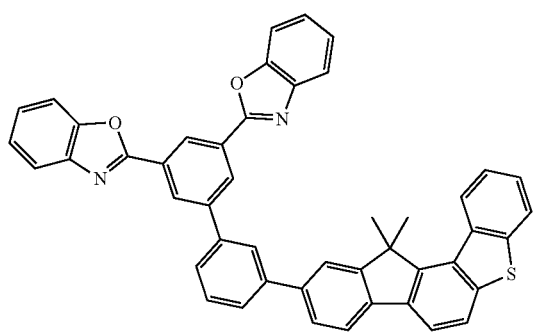
176
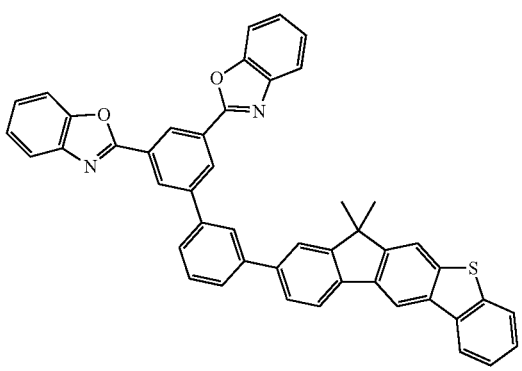

-continued
177
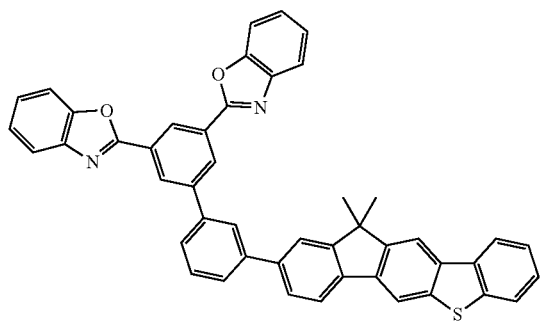
178
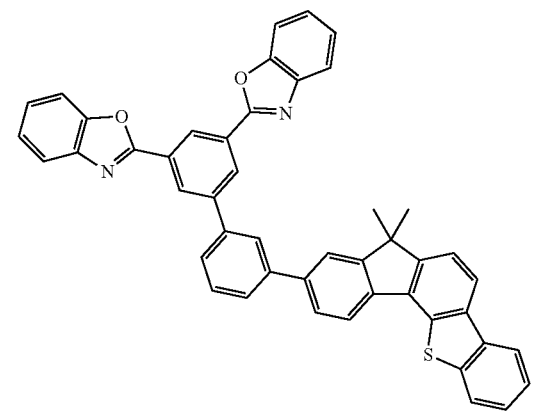
179
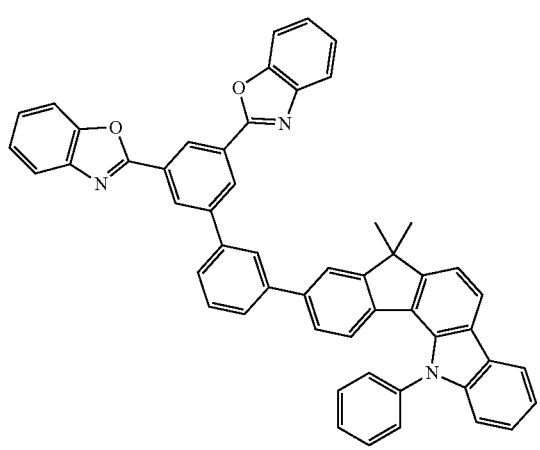
180
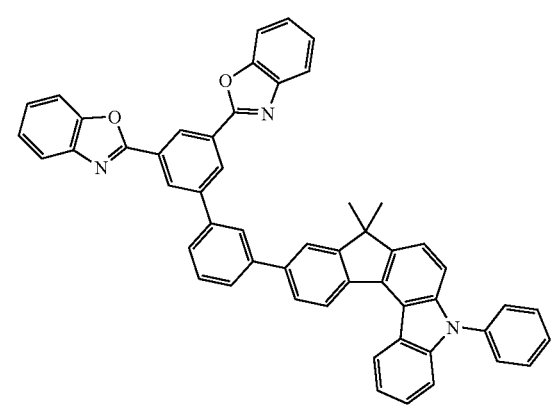
181
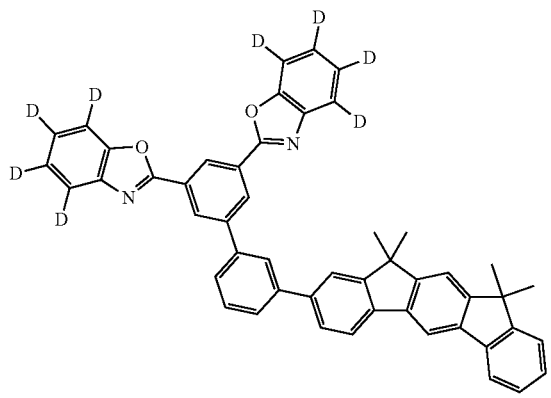
182
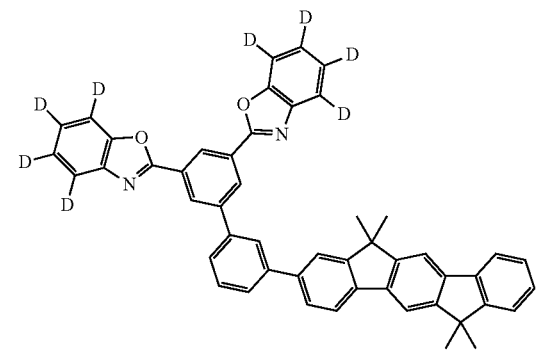

-continued
183
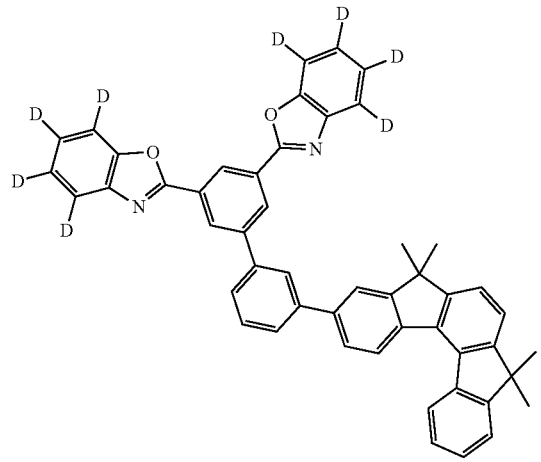
184
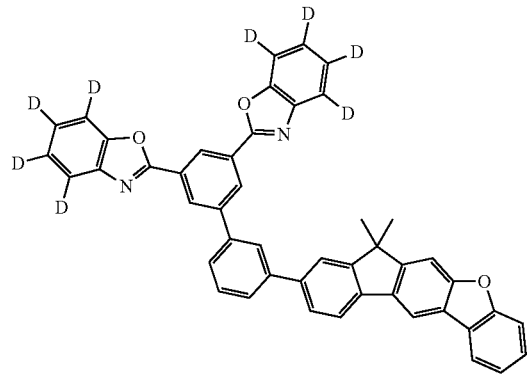
185
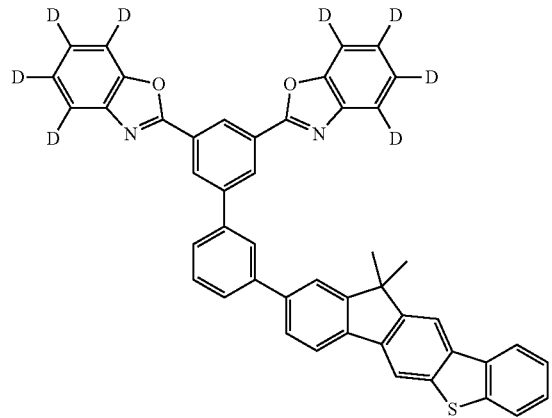
186
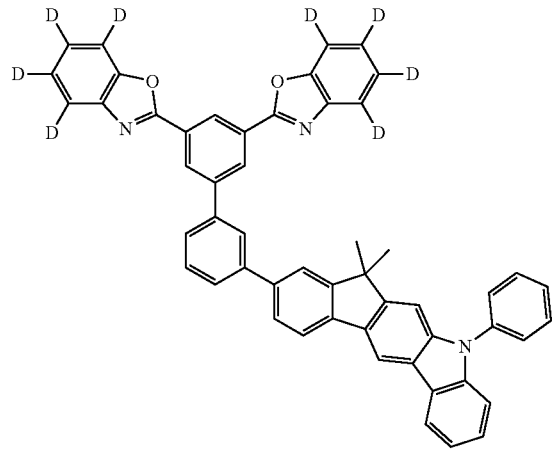
187
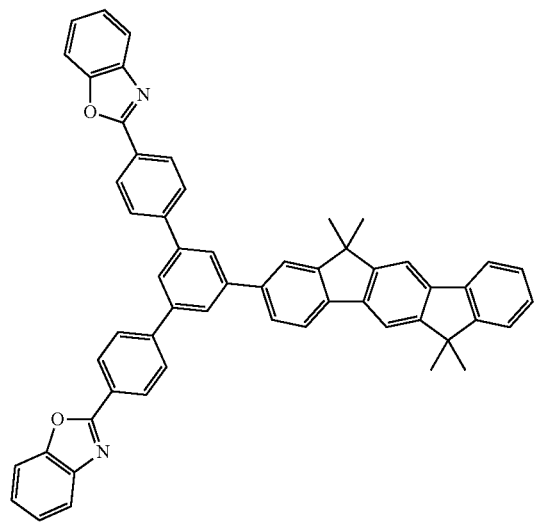
188
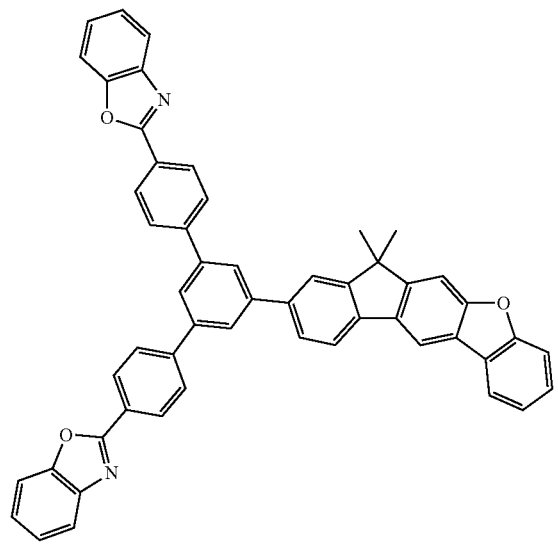

-continued
189
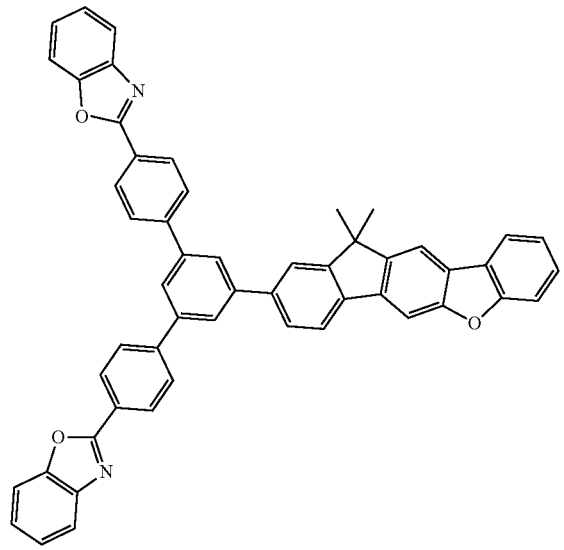
190
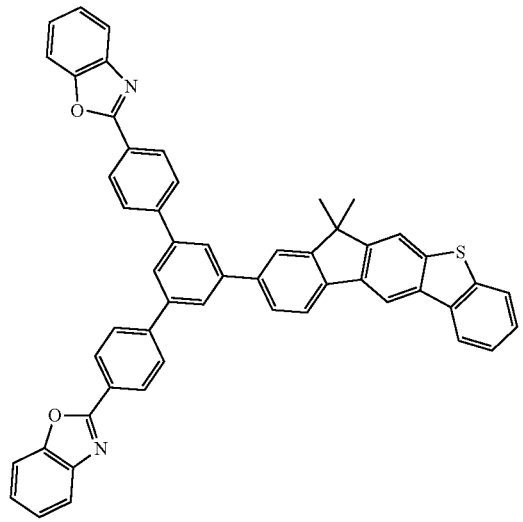
191
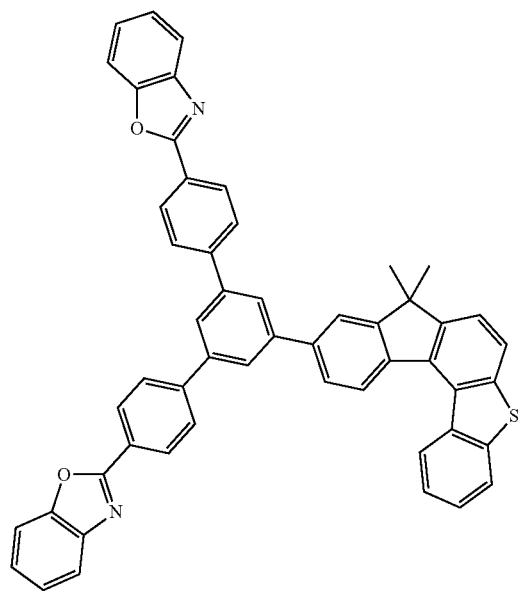
192
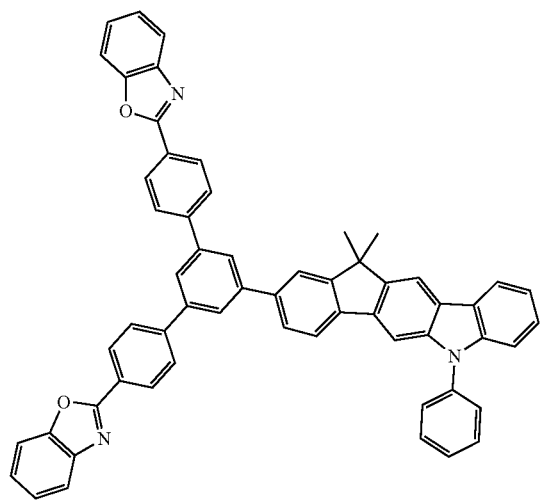
193
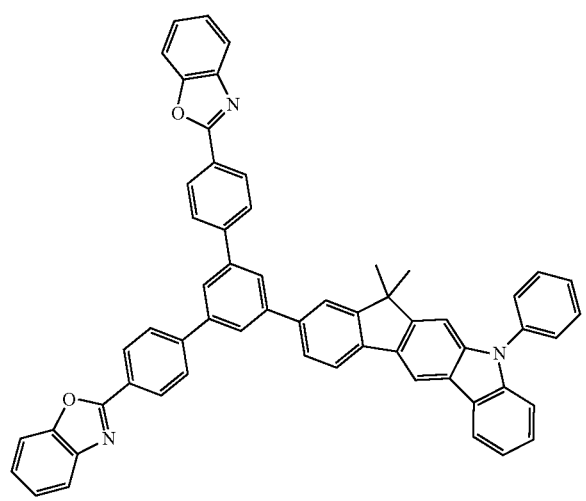
194
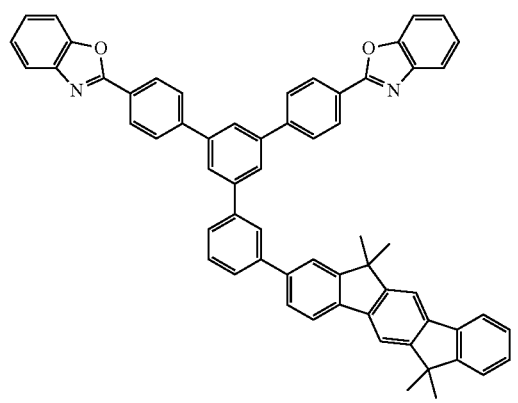

-continued
| | |
|---|---|
| 195 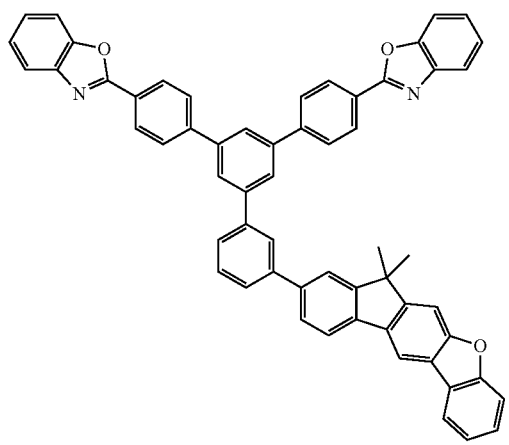 | 196 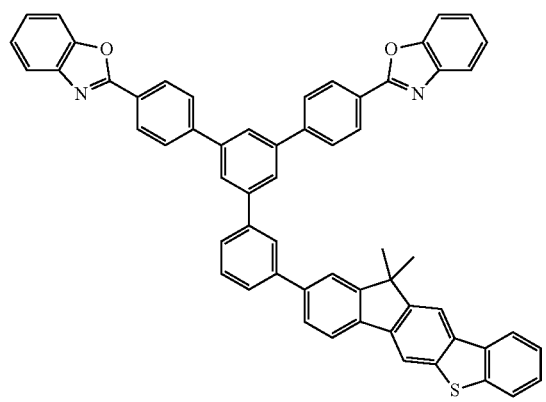 |
| 197 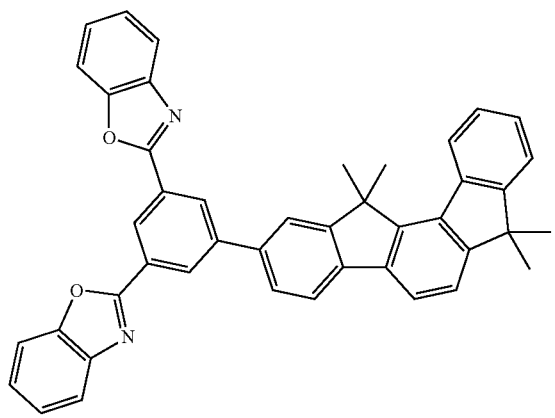 | 198 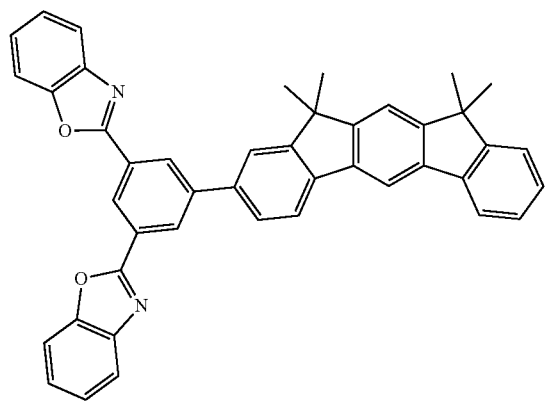 |
| 199 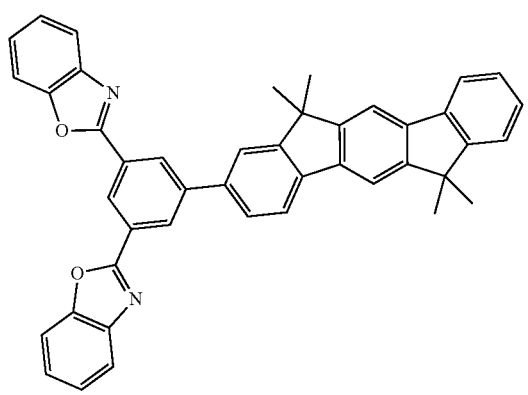 | 200 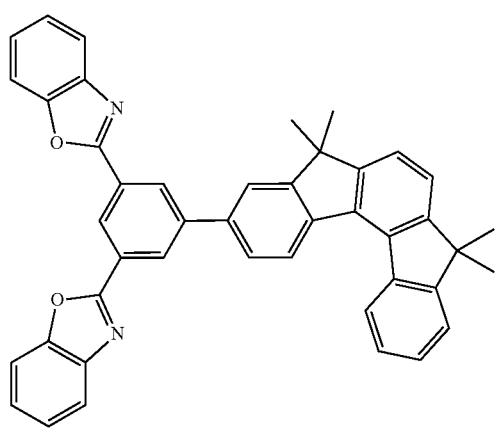 |

-continued
| 201 | 202 |
|---|---|
| 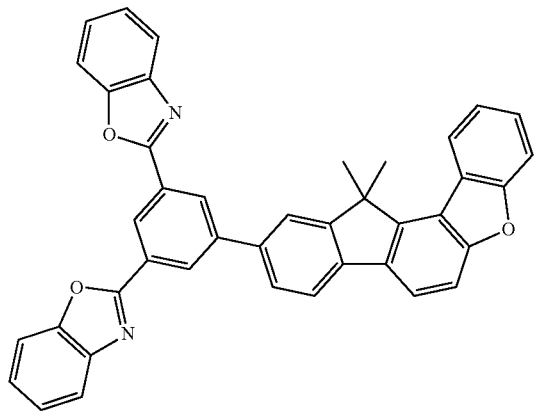 | 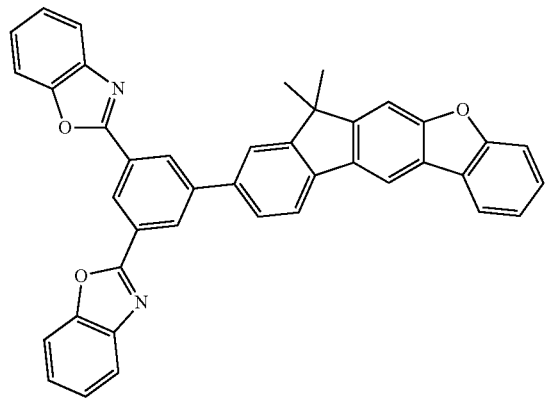 |
| 203 | 204 |
| 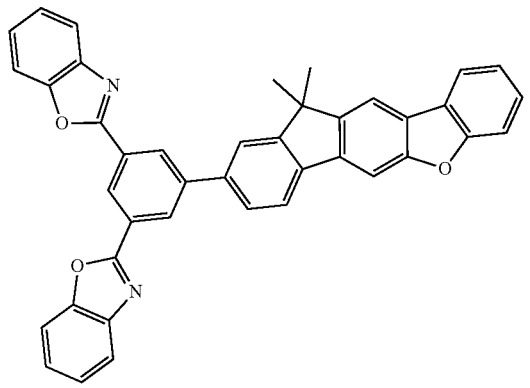 | 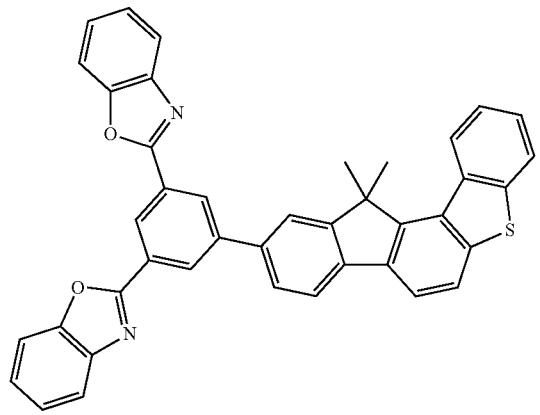 |
| 205 | 206 |
| 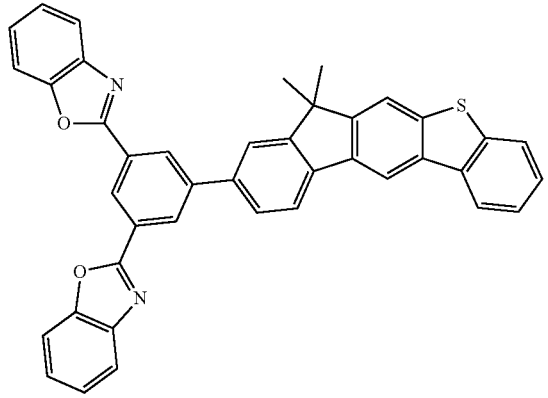 | 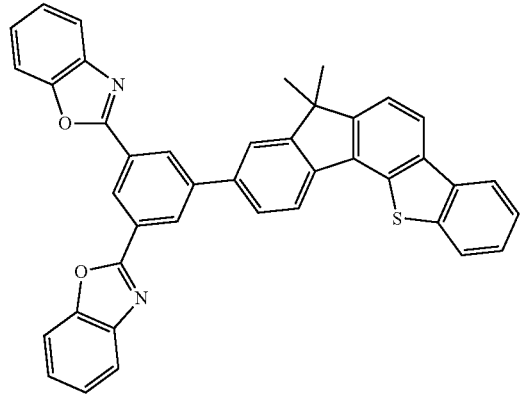 |
| 207 | 208 |
| 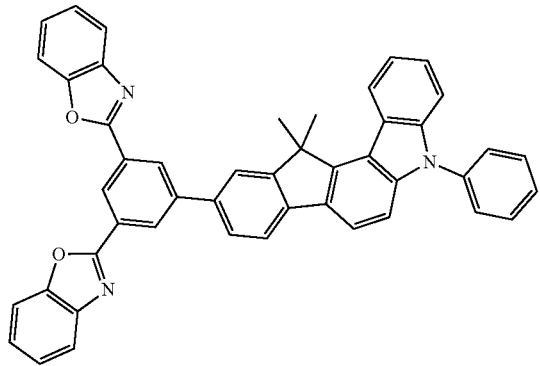 | 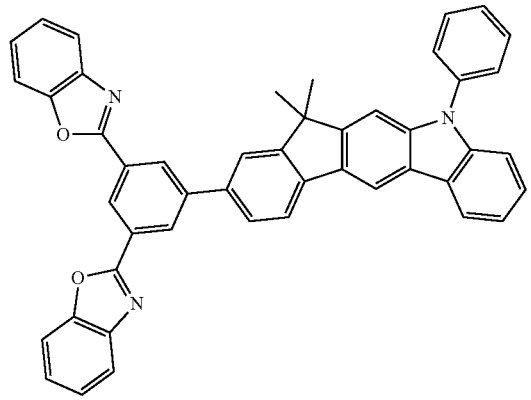 |

-continued
209
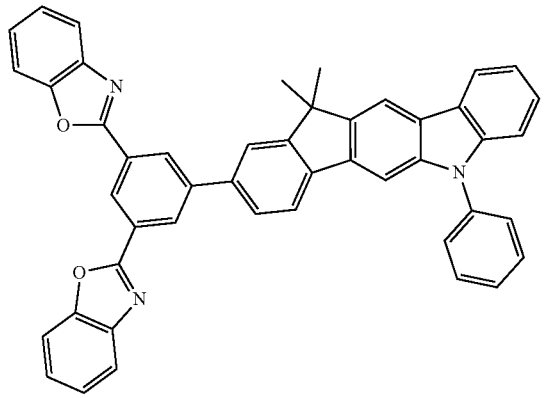
210
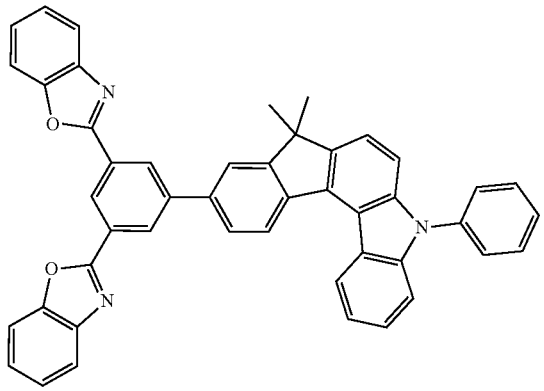
211
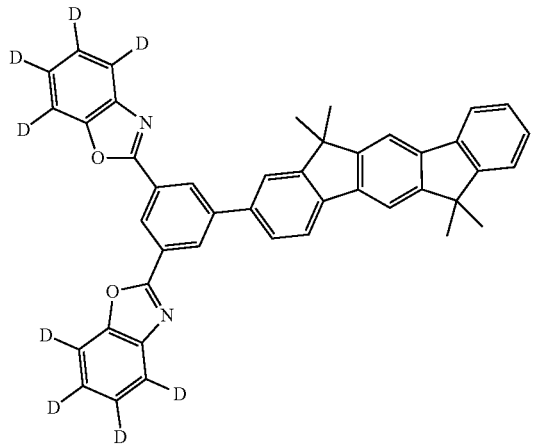
212
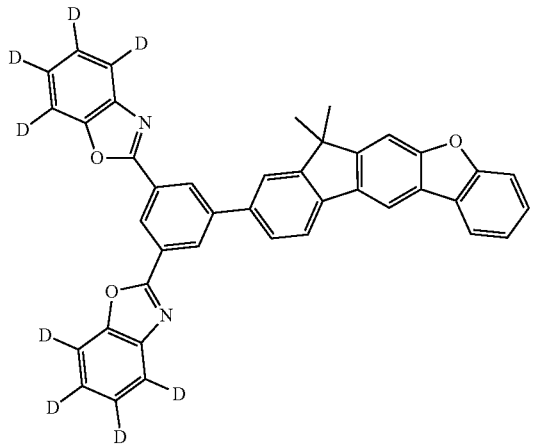
213
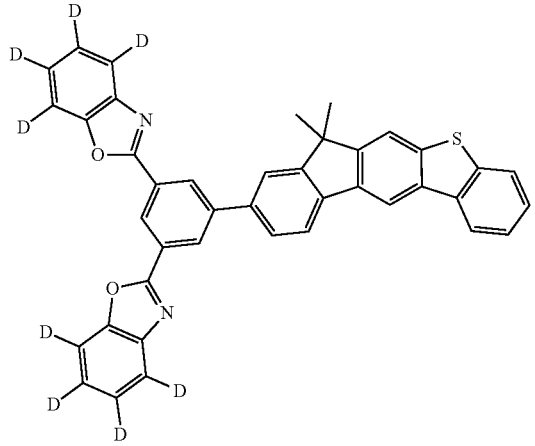
214
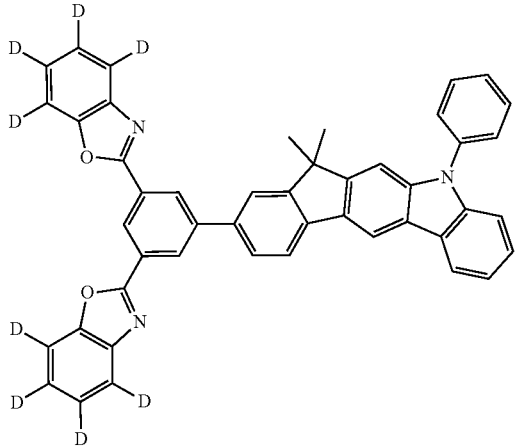

215
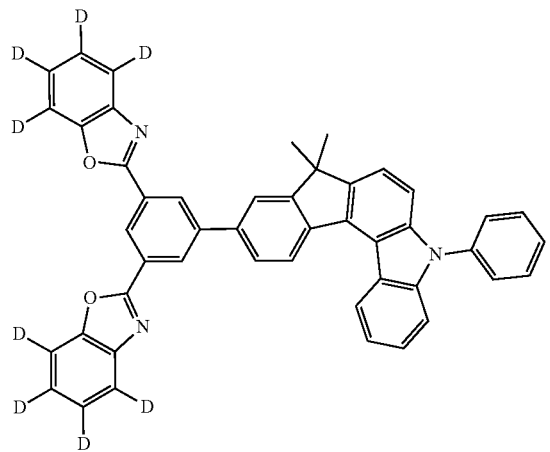
216
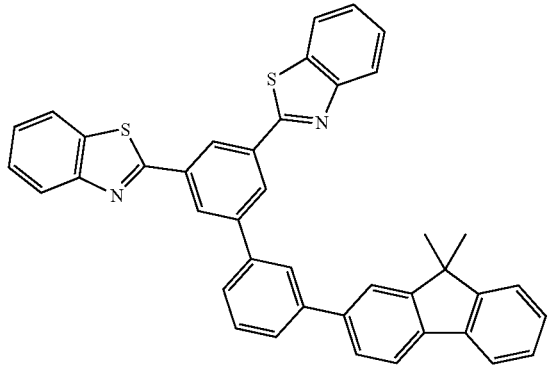
217
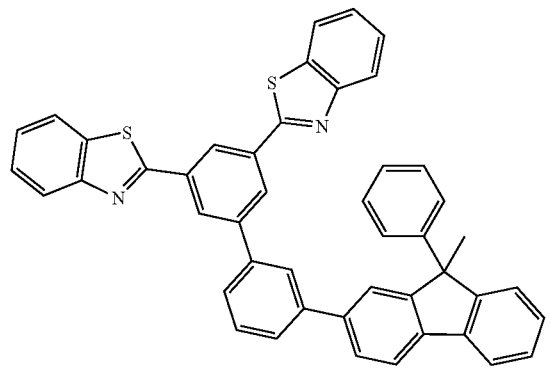
218
219
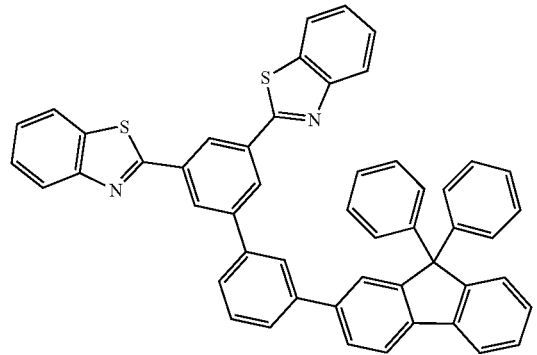
220
221
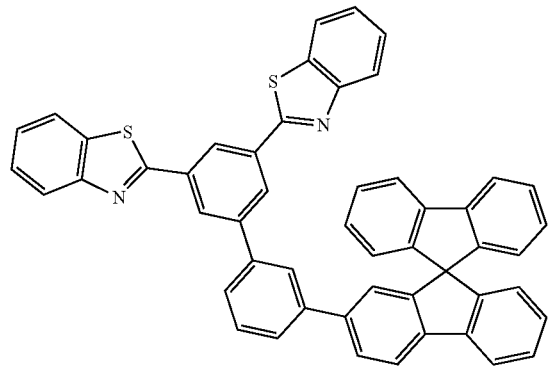
222
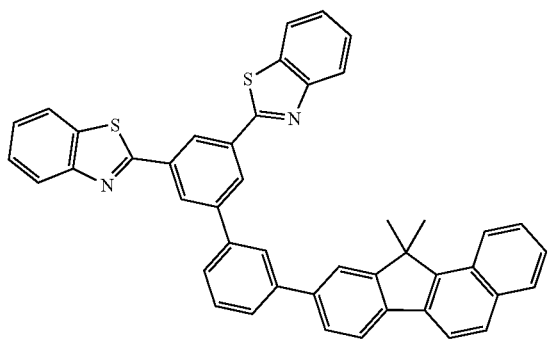

-continued
223
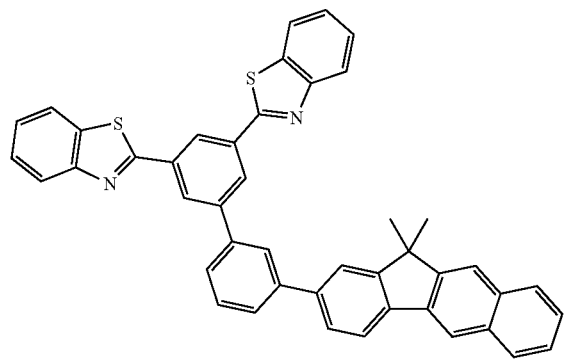
224
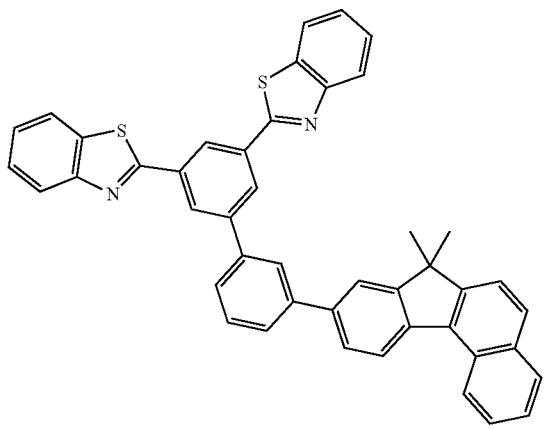
225
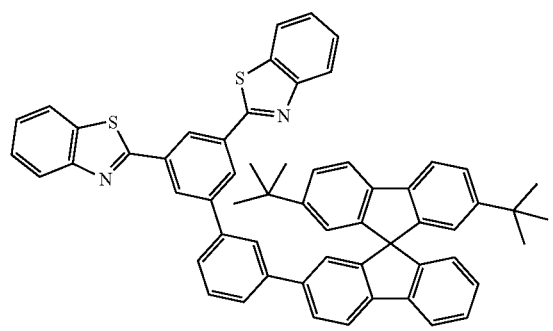
226
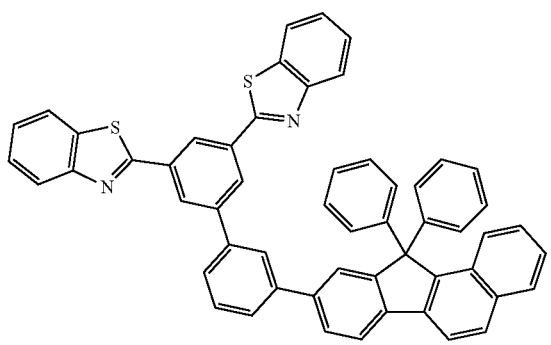
227
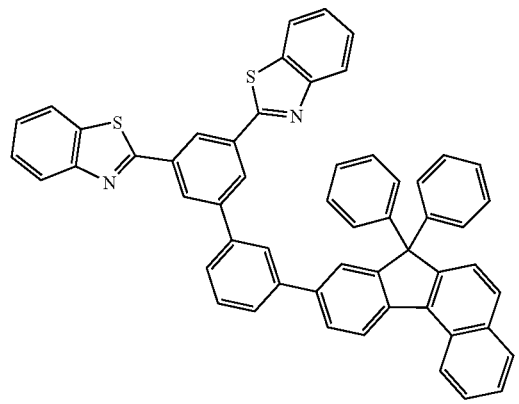
228
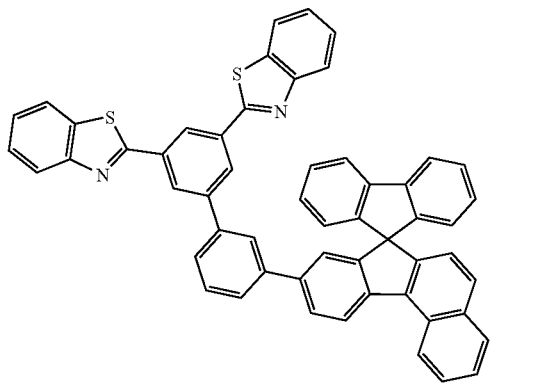
229
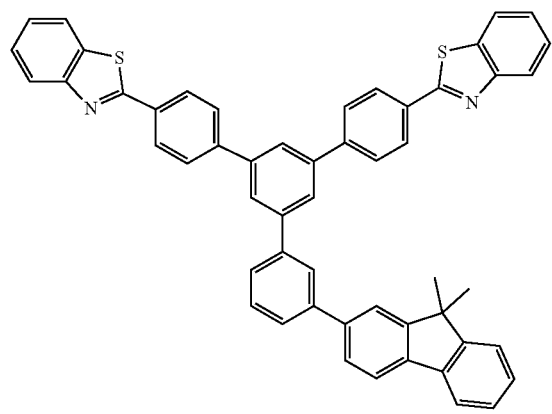
230
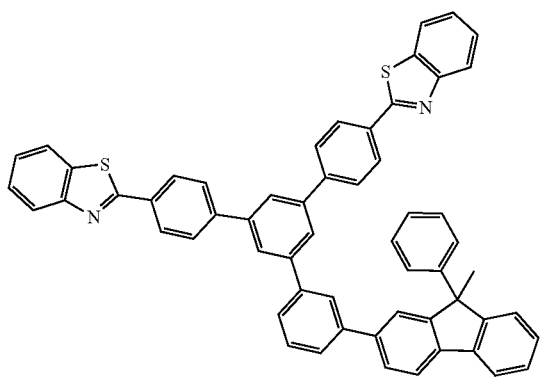

-continued
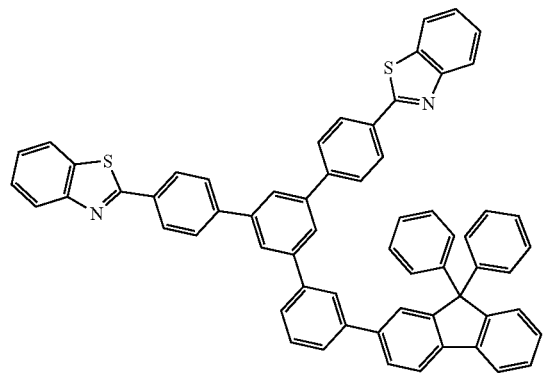
231
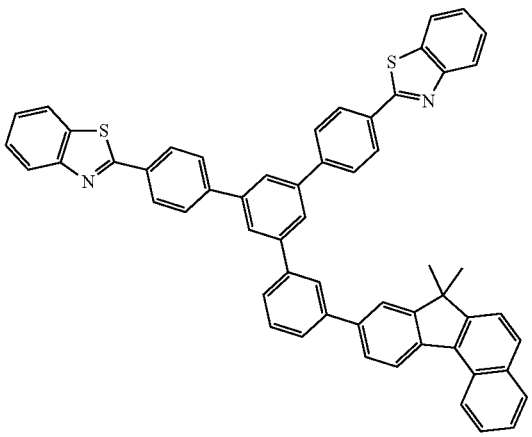
232
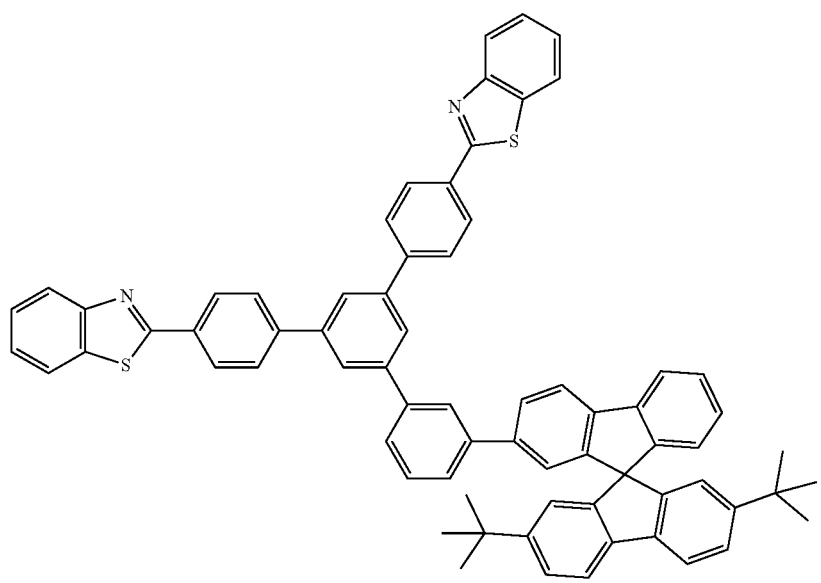
233
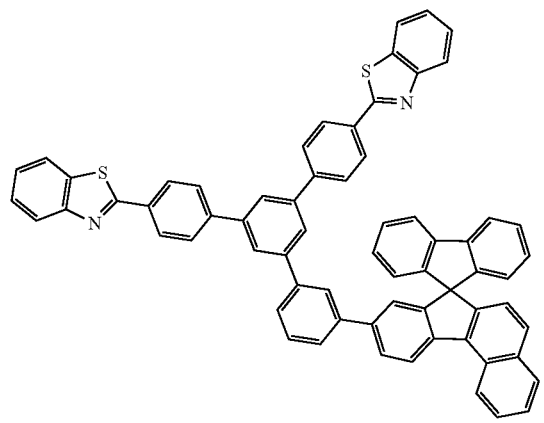
234
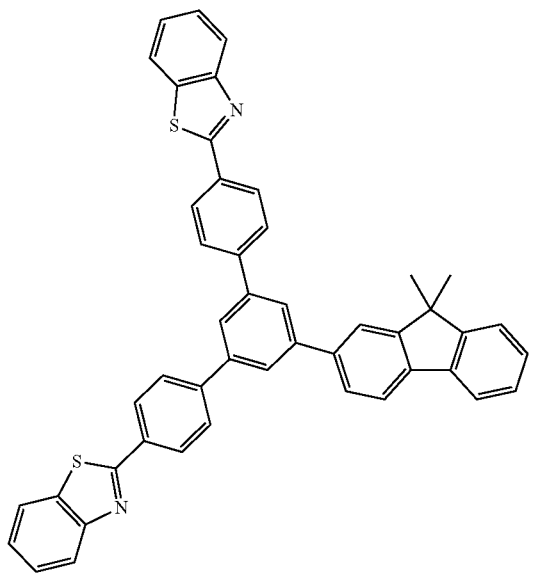
235

-continued
236
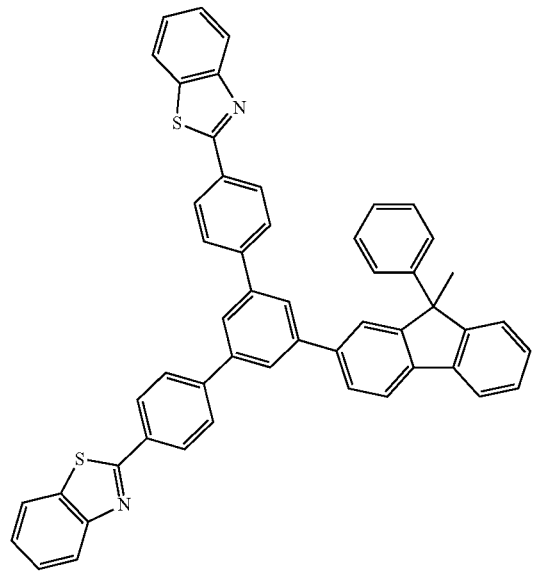
237
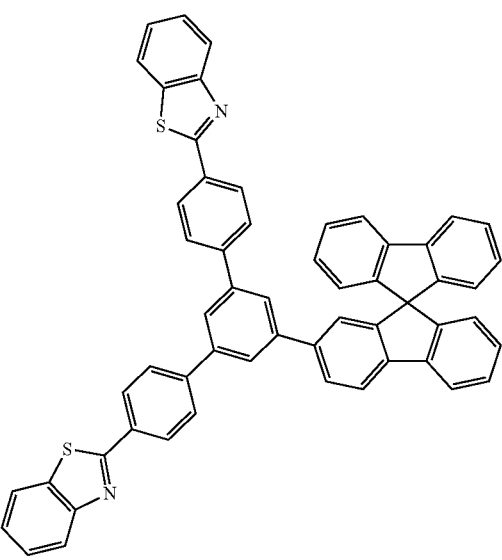
238
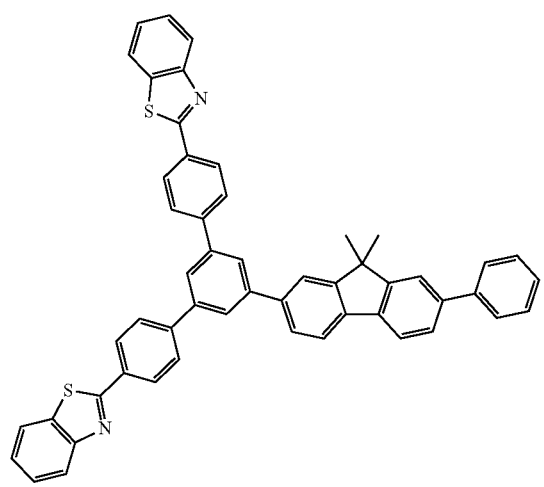
239
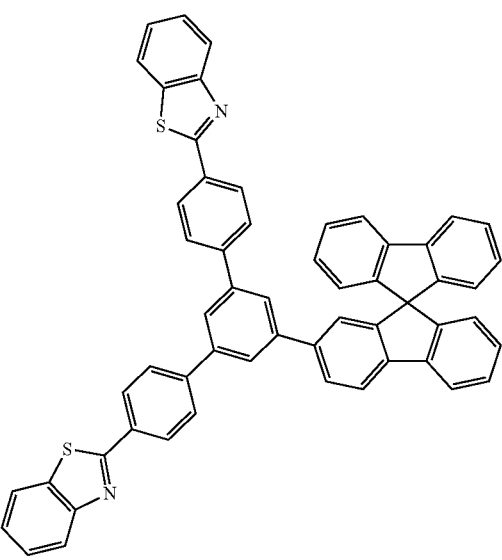
240
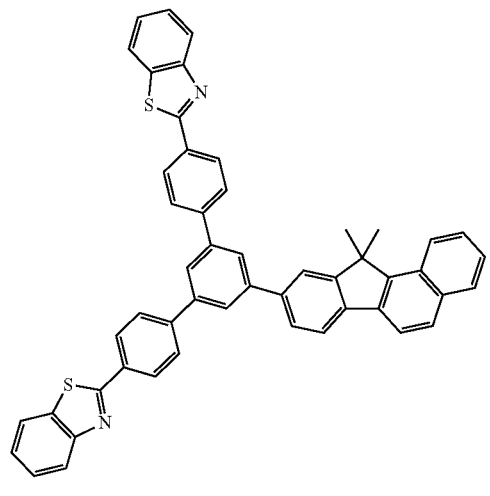
241
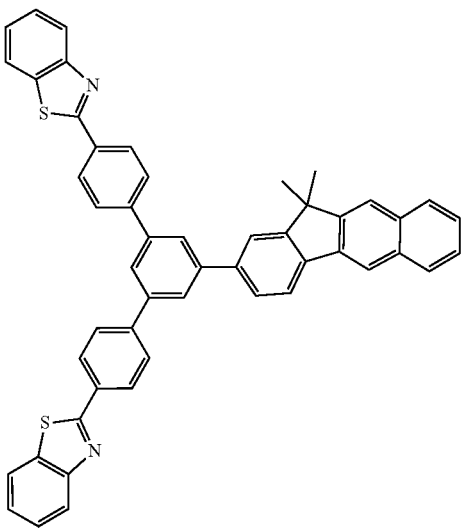

103
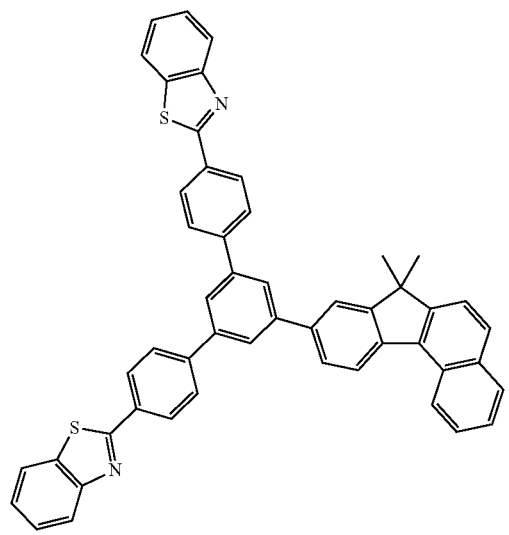
104
242
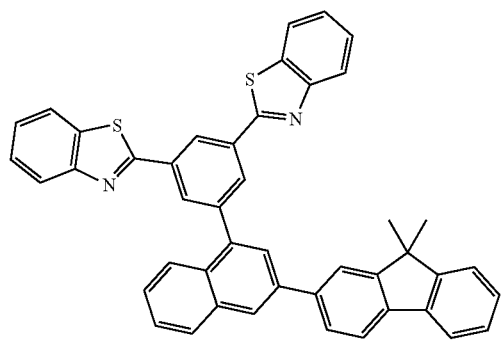
243
244
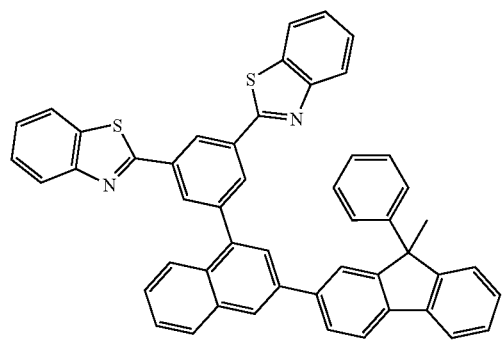
245
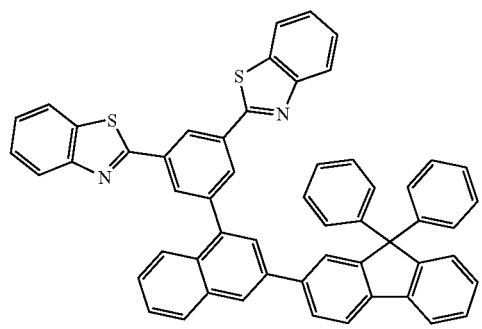
246
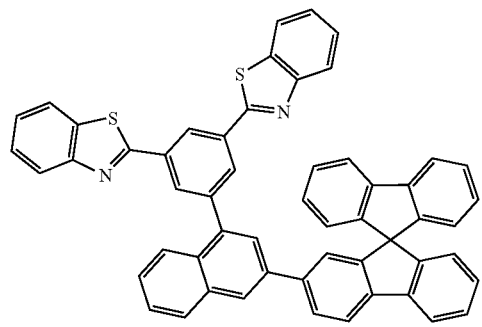
247
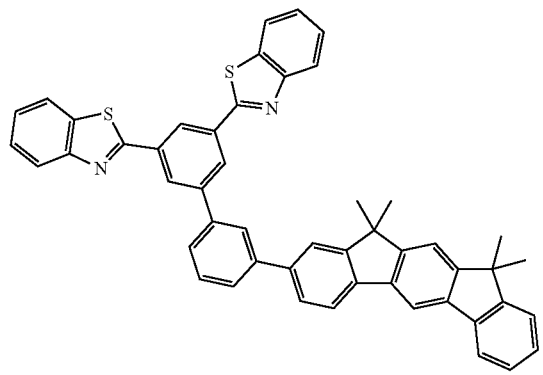

-continued
248
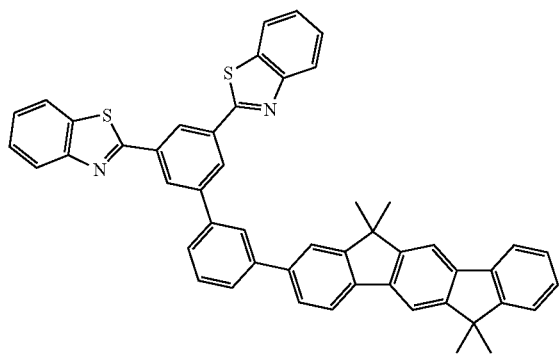
249
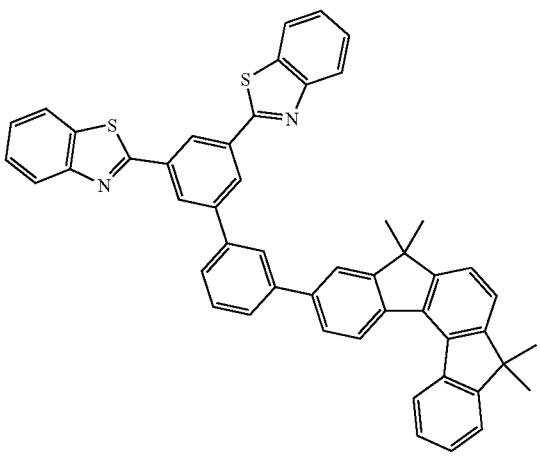
250
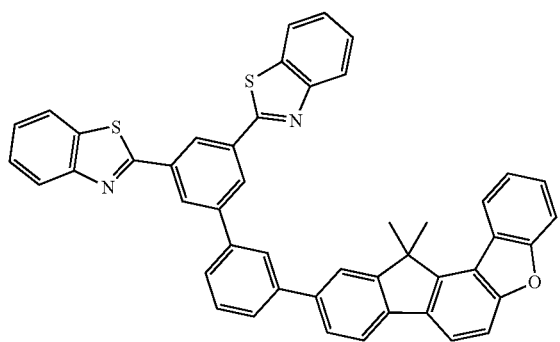
251
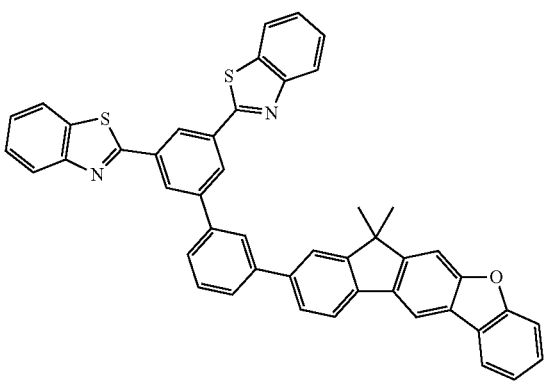
252
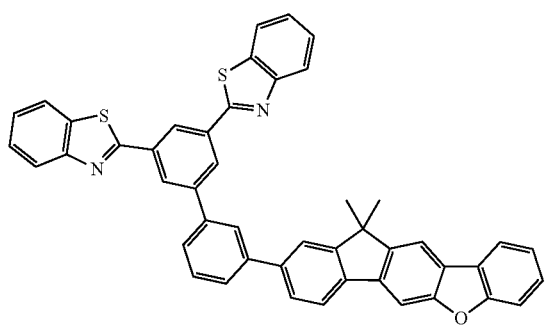
253
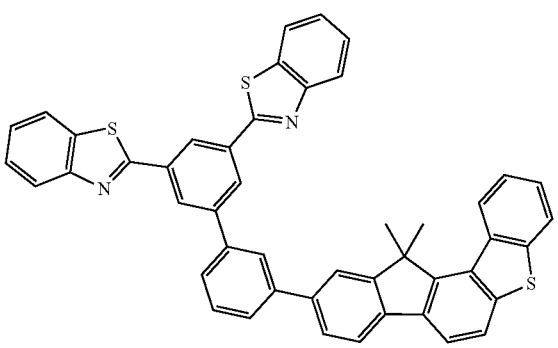
254
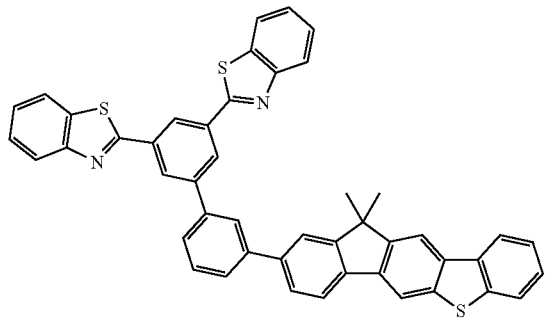
255
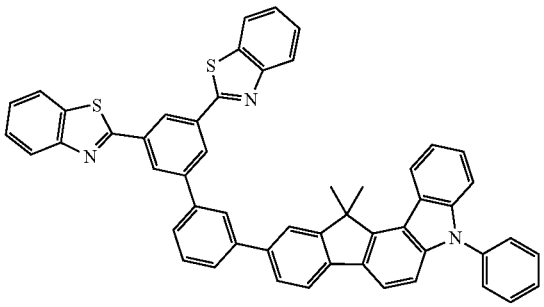

-continued
256
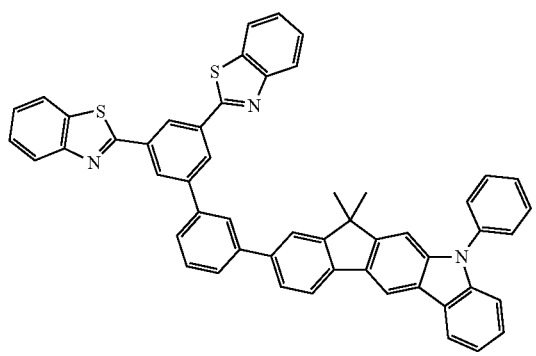
257
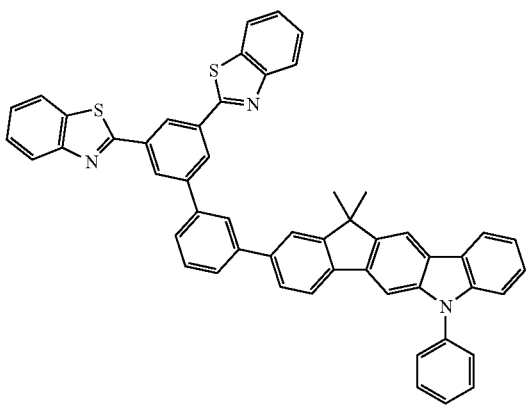
258
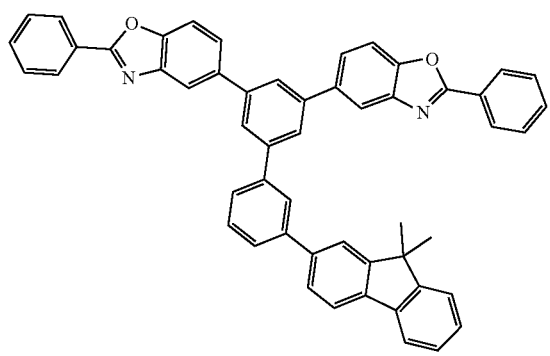
259
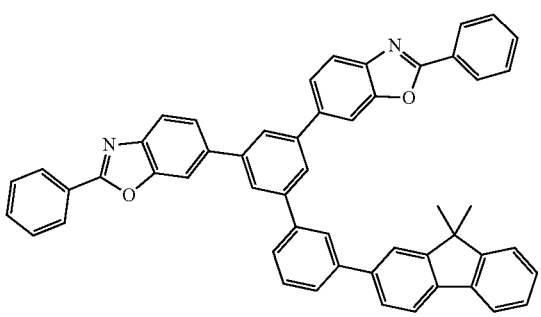
260
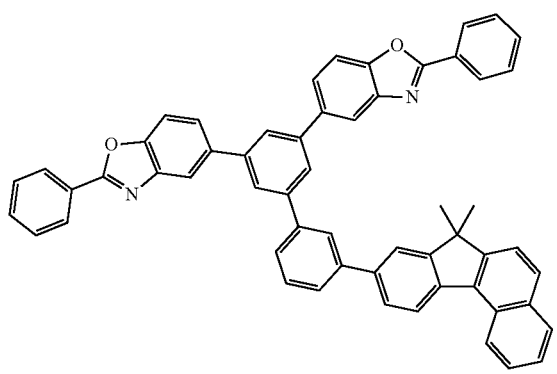
261
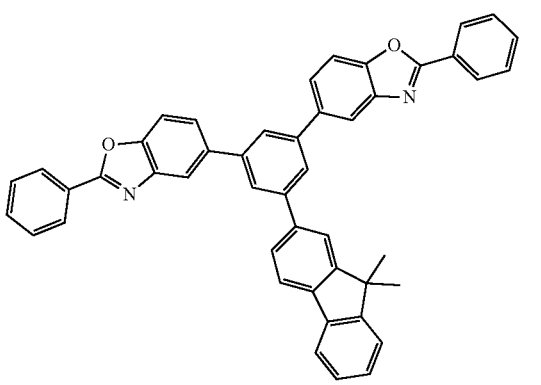
262
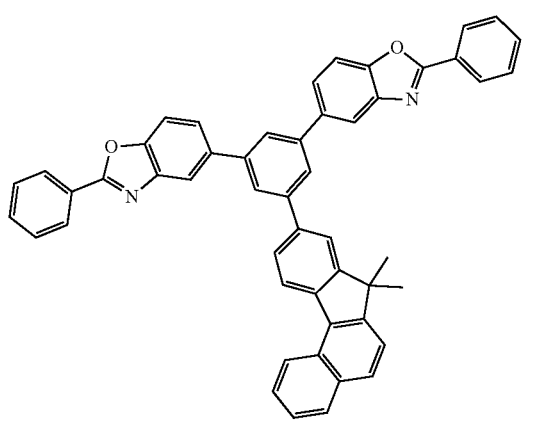
263
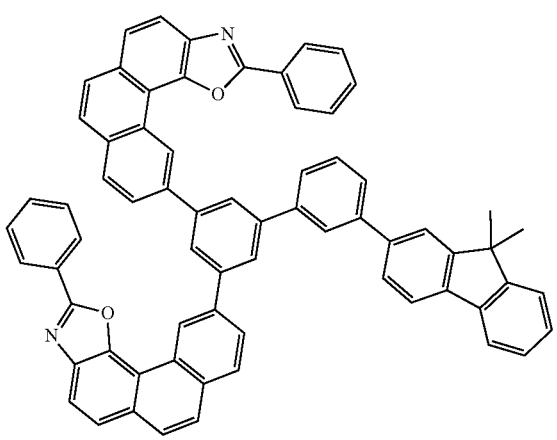

-continued
264
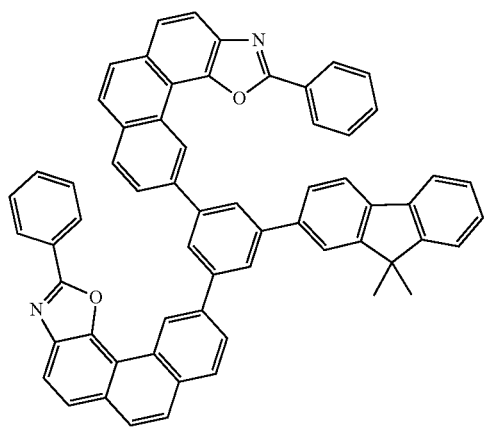
265
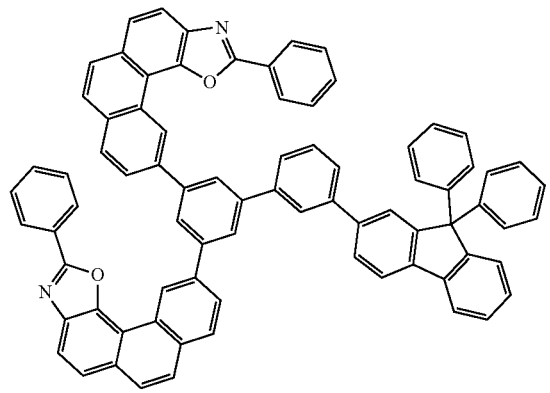
266
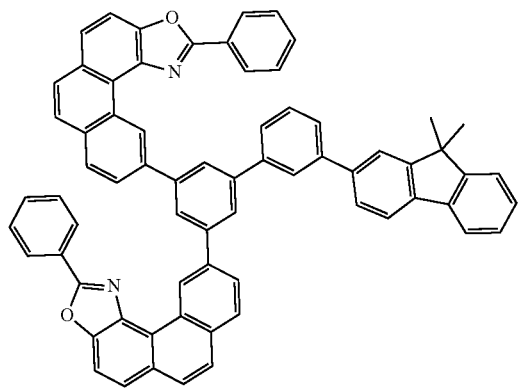
267
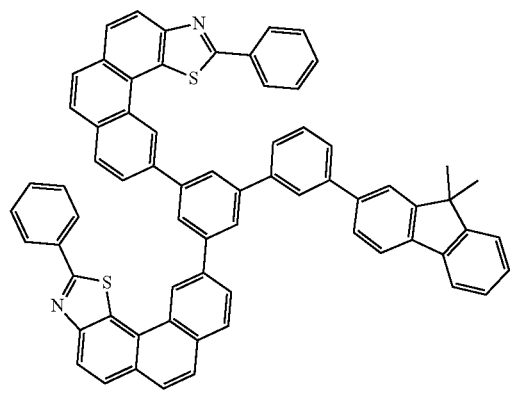
268
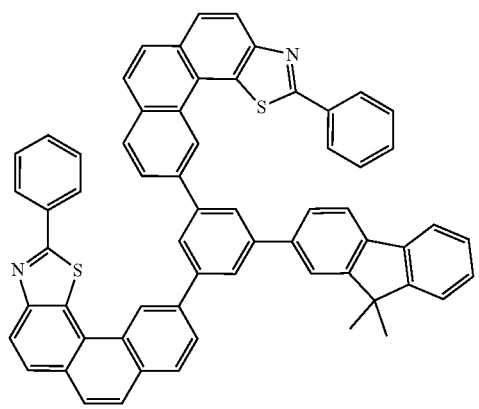
269
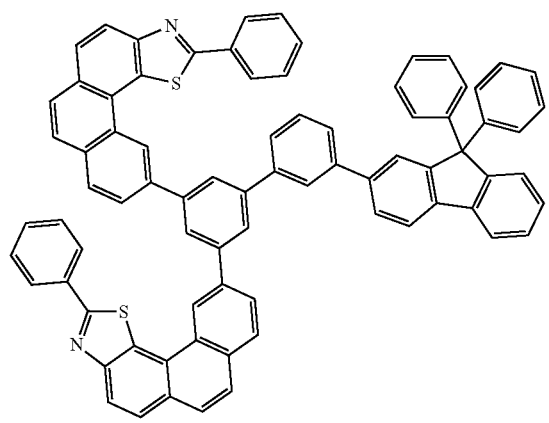
270
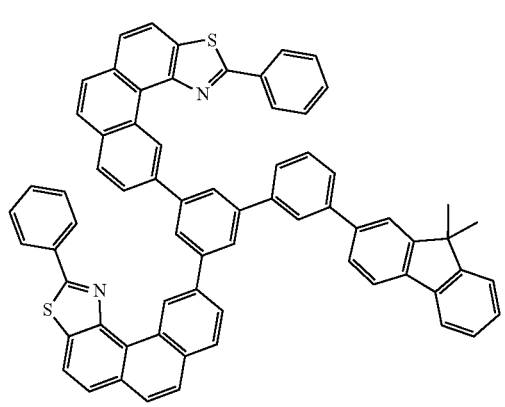
271
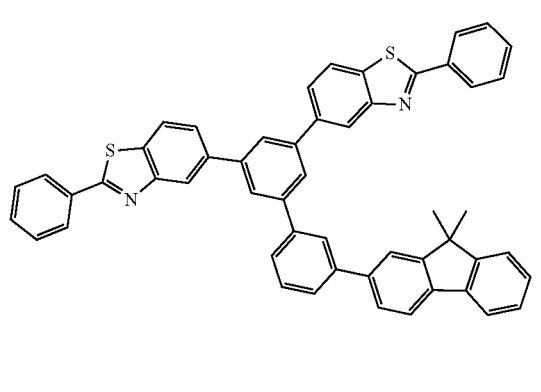

-continued
272
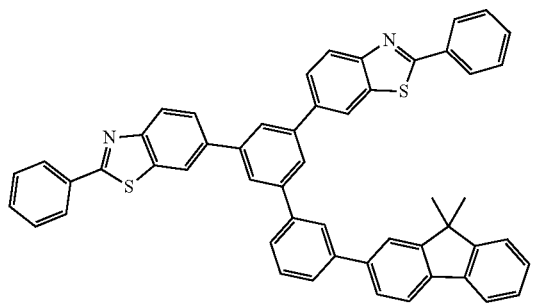
273
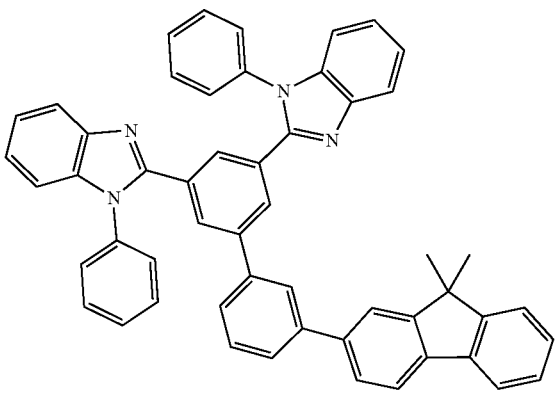
274
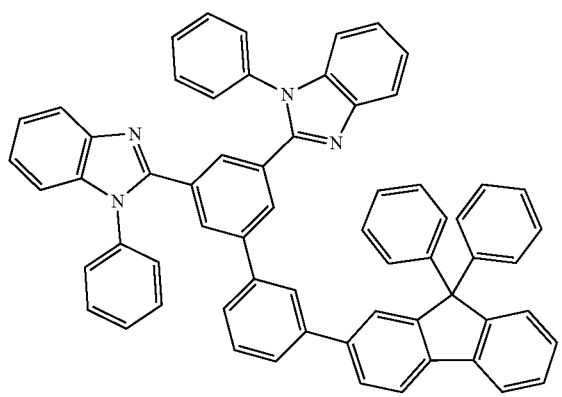
275
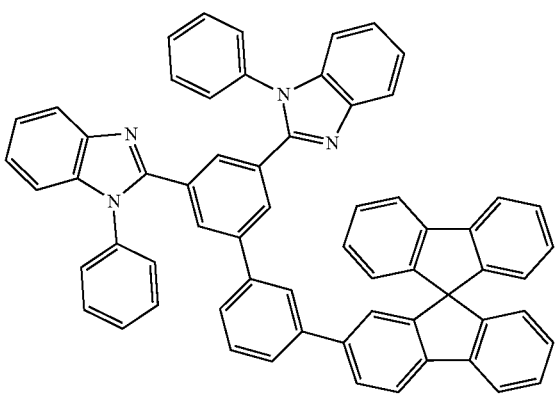
276
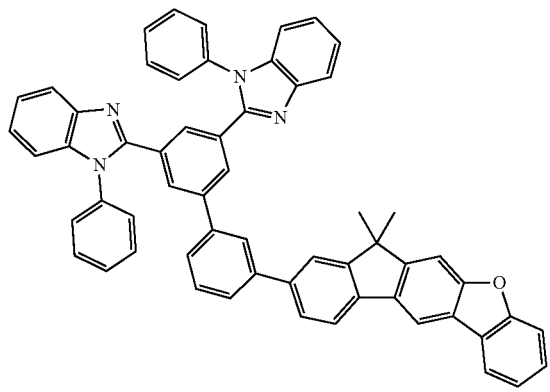
277
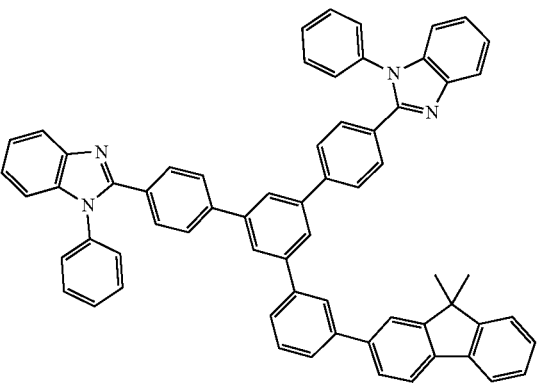
278
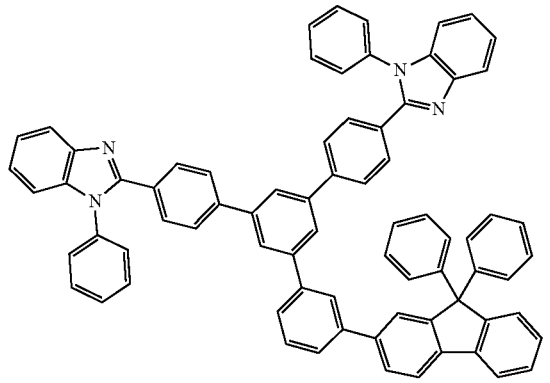
279
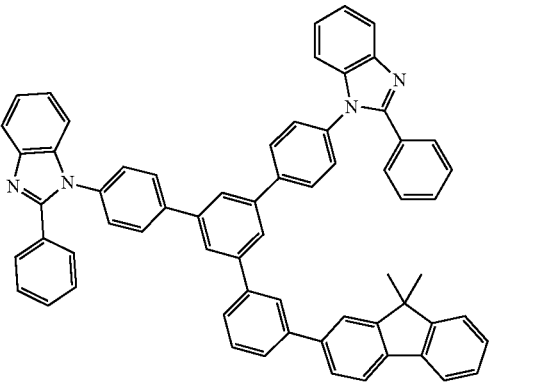

280
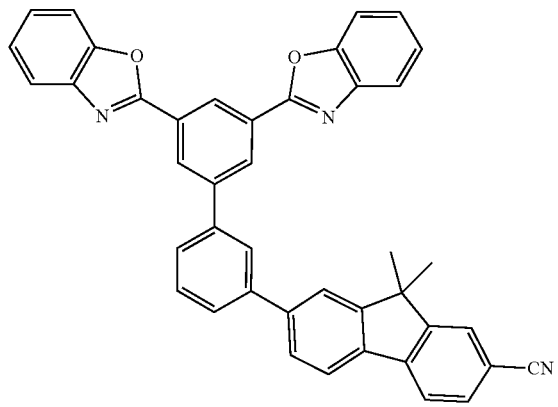
281
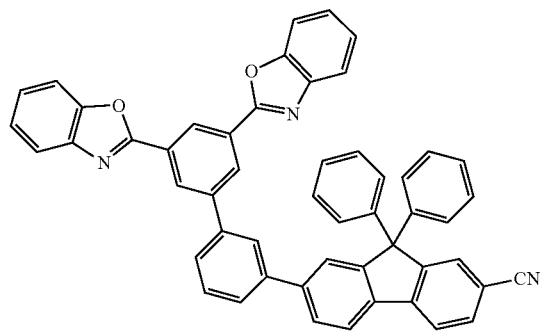
282
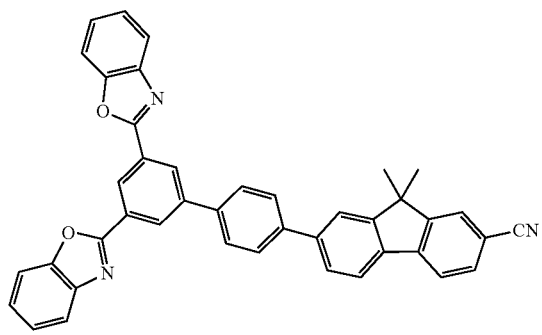
283
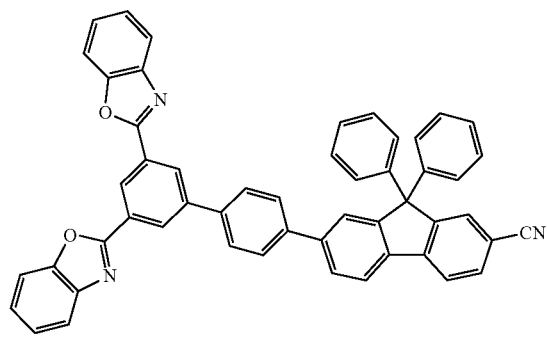
284
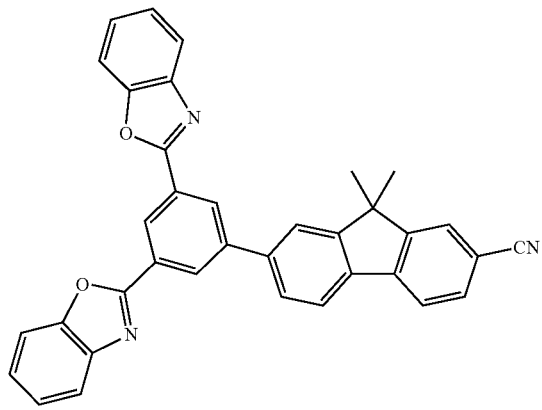
285
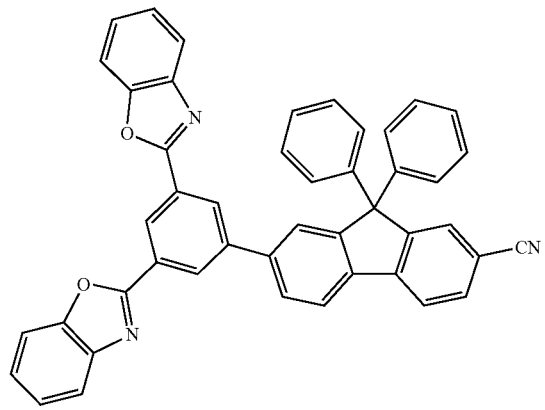
286
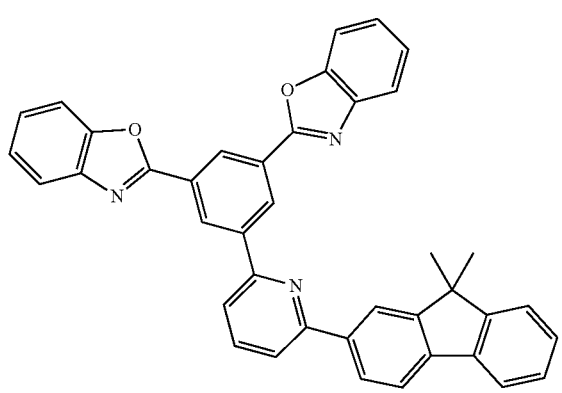
287
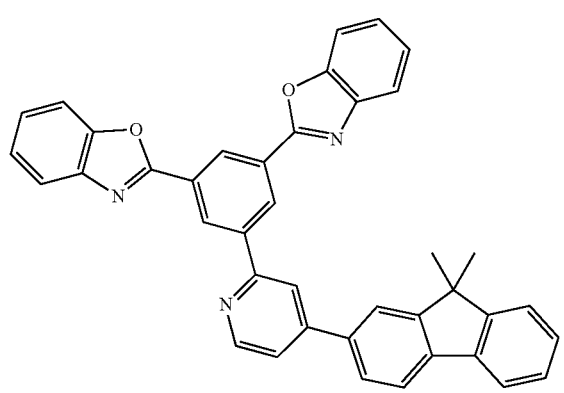

-continued
288
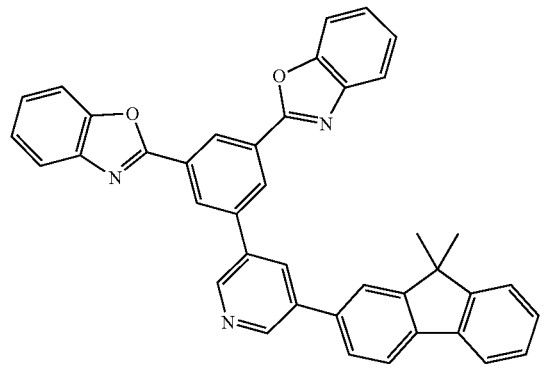
289
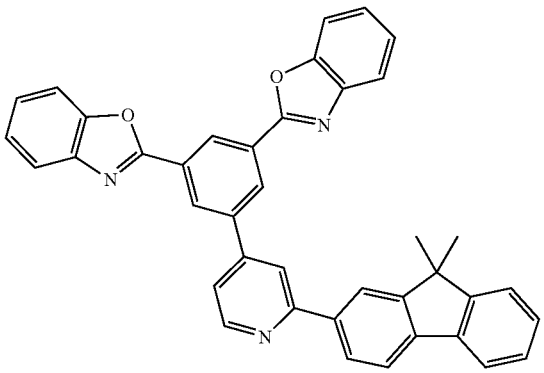
290
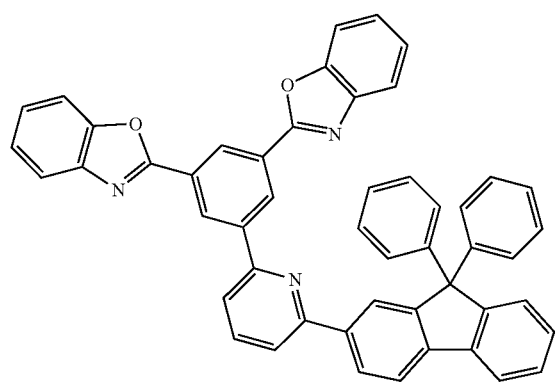
291
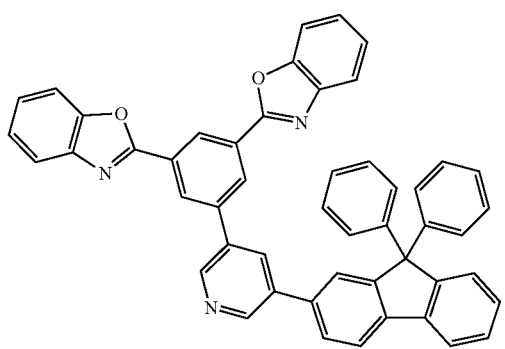
292
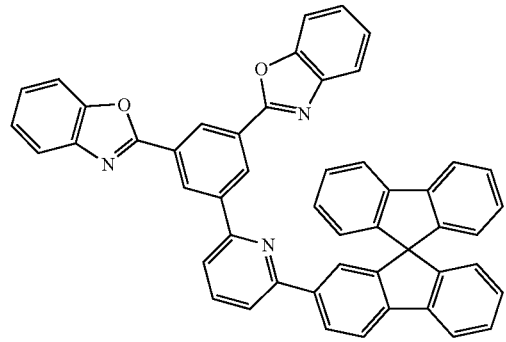
293
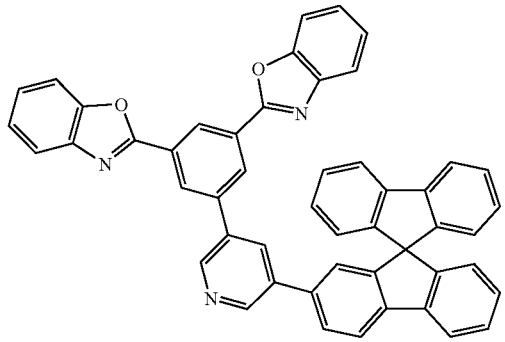
294
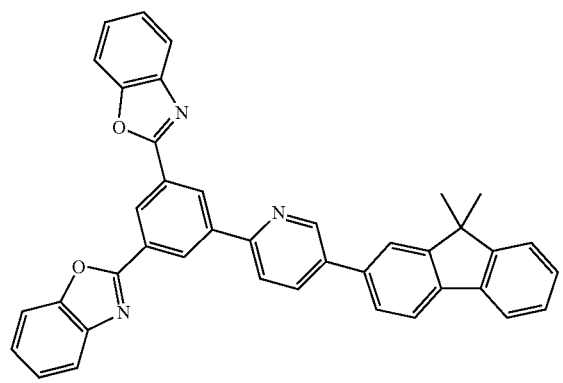
295
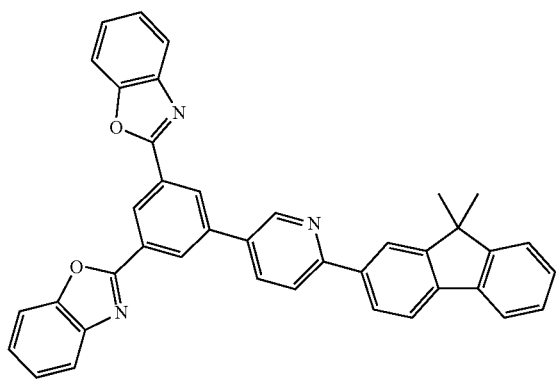

-continued
296
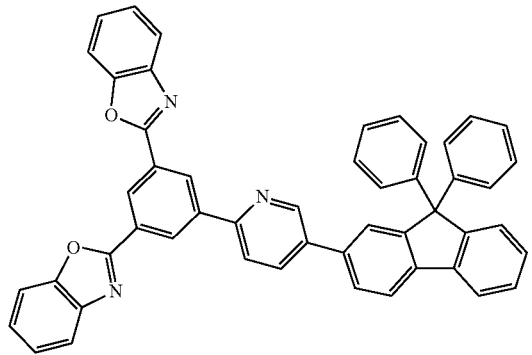
297
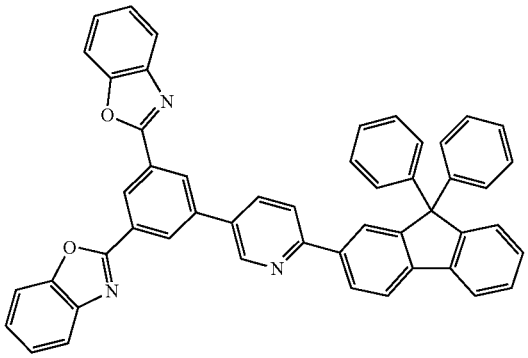
298
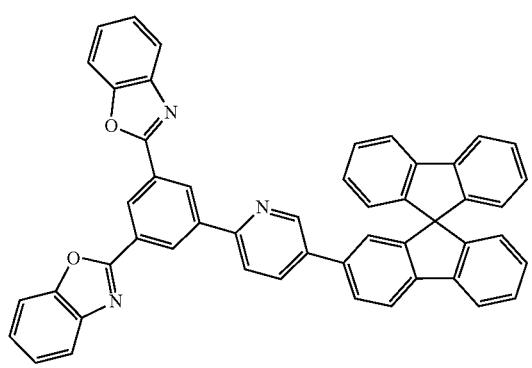
299
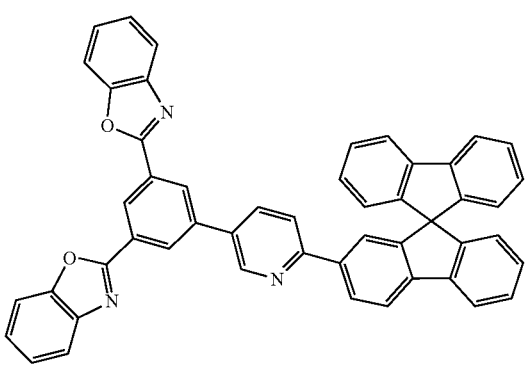
300
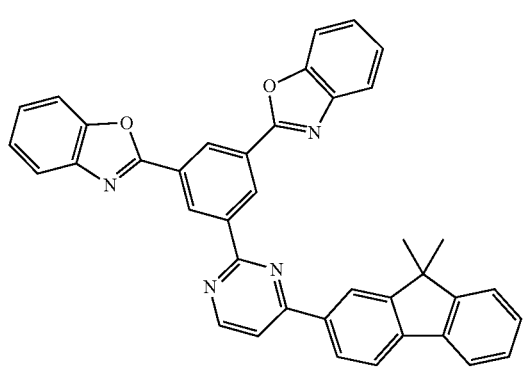
301
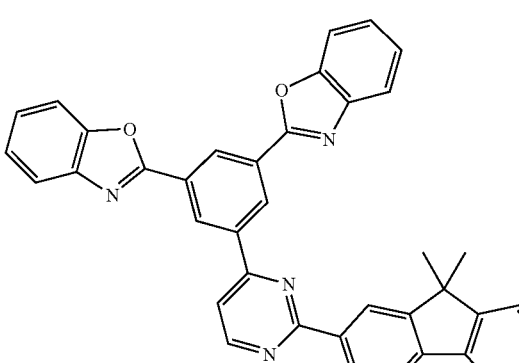
302
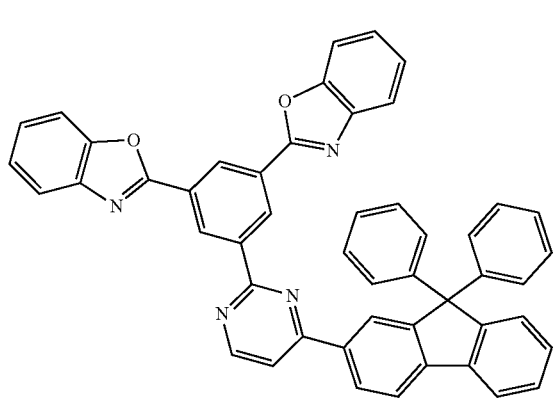
303
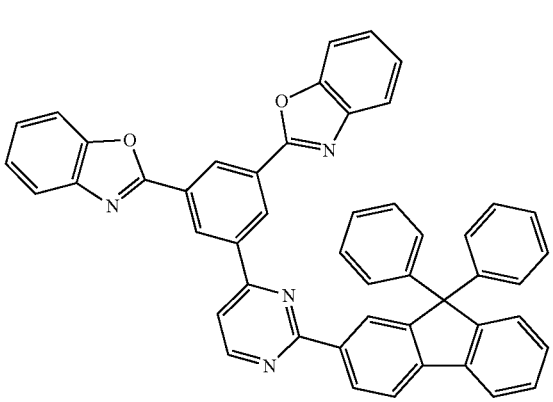

-continued
| 304 | 305 |
|---|---|
| 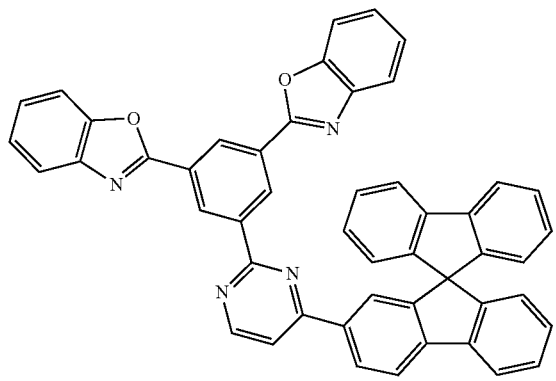 | 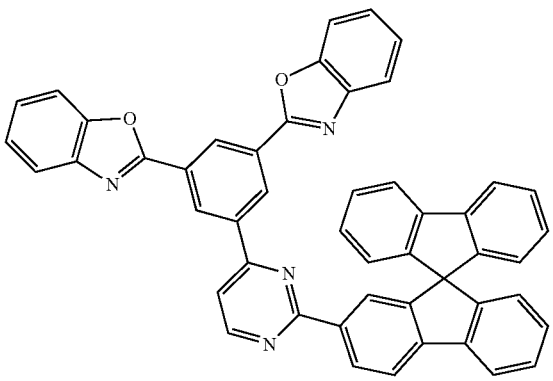 |
| 306 | 307 |
| 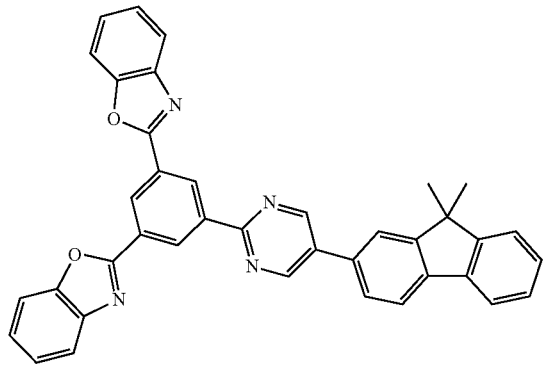 | 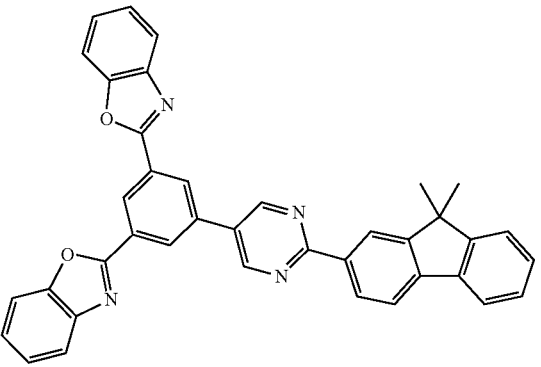 |
| 308 | 309 |
| 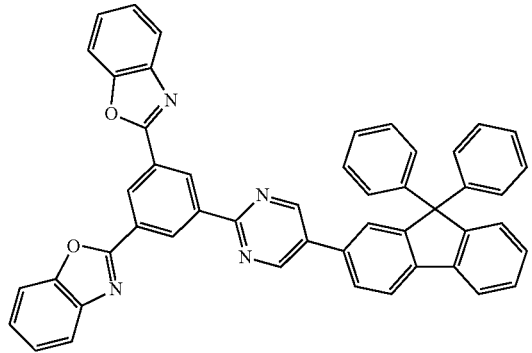 | 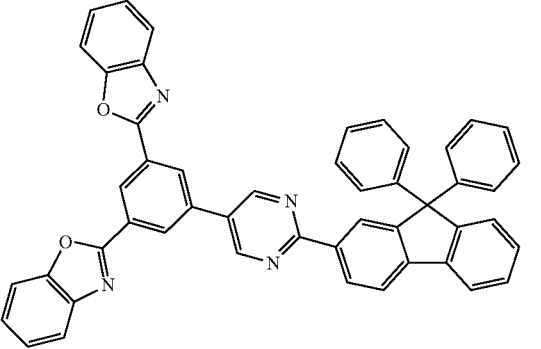 |
| 310 | 311 |
| 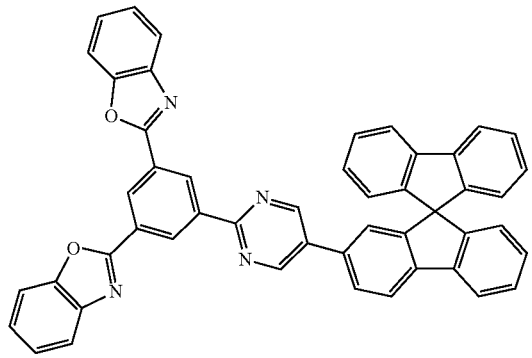 | 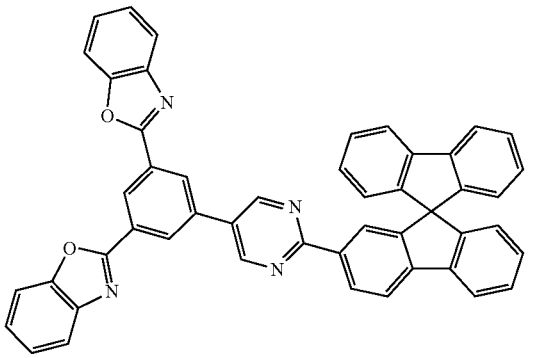 |

-continued
312
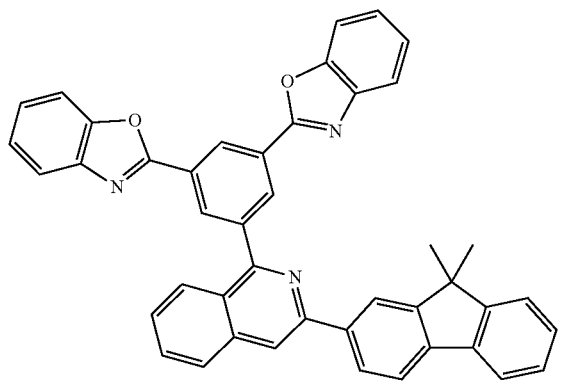
313
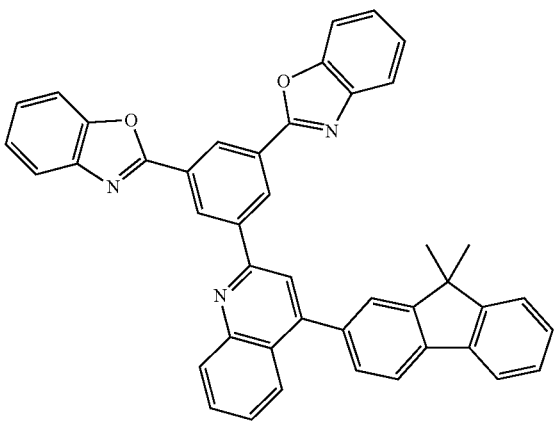
314
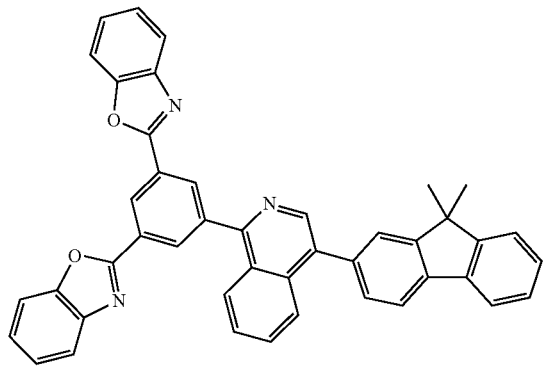
315
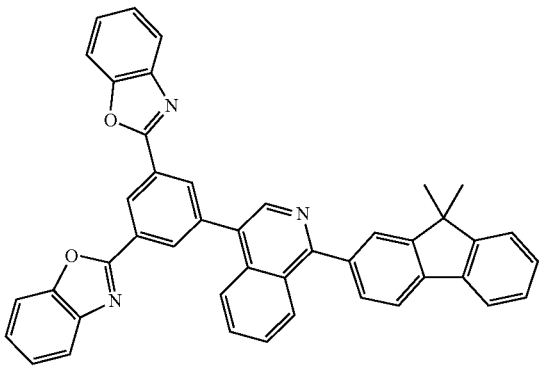
316
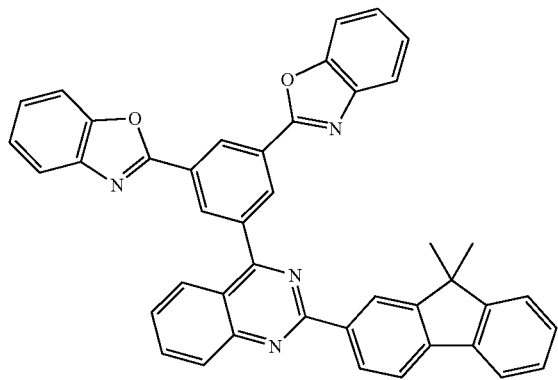
317
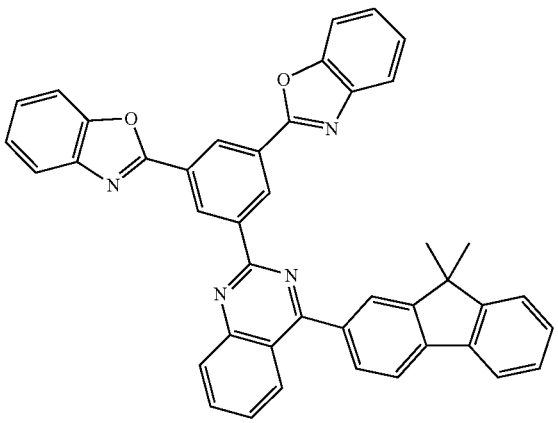
318
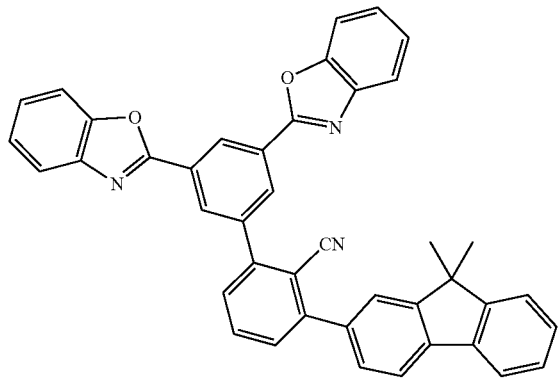
319
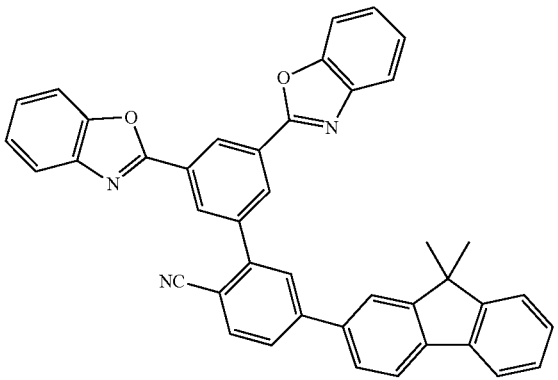

-continued
320
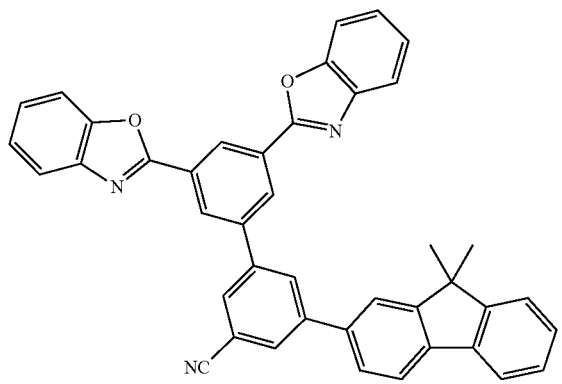
321
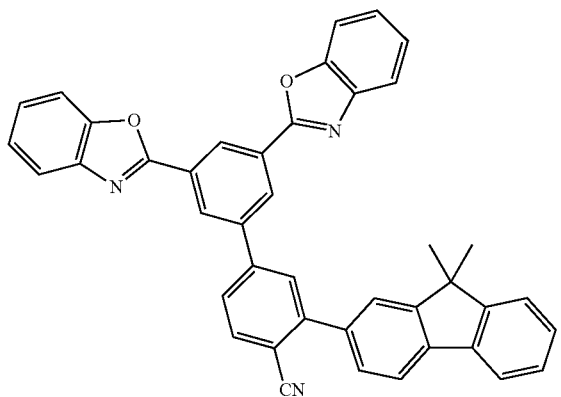
322
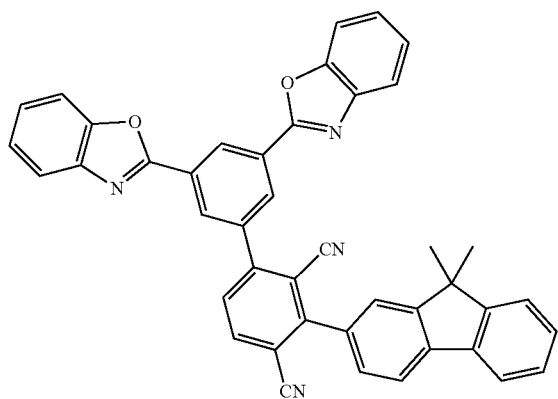
323
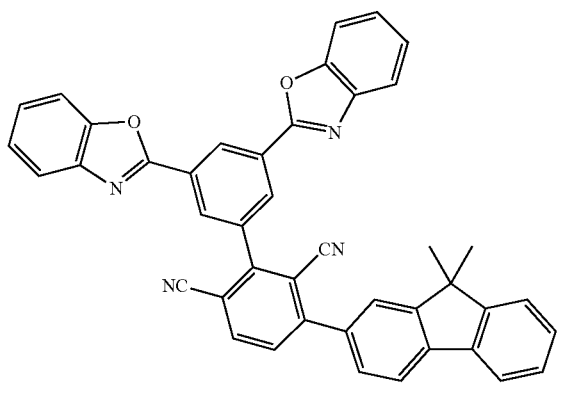
324
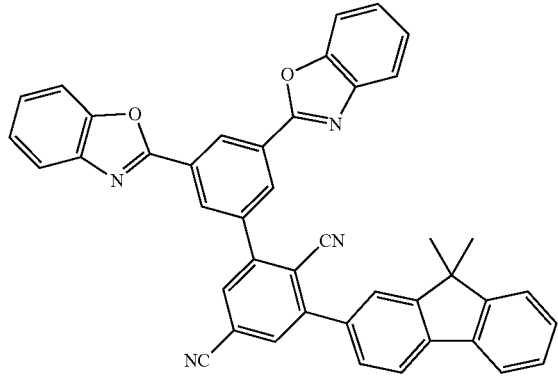
325
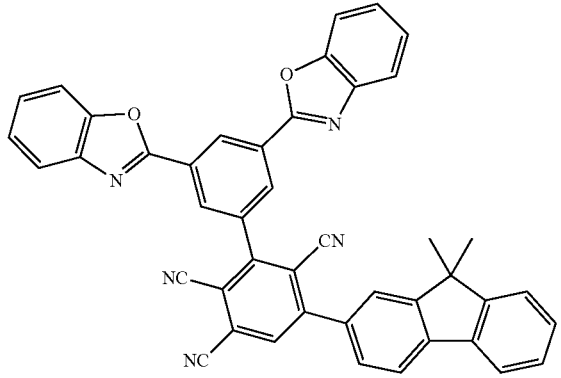
326
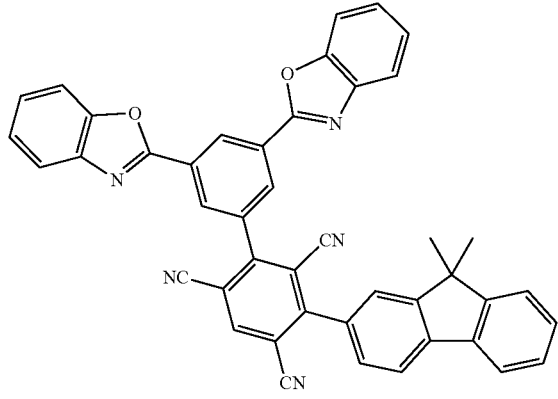
327
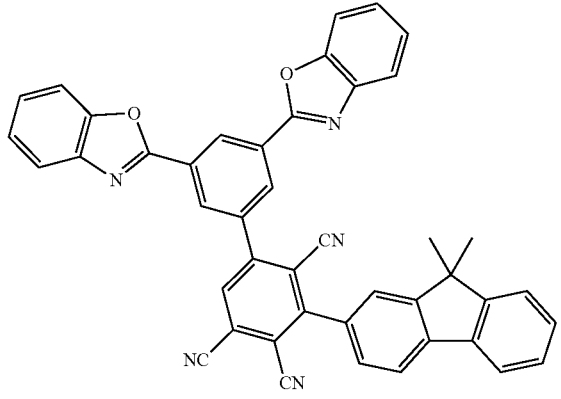

328
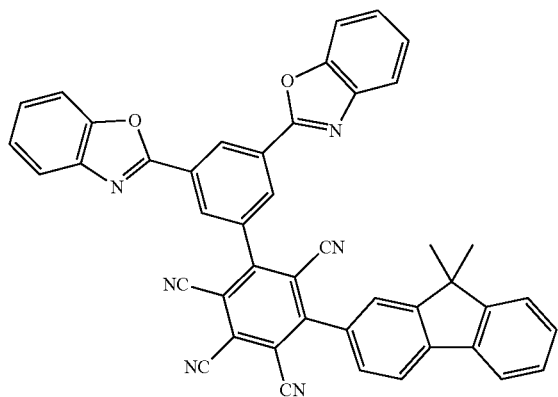
329
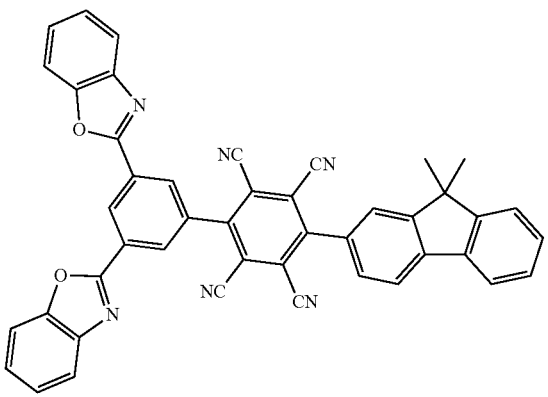
330
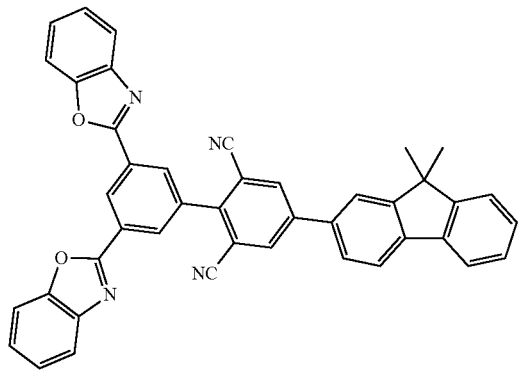
331
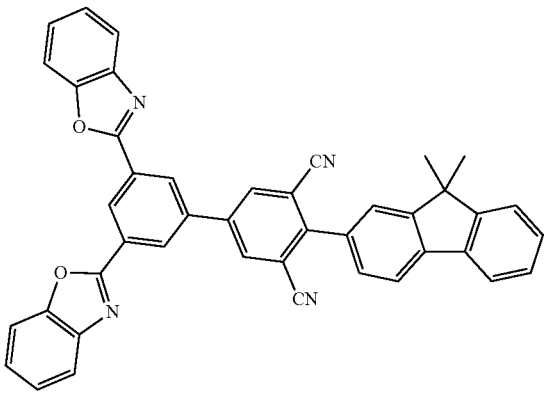
332
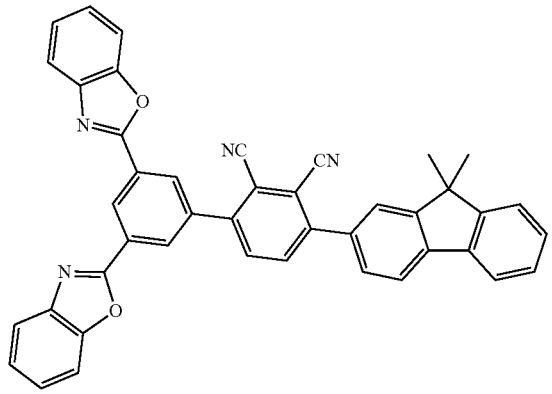
333
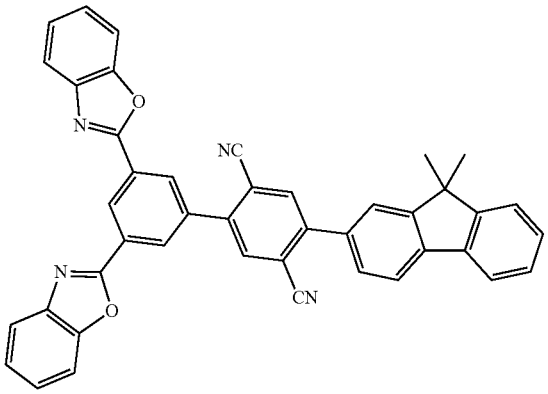
334
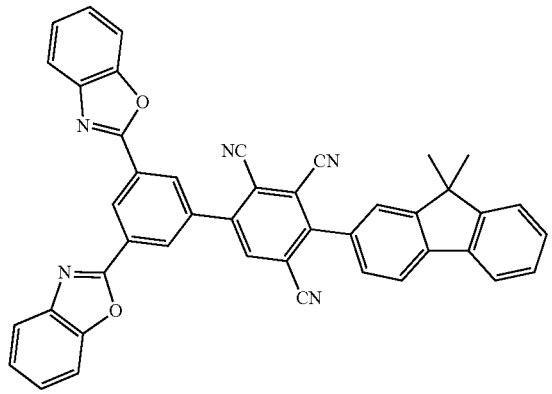
335
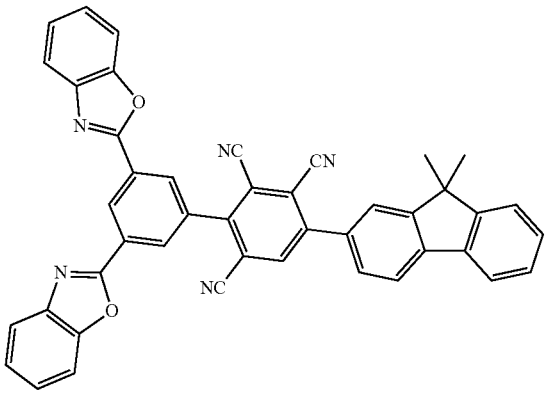

-continued
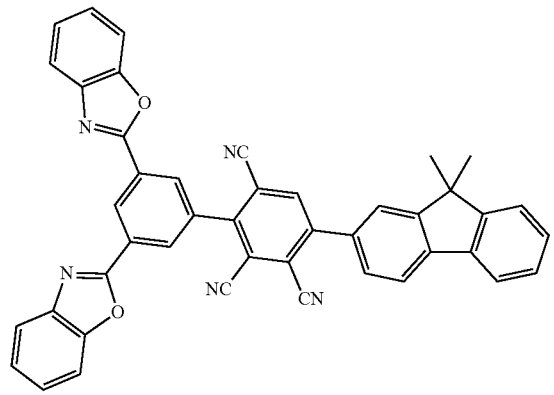
336
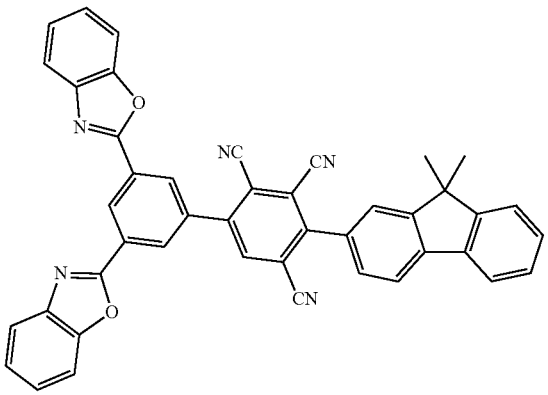
337
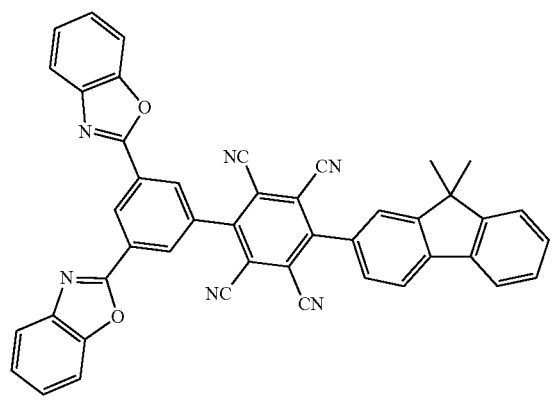
338
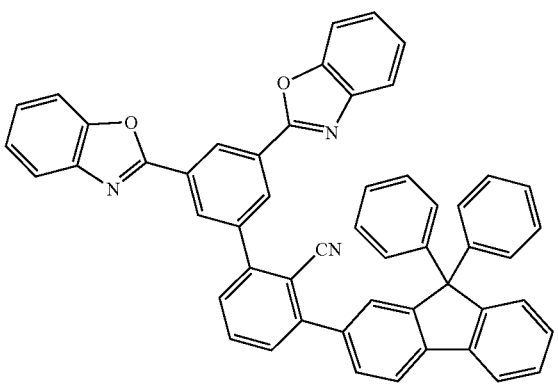
339
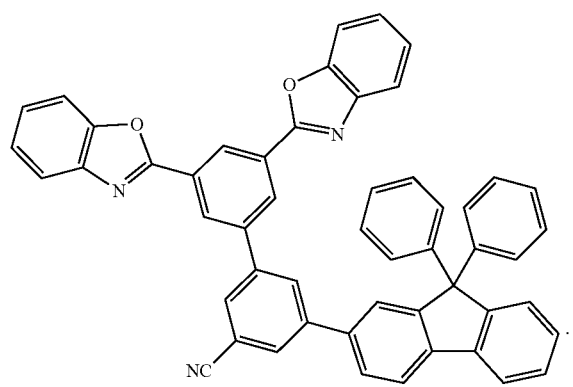
340
For a more detailed description of the present disclosure, the present disclosure also provides a route for the synthesis of the compound as shown in Formula I, but the present disclosure is not limited thereto.
1. Synthesis of Intermediate d:
when $L_1$ is not a single bond,
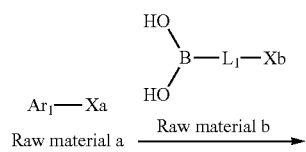
-continued
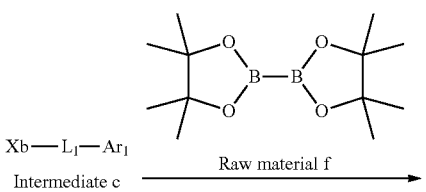

-continued

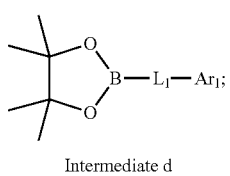

Intermediate d when $L_1$ is a single bond,

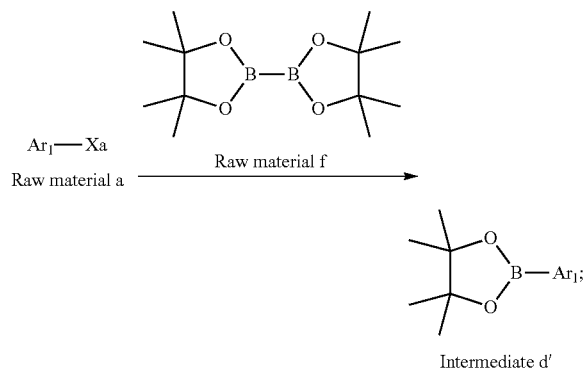

2. Synthesis of Intermediate i:

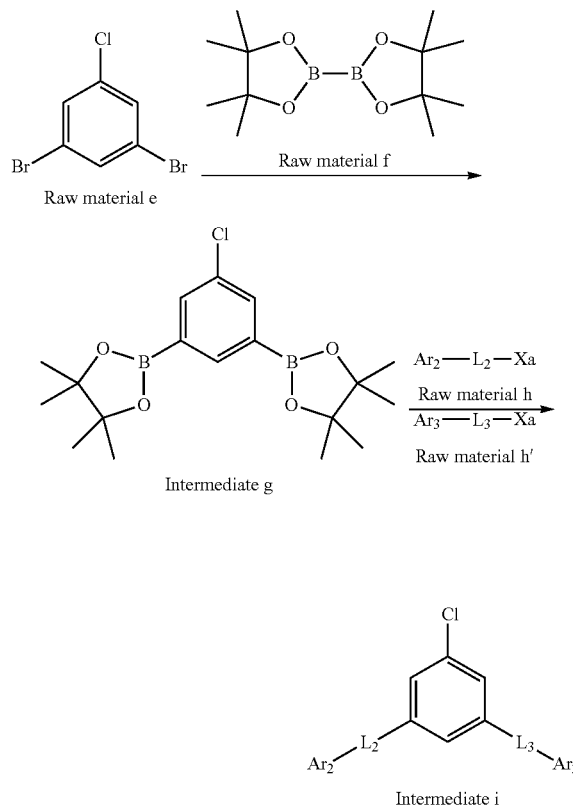

3. Synthesis of the Compound of the Present Disclosure: when $L_1$ is not a single bond,

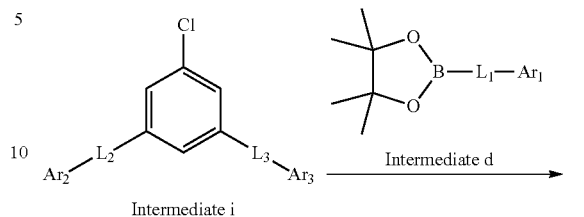

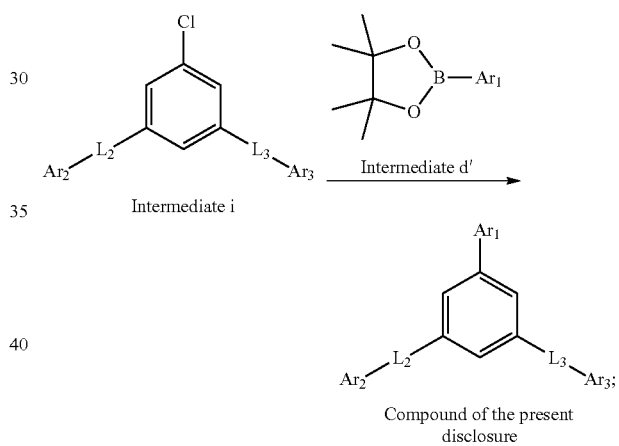

when $L_1$ is a single bond, wherein $Ar_1$ to $Ar_3$ and $L_1$ to $L_3$ are defined as the above, and Xa and Xb are independently selected from any one of Cl, Br or I.

The present disclosure further provides an organic electroluminescent device which includes an anode, a cathode, and an organic layer disposed between the anode and the cathode, wherein the organic layer includes the heterocyclic compound described above.

The organic electroluminescent device provided by the present disclosure may be prepared by using materials and methods known in the related art, except that one or more organic layers of the organic electroluminescent device may include the heterocyclic compound provided by the present disclosure.

Preferably, the organic layer includes a hole blocking layer and an electron transport layer, wherein the electron transport layer or the hole blocking layer includes the heterocyclic compound provided by the present disclosure.

Preferably, the hole blocking layer includes the heterocyclic compound provided by the present disclosure.

The organic layer of the organic electroluminescent device provided by the present disclosure may be formed in a single-layer structure or in a multilayer structure in which the preceding organic layers are stacked. For example, the organic layer of the organic electroluminescent device in this specification may include an emissive layer, a hole injection layer, a hole transport layer, a hole blocking layer, an electron blocking layer, an electron transport layer, an electron injection layer, etc. Meanwhile, each organic layer may also include one or more layers, for example, the hole transport layer includes a first hole transport layer and a second hole transport layer. However, the structure of the organic electroluminescent device is not limited thereto and may include more or less organic layers.

In the organic electroluminescent device provided by the present disclosure, the materials of the organic layer can be any material used for the layer in the related art.

The anode material of the present disclosure is usually a material having a high work function to facilitate the injection of holes into the organic layer. Specific examples of materials that may be used in the present disclosure may include: metals, such as vanadium, chromium, copper, zinc and gold, or alloys thereof; metal oxides, such as zinc oxide, indium oxide, indium tin oxide (ITO), and indium zinc oxide (IZO); combinations of metals and oxides, such as ZnO:Al or $SnO_2$:Sb; and conducting polymers, such as poly(3-methylthiophene), polypyrrole, polyaniline, poly[3,4-(ethylene-1,2-dioxy)thiophene] (PEDT), etc., but are not limited thereto.

The cathode material of the present disclosure is usually a material having a low work function to facilitate the injection of electrons into the organic layer. Specific examples of materials that may be used in the present disclosure may include: metals, such as magnesium, calcium, sodium, potassium, titanium, indium, yttrium, lithium, aluminum, silver, tin, and lead, or alloys thereof; and a multilayer material, such as LiF/Al or $LiO_2$/Al, but not limited thereto.

The hole injection material of the present disclosure is preferably a material having a good hole-acceptance ability, and the highest occupied molecular orbital (HOMO) of the hole injection material is preferably a value between the work function of the anode material and the HOMO of an adjacent organic material layer. Specific examples of hole injection materials that may be used in the present disclosure may include phthalocyanine compounds (such as copper phthalocyanine), N,N'-bis[4-[bis(3-methylphenyl)amino]phenyl]-N,N'-diphenyl-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), N,N'-bis(naphth-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, hexaazatriphenylenehexacabonitrile (HAT), etc., but are not limited thereto.

The hole transport material of the present disclosure is preferably a material having a high hole mobility, which can accept holes from the anode or the hole injection layer and transport the holes into the emissive layer. Specific examples of hole transport materials that may be used in the present disclosure may include carbazole derivatives (such as N-phenylcarbazole and polyvinylcarbazole), fluorene derivatives, N,N'-diphenyl-N,N'-bis(3-methylphenyl)-1,1'-biphenyl-4,4'-diamine (TPD), triphenylamine derivatives (such as 4,4',4''-tris(carbazol-9-yl)triphenylamine), N,N'-diphenyl-N,N'-(1-naphthyl)-1,1'-biphenyl-4,4'-diamine (NPB), 4-[1-[4-[bis(4-methylphenyl)amino]phenyl]cyclohexyl]-N-(3-methylphenyl)-N-(4-methylphenyl)-(4-methylphenyl)-aniline (TAPC), N,N,N',N'-tetrakis(3-methylphenyl)-3,3'-dimethylbiphenyldiamine (HMTPD), 9,9'-(1,3-phenyl)di-9H-carbazole (mCP), etc., but are not limited thereto.

The emissive layer material of the present disclosure may include a fluorescent material or a phosphorescent material. When the phosphorescent luminescent material is used, in order to avoid the concentration quenching of the phosphorescent material, the phosphorescent material is usually used as a doped material and co-deposited with other matrix materials (host materials) to prepare the emissive layer, and the amount of the phosphorescent material is preferably 0.1% to 70% by mass, more preferably 0.1% to 30% by mass, further preferably 1% to 30% by mass, further preferably 1% to 20% by mass, and particularly preferably 1% to 10% by mass.

Specific examples of fluorescent materials that may be used in the present disclosure may include fused polycyclic aromatic derivatives, styrene amine derivatives, fused ring amine derivatives, boron-containing compounds, pyrrole derivatives, indole derivatives, carbazole derivatives, etc., but are not limited thereto. Specific examples of phosphorescent materials that may be used in the present disclosure may include heavy metal complexes (such as iridium complexes, platinum complexes, osmium complexes, etc.), rare earth metal complexes with phosphorescence (such as terbium complexes, europium complexes, etc.), etc., but are not limited thereto.

Specific examples of host materials that may be used in the present disclosure may include fused aromatic ring derivatives, heterocyclic compounds, etc. Specifically, the fused aromatic ring derivatives include anthracene derivatives, pyrene derivatives, naphthalene derivatives, pentacene derivatives, phenanthrene derivatives, fluoranthene derivatives, etc., and the heterocyclic compounds include carbazole derivatives, dibenzofuran derivatives, dibenzothiophene derivatives, pyrimidine derivatives, etc., both of which are not limited thereto.

The electron transport material of the present disclosure is preferably a substance having a good electron mobility. Specific examples may include metal chelates, oxazoxazole derivatives, thiazole derivatives, diazole derivatives, azabenzene derivatives, diazanthracene derivatives, silicon-containing heterocyclic compounds, boron-containing heterocyclic compounds, cyano compounds, quinoline derivatives, phenanthroline derivatives, benzimidazole derivatives, etc., but are not limited thereto. Preferably, the electron transport material is selected from the heterocyclic compound provided by the present disclosure.

The electron injection material of the present disclosure is preferably a substance having the ability to transport electrons and an effect of injecting electrons from the cathode. Examples of electron injection materials that may be used in the present disclosure include alkali metal salts (such as lithium fluoride and cesium fluoride); alkaline-earth metal salts (such as magnesium fluoride); metal complexes of hydroxyquinoline derivatives such as hydroxyquinoline lithium; metal oxides (such as aluminum oxide), etc., but not limited thereto. These compounds can be used alone or in combination with other materials.

The hole blocking material of the present disclosure is preferably a material having a high triplet energy level and a suitable HOMO energy level. Specific examples may include oxadiazole derivatives, triazole derivatives, quinoline derivatives, diazaphenanthrene derivatives, anthraquinone derivatives, anthrone derivatives, azabenzene derivatives, imidazole derivatives, etc., but are not limited thereto. Preferably, the hole blocking material is selected from the heterocyclic compound provided by the present disclosure.

The organic layer material of the present disclosure, when used, can form a single-layer structure by forming a film from the organic layer material of the present disclosure alone, or can form a single-layer structure by forming a film from a mixture with other materials, or can form a laminated structure of single layers where the film are formed from the organic layer material of the present disclosure alone, a laminated structure of single layers where the film are formed from a mixture with other materials, or a laminated structure of single layers where the film are formed from the organic layer material of the present disclosure alone and single layers where the film are formed from a mixture with other materials, but are not limited thereto.

The organic electroluminescent device of the present disclosure can be manufactured by sequentially stacking the above structures. Known manufacturing methods such as the dry film forming method and the wet film forming method can be used as the manufacturing method. Specific examples of the dry film forming method include vacuum evaporation method, sputtering method, plasma method, ion plating method, etc. Specific examples of the wet film forming method include spin coating method, impregnation method, tape casting method, ink-jet method, etc. However, the manufacturing methods are not limited thereto.

The organic light-emitting device of the present disclosure can be widely used in the fields of panel display, lighting sources, flexible OLEDs, electronic papers, organic solar cells, organic photoreceptors or organic thin-film transistor, signboards, signal lamps, etc.

The manufacture of the above-mentioned organic electroluminescent device will be described in detail in the following examples. However, the following examples are only for illustration of this specification and the scope of this specification is not limited to these examples.

Preparation and Characterization of Compounds

Raw Materials, Reagents, and Characterization Equipment:

The sources of raw materials used in the examples described below are not particularly limited in the present disclosure, and the raw materials may be commercially available products or be prepared in a preparation method known to those skilled in the art.

Mass spectrometry was performed using G2-Si quadrupole-time-of-flight mass spectrometry produced by WATER CORPORATION, UK, with chloroform as the solvent;

Element analysis was performed using Vario EL cube elemental analyzer produced by ELEMENTAR CO., GERMANY, with sample mass of 5 mg to 10 mg;

Nuclear magnetic resonance ($^1$H NMR) was performed using Bruker-510 nuclear magnetic resonance spectrometer produced by BRUKER CO., GERMANY, in 600 MHz, with $CDCl_3$ as solvent and TMS as internal standard.

SYNTHESIS EXAMPLE 1

Synthesis of Compound 1

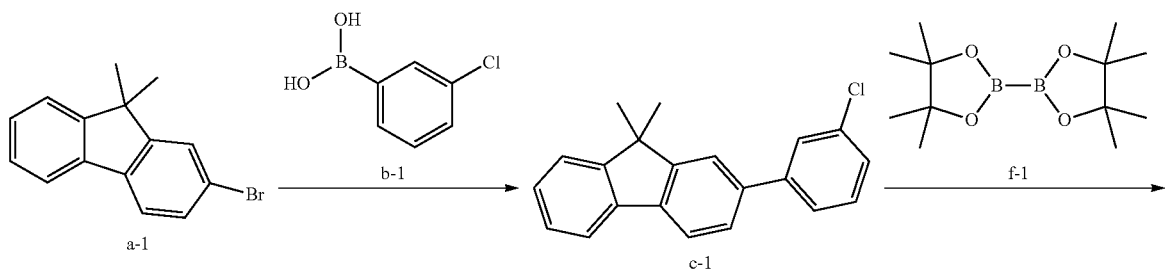

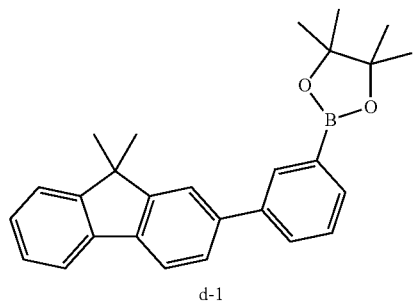

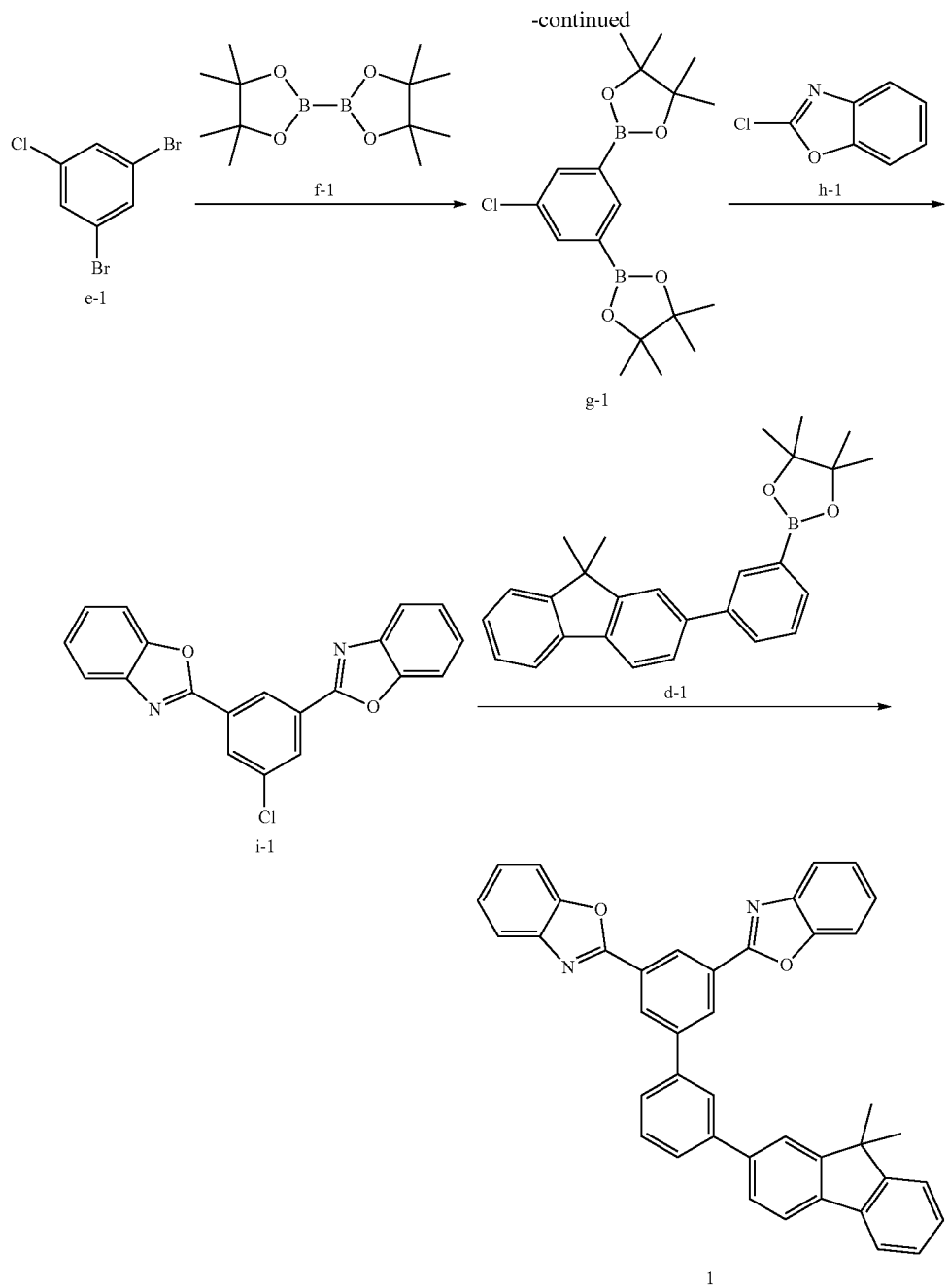

Preparation of Intermediate d-1:

Under the protection of nitrogen, 400 mL of tetrahydrofuran, raw material a-1 (80 mmol, 21.76 g), raw material b-1 (80 mmol, 12.51 g), pd(dppf)Cl$_2$ (0.2 mmol, 0.15 g), and potassium acetate (100 mmol, 9.8 g) were added to a three-mouth flask, the mixture was stirred, and the mixed solution of the above reactants was heated to reflux at 80° C. for 5 hours. After the reaction was complete, the mixed solution was cooled, 400 mL of water was added, and the mixture was filtered and dried in a vacuum oven. The resulting residue was separated and purified by silica gel column to give Intermediate c-1 (20.72 g, 85% yield). The analysis results of Intermediate c-1 were as follows. The purity detected by HPLC was greater than or equal to 99.5%. Mass spectrum m/z: 304.1051 (theoretical value: 304.1019).

Under the protection of nitrogen, 200 mL of tetrahydrofuran, raw material c-1 (40 mmol, 12.20 g), raw material f-1 (40 mmol, 10.16 g), pd(dppf)Cl$_2$ (0.2 mmol, 0.15 g), and potassium acetate (100 mmol, 9.80 g) were added to a three-mouth flask, the mixture was stirred, and the mixed solution of the above reactants was heated to reflux at 100° C. for 7 hours. After the reaction was complete, the mixed solution was cooled, 200 mL of water was added, and the mixture was filtered and dried in a vacuum oven. The resulting residue was separated and purified by silica gel column to give Intermediate d-1 (13.47 g, 86% yield). The analysis results of Intermediate d-1 were as follows. The purity detected by HPLC was greater than or equal to 99.4%. Mass spectrum m/z: 396.2245 (theoretical value: 396.2261).

Preparation of Intermediate g-1:

Under the protection of nitrogen, 200 mL of tetrahydrofuran, raw material e-1 (40 mmol, 10.7 g), raw material f-1 (80 mmol, 20.32 g), pd(dppf)Cl$_2$ (0.2 mmol, 0.15 g), and potassium acetate (100 mmol, 9.80 g) were added to a three-mouth flask, the mixture was stirred, and the mixed solution of the above reactants was heated to reflux at 100° C. for 7 hours. After the reaction was complete, the mixed solution was cooled, 200 mL of water was added, and the mixture was filtered and dried in a vacuum oven. The resulting residue was separated and purified by silica gel column to give Intermediate g-1 (11.37 g, 78% yield). The analysis results of Intermediate g-1 were as follows. The purity detected by HPLC was greater than or equal to 99.4%. Mass spectrum m/z: 364.1729 (theoretical value: 364.1784).

Preparation of Intermediate i-1:

Under the protection of nitrogen, 200 mL of DMF, raw material h-1 (60 mmol, 9.18 g), raw material g-1 (30 mmol, 10.94 g), and pd(dppf)Cl$_2$ (0.2 mmol, 0.15 g) were added to a three-mouth flask and stirred, then K$_3$PO$_4$ aqueous solution (30 mmol, 6.38 g) was added, and the mixture was heated to 150° C. and refluxed for 24 hours. The sample was collected and spotted on a plate, which showed that the reaction was complete. The reaction was naturally cooled, the reaction product was extracted with 400 mL of dichloromethane, the layers were separated, the extracts were dried with anhydrous sodium sulfate and filtered, and the filtrate was rotary evaporated and purified by silica gel column to give Intermediate i-1 (7.80 g, 75% yield). The analysis results of Intermediate i-1 were as follows. The purity detected by HPLC was greater than or equal to 99.6%.

Mass pectrum m/z: 346.0541 (theoretical value: 346.0509).

Preparation of Compound 1:

Under the protection of nitrogen, 100 mL of tetrahydrofuran, raw material i-1 (20 mmol, 6.94 g), raw material d-1 (20 mmol, 7.93 g), pd$_2$(dba)$_3$ (0.2 mmol, 0.18 g), 50% tri-tert-butyl phosphine (0.2 mL, 0.4 mmol), and sodium tert-butoxide (30 mmol, 2.88 g) were added to a three-mouth flask, the mixture was stirred, and the mixed solution of the above reactants was heated to reflux at 100° C. for 10 hours. The sample was collected and spotted on a plate, which showed that the reaction was complete. The reaction was naturally cooled, the reaction product was extracted with 200 mL of dichloromethane, the layers were separated, the extracts were dried with anhydrous sodium sulfate and filtered, and the filtrate was rotary evaporated and purified by silica gel column to give Compound 1 (8.13 g, 70% yield). The purity detected by HPLC was greater than or equal to 99.2%.

Mass spectrum m/z: 580.2180 (theoretical value: 580.2151). Theoretical element content (%) of C$_{41}$H$_{28}$N$_2$O$_2$: C, 84.80; H, 4.86; N, 4.82. Measured elemental content (%): C, 84.84; H, 4.80; N, 4.77. $^1$H NMR (600 MHz, CDCl$_3$) (δ, ppm): 8.42 (s, 1H), 8.11 (s, 1H), 8.10 (s, 1H), 7.98 (s, 1H), 7.78 (d, 1H), 7.73-7.69 (m, 3H), 7.67-7.63 (m, 2H), 7.62-7.59 (m, 2H), 7.58-7.56 (m, 1H), 7.51 (t, 1H), 7.48 (s, 1H), 7.46-7.43 (m, 1H), 7.38-7.31 (m, 6H), 1.54 (s, 6H). The above results confirmed that the given product was the target product.

SYNTHESIS EXAMPLE 2

Synthesis of Compound 4

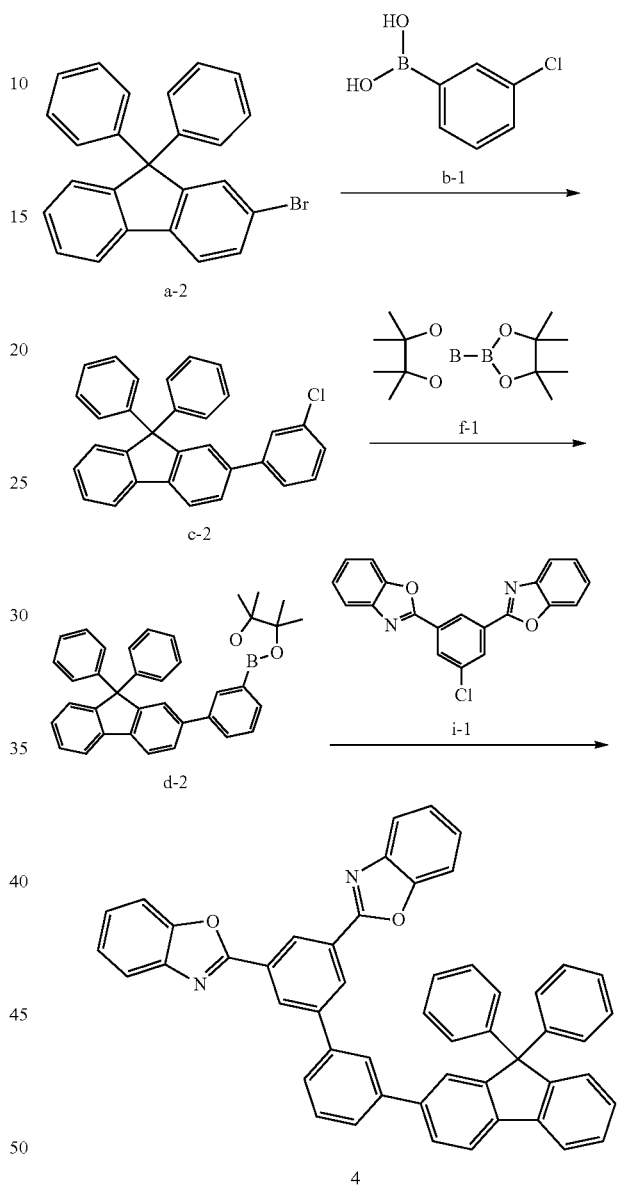

Compound 4 (10.14 g) was given according to the same preparation method as described in Synthesis Example 1 except that a-1 in Synthesis Example 1 was replaced with an equimolar amount of a-2. The purity detected by HPLC was greater than or equal to 99.6%.

Mass spectrum m/z: 704.2408 (theoretical value: 704.2464). Theoretical element content (%) of C$_{51}$H$_{32}$N$_2$O$_2$: C, 86.91; H, 4.58; N, 3.97. Measured elemental content (%): C, 86.96; H, 4.60; N, 3.94. $^1$H NMR (600 MHz, CDCl$_3$) (δ, ppm):8.42 (s, 1H), 8.11 (s, 1H), 8.10 (s, 1H), 7.98 (s, 1H), 7.90 (d, 1H), 7.87-7.81 (m, 1H), 7.75-7.69 (m, 2H), 7.67 (dd, 1H), 7.66-7.63 (m, 1H), 7.62 (d, 1H), 7.60 (d, 1H), 7.60 (s, 1H), 7.58-7.55 (m, 1H), 7.51 (t, 1H), 7.43-7.39 (m, 1H), 7.38-7.31 (m, 6H), 7.31-7.23 (m, 6H), 7.06-7.00 (m, 4H). The above results confirmed that the given product was the target product.

SYNTHESIS EXAMPLE 3

Synthesis of Compound 5

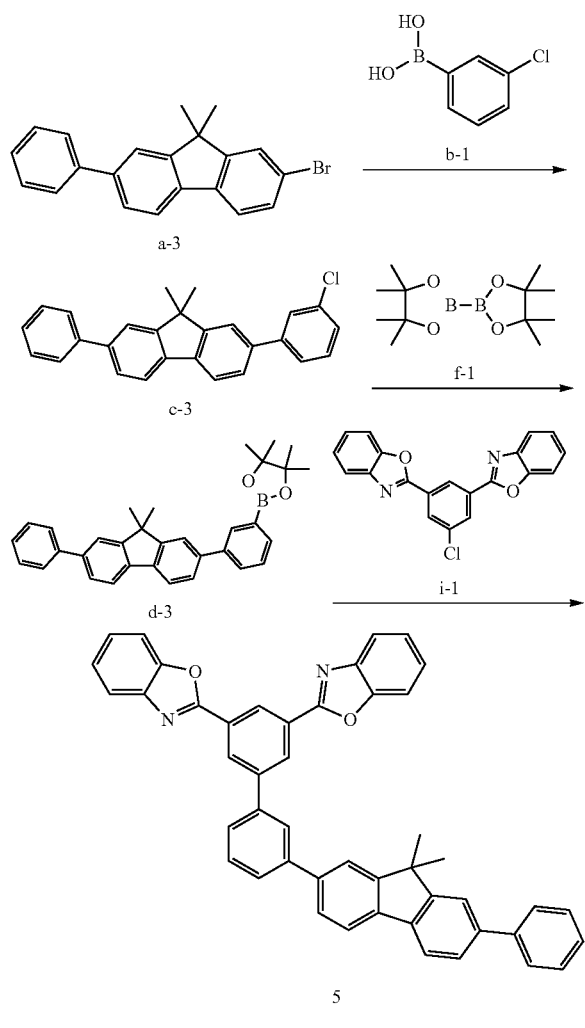

Compound 5 (8.54 g) was given according to the same preparation method as described in Synthesis Example 1 except that a-1 in Synthesis Example 1 was replaced with an equimolar amount of a-3. The purity detected by HPLC was greater than or equal to 99.5%.

Mass spectrum m/z: 656.2419 (theoretical value: 656.2464). Theoretical element content (%) of $C_{47}H_{32}N_2O_2$: C, 85.95; H, 4.91; N, 4.27. Measured elemental content (%): C, 85.98; H, 4.85; N, 4.33. $^1$H NMR (600 MHz, CDCl$_3$) (δ, ppm): 8.42 (s, 1H), 8.11 (s, 1H), 8.10 (s, 1H), 7.98 (s, 1H), 7.78 (dd, 2H), 7.72-7.69 (m, 2H), 7.67-7.63 (m, 3H), 7.62-7.58 (m, 4H), 7.58-7.56 (m, 1H), 7.54-7.51 (m, 2H), 7.50 (s, 1H), 7.47-7.42 (m, 2H), 7.41-7.31 (m, 5H), 1.55 (s, 6H). The above results confirmed that the obtained product was the target product.

SYNTHESIS EXAMPLE 4

Synthesis of Compound 9

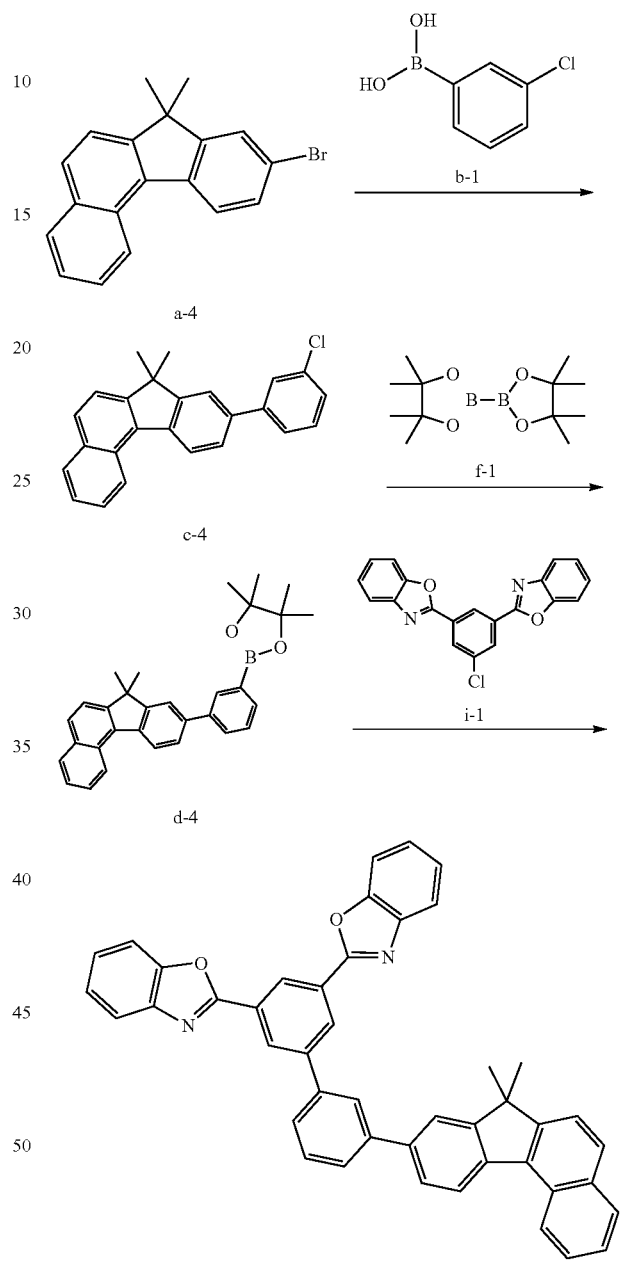

Compound 9 (7.82 g) was given according to the same preparation method as described in Synthesis Example 1 except that a-1 in Synthesis Example 1 was replaced with an equimolar amount of a-4. The purity detected by HPLC was greater than or equal to 99.7%.

Mass spectrum m/z: 630.2347 (theoretical value: 630.2307). Theoretical element content (%) of $C_{45}H_{30}N_2O_2$: C, 85.69; H, 4.79; N, 4.44. Measured elemental content (%): C, 85.73; H, 4.80; N, 4.40.

SYNTHESIS EXAMPLE 5

Synthesis of Compound 10

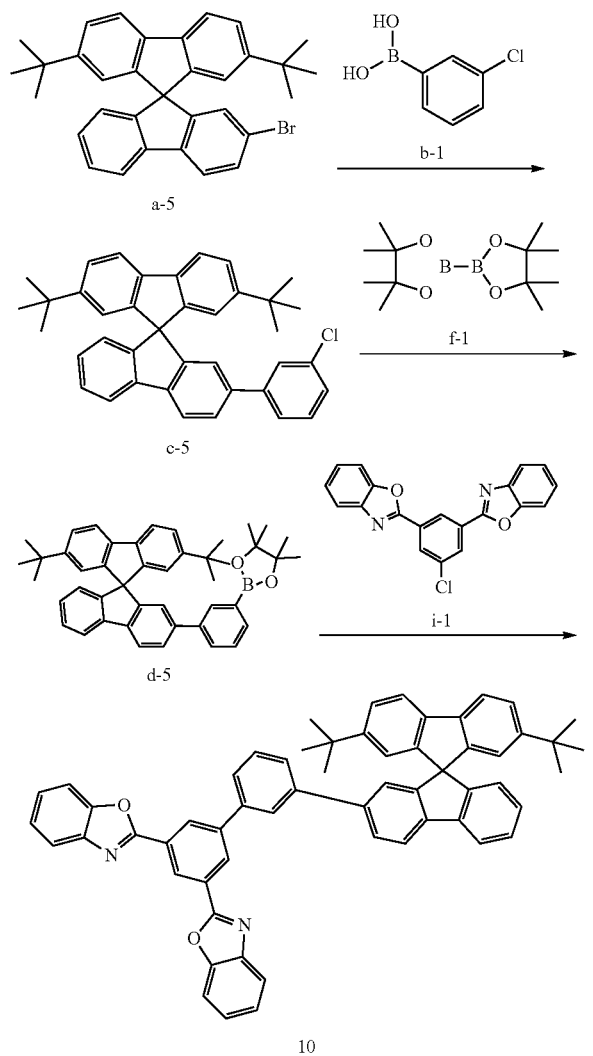

Compound 10 (9.94 g) was given according to the same preparation method as described in Synthesis Example 1 except that a-1 in Synthesis Example 1 was replaced with an equimolar amount of a-5. The purity detected by HPLC was greater than or equal to 99.2%.

Mass spectrum m/z: 814.3522 (theoretical value: 814.3559). Theoretical element content (%) of $C_{59}H_{46}N_2O_2$: C, C, 86.95; H, 5.69; N, 3.44. Measured elemental content (%): C, 86.99; H, 5.71; N, 3.39. $^1$H NMR (600 MHz, CDCl$_3$) (δ, ppm): 8.42 (s, 1H), 8.11 (s, 1H), 8.10 (s, 1H), 7.98 (s, 1H), 7.90 (d, 1H), 7.84 (dd, 1H), 7.75 (d, 2H), 7.73-7.69 (m, 2H), 7.67 (dd, 1H), 7.65-7.64 (m, 1H), 7.63-7.59 (m, 2H), 7.59-7.55 (m, 2H), 7.51 (t, 1H), 7.40-7.28 (m, 8H), 7.16 (s, 1H), 7.16 (s, 1H), 7.10 (dd, 1H), 1.32 (s, 18H). The above results confirmed that the obtained product was the target product.

SYNTHESIS EXAMPLE 6

Synthesis of Compound 17

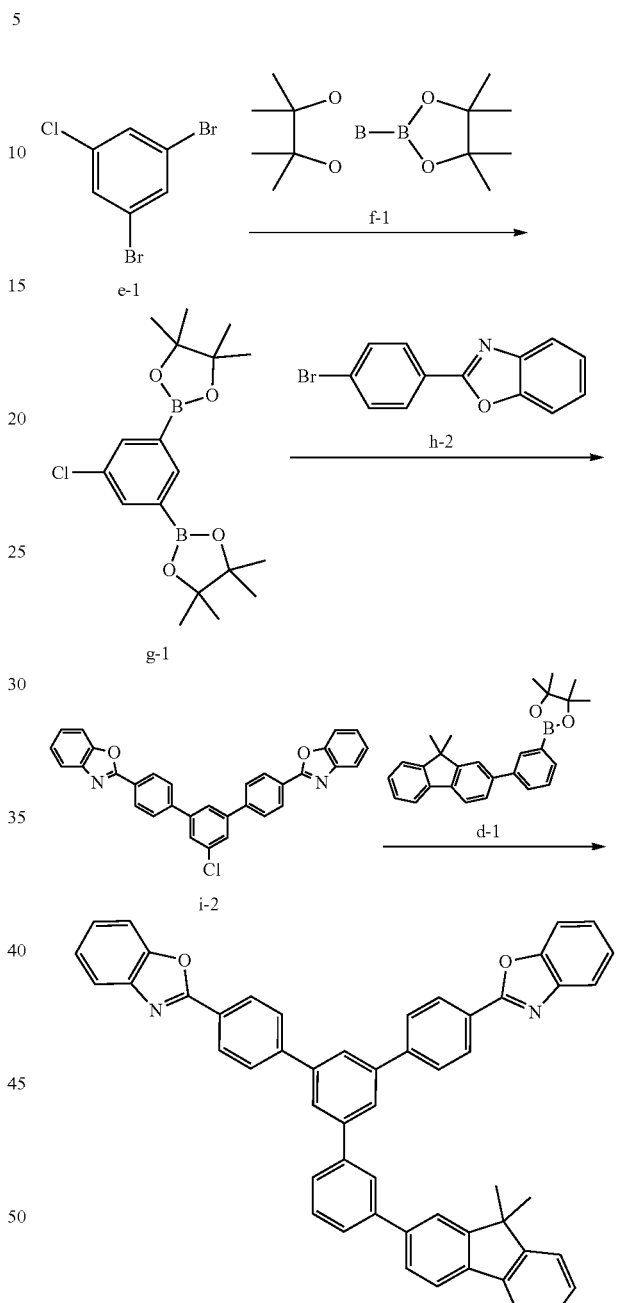

Compound 17 (10.99 g) was given according to the same preparation method as described in Synthesis Example 1 except that h-1 in Synthesis Example 1 was replaced with an equimolar amount of h-2. The purity detected by HPLC was greater than or equal to 99.7%.

Mass spectrum m/z: 732.2755 (theoretical value: 732.2777). Theoretical element content (%) of $C_{53}H_{36}N_2O_2$: C, 86.86; H, 4.95; N, 3.82. Measured elemental content (%): C, 86.84; H, 4.95; N, 3.81. The above results confirmed that the obtained product was the target product.

SYNTHESIS EXAMPLE 7
Synthesis of Compound 51
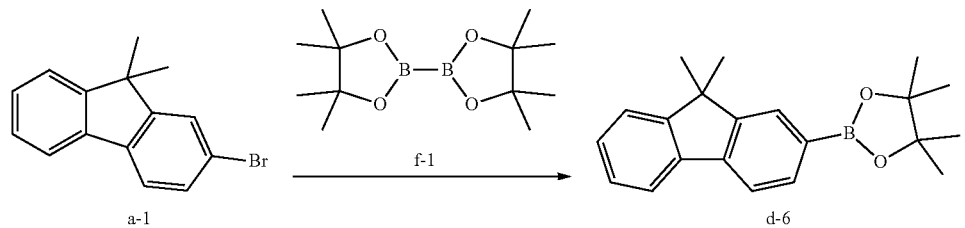
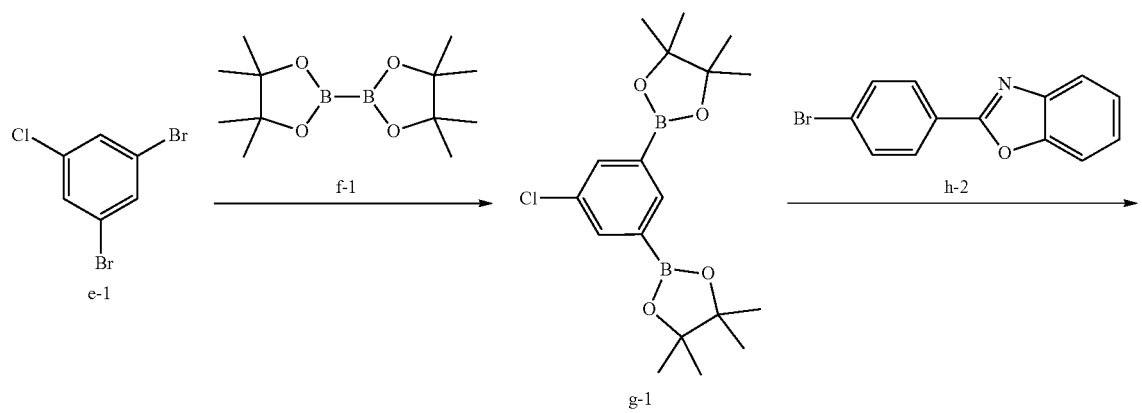
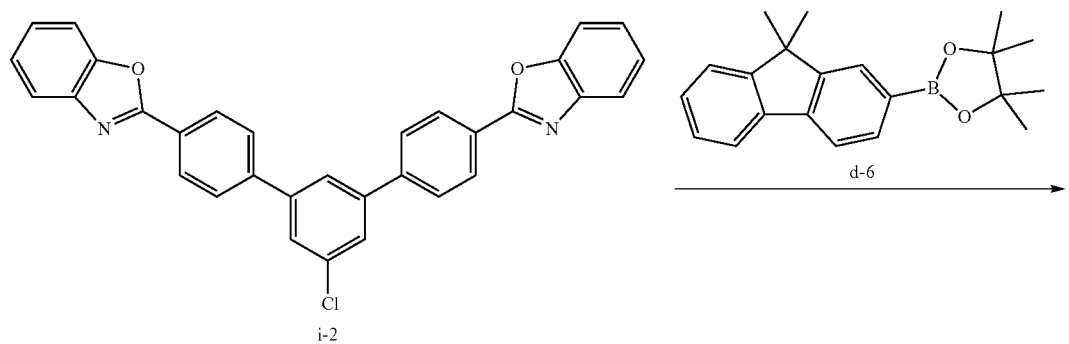

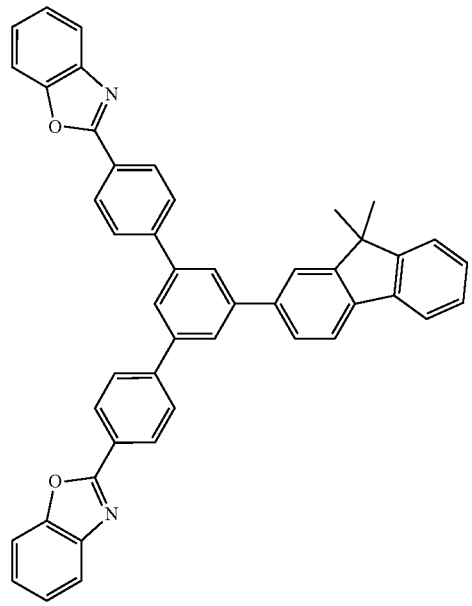

51

Preparation of Intermediate d-6:

Under the protection of nitrogen, 200 mL of tetrahydrofuran, raw material a-1 (40 mmol, 12.20 g), raw material f-1 (40 mmol, 10.16 g), pd(dppf)Cl₂ (0.2 mmol, 0.15 g), and potassium acetate (100 mmol, 9.80 g) were added to a three-mouth flask, the mixture was stirred, and the mixed solution of the above reactants was heated to reflux at 100° C. for 7 hours. After the reaction was complete, the mixed solution was cooled, 200 mL of water was added, and the mixture was filtered and dried in a vacuum oven. The resulting residue was separated and purified by silica gel column to give Intermediate d-6 (10.76 g, 84% yield). The analysis results of Intermediate d-6 were as follows. The purity detected by HPLC was greater than or equal to 99.4%. Mass spectrum m/z: 320.1985 (theoretical value: 320.1948).

Preparation of Compound 51:

Under the protection of nitrogen, 100 mL of tetrahydrofuran, raw material i-2 (20 mmol, 9.98 g), Intermediate d-6 (20 mmol, 6.40g), pd₂(dba)₃ (0.2 mmol, 0.18 g), 50% tri-tert-butyl phosphine (0.2 mL, 0.4 mmol), and sodium tert-butoxide (30 mmol, 2.88 g) were added to a three-mouth flask, the mixture was stiffed, and the mixed solution of the above reactants was heated to reflux at 100° C. for 10 hours. The sample was collected and spotted on a plate, which showed that the reaction was complete. The reaction was naturally cooled, the reaction product was extracted with 200 mL of dichloromethane, the layers were separated, the extracts were dried with anhydrous sodium sulfate and filtered, and the filtrate was rotary evaporated and purified by silica gel column to give Compound 51 (9.46 g, 72% yield). The purity detected by HPLC was greater than or equal to 99.6%.

Mass spectrum m/z: 656.2429 (theoretical value: 656.2464). Theoretical element content (%) of $C_{47}H_{32}N_2O_2$: C, 85.95; H, 4.91; N, 4.27. Measured elemental content (%): C, 85.98; H, 4.87; N, 4.27. The above results confirmed that the obtained product was the target product.

SYNTHESIS EXAMPLE 8

Synthesis of Compound 82

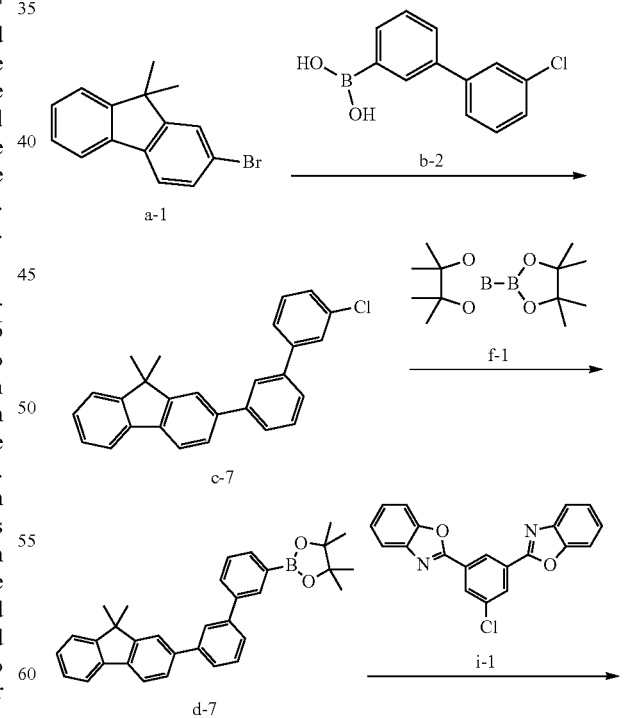

147
-continued

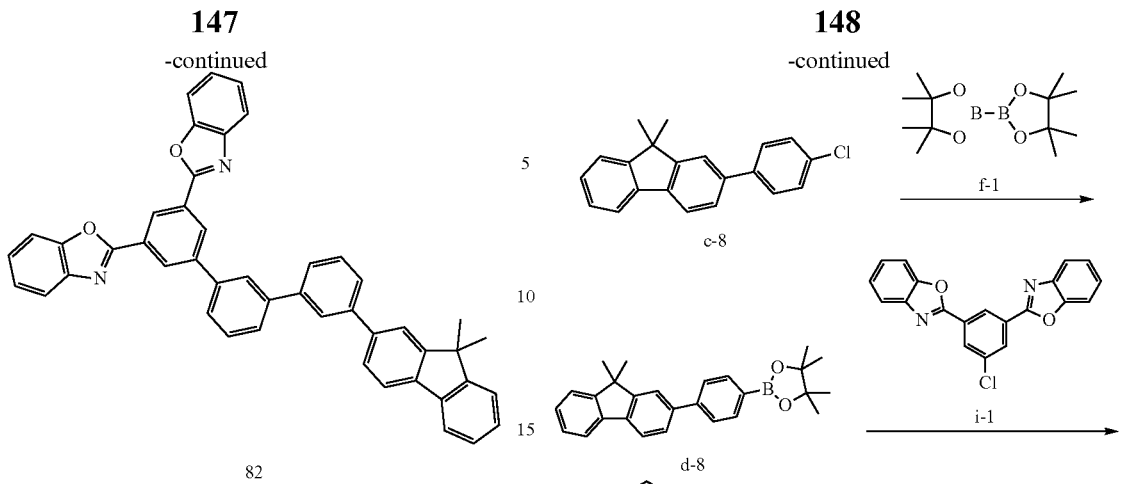

82

Compound 82 (8.54 g) was given according to the same preparation method as described in Synthesis Example 1 except that b-1 in Synthesis Example 1 was replaced with an equimolar amount of b-2. The purity detected by HPLC was greater than or equal to 99.3%.

Mass spectrum m/z: 656.2418 (theoretical value: 656.2464). Theoretical element content (%) of $C_{47}H_{32}N_2O_2$: C, 85.95; H, 4.91; N, 4.27. Measured elemental content (%): C, 85.93; H, 4.91; N, 4.29. $^1$H NMR (600 MHz, CDCl$_3$) (δ, ppm): 8.31 (s, 1H), 8.29 (s, 1H), 8.27 (s, 1H), 8.12 (s, 1H), 8.04 (s, 1H), 7.98-7.96 (m, 2H), 7.84-7.82 (m, 2H), 7.81-7.79 (m, 1H), 7.77-7.73 (m, 2H), 7.72-7.71 (m, 1H), 7.68-7.61 (m, 7H), 7.55-7.52 (m, 1H), 7.46-7.73 (m, 1H), 7.39-7.36 (m, 4H), 1.72 (s, 6H). The above results confirmed that the obtained product was the target product.

SYNTHESIS EXAMPLE 9

Synthesis of Compound 147

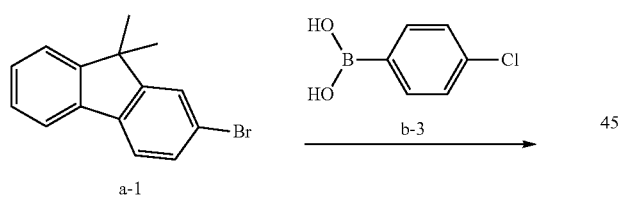

148
-continued c-8 d-8

147

Compound 147 (8.25g) was given according to the same preparation method as described in Synthesis Example 1 except that b-1 in Synthesis Example 1 was replaced with an equimolar amount of b-3. The purity detected by HPLC was greater than or equal to 99.5%.

Mass spectrum m/z: 580.2193 (theoretical value: 580.2151). Theoretical element content (%) of $C_{41}H_{28}N_2O_2$: 84.80; H, 4.86; N, 4.82. Measured elemental content (%): 84.78; H, 4.90; N, 4.81. The above results confirmed that the obtained product was the target product.

SYNTHESIS EXAMPLE 10

Synthesis of Compound 171

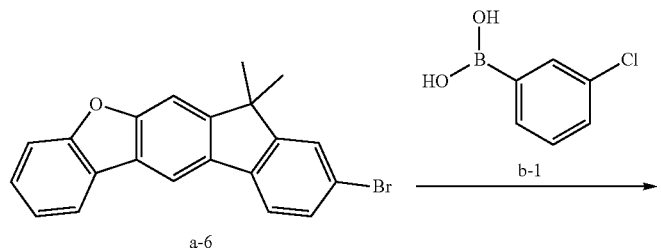

-continued
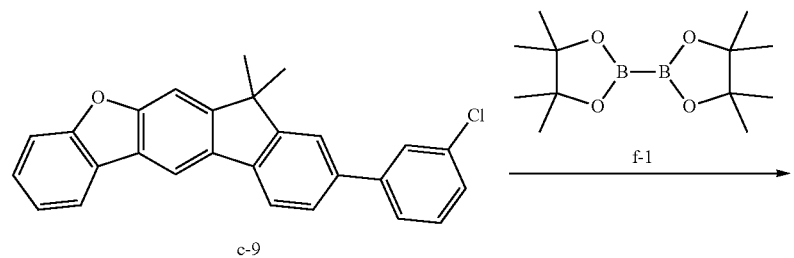
c-9
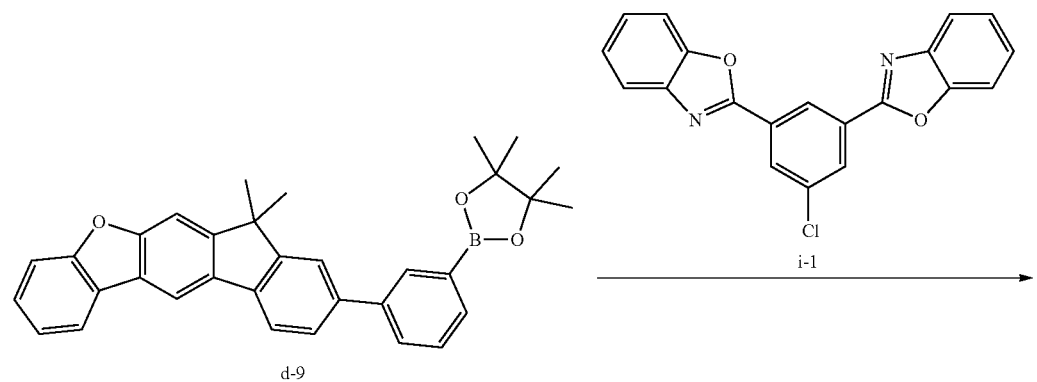
d-9
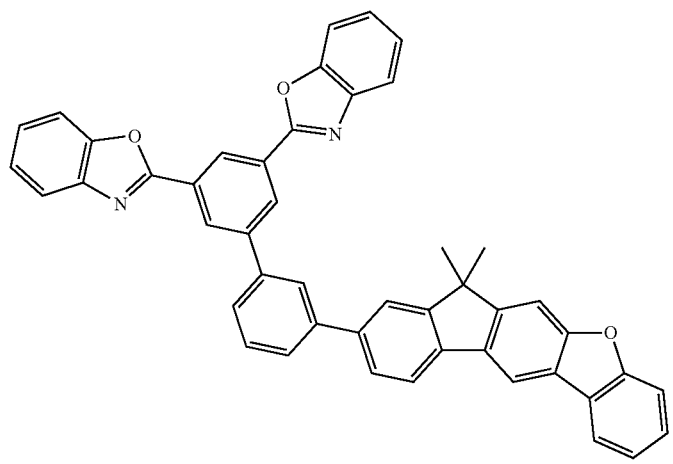
171

Compound 171 (7.92 g) was given according to the same preparation method as described in Synthesis Example 1 except that a-1 in Synthesis Example 1 was replaced with an equimolar amount of a-6. The purity detected by HPLC was greater than or equal to 99.1%.

Mass spectrum m/z: 670.2284 (theoretical value: 670.2256). Theoretical element content (%) of $C_{47}H_{30}N_2O_3$: C, 84.16; H, 4.51; N, 4.18. Measured elemental content (%): C, 84.18; H, 4.51; N, 4.15. The above results confirmed that the obtained product was the target product.

SYNTHESIS EXAMPLE 11

Synthesis of Compound 216

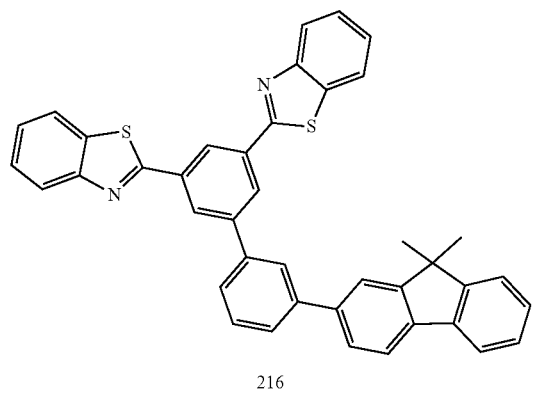

216

Compound 216 (8.58 g) was given according to the same preparation method as described in Synthesis Example 1 except that h-1 in Synthesis Example 1 was replaced with an equimolar amount of h-3. The purity detected by HPLC was greater than or equal to 99.4%.

Mass spectrum m/z: 612.1615 (theoretical value: 612.1694). Theoretical element content (%) of $C_{41}H_{28}N_2S_2$: C, 80.36; H, 4.61; N, 4.57. Measured elemental content (%): C, 80.40; H, 4.60; N, 4.55. The above results confirmed that the obtained product was the target product.

SYNTHESIS EXAMPLE 12

Synthesis of Compound 258

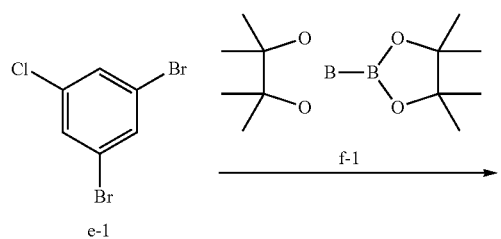

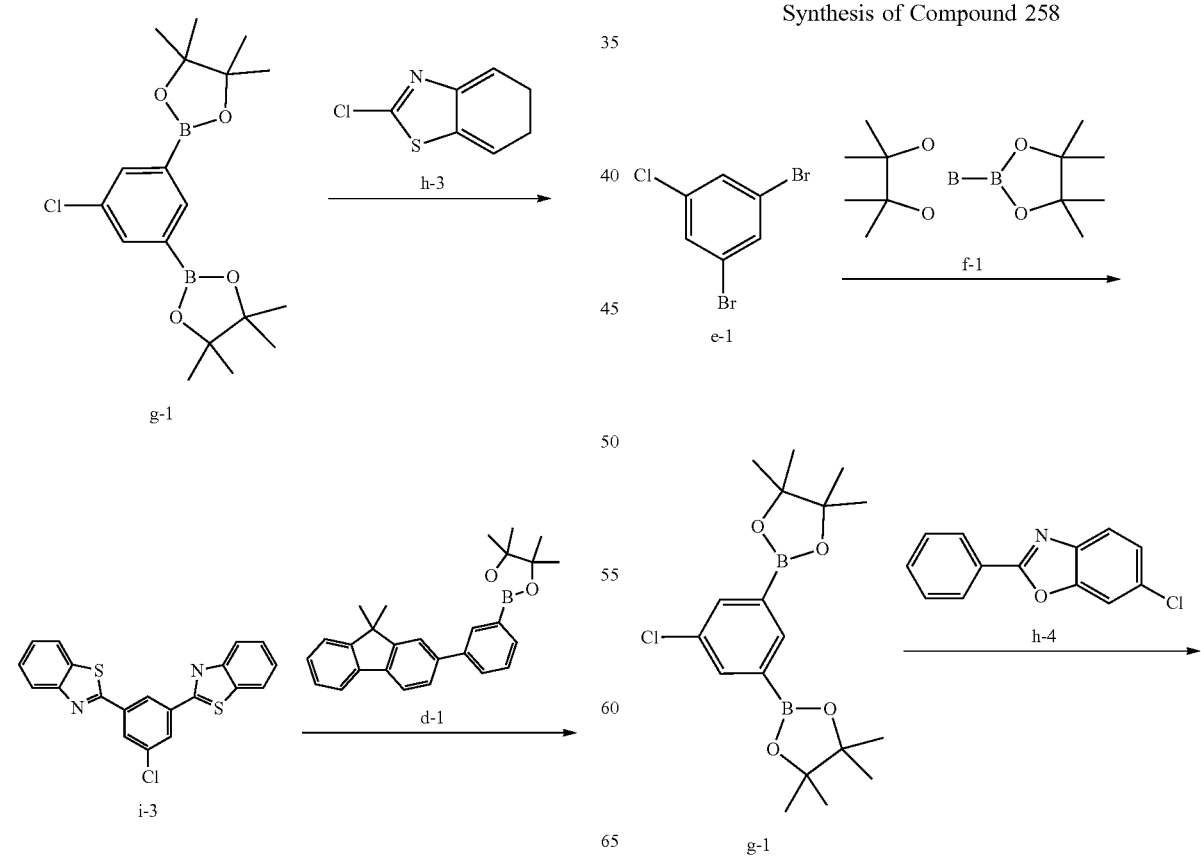

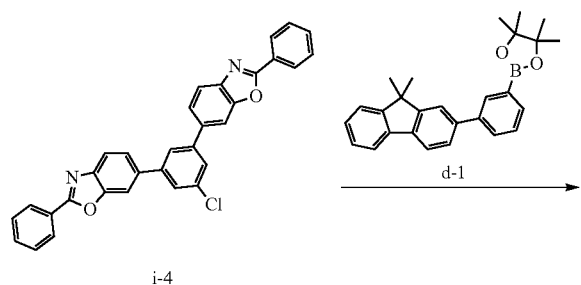

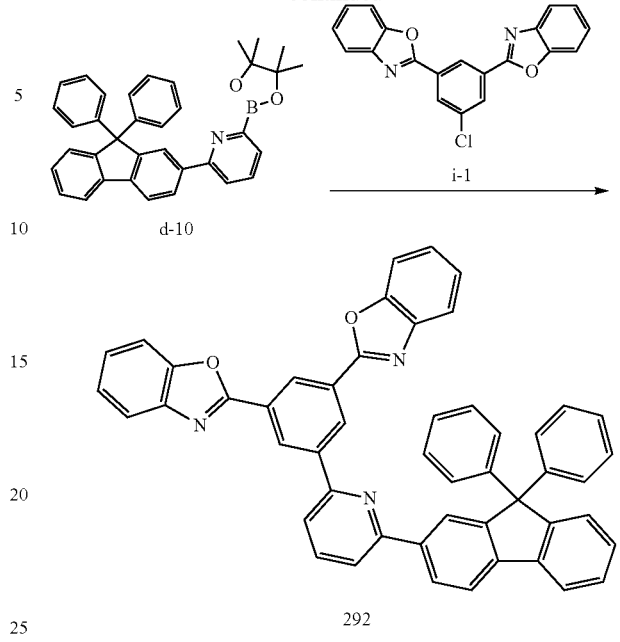

Compound 258 (9.97 g) was given according to the same preparation method as described in Synthesis Example 1 except that h-1 in Synthesis Example 1 was replaced with an equimolar amount of h-4. The purity detected by HPLC was greater than or equal to 99.3%.

Mass spectrum m/z: 732.2709 (theoretical value: 732.2777). Theoretical element content (%) of $C_{53}H_{36}N_2O_2$: C, 86.86; H, 4.95; N, 3.82. Measured elemental content (%): C, 86.87; H, 4.95; N, 3.79. The above results confirmed that the obtained product was the target product.

SYNTHESIS EXAMPLE 13

Synthesis of Compound 292

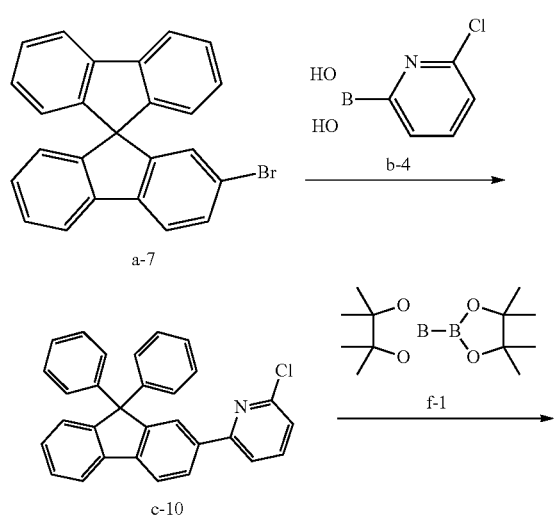

Compound 292 (10.42 g) was given according to the same preparation method as described in Synthesis Example 1 except that a-1 and b-1 in Synthesis Example 1 were replaced with equimolar amounts of a-7 and b-4. The purity detected by HPLC was greater than or equal to 99.3%.

Mass spectrum m/z: 705.2215 (theoretical value: 703.2260). Theoretical element content (%) of $C_{50}H_{29}N_3O_2$: C, 85.33; H, 4.15; N, 5.97. Measured elemental content (%): C, 85.35; H, 4.13; N, 5.98. $^1$H NMR (600 MHz, CDCl$_3$) (δ, ppm): 8.52 (s, 1H), 8.32 (s, 1H), 8.32 (s, 1H), 7.93 (d, 2H), 7.85-7.84 (m, 3H), 7.76 (dd, 1H), 7.72-7.70 (m, 3H), 7.63 (s, 1H), 7.62-7.56 (m, 3H), 7.39-7.30 (m, 10H), 7.10 (dd, 1H), 7.06 (dd, 2H). The above results confirmed that the obtained product was the target product.

DEVICE EXAMPLE 1

An ITO glass substrate was subjected to ultrasonic cleaning twice with 5% glass cleaning liquid for 20 minutes each time and then subjected to ultrasonic cleaning twice with deionized water for 10 minutes each time. The ITO glass substrate was subjected to ultrasonic cleaning sequentially with acetone and isoacetone for 20 minutes and dried at 120° C. The ITO glass substrate was then transferred to a vacuum deposition device.

On the transparent ITO glass substrate prepared as above, hexaazatriphenylenehexacabonitrile (HAT) with a thickness of 50 Å was evaporated to form a hole injection layer; Compound HT-1 with a thickness of 1300 Å was evaporated on the hole injection layer to form a hole transport layer; subsequently, BH and BD in a weight ratio of 25:1 with a thickness of 200 Å were deposited by vacuum deposition on the hole transport layer to form an emissive layer; Compound 1 of Synthetic Example 1 of the present disclosure with a thickness of 80 Å was evaporated on the emissive layer to form a hole blocking layer, and Compound ET-1 was evaporated on the hole blocking layer to form an electron transport layer with a thickness of 300 Å. Lithium fluoride (LiF) with a thickness of 10 Å was evaporated on the electron transport layer to form an electron injection layer, and finally aluminum with a thickness of 1000 Å was evaporated to form a cathode.
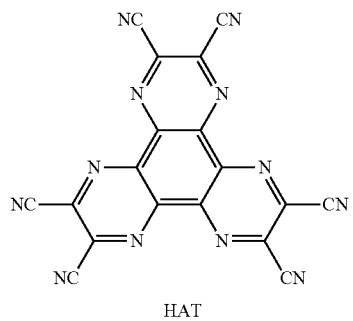
HAT
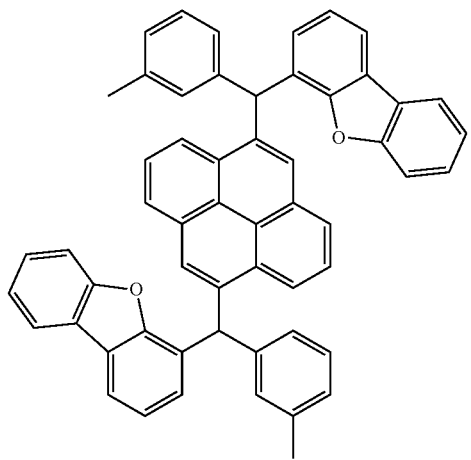
BD
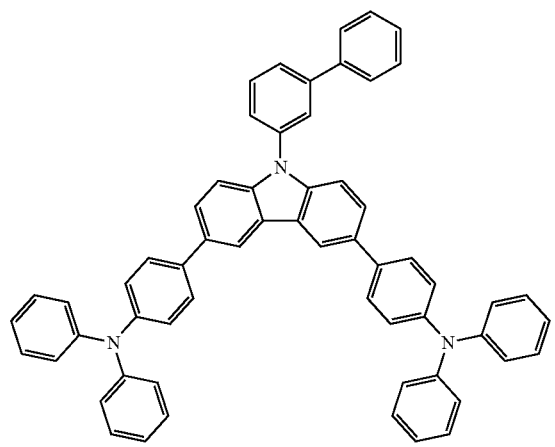
HT-1
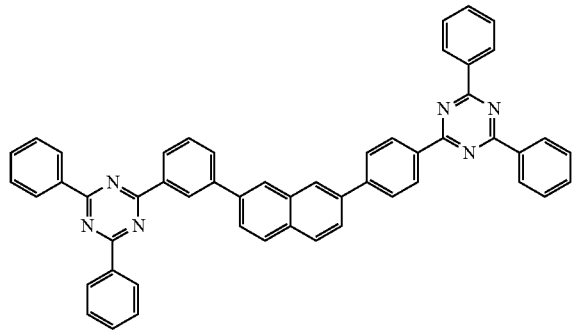
ET-1
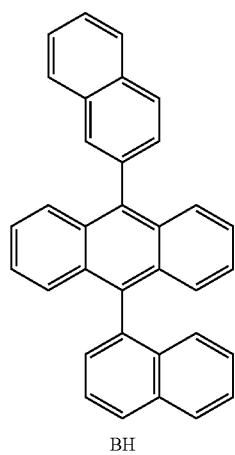
BH
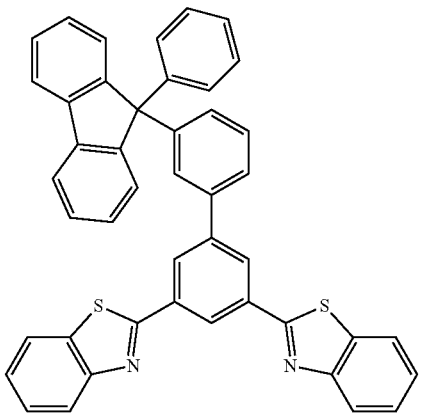
Comparative compound 1

-continued

Comparative compound 2

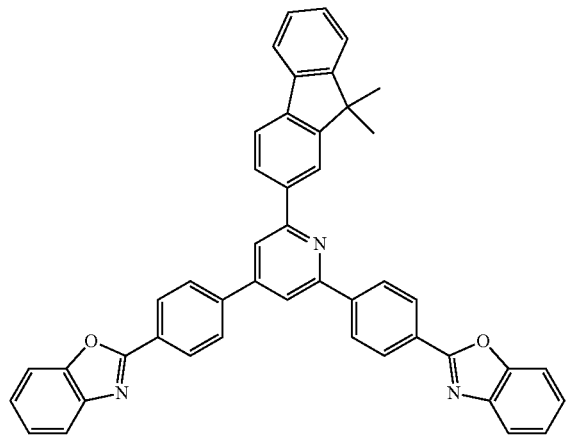

Comparative compoud 3

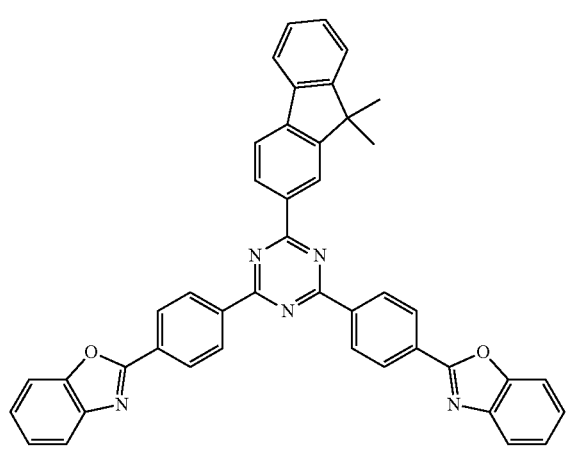

DEVICE EXAMPLES 2 TO 13

Except that Compound 4, Compound 5, Compound 9, Compound 10, Compound 17, Compound 51, Compound 82, Compound 147, Compound 171, Compound 216, Compound 258, and Compound 292 of the present disclosure were respectively used as the hole blocking layer in place of Compound 1 in Device Example 1, the organic electroluminescent devices were prepared according to the same synthesis method as in Device Example 1.

DEVICE EXAMPLE 14

An ITO glass substrate was cleaned according to the manner described in Device Example 1. Hexaazatriphenylenehexacabonitrile (HAT) with a thickness of 50 Å was evaporated on the ITO glass substrate to form a hole injection layer; Compound HT-1 with a thickness of 1300 Å was evaporated on the hole injection layer to form a hole transport layer; subsequently, BH and BD in a weight ratio of 25:1 with a thickness of 200 Å were deposited by vacuum deposition on the hole transport layer to form an emissive layer; Compound 1 of Synthetic Example 1 of the present disclosure with a thickness of 300 Å was evaporated on the emissive layer to form an electron transport layer, lithium fluoride (LiF) with a thickness of 10 Å was evaporated on the electron transport layer to form an electron injection layer, and finally aluminum with a thickness of 1000 Å was evaporated to form a cathode.

DEVICE EXAMPLES 15 TO 26

Except that Compound 4, Compound 5, Compound 9, Compound 10, Compound 17, Compound 51, Compound 82, Compound 147, Compound 171, Compound 216, Compound 258, and Compound 292 of the present disclosure were respectively used as the electron transport layer in place of Compound 1 in Device Example 14, the organic electroluminescent devices were prepared according to the same synthesis method as in Device Example 14.

COMPARATIVE EXAMPLES 1 TO 3

Except that Comparative Compound 1, Comparative Compound 2, and Comparative Compound 3 were used as the hole blocking layer in place of Compound 1 in Device Example 1, the organic electroluminescent devices were prepared according to the same synthesis method as in Device Example 1.

COMPARATIVE EXAMPLES 4 TO 6

Except that Comparative Compound 1, Comparative Compound 2, and Comparative Compound 3 were used as the electron transport layer in place of Compound 1 in Device Example 14, the organic electroluminescent devices were prepared according to the same synthesis method as in Device Example 14.

The devices were prepared by using a vacuum evaporation system, and the preparation was completed by consecutive evaporation under uninterrupted vacuum. The materials used herein were respectively placed in quartz crucibles with different evaporation sources, and the temperature of evaporation sources could be controlled independently. The thermal evaporation rate of organic materials was generally 0.1 nm/s, and the evaporation rate of doped materials was adjusted according to the doping ratio; the evaporation rate of electrode metals was 0.4 nm/s to 0.6 nm/s. In the film manufacture process, the vacuum degree of the system was maintained below $5 \times 10^{-5}$ Pa.

Test software, a computer, K2400 SourceMeter produced by KEITHLEY, USA, and PR788 SpectraScan produced by PHOTO RESEARCH, USA were combined into a joint IVL test system to test the luminous efficiency and CIE color coordinates of the organic electroluminescent devices. The lifetime was tested by M6000 OLED lifetime test system produced by MCSCIENCE CO. The test environment was the atmospheric environment, and the temperature was room temperature. For the organic electroluminescent devices prepared according to the above method, the drive voltage and the luminous efficiency were measured at a current density of 10 mA/cm2, and the time (T90) of reaching 90% of initial luminance was measured at a current density of 20 mA/cm2. The test results of luminescence characteristics of devices in Device Examples 1 to 26 and Comparative Examples 1 to 6 of the present disclosure are shown in Table 1.

TABLE 1 luminescence characteristic test of organic electroluminescent devices

| Device Examples | Hole blocking layer | Electron transport layer | Drive voltage | Luminous efficiency | Lifetime (T90) |
|---|---|---|---|---|---|
| Device Example 1 | Compound 1 | ET-1 | 4.3 | 9.10 | 206 |
| Device Example 2 | Compound 4 | ET-1 | 4.3 | 9.06 | 203 |
| Device Example 3 | Compound 5 | ET-1 | 4.3 | 8.91 | 190 |
| Device Example 4 | Compound 9 | ET-1 | 4.4 | 8.75 | 181 |
| Device Example 5 | Compound 10 | ET-1 | 4.4 | 8.84 | 188 |
| Device Example 6 | Compound 17 | ET-1 | 4.5 | 8.66 | 172 |
| Device Example 7 | Compound 51 | ET-1 | 4.5 | 8.59 | 168 |
| Device Example 8 | Compound 82 | ET-1 | 4.4 | 8.79 | 187 |
| Device Example 9 | Compound 147 | ET-1 | 4.6 | 8.53 | 164 |
| Device Example 10 | Compound 171 | ET-1 | 4.4 | 8.70 | 179 |
| Device Example 11 | Compound 216 | ET-1 | 4.3 | 8.95 | 197 |
| Device Example 12 | Compound 258 | ET-1 | 4.5 | 8.64 | 170 |
| Device Example 13 | Compound 292 | ET-1 | 4.3 | 8.95 | 195 |
| Comparative Example 1 | Comparative Compound 1 | ET-1 | 4.8 | 6.05 | 135 |
| Comparative Example 2 | Comparative Compound 2 | ET-1 | 4.6 | 7.52 | 155 |
| Comparative Example 3 | Comparative Compound 3 | ET-1 | 4.7 | 6.98 | 147 |
| Device Example 14 | — | Compound 1 | 4.5 | 8.40 | 184 |
| Device Example 15 | — | Compound 4 | 4.5 | 8.31 | 181 |
| Device Example 16 | — | Compound 5 | 4.6 | 8.22 | 175 |
| Device Example 17 | — | Compound 9 | 4.7 | 8.06 | 170 |
| Device Example 18 | — | Compound 10 | 4.6 | 8.15 | 173 |
| Device Example 19 | — | Compound 17 | 4.7 | 7.77 | 162 |
| Device Example 20 | — | Compound 51 | 4.8 | 7.68 | 159 |
| Device Example 21 | — | Compound 82 | 4.5 | 8.27 | 177 |
| Device Example 22 | — | Compound 147 | 4.7 | 7.85 | 165 |
| Device Example 23 | — | Compound 171 | 4.6 | 7.92 | 169 |
| Device Example 24 | — | Compound 216 | 4.4 | 8.46 | 187 |
| Device Example 25 | — | Compound 258 | 4.8 | 7.50 | 156 |
| Device Example 26 | — | Compound 292 | 4.4 | 8.59 | 189 |
| Comparative Example 4 | — | Comparative Compound 1 | 5.0 | 6.08 | 118 |
| Comparative Example 5 | — | Comparative Compound 2 | 4.9 | 6.95 | 133 |
| Comparative Example 6 | — | Comparative Compound 3 | 4.8 | 6.53 | 140 |

As can be seen from the results in Table 1, the compound of the present disclosure can be applied to the preparation of OLED light-emitting devices and obtains good performance. When the compound of the present disclosure is used as the hole blocking material and electron transport material of an organic electroluminescent device, the drive voltage, luminous efficiency, and lifetime of the device are greatly improved. The compound of the present disclosure, when used as the hole blocking material and electron transport material, in particular, as the hole blocking material, has a good application effect in the OLED light-emitting device and has a good industrialization prospect.

It is to be noted that the present disclosure has been described in particular through some embodiments, but without departing from the principle of the present disclosure, modifications in various forms or details may be made to the present disclosure by those of ordinary skill in the art, and such modifications fall within the scope of the present disclosure.

What is claimed is:

1. A heterocyclic compound, having a structure as shown in Formula I:

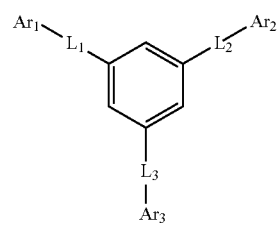

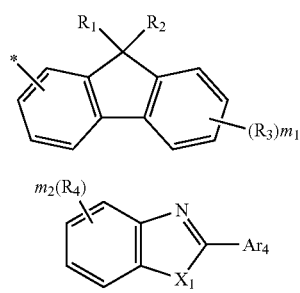

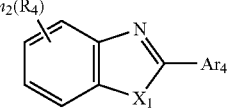

wherein, in the structure as shown in Formula I, $Ar_1$ is selected from a structure as shown in Formula II, and $Ar_2$ and $Ar_3$ are identical to each other or different from each other and independently selected from a structure as shown in Formula III;

wherein $L_1$ is independently selected from a single bond or any one of the following groups:

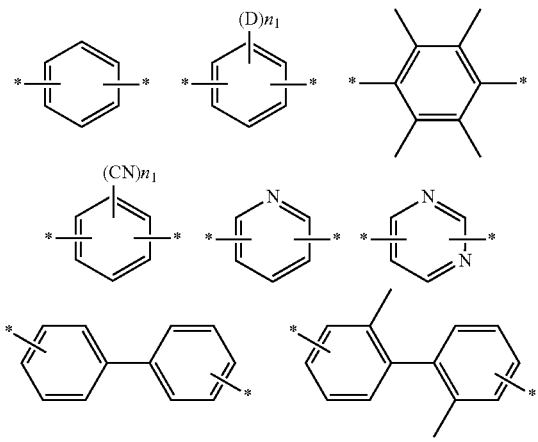

161

-continued

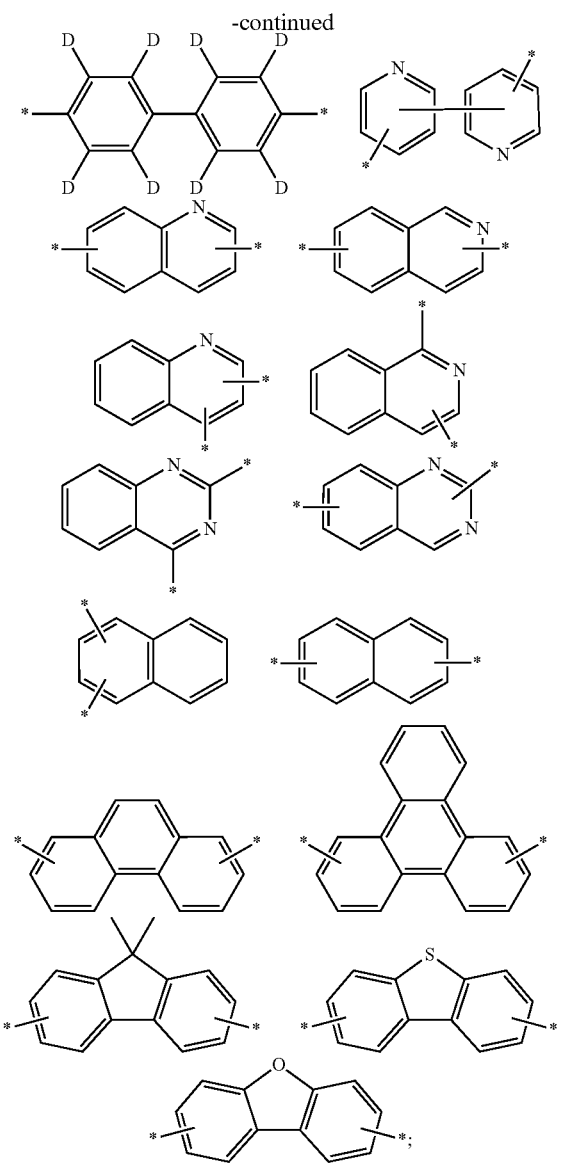

wherein $n_1$ is an integer selected from 1 to 4;
$L_2$ to $L_3$ are identical to each other or different from each other and independently selected from any one of a single bond, substituted or unsubstituted C6 to C30 arylene or substituted or unsubstituted C3 to C30 heteroarylene;
* is the attachment site between $L_1$ and $Ar_1$, the attachment site between $L_2$ and $Ar_2$ is any position on the structure as shown in Formula III, and the attachment site between $L_3$ and $Ar_3$ is any position on the structure as shown in Formula III;
in the structure as shown in Formula II, $R_1$ and $R_2$ are identical to each other or different from each other and independently selected from any one of hydrogen, C1 to C12 alkyl, substituted or unsubstituted phenyl, or $R_1$ and $R_2$ are joined to form a substituted or unsubstituted ring, wherein substituted refers to mono- or multi-substitution with any of the following groups: deuterium, methyl, ethyl, tert-butyl, phenyl, biphenyl or naphthyl;
$R_3$ is selected from any one of hydrogen, deuterium, halogen, cyano, hydroxyl, amino, sulfanyl, adamantyl,

162 norcamphanyl, substituted or unsubstituted C1 to C12 alkyl, substituted or unsubstituted C2 to C12 alkenyl or substituted or unsubstituted C6 to C30 aryl;
$m_1$ is an integer selected from 0 to 4, and when $m_1$ is greater than 1, two or more $R_3$ are identical to each other or different from each other, or two adjacent $R_3$ are joined to form a ring; and
wherein the structure as shown in Formula III is selected from any one of the following groups:

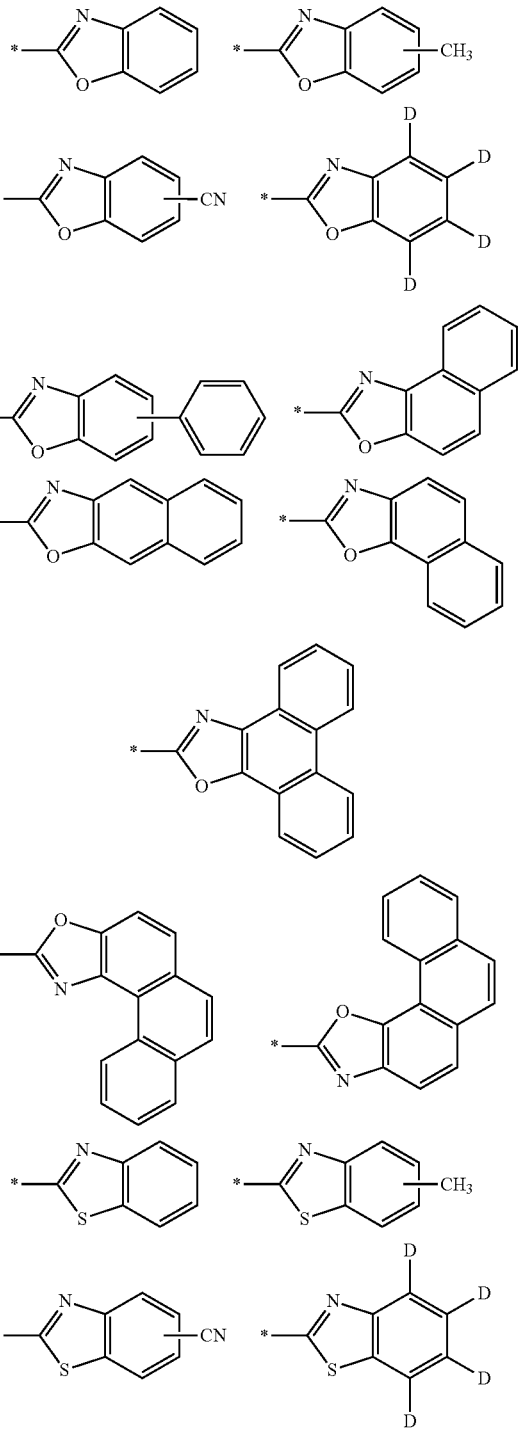

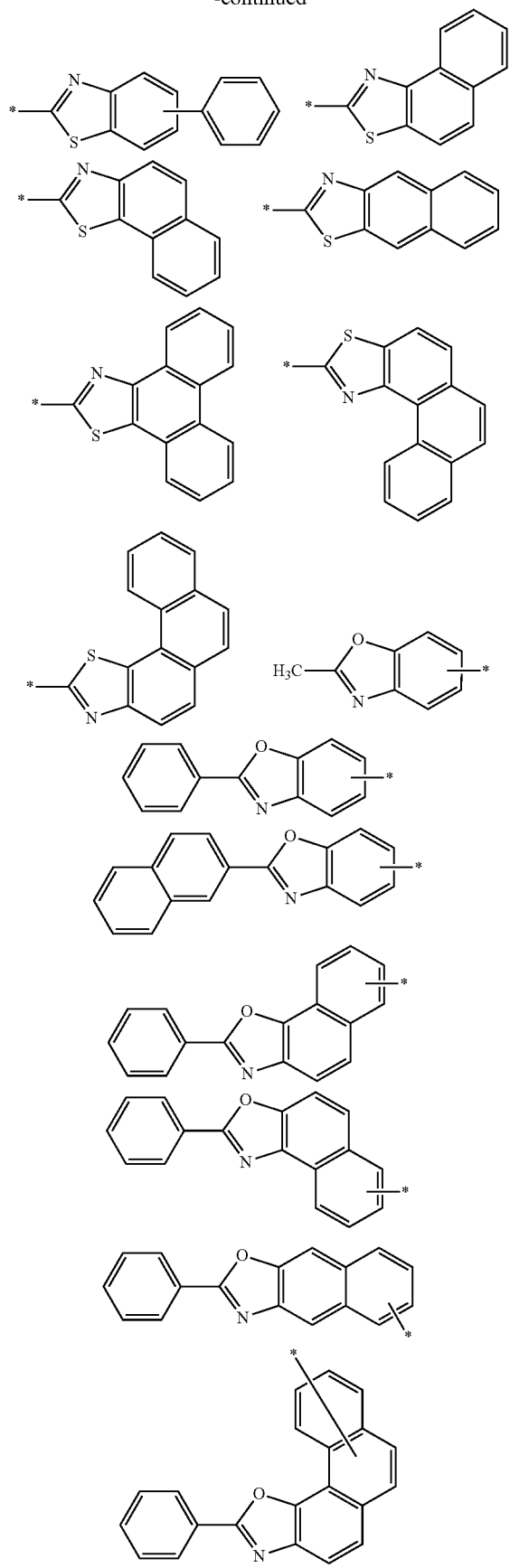
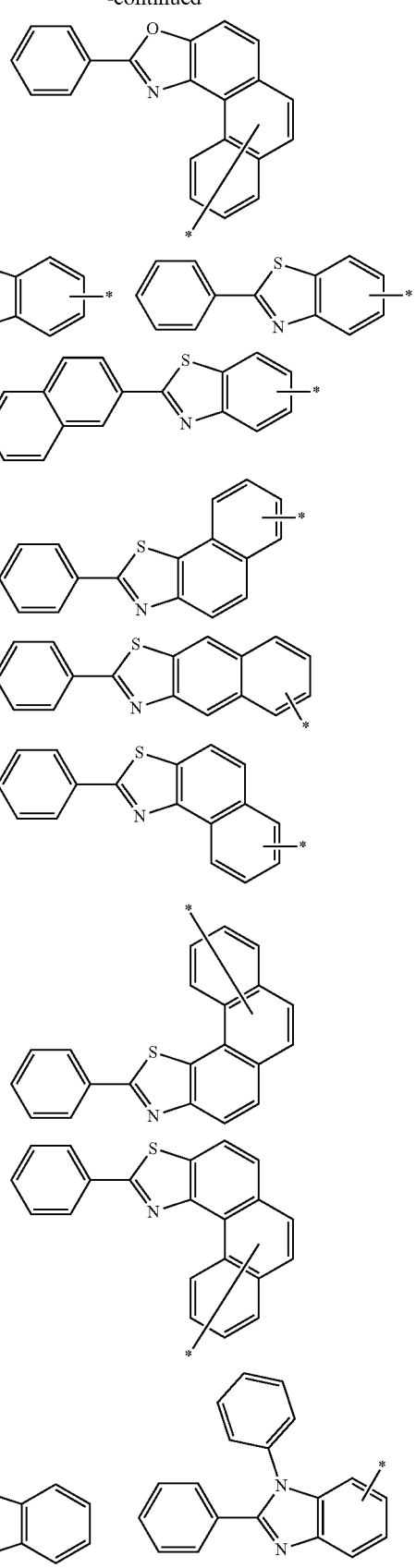

-continued

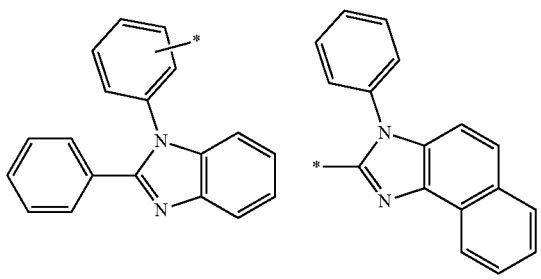

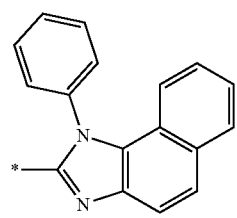

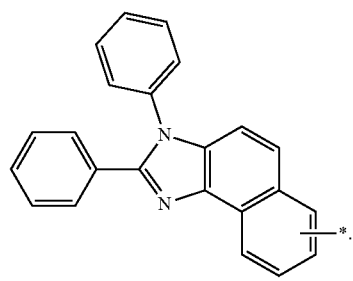

2. The heterocyclic compound according to claim 1, wherein the structure as shown in Formula II is selected from any one of structures as shown in Formula II-1 to Formula II-4:

II-1

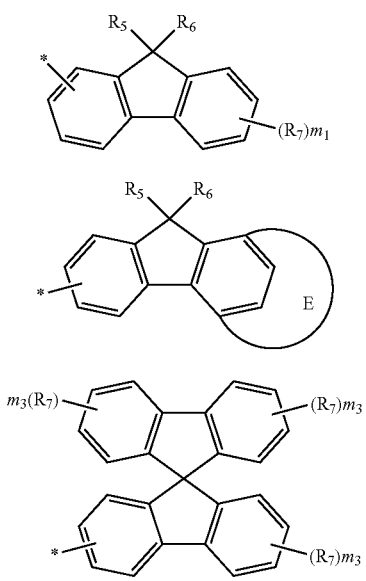

-continued

II-4

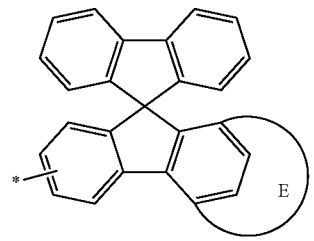

wherein, * represents an attachment site to $L_1$;
$R_5$ and $R_6$ are identical to each other or different from each other and independently selected from any one of hydrogen, methyl, ethyl or phenyl;
$R_7$ is selected from any one of hydrogen, deuterium, cyano, adamantyl, norcamphanyl, substituted or unsubstituted C1 to C6 alkyl or substituted or unsubstituted C6 to C18 aryl;
$m_3$ is an integer selected from 0 to 4, and when $m_3$ is greater than 1, two or more $R_7$ are identical to each other or different from each other;
ring E is selected from any one of the following structures:

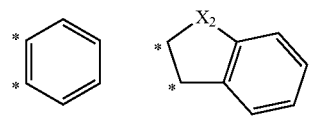

wherein, * represents a fusion site; and
$X_2$ is selected from any one of C—$R_8R_9$, N—$R_{10}$, O or S;
$R_8$ and $R_9$ are identical to each other or different from each other and independently selected from any one of hydrogen, substituted or unsubstituted C1 to C12 alkyl or substituted or unsubstituted C6 to C30 aryl; and
$R_{10}$ is selected from any one of substituted or unsubstituted C1 to C12 alkyl, substituted or unsubstituted C6 to C30 aryl or substituted or unsubstituted C3 to C30 heteroaryl.

3. The heterocyclic compound according to claim 1, wherein the structure as shown in Formula II is selected from any one of the following groups:

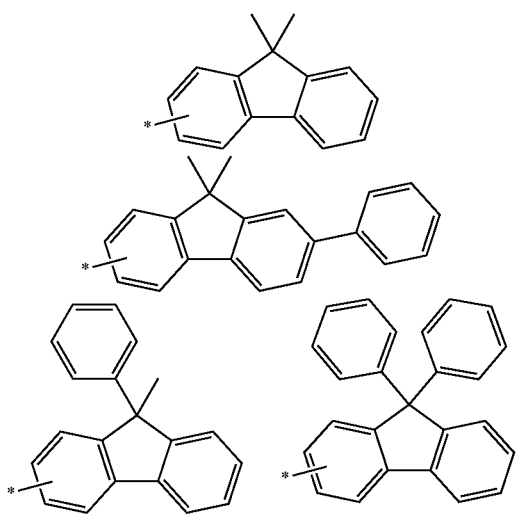

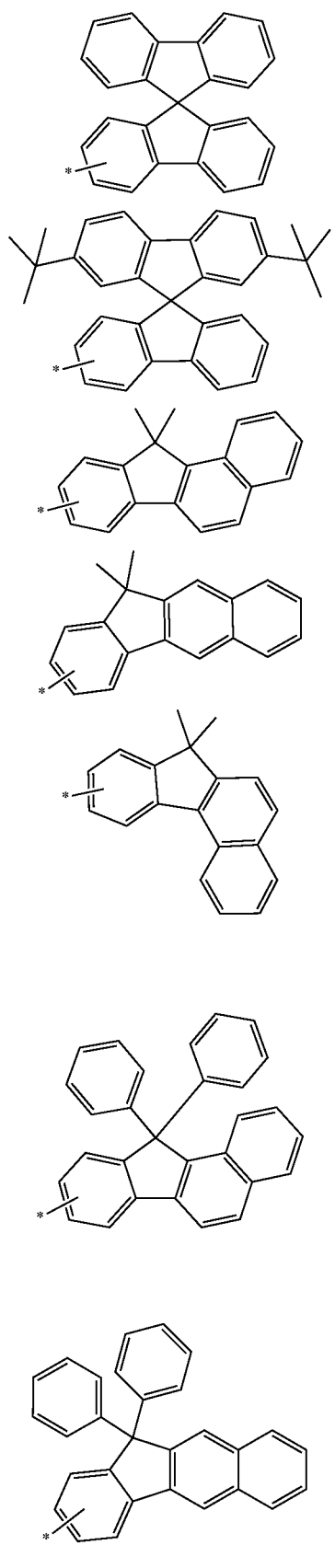
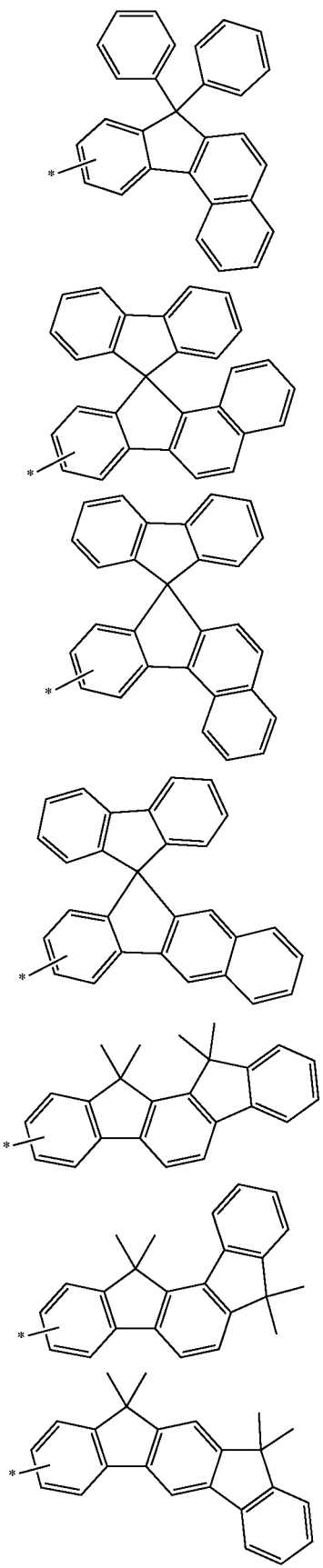

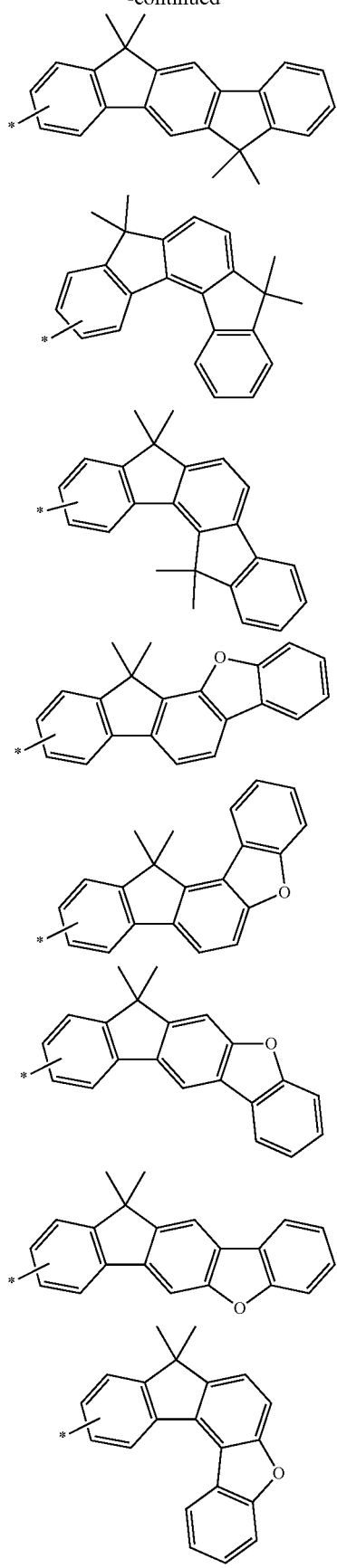
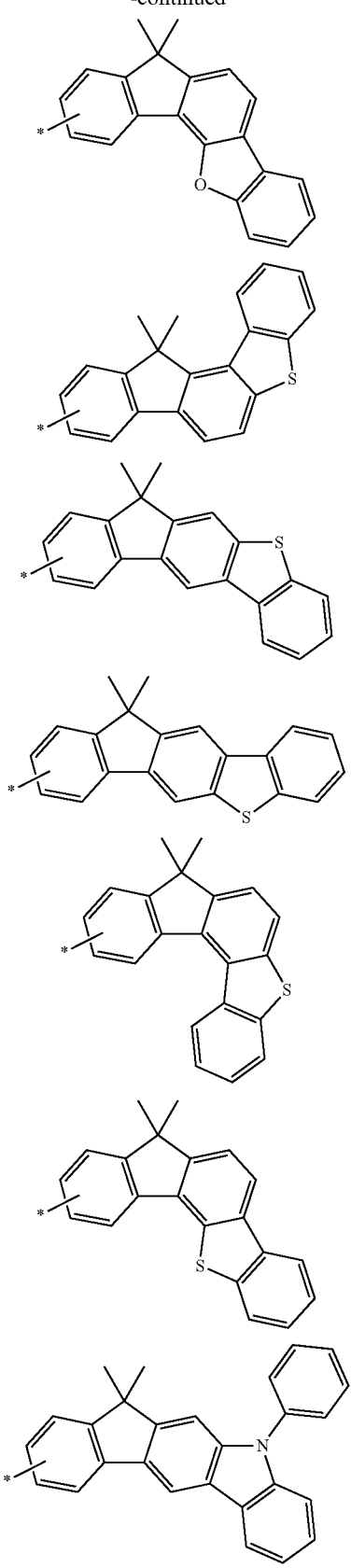

171
-continued
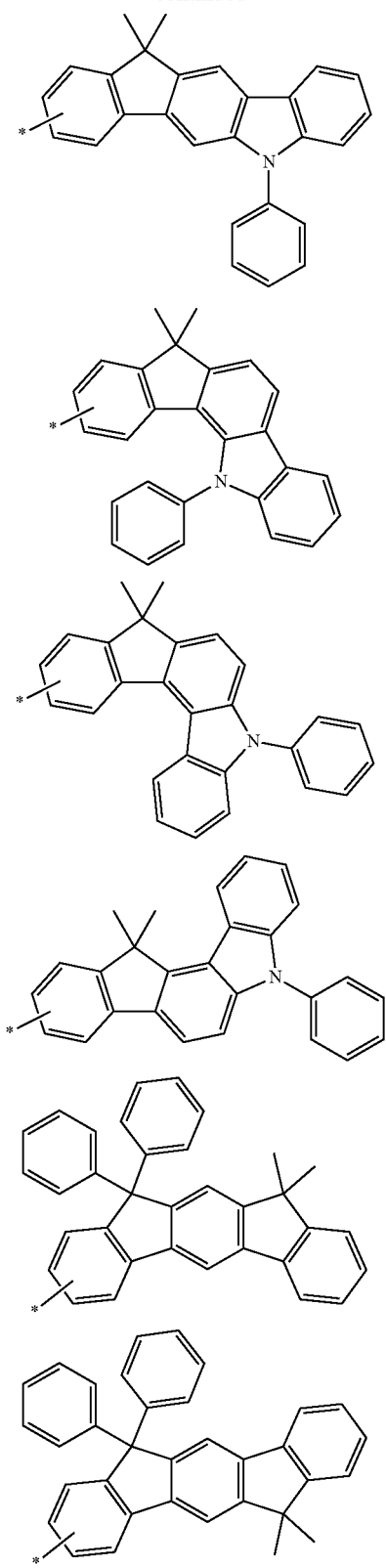
172
-continued
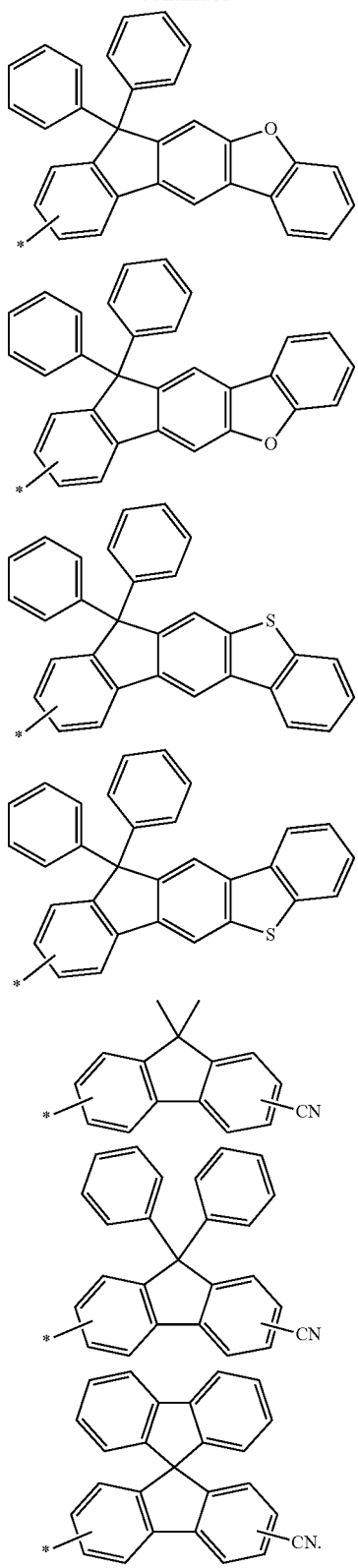
4. The heterocyclic compound according to claim 1, wherein $L_2$ and $L_3$ are identical to each other or different from each other and independently selected from a single bond or any one of the following groups:

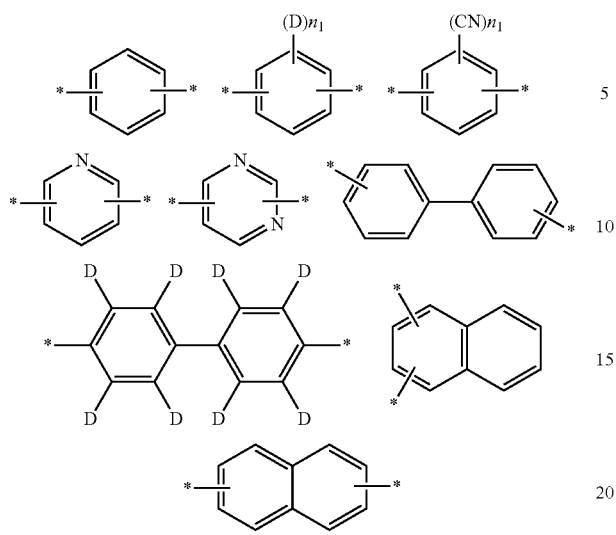
wherein $n_1$ is an integer selected from 1 to 4.
5. The heterocyclic compound according to claim 1, wherein the structure as shown in Formula I is selected from any one of the following structures:
1
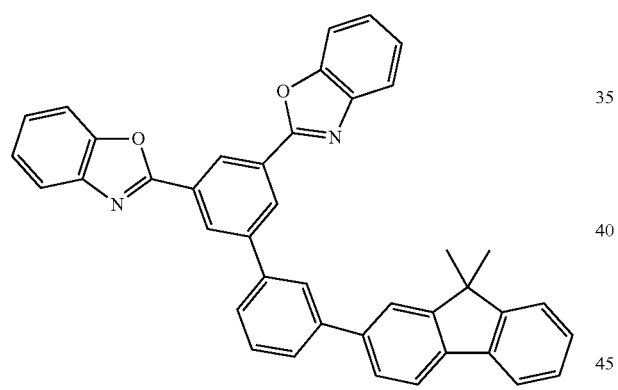
2
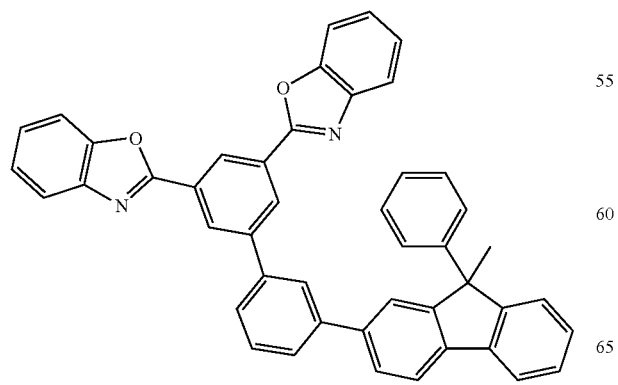
3
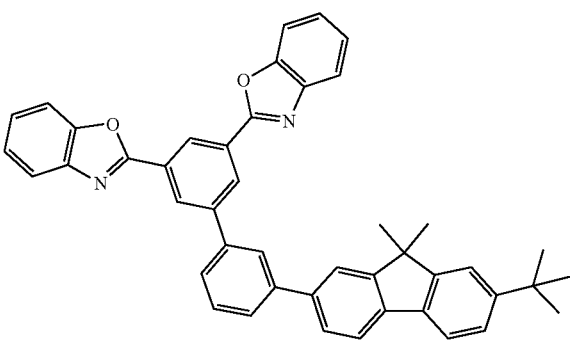
4
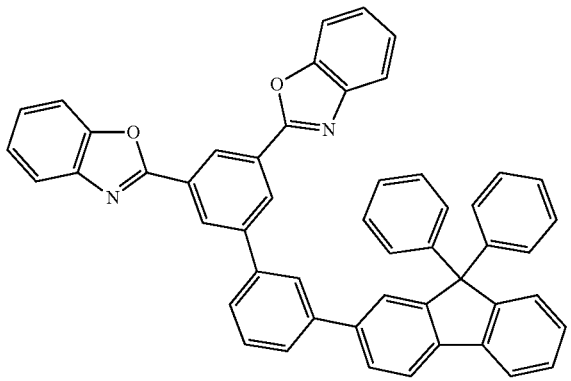
5
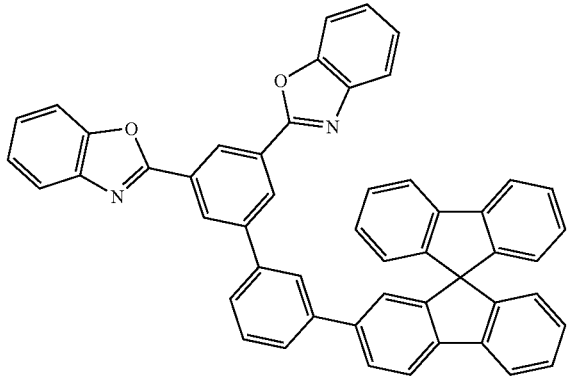
6

175
-continued
7
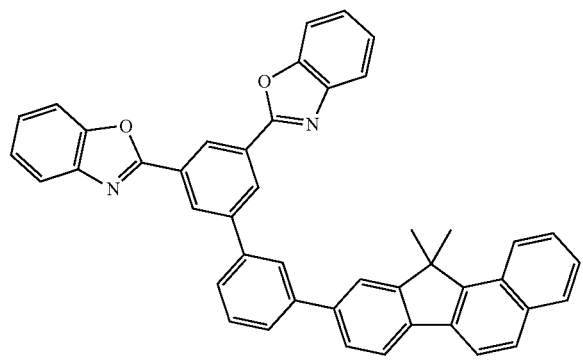
8
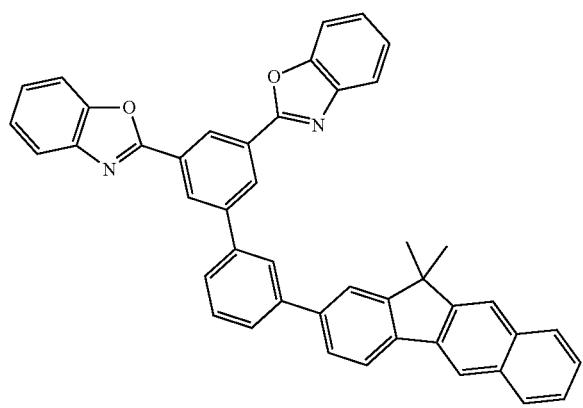
9
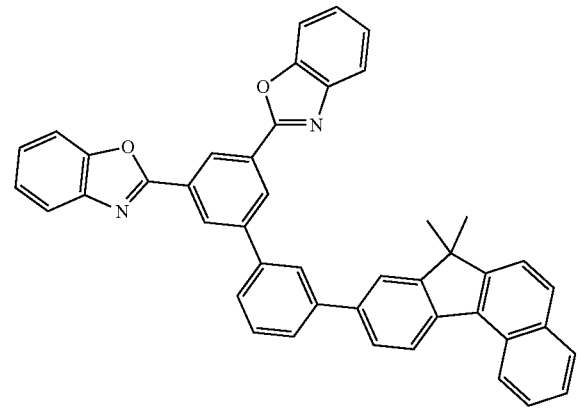
10
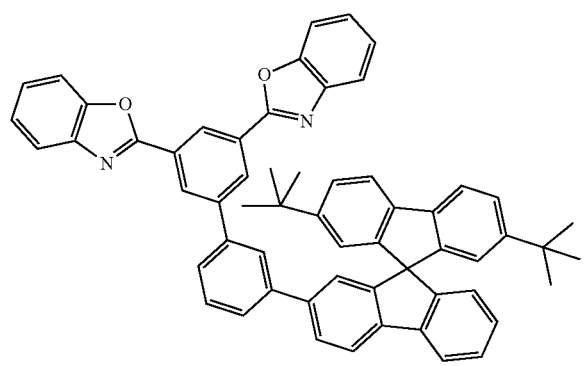
176
-continued
11
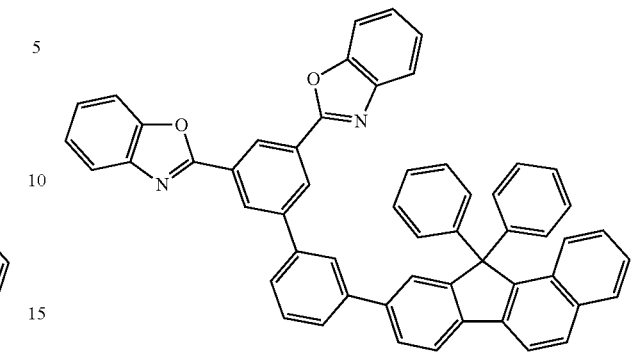
12
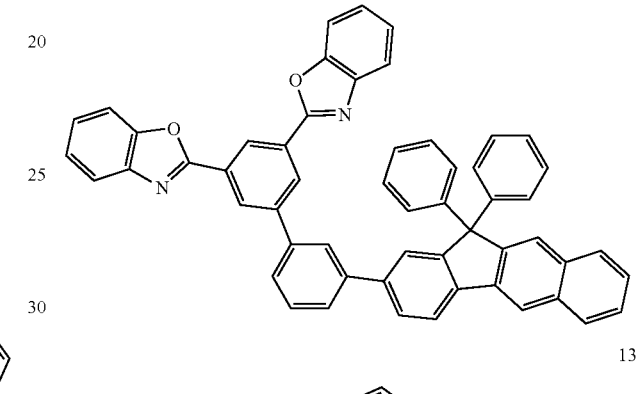
13
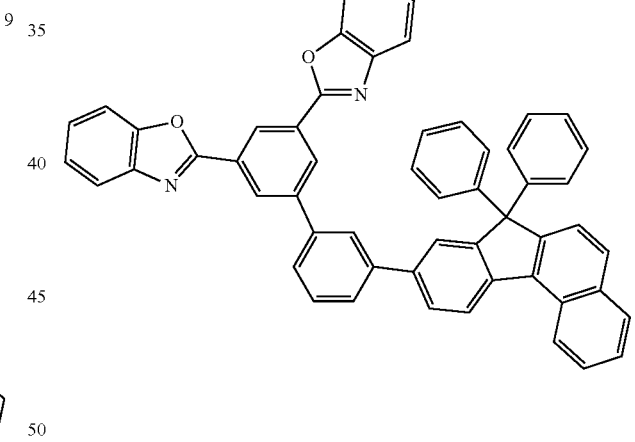
14
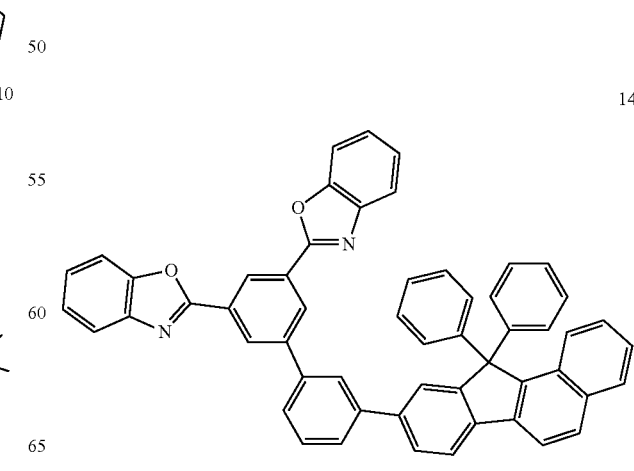

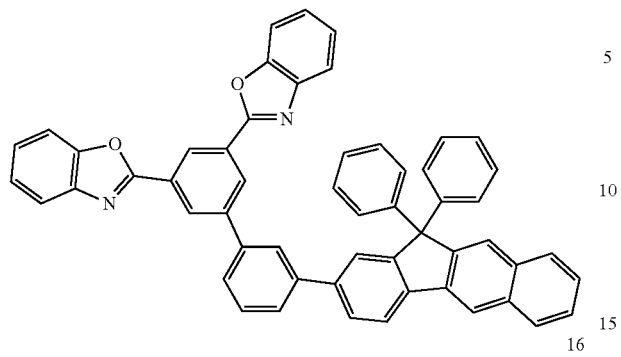
15
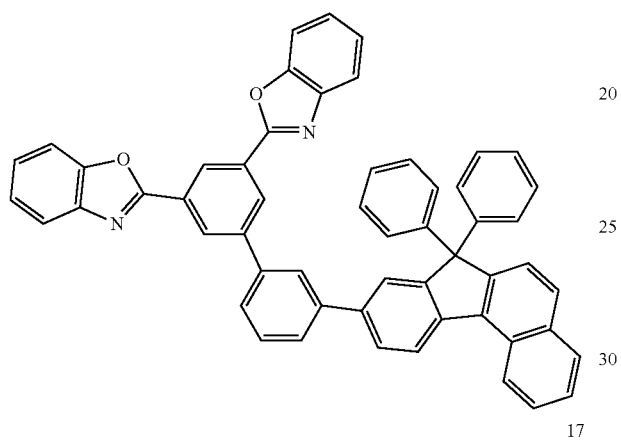
16
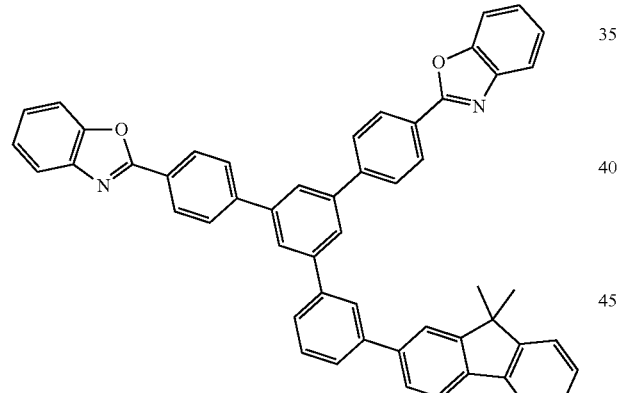
17
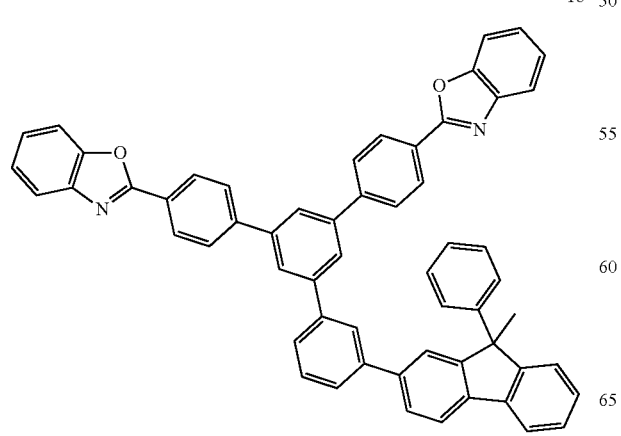
18
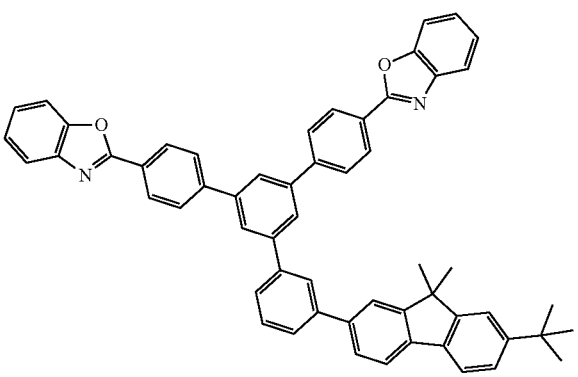
19
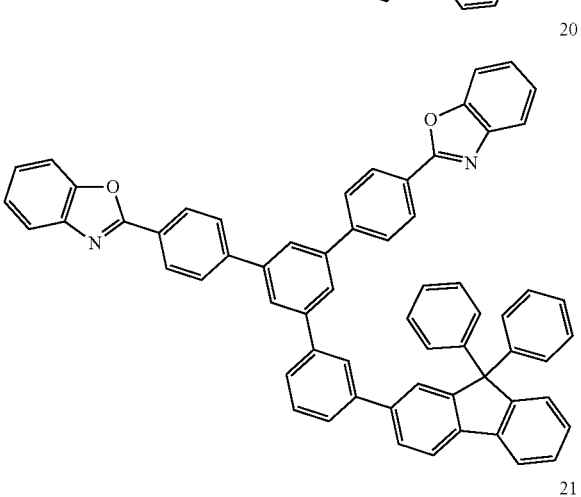
20

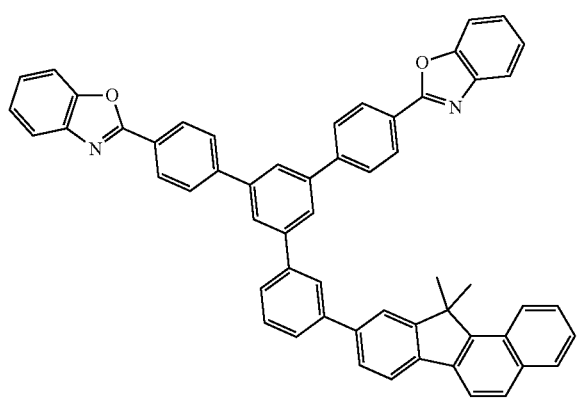
23
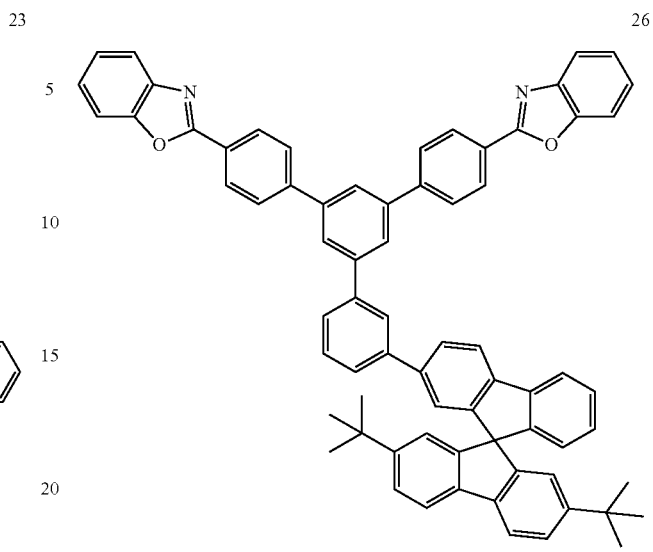
26
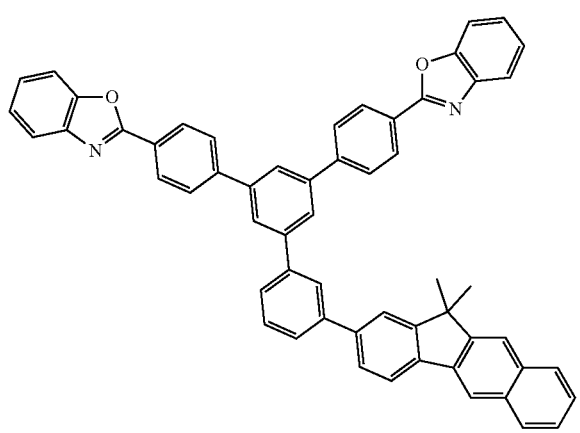
24
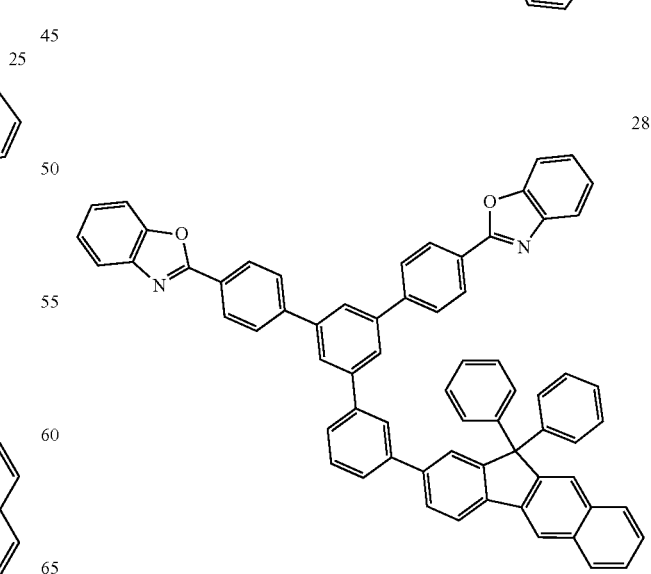
27
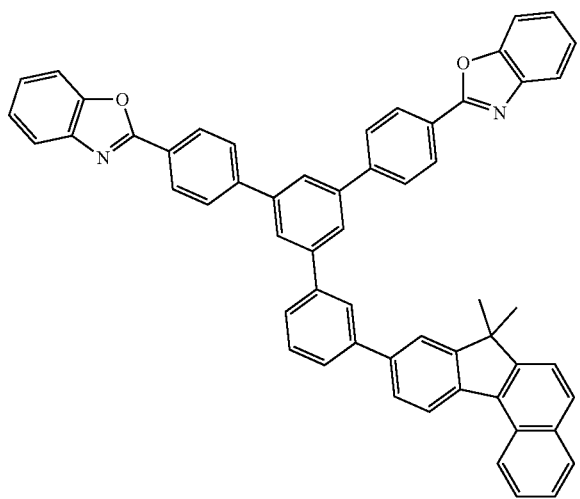
25
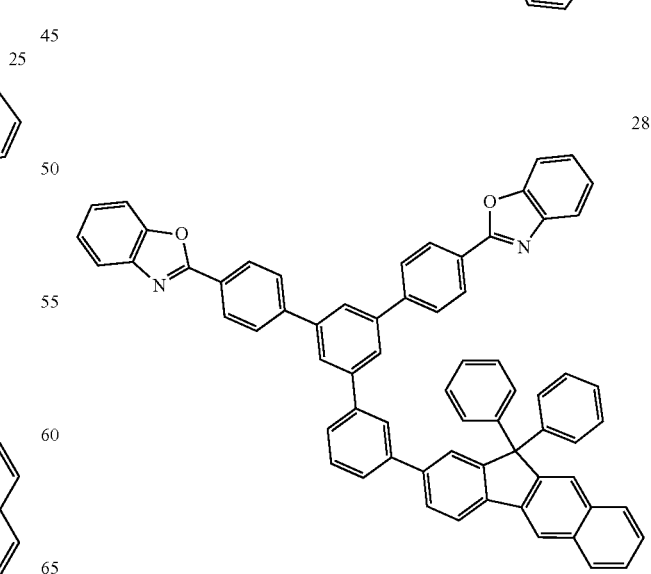
28

29
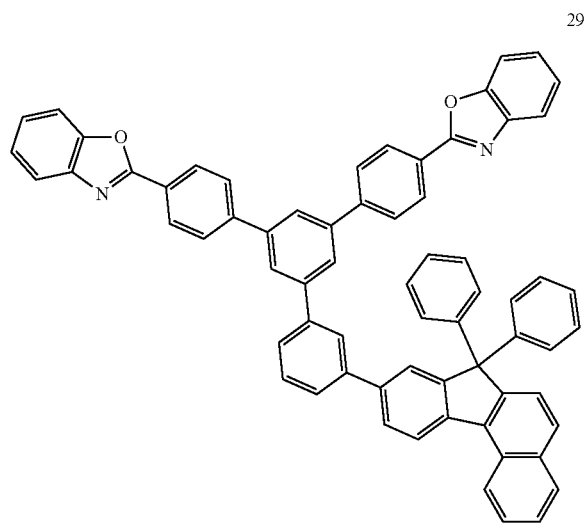
30
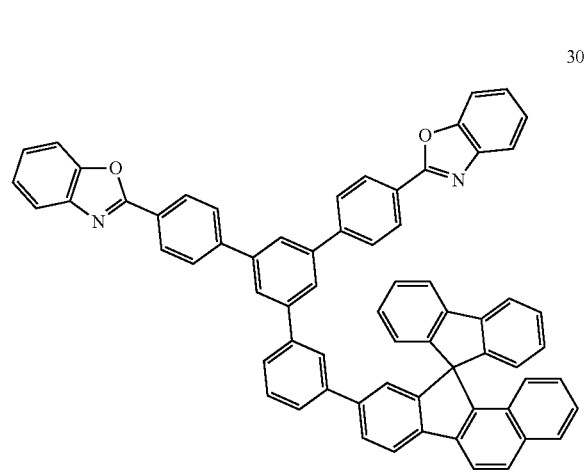
31
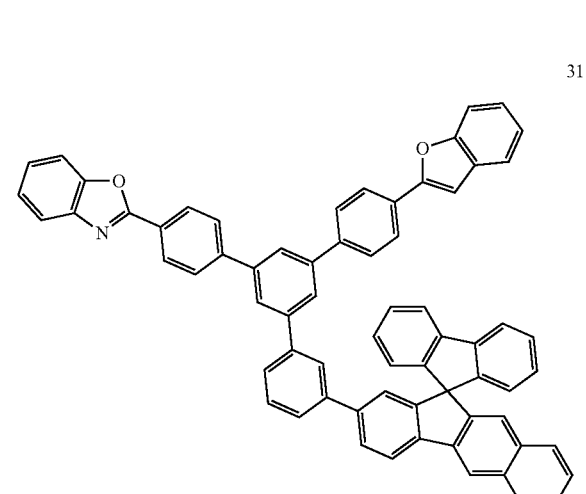
32
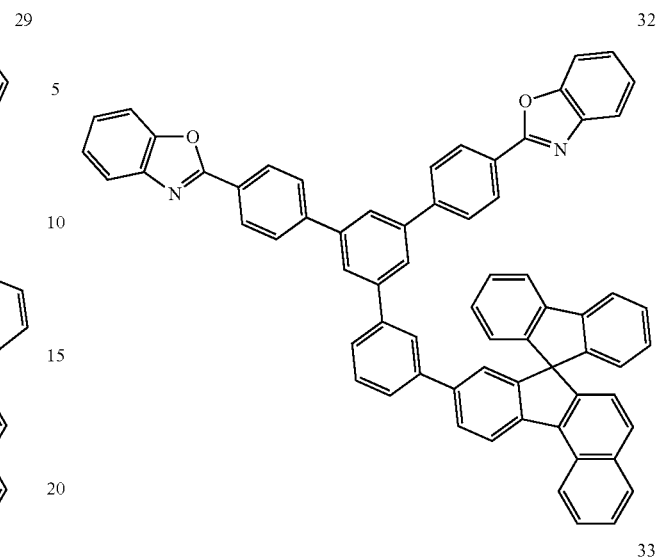
33
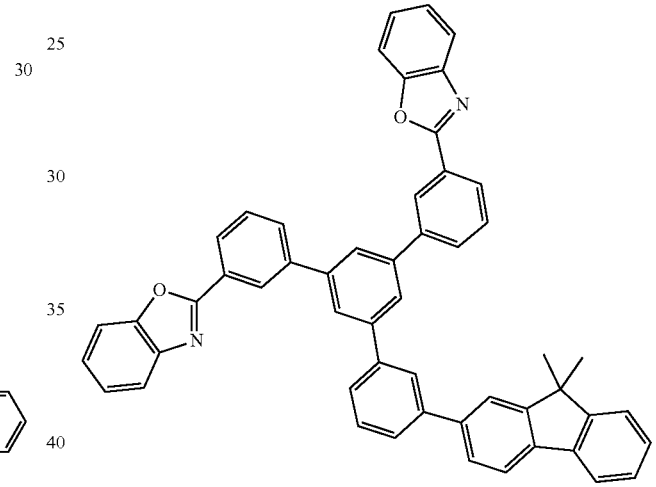
34
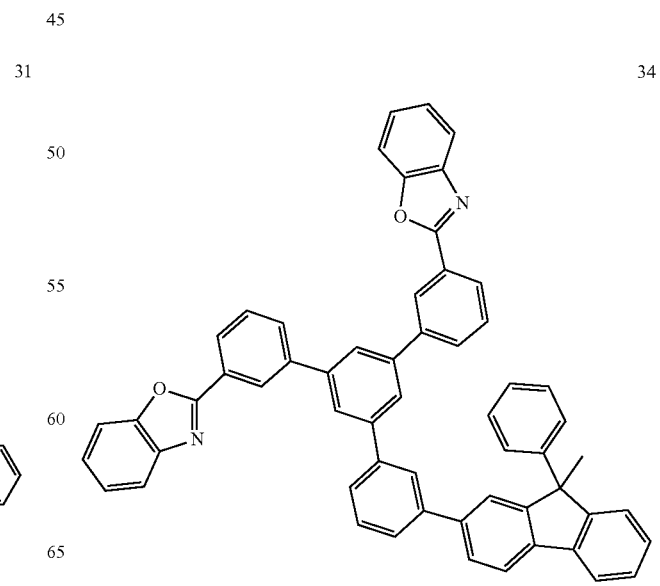

35
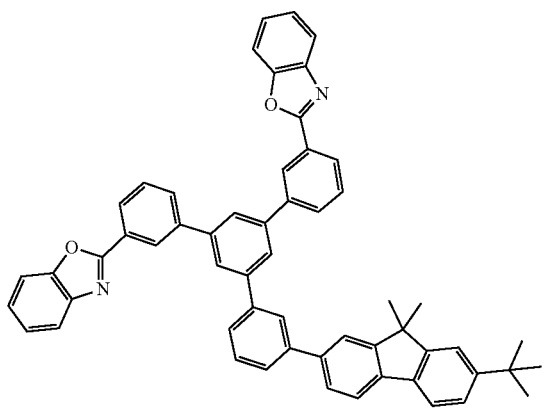
36
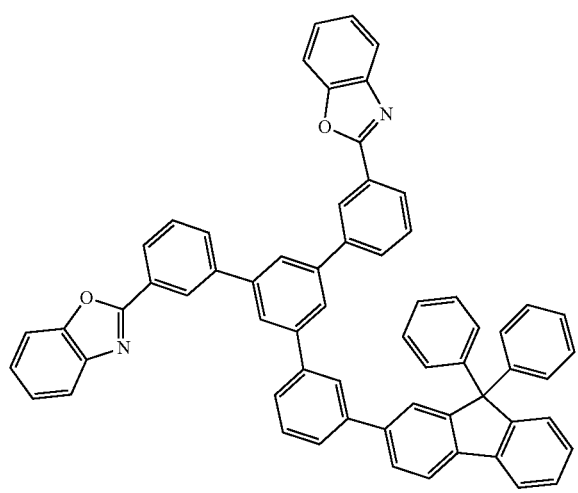
37
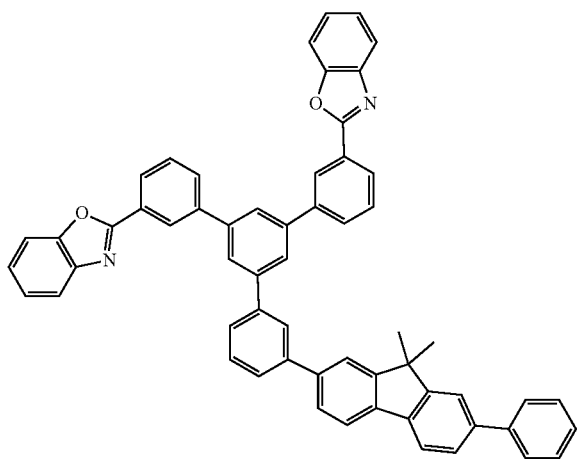
38
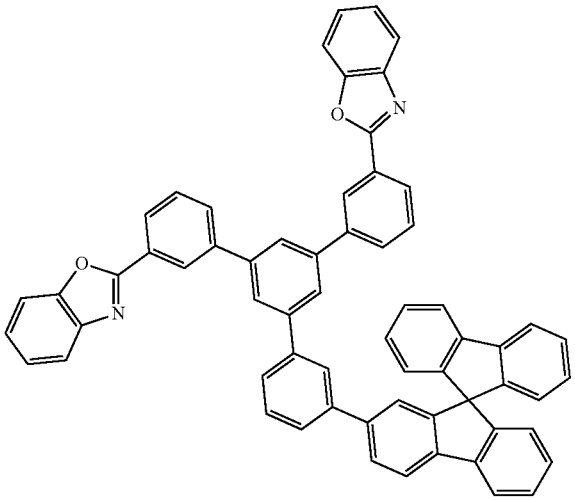
39
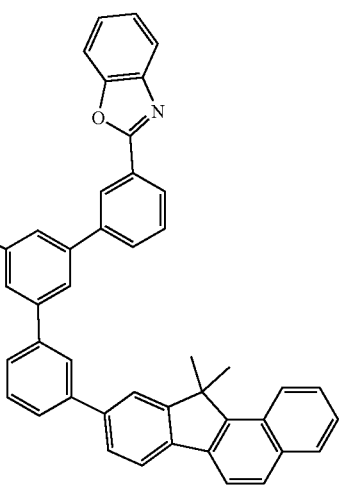
40
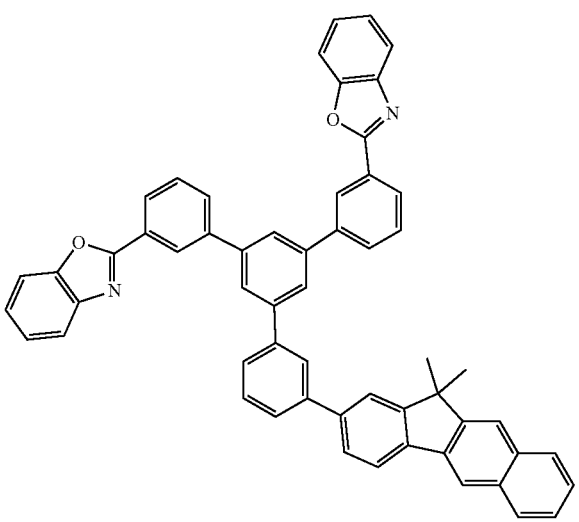

41
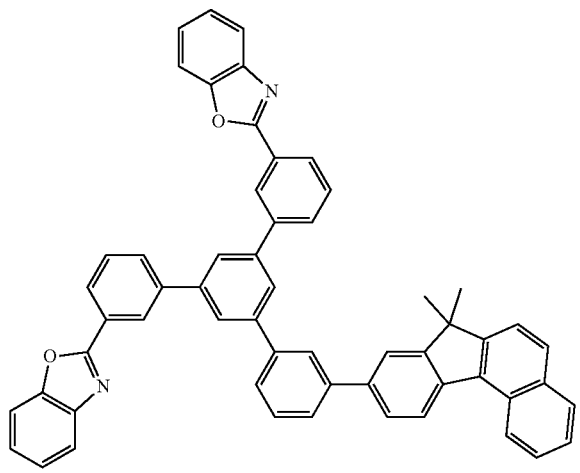
42
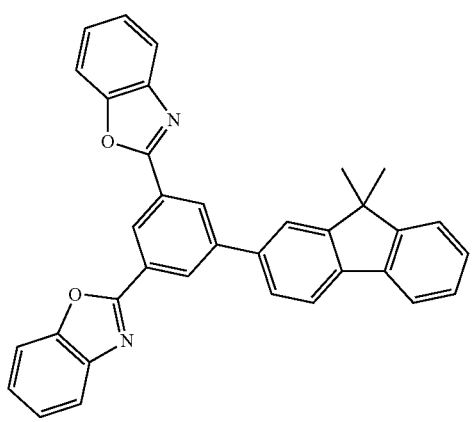
43
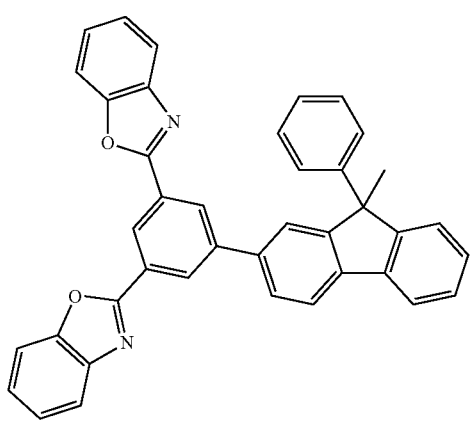
44
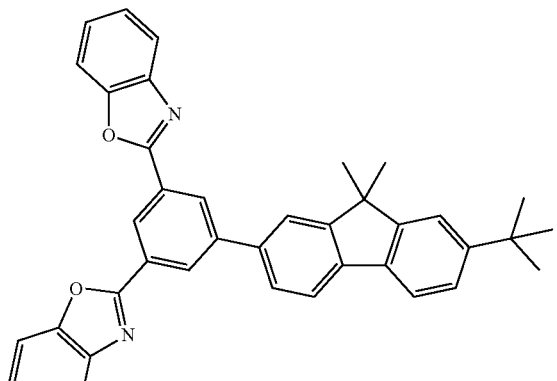
45
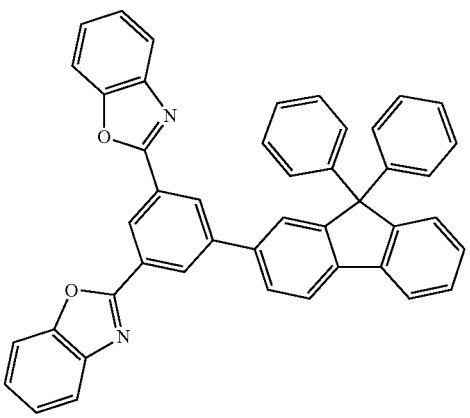
46
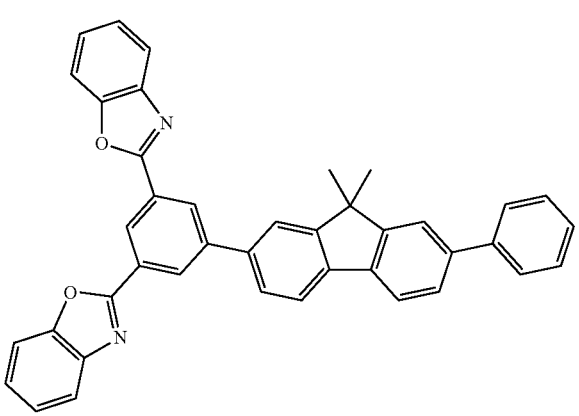

47
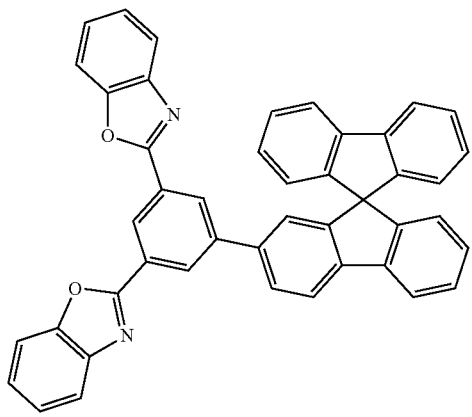
48
50
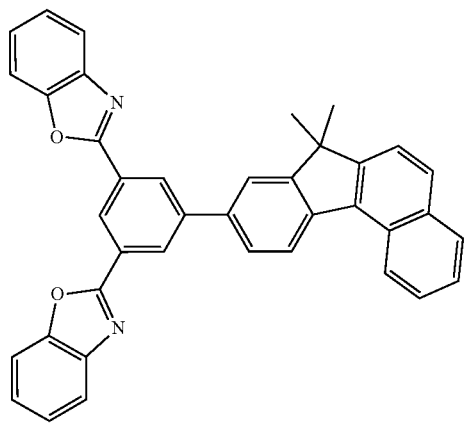
49
51

52
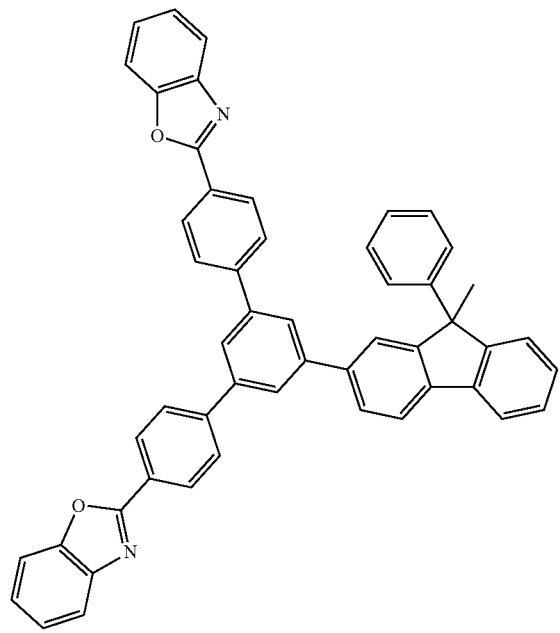
53
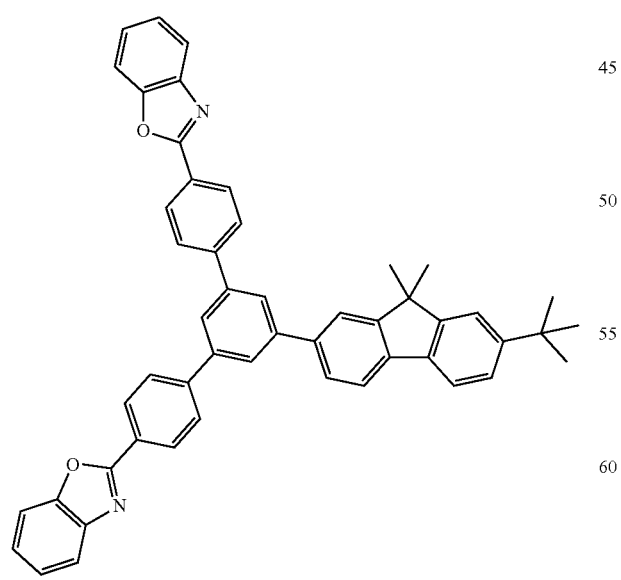
54
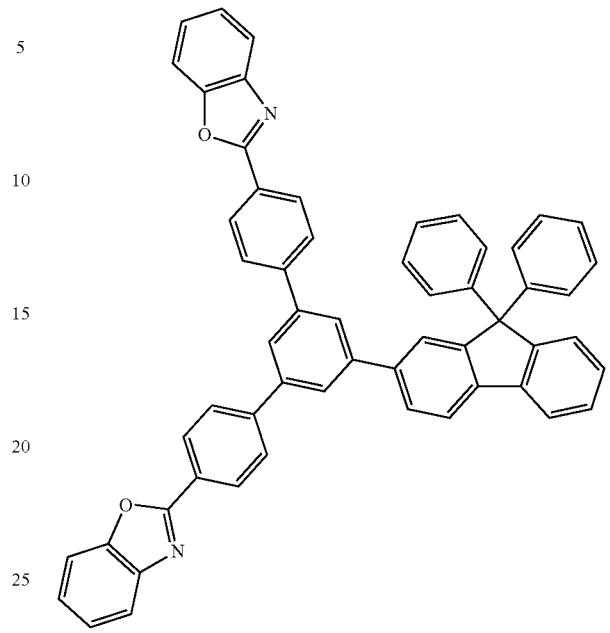
55
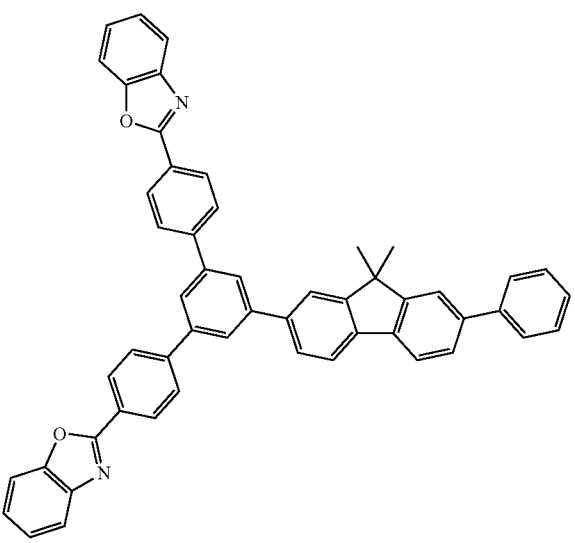

191
-continued
56
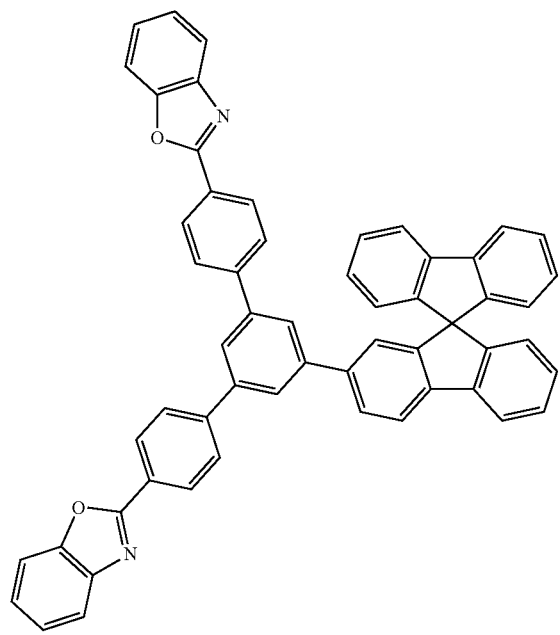
57
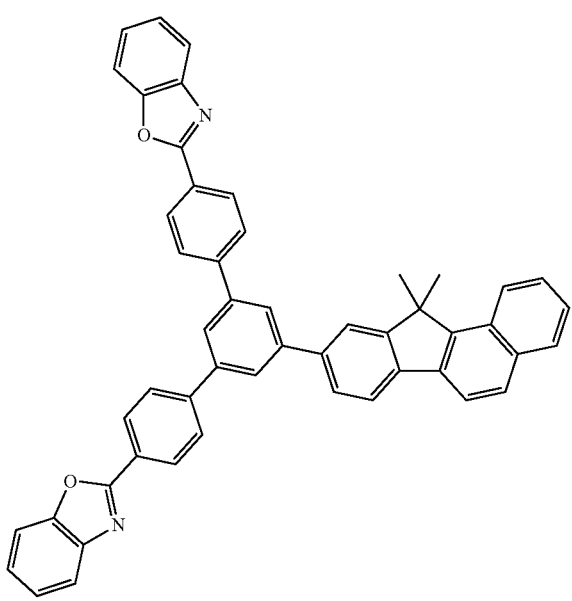
192
-continued
58
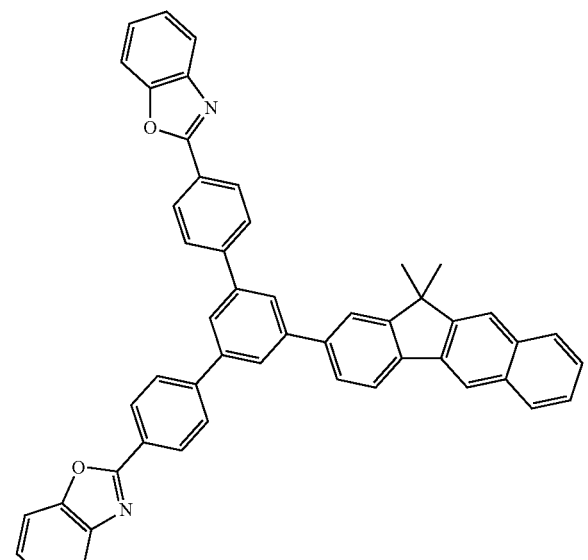
59
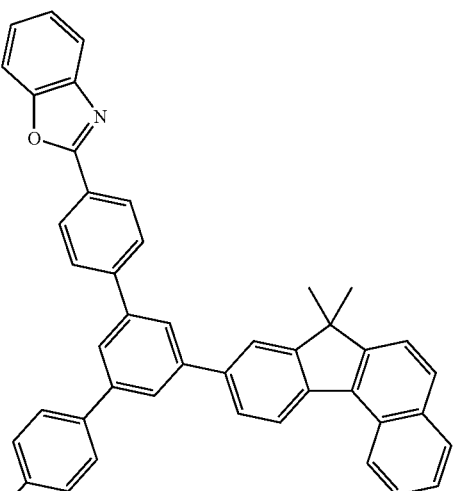

193
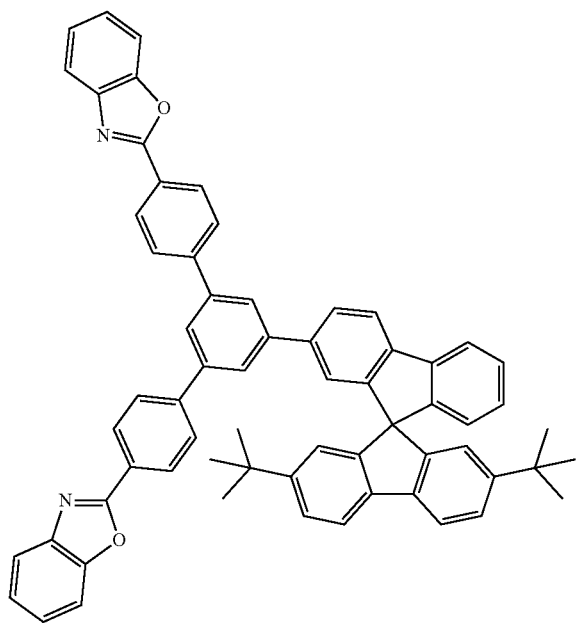
194
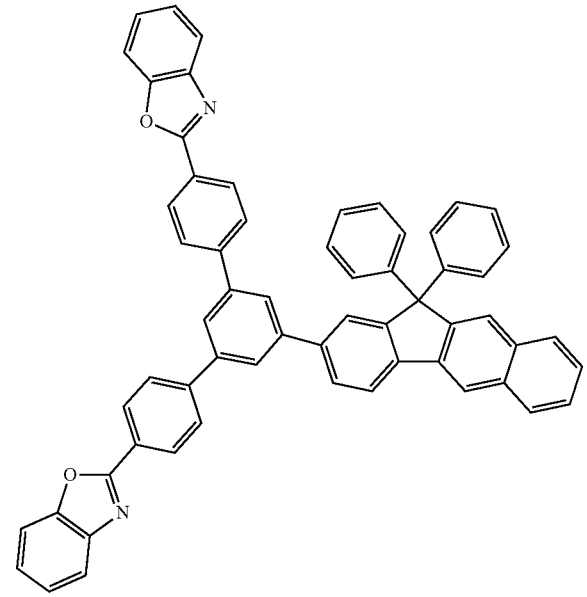
61
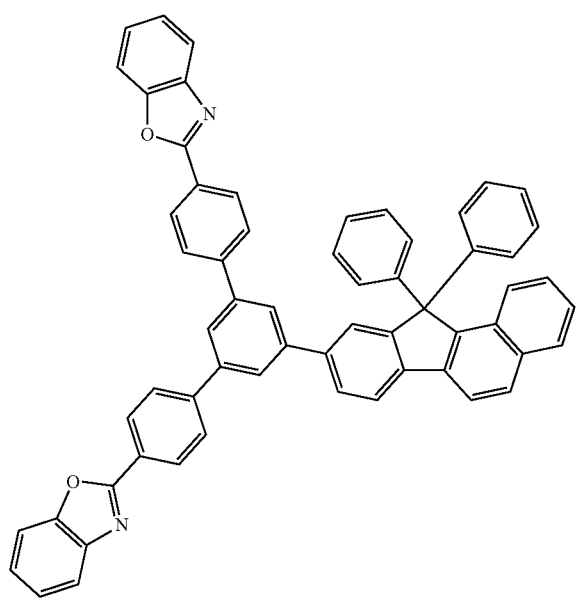
63
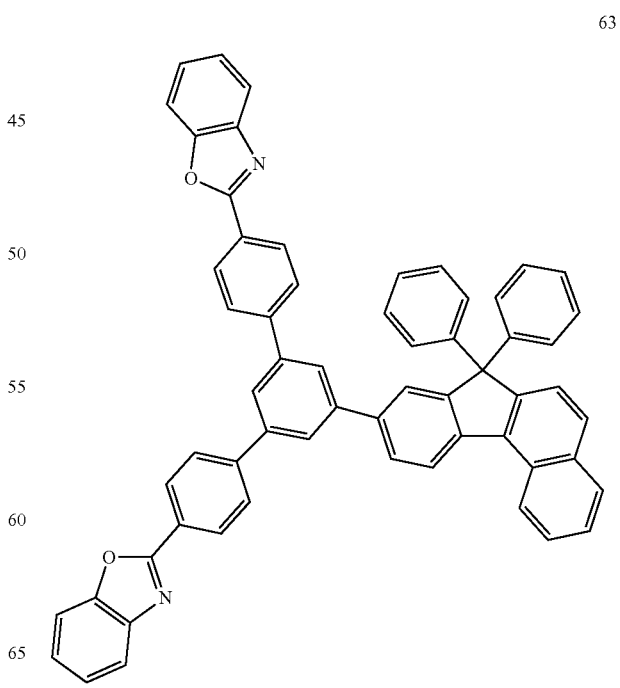

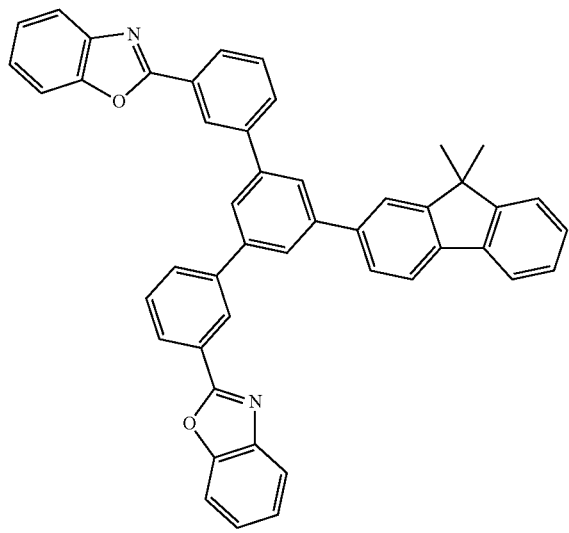
64
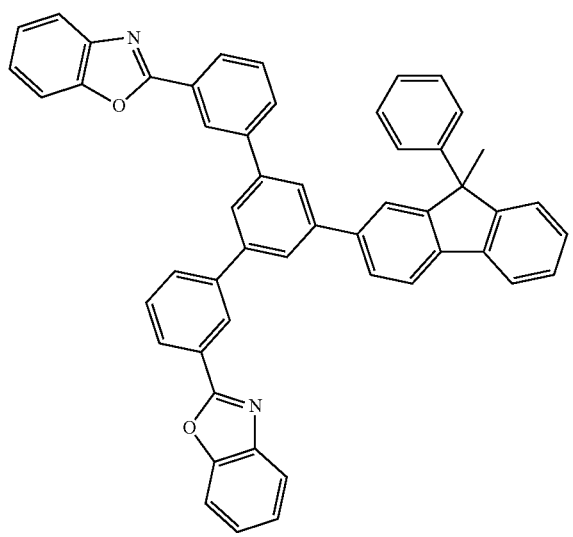
65
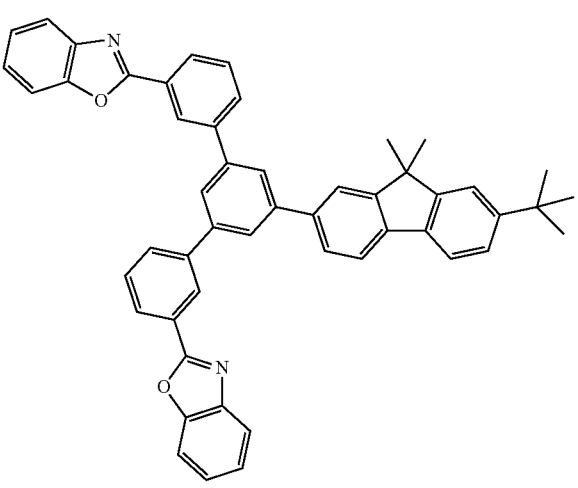
66
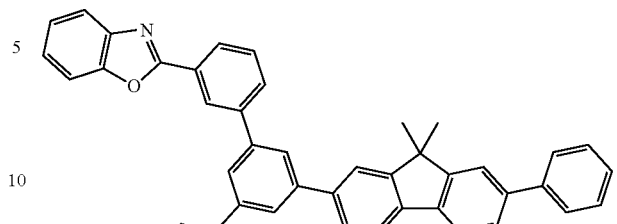
67
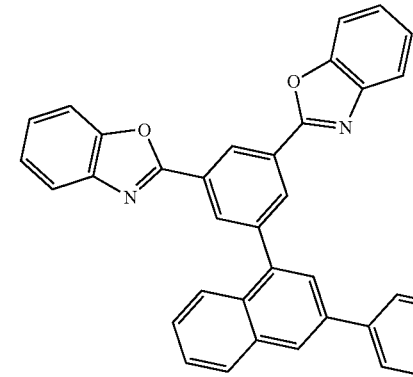
68
69

-continued
70
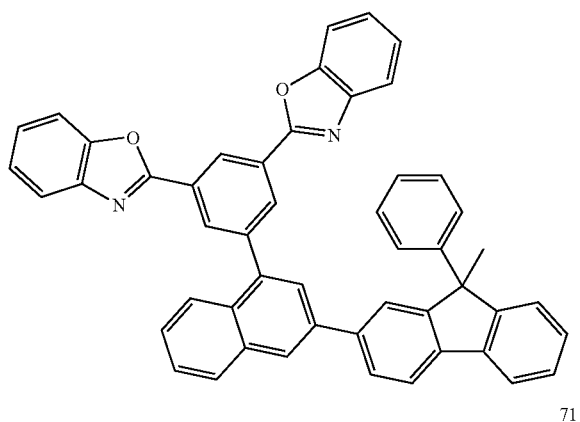
71
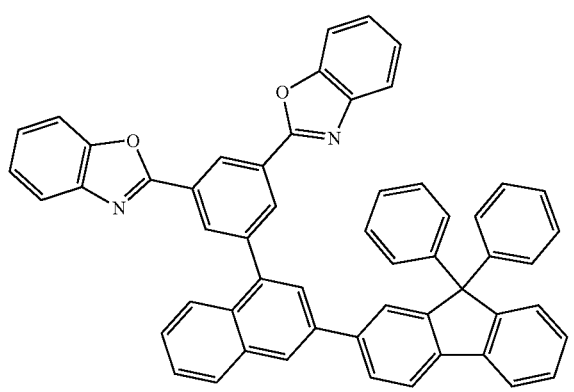
72
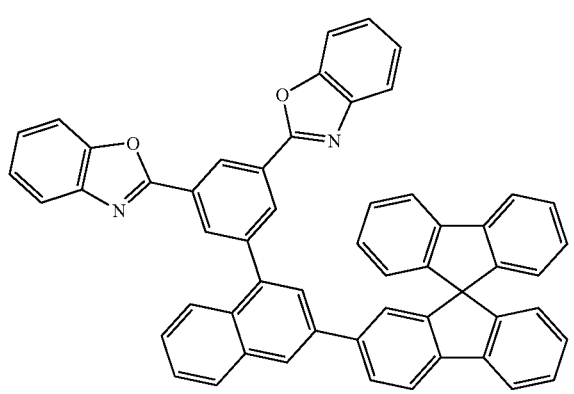
73
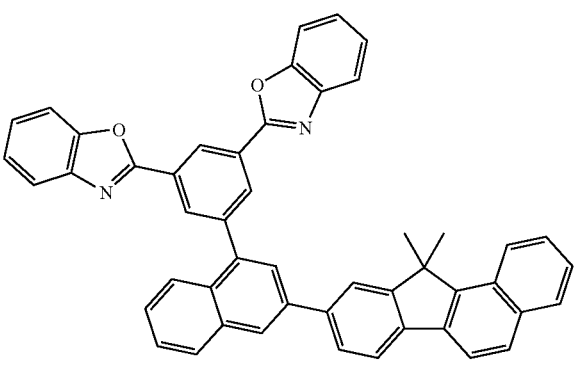
-continued
74
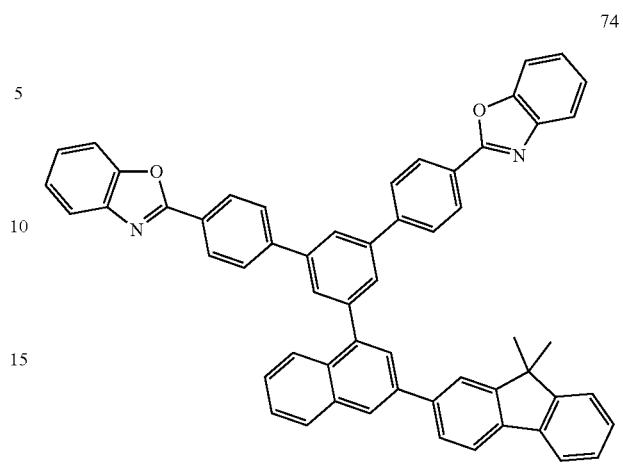
75
76

77
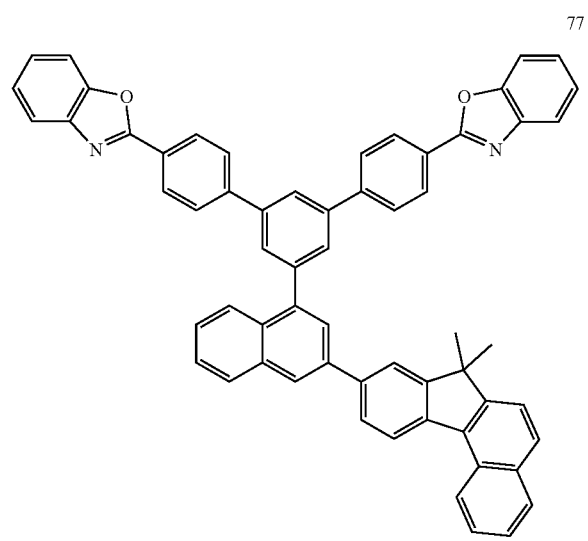
78
79
80
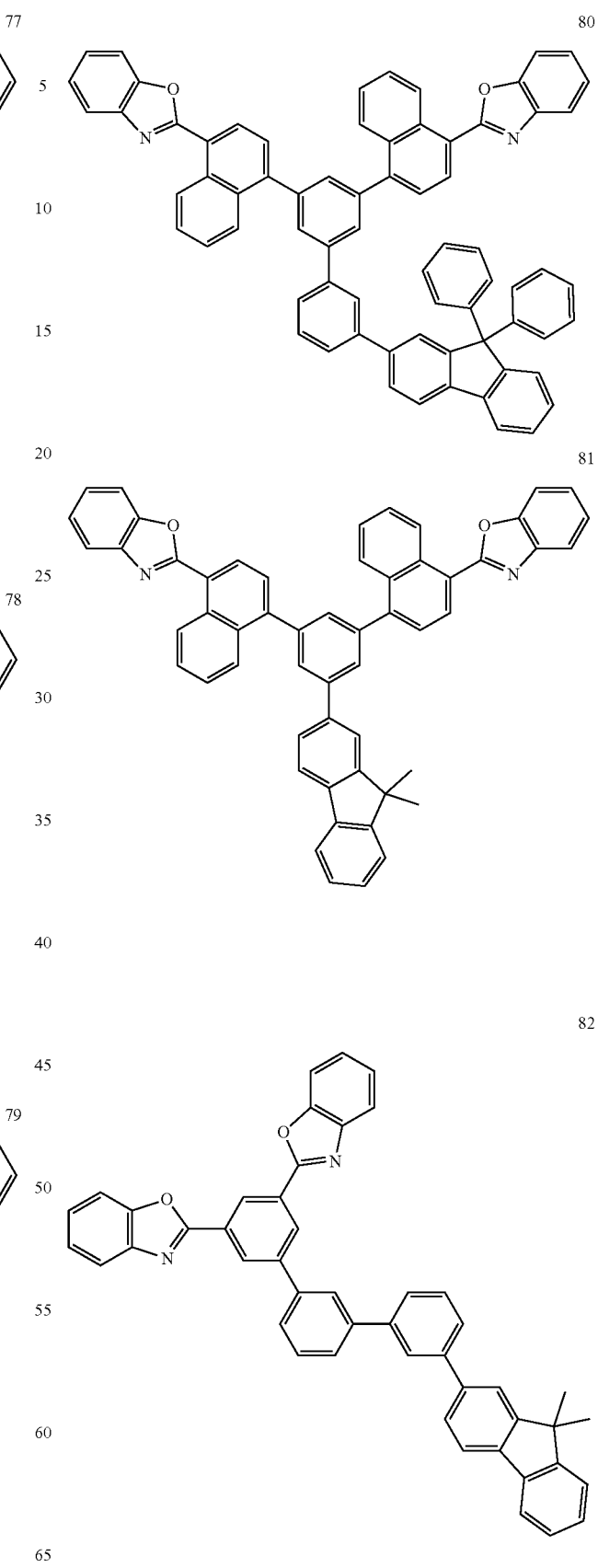
81
82

83
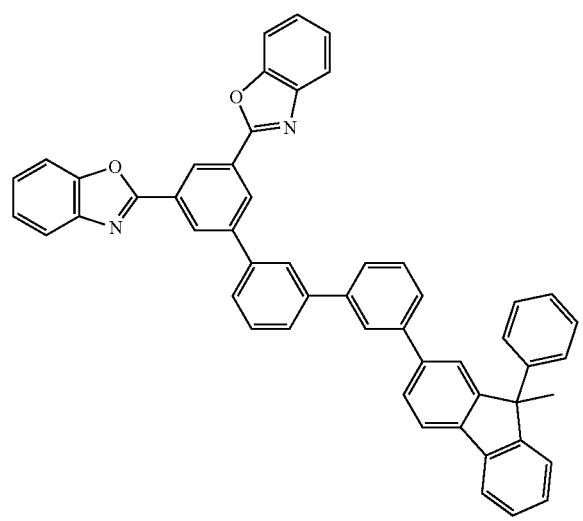
84
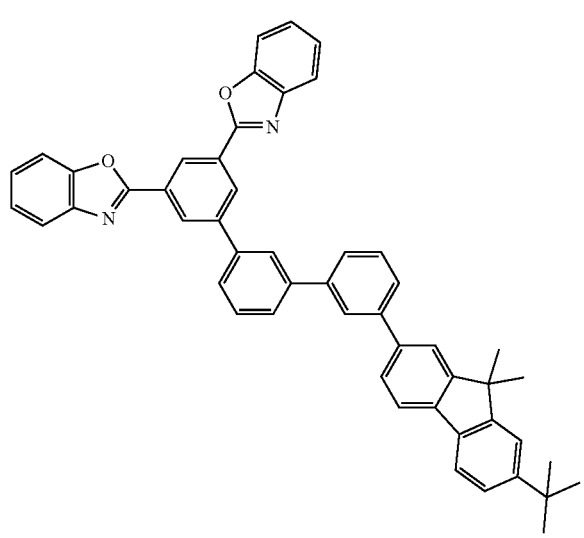
85
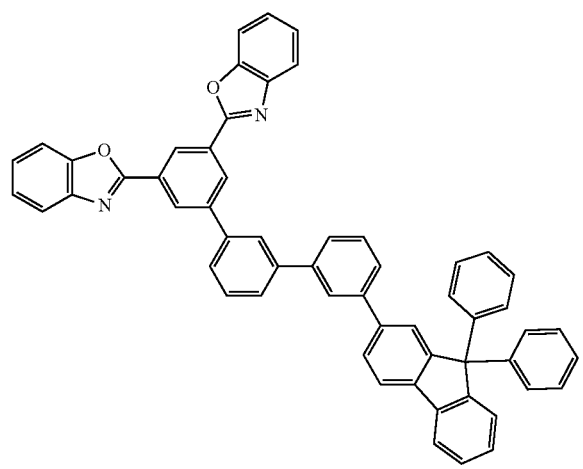
86
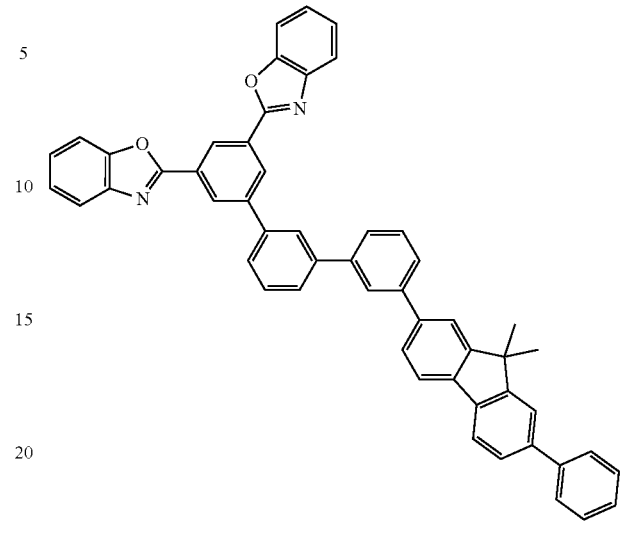
87
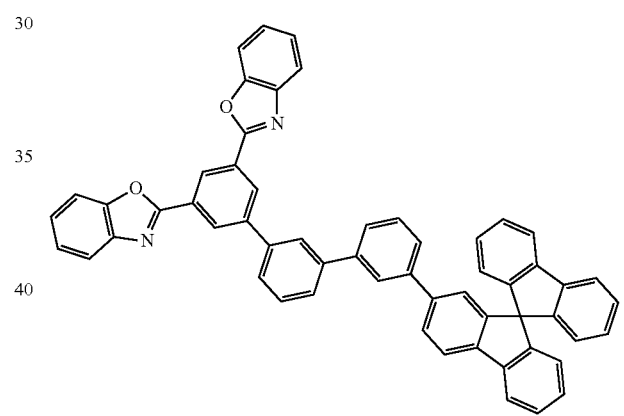
88
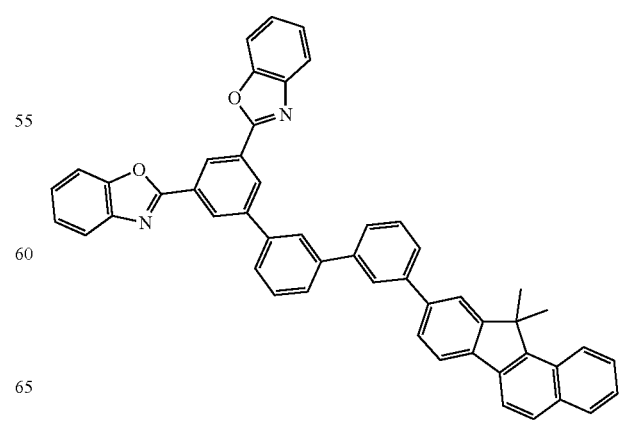

89
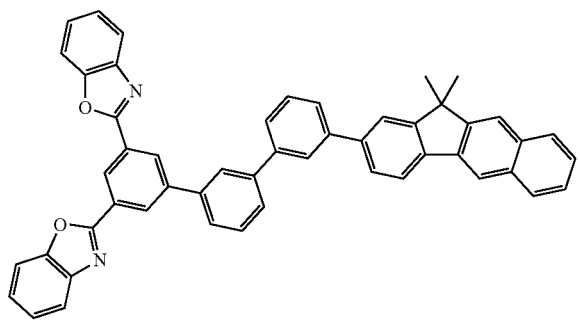
90
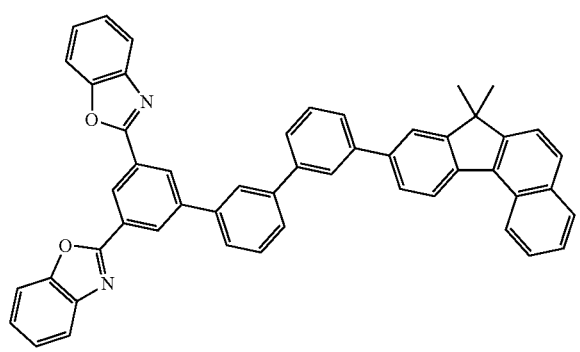
91
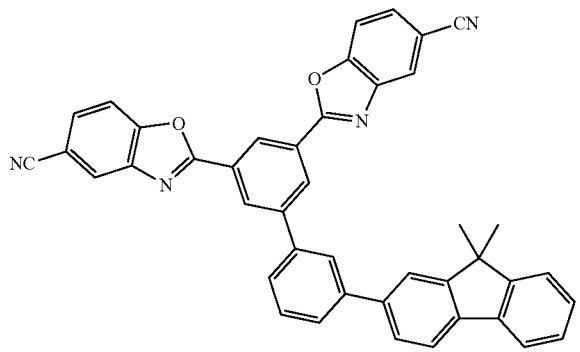
92
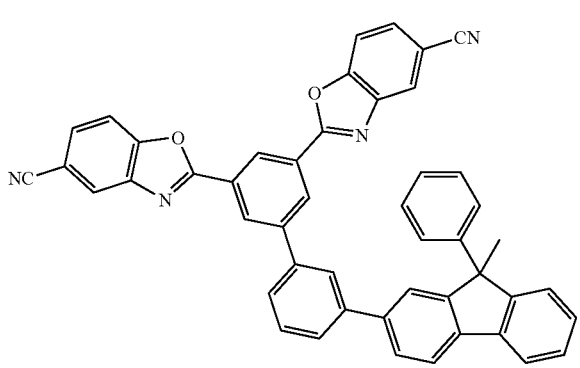
93
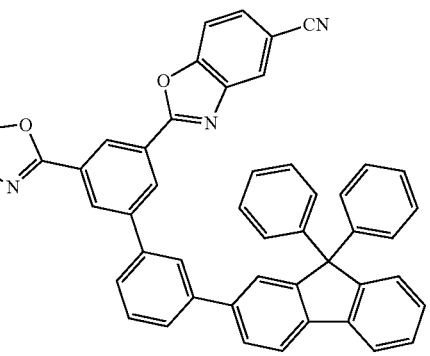
94
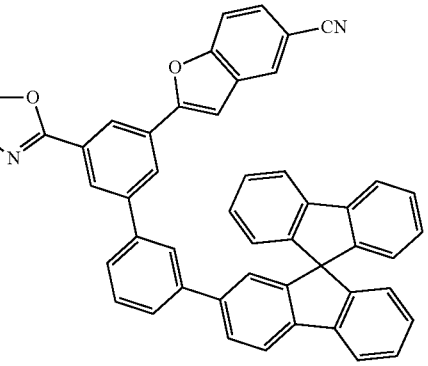
95
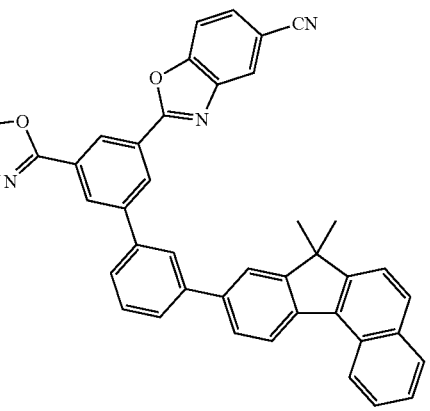
96
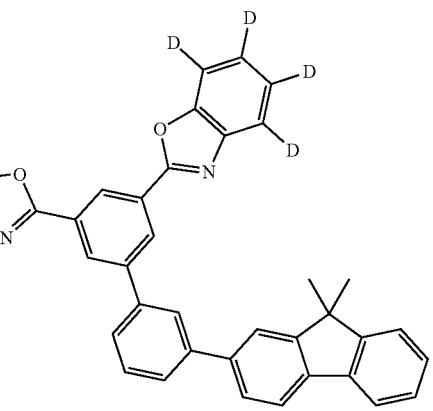

97
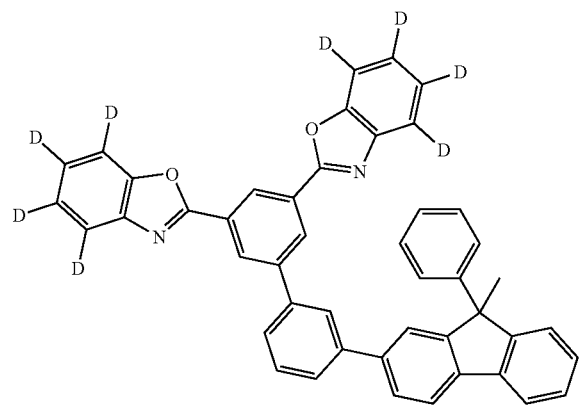
98
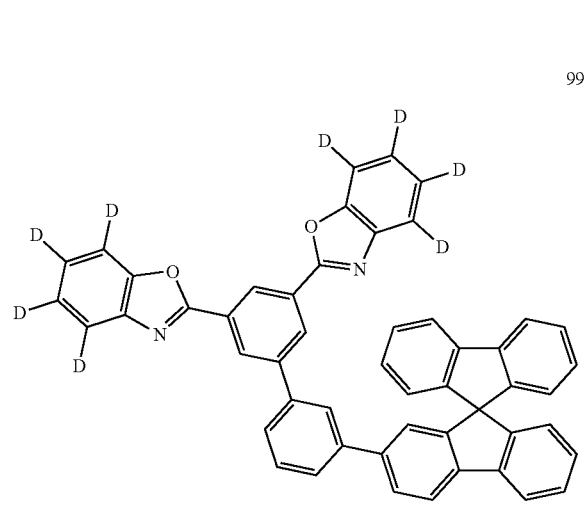
99
100
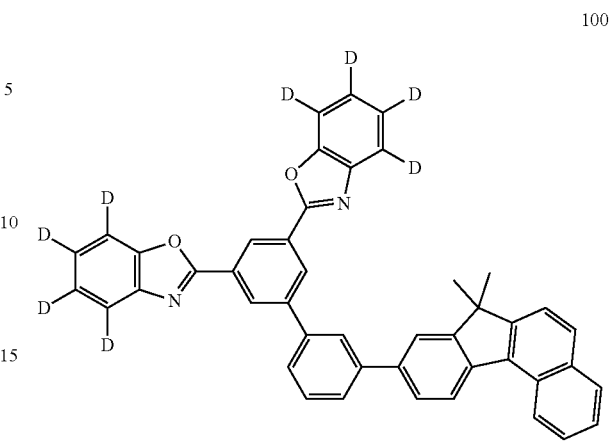
101
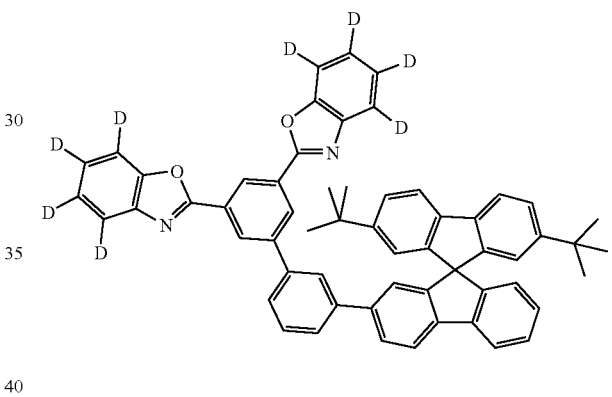
102
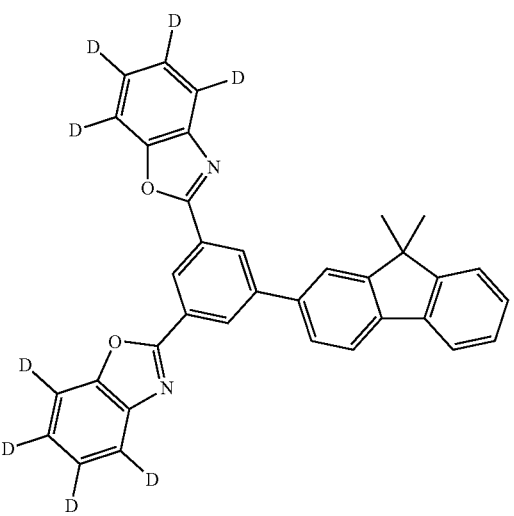

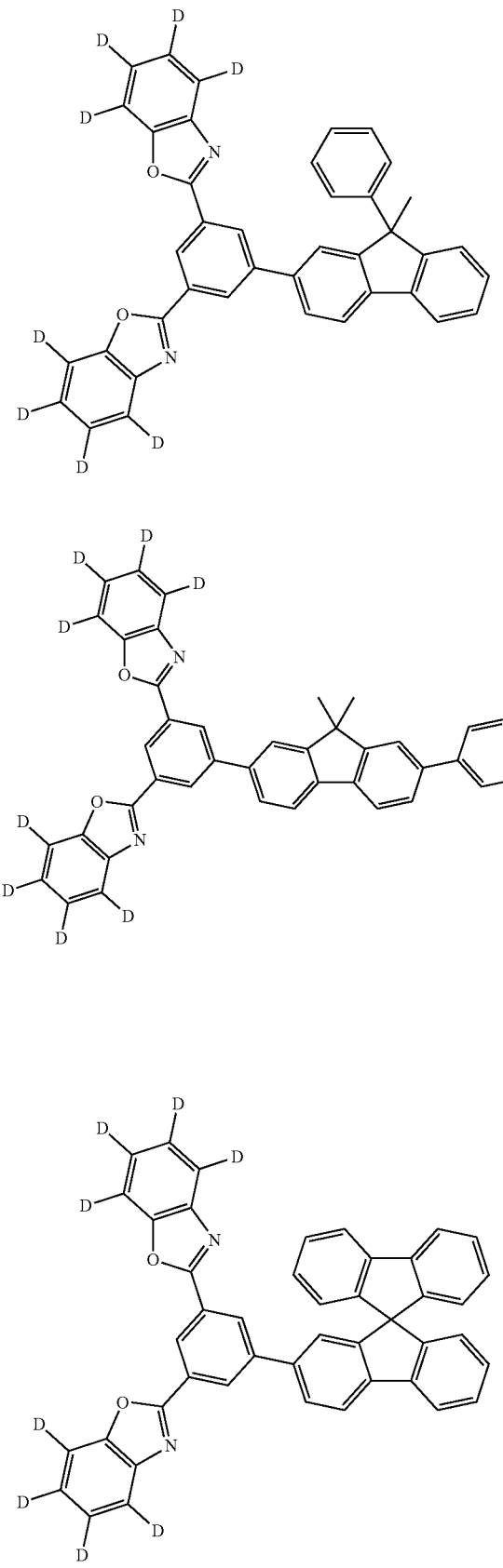
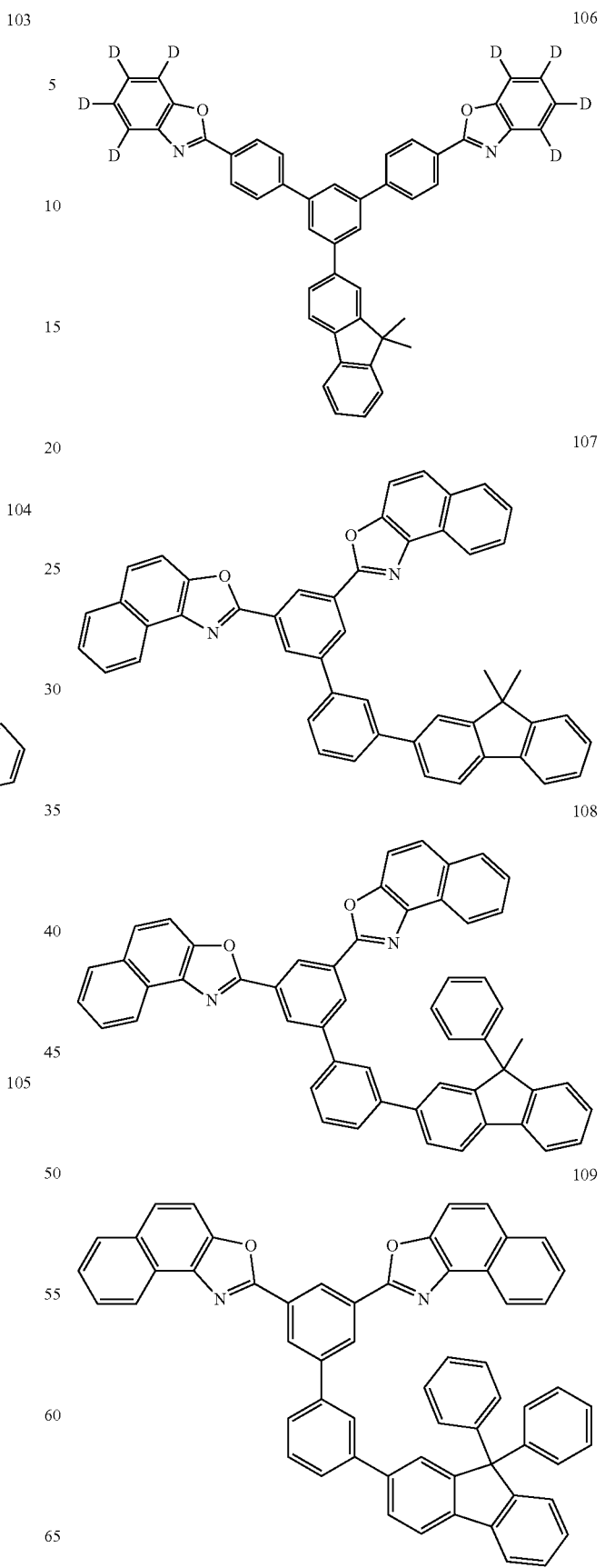

209
-continued
110
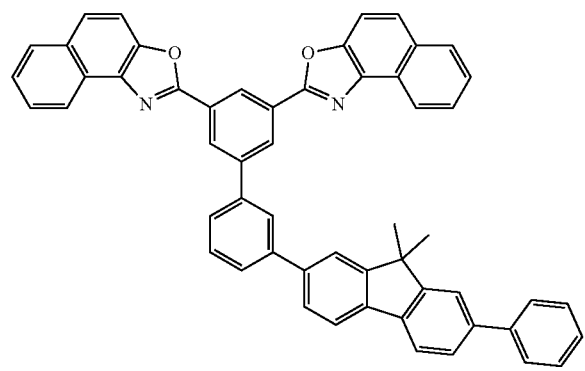
111
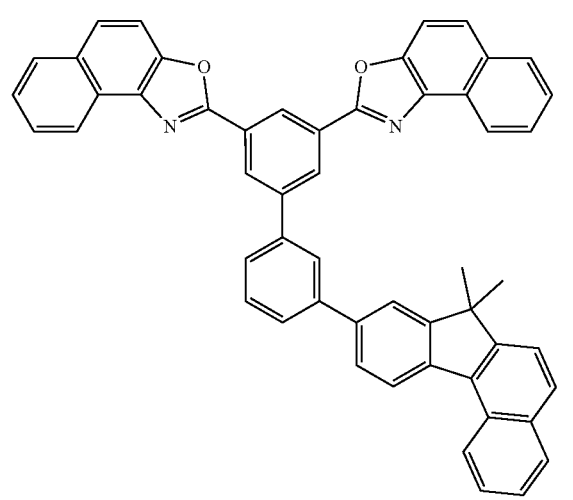
112
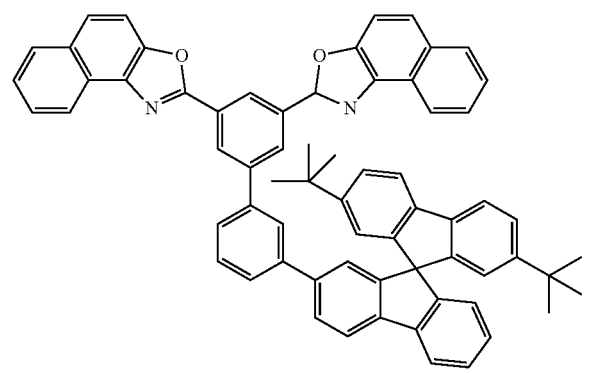
210
-continued
113
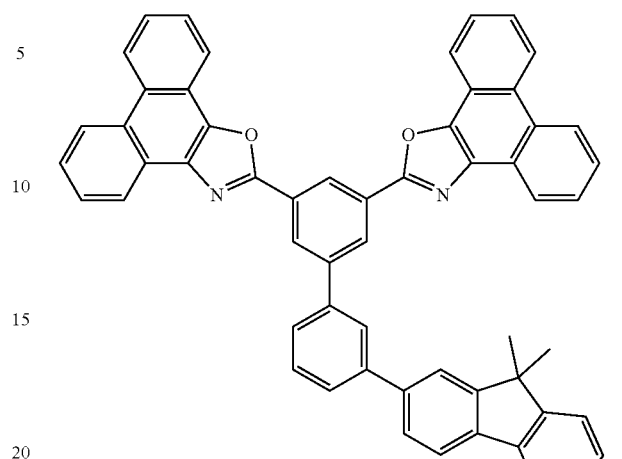
114
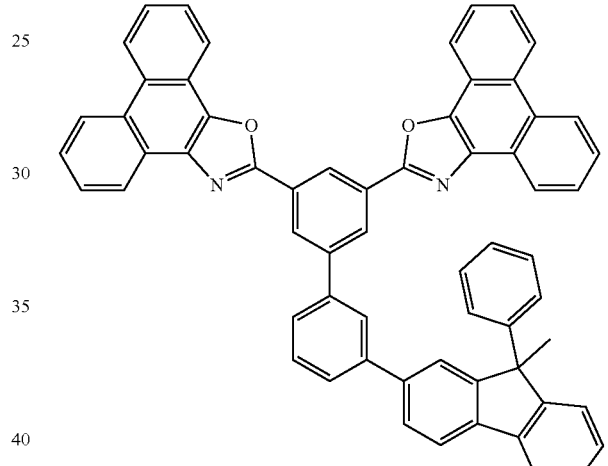
115
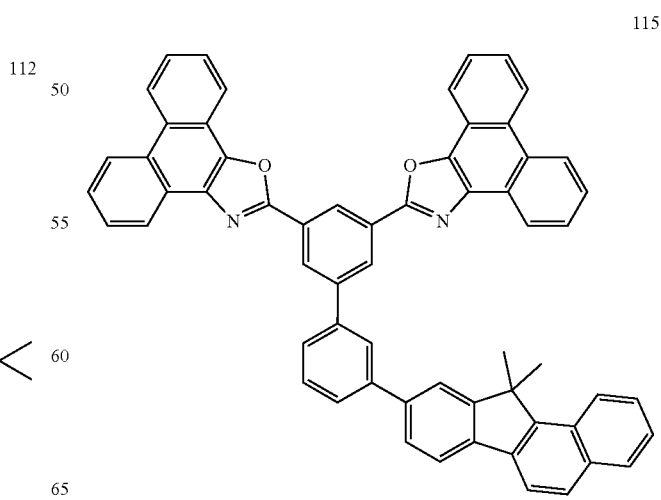

116
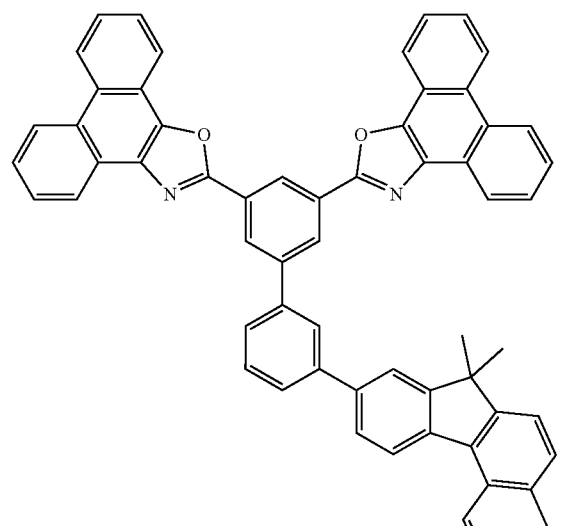
117
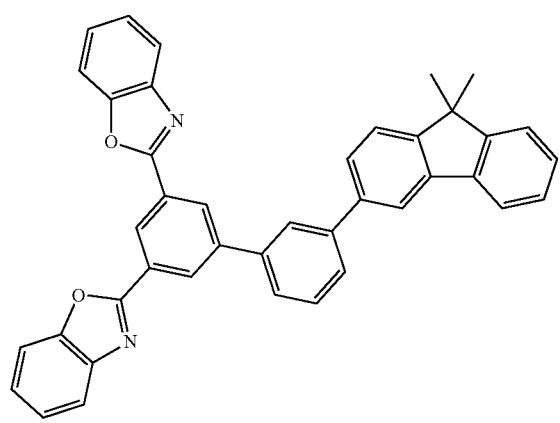
118
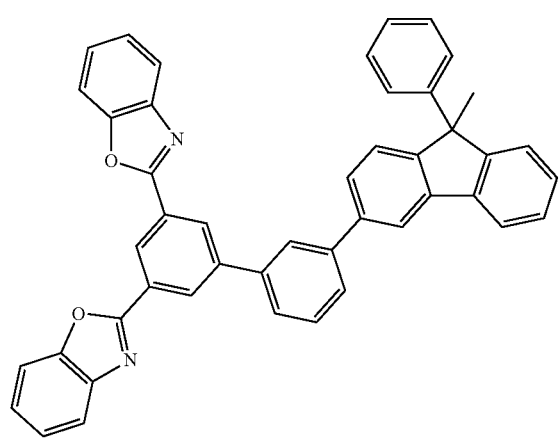
119
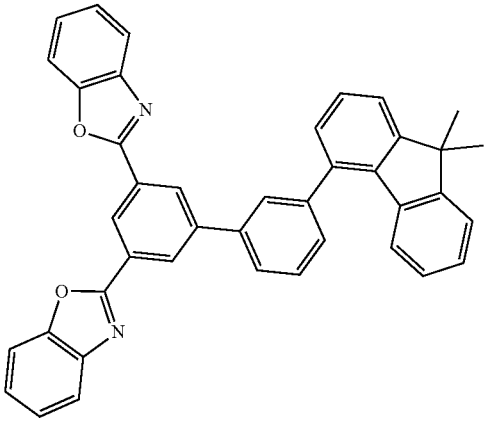
120
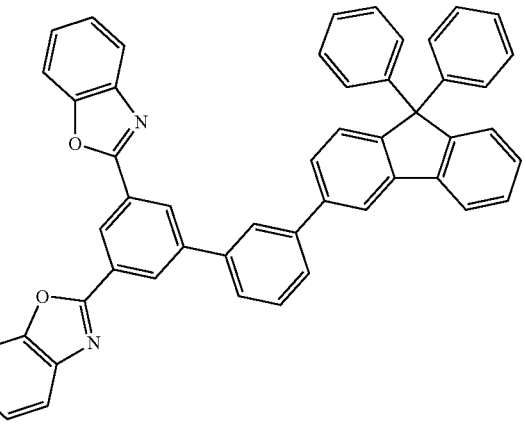
121
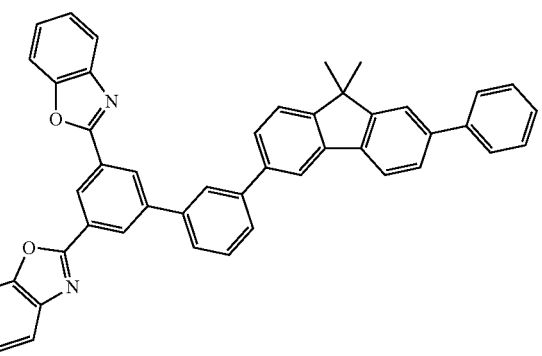
122
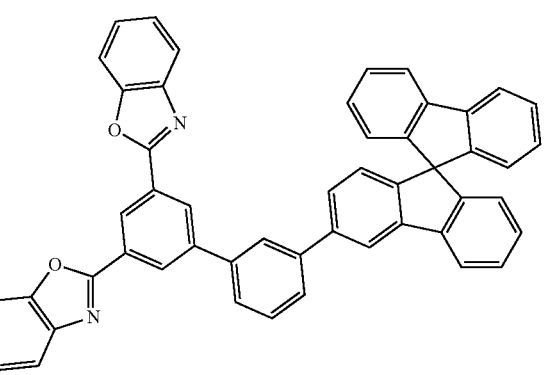

213
-continued
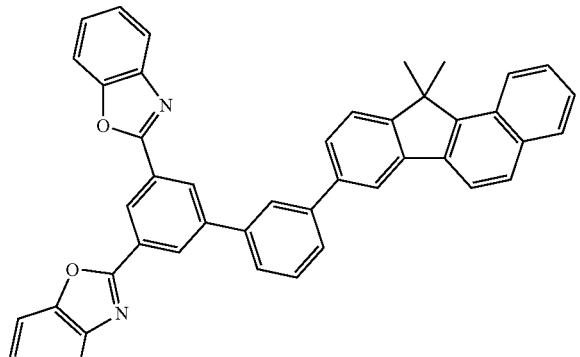
123
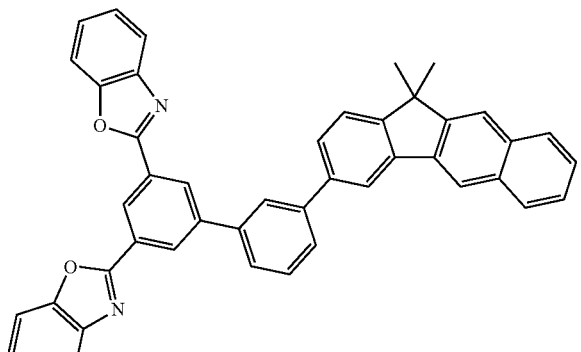
124
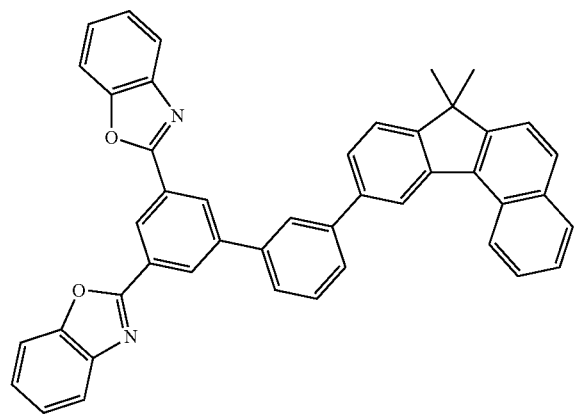
125
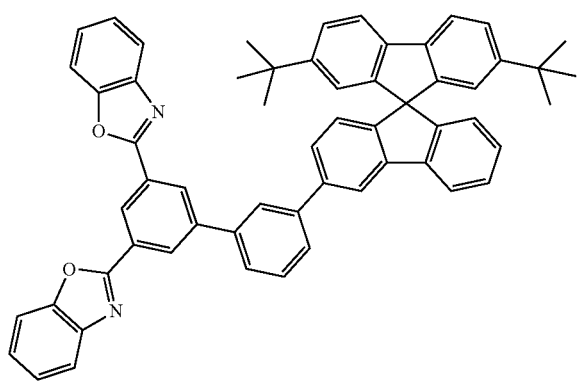
126
214
-continued
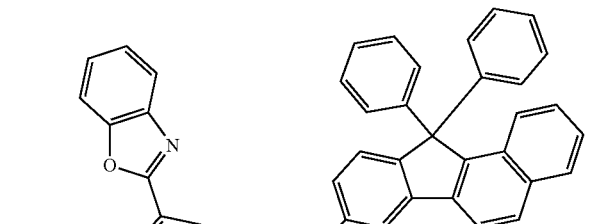
127
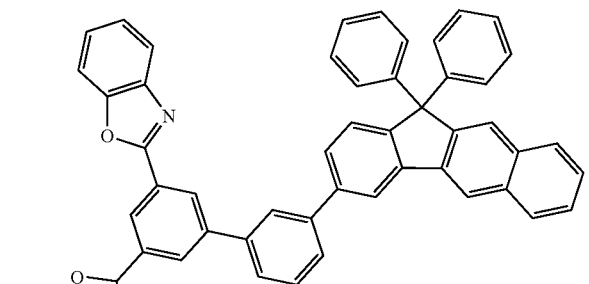
128
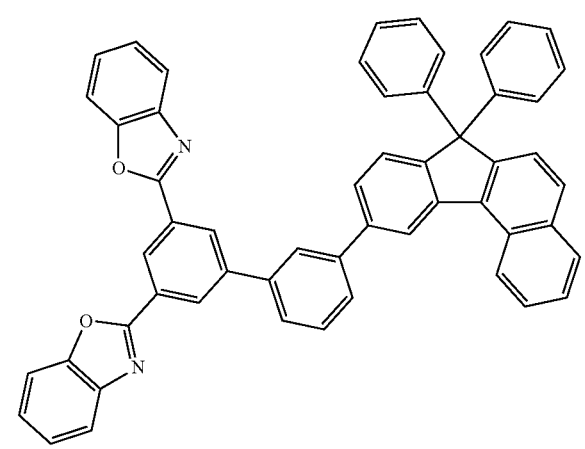
129

215
-continued
130
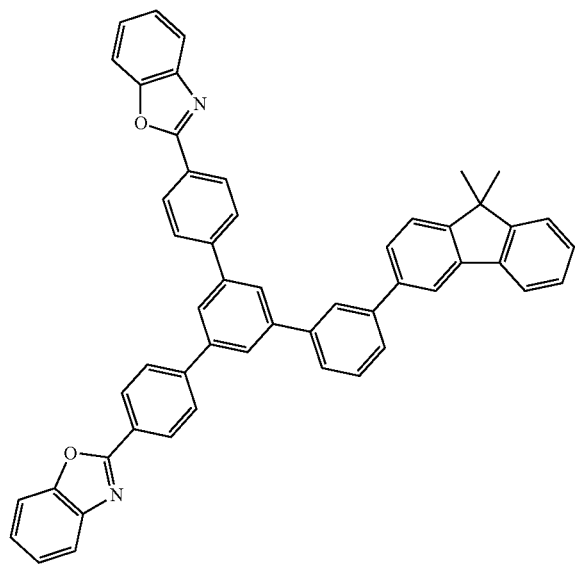
131
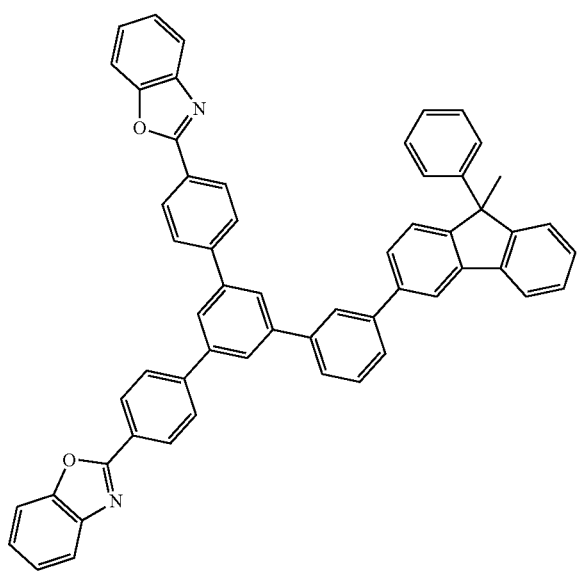
216
-continued
132
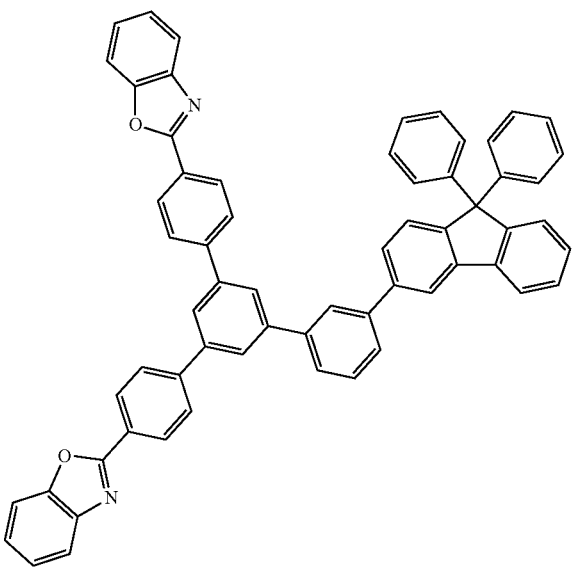
133
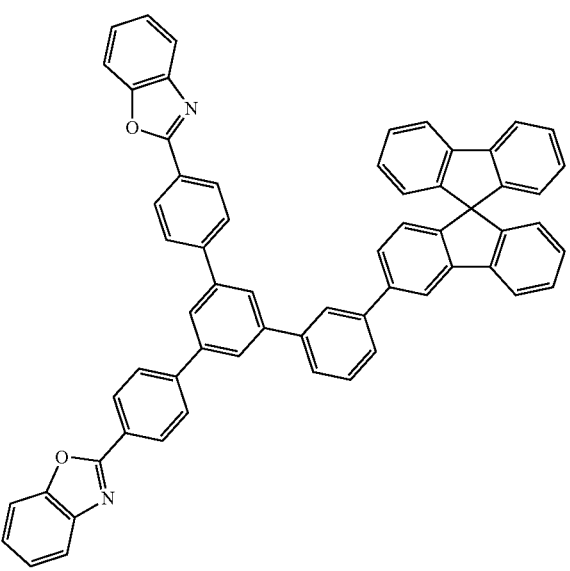

134
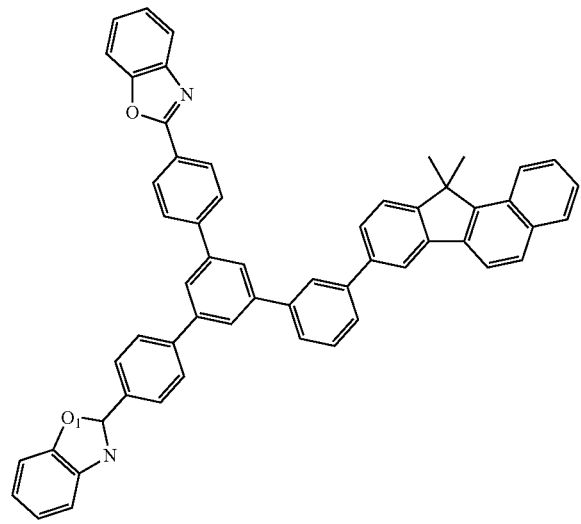
135
138
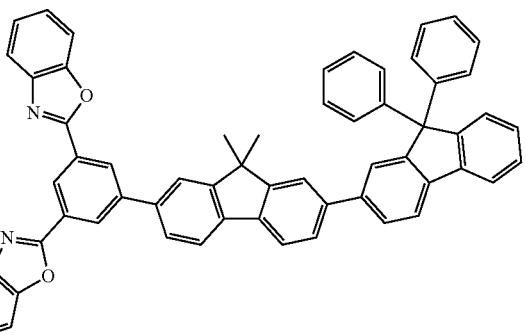
139
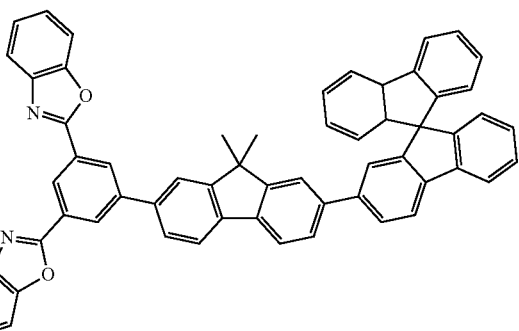
136
140
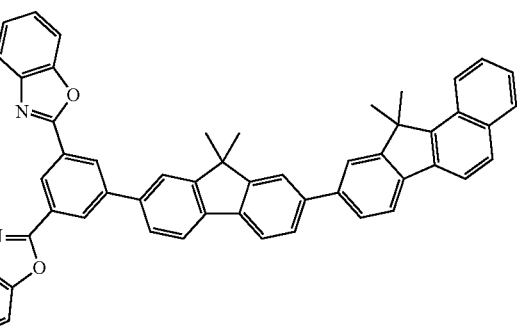
137
141
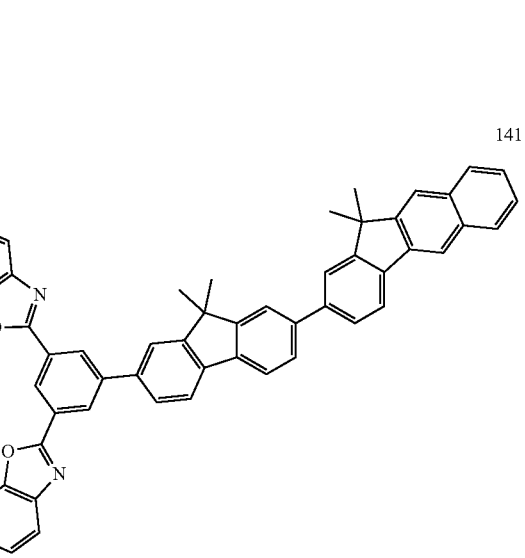

142
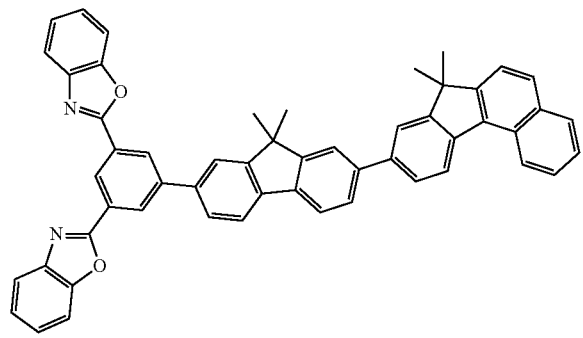
143
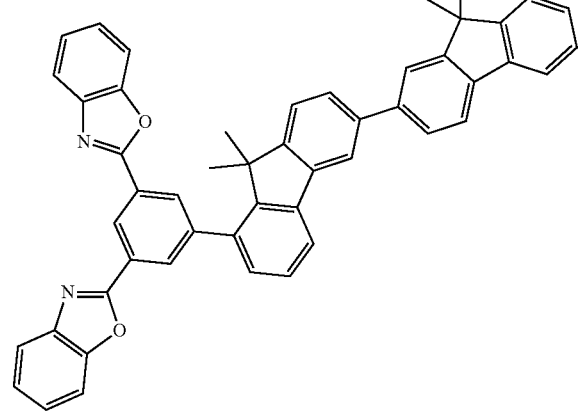
144
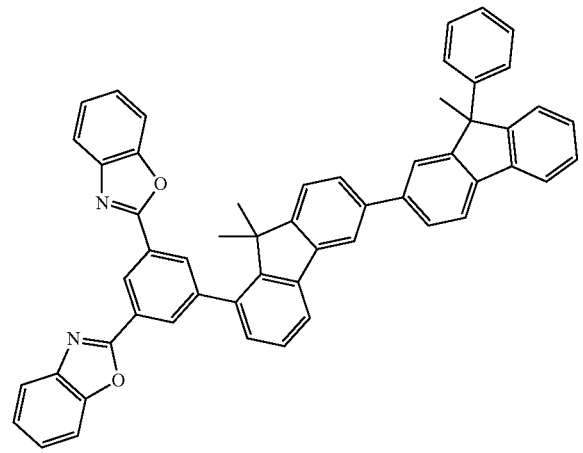
145
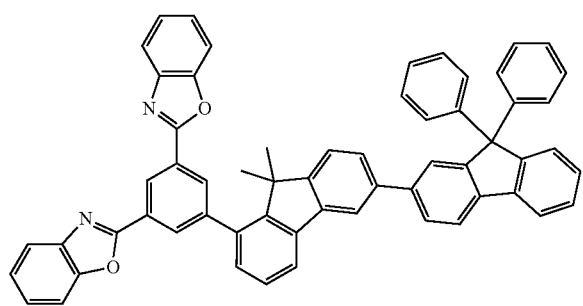
146
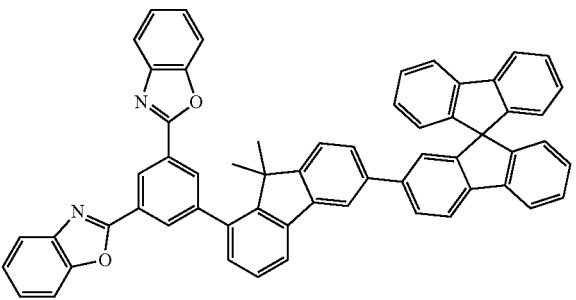
147
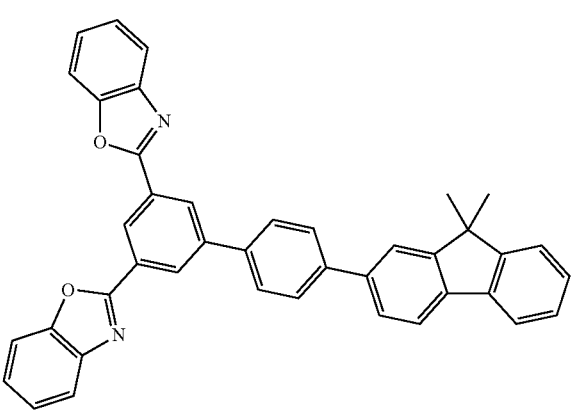
148
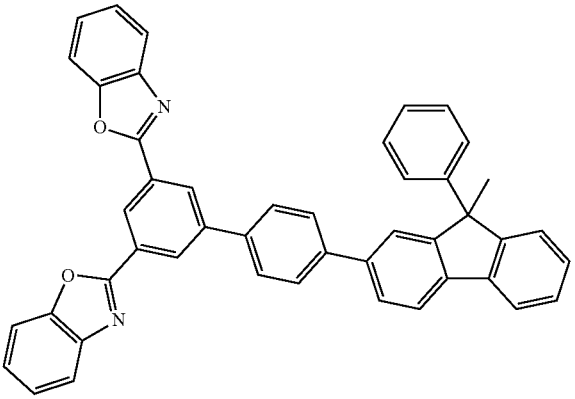
149
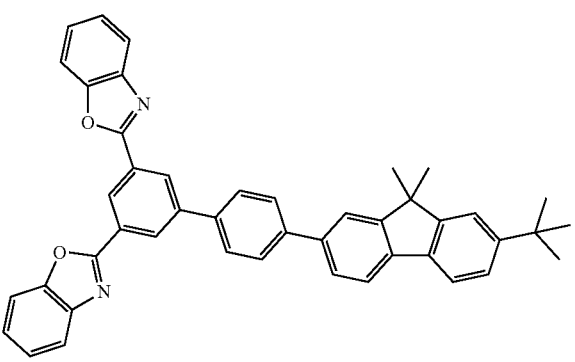

-continued
150
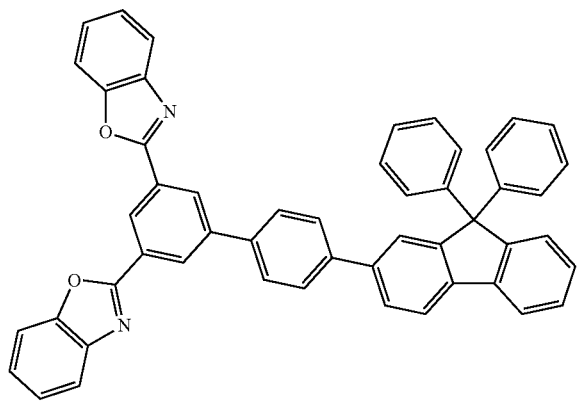
151
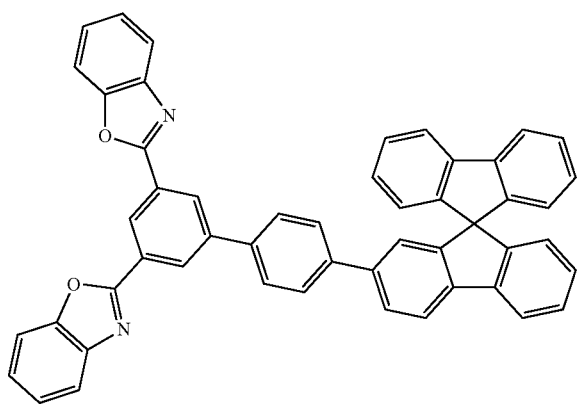
152
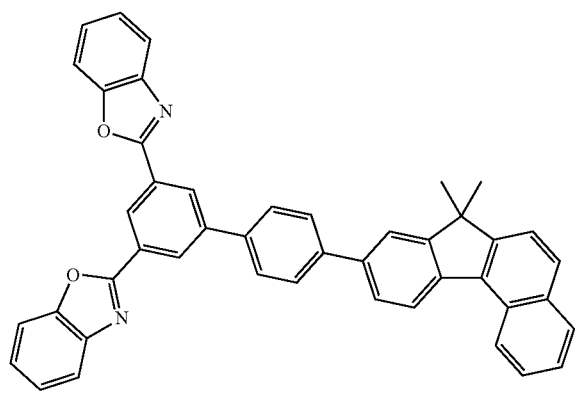
-continued
153
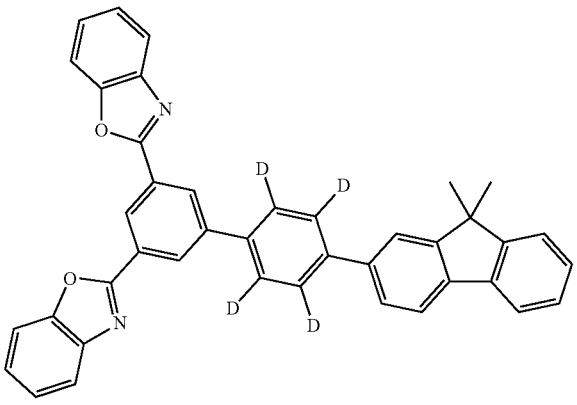
154
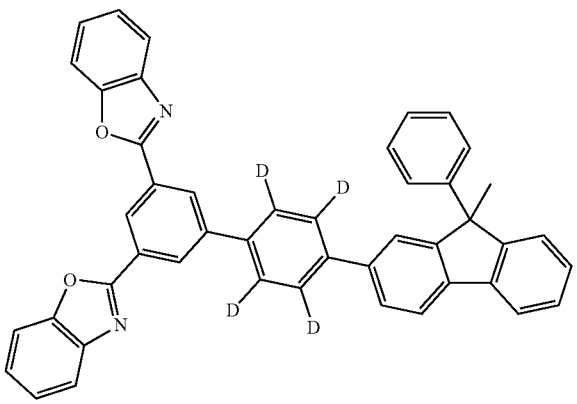
155
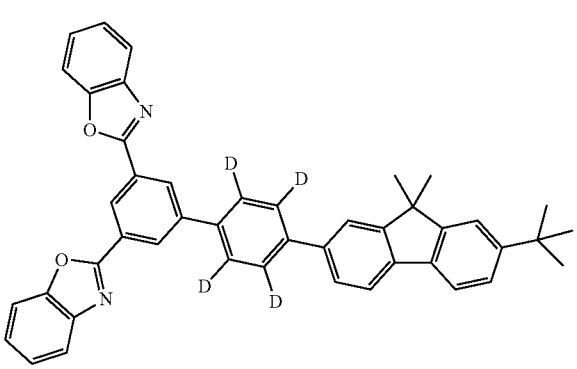
156
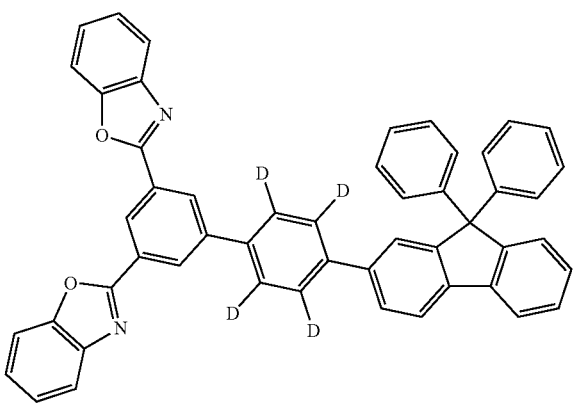

157
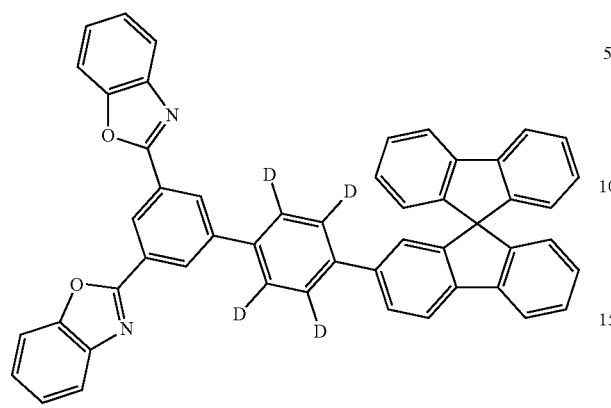
158
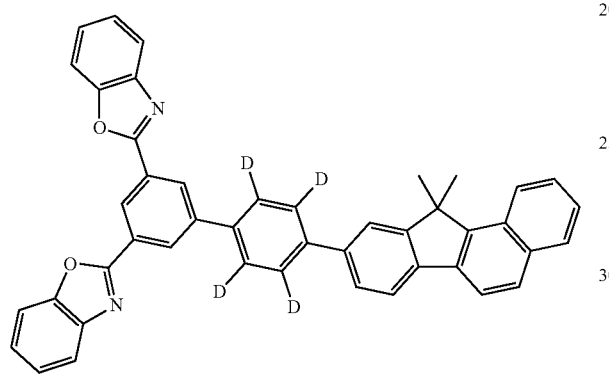
159
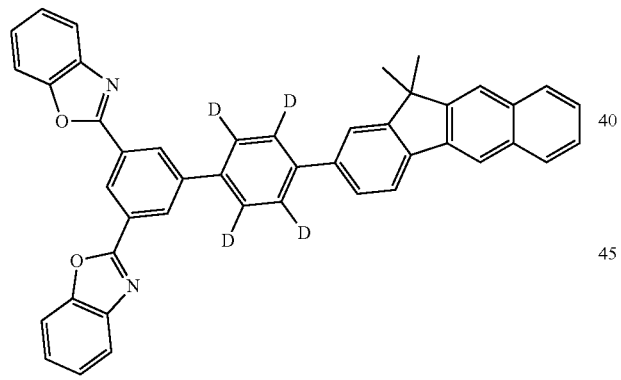
160
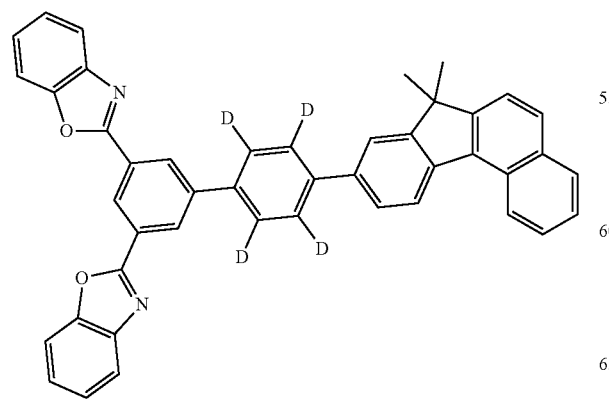
161
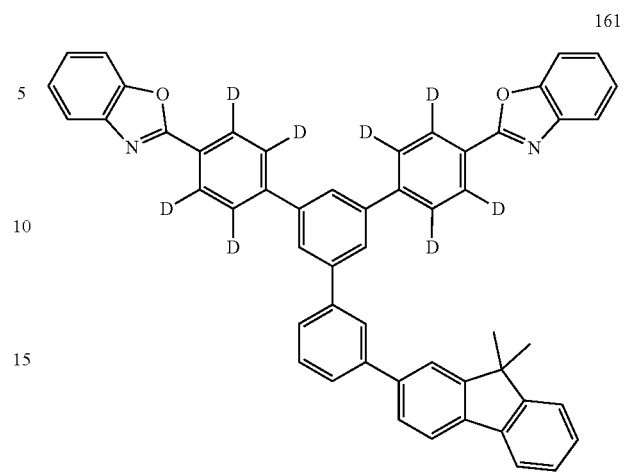
162
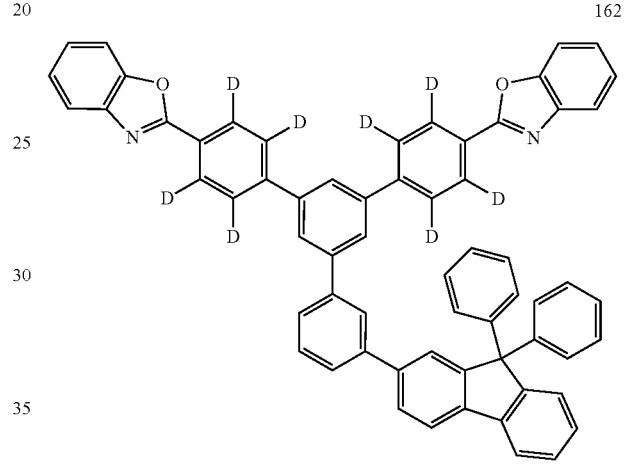
163
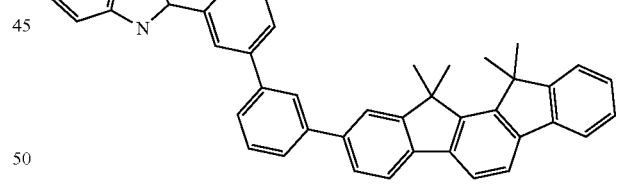
164
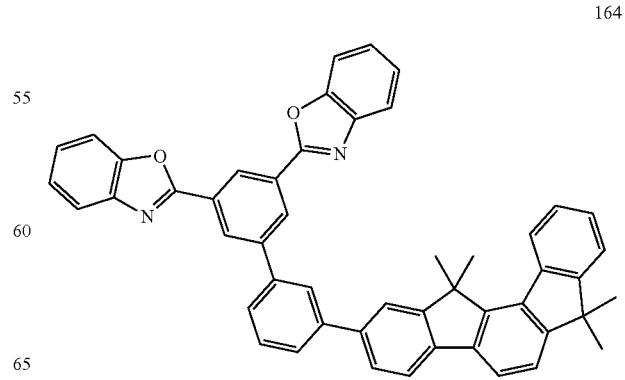

165
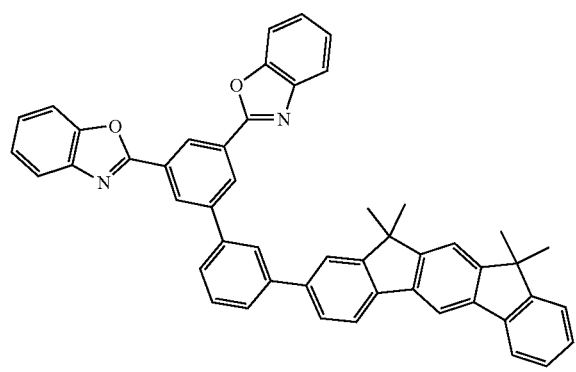
166
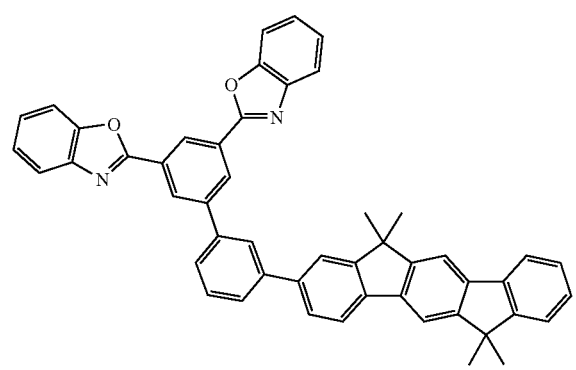
167
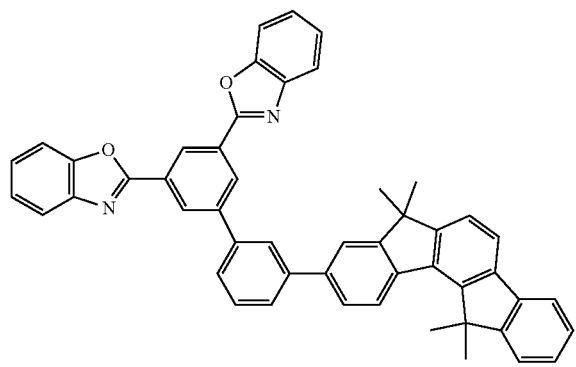
168
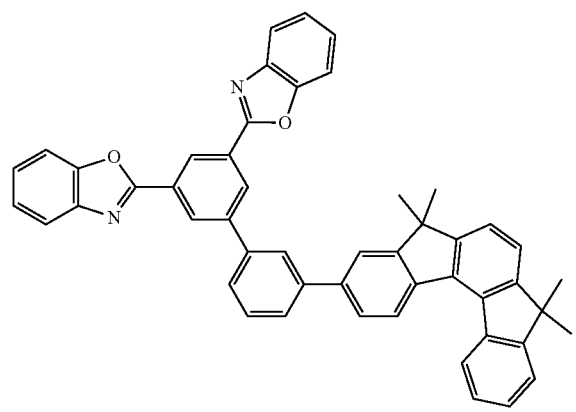
169
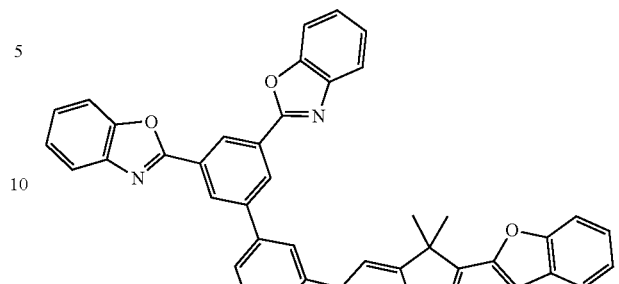
170
171
172
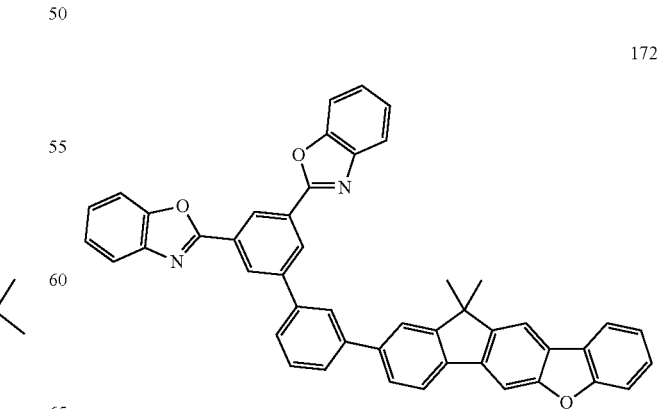

173
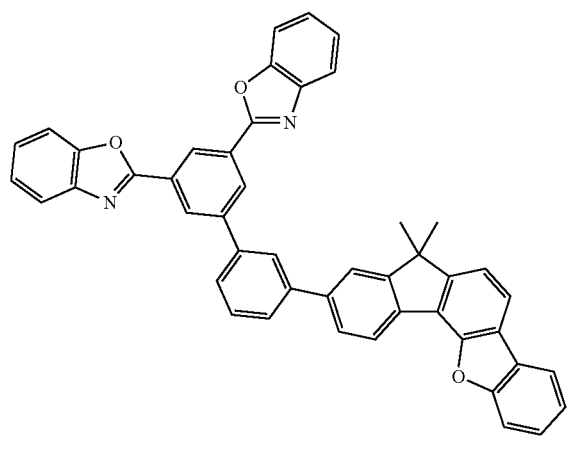
174
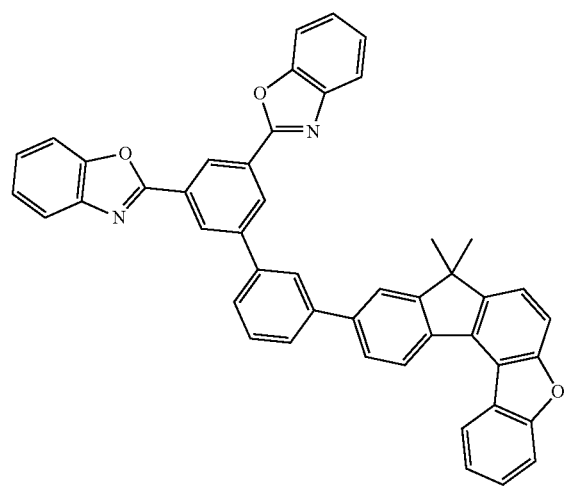
175
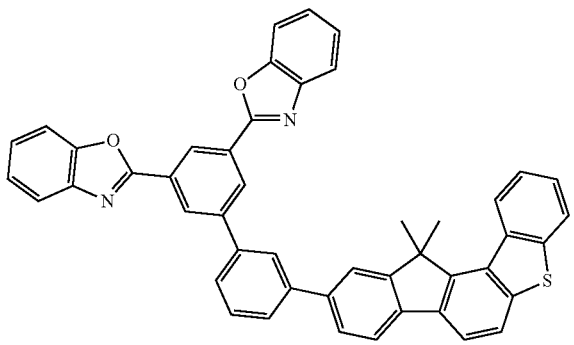
176
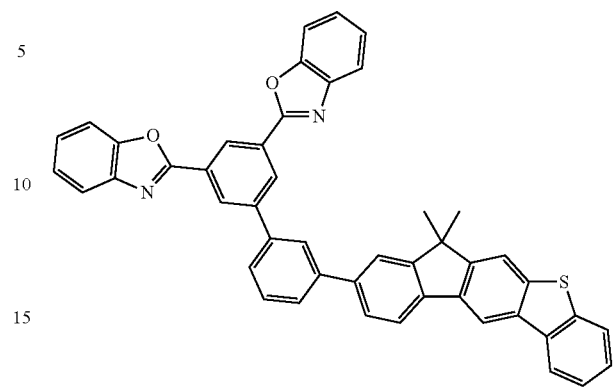
177
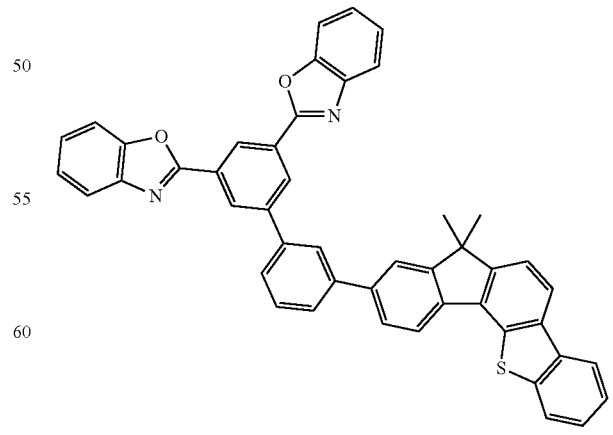
178

-continued
179
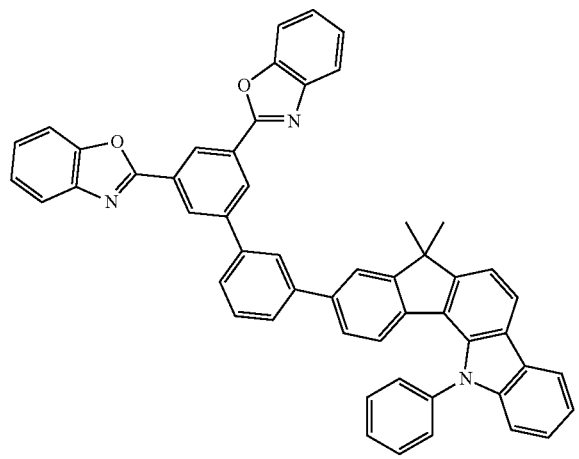
180
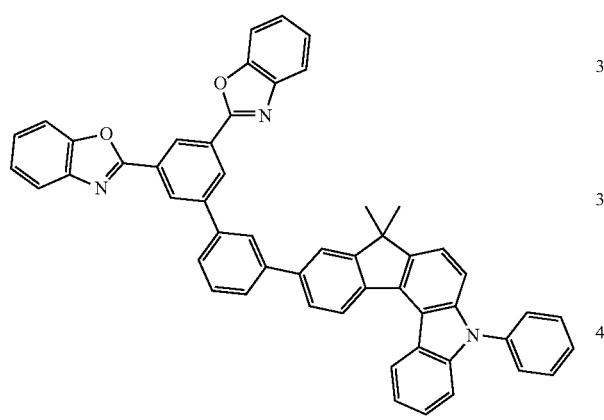
181
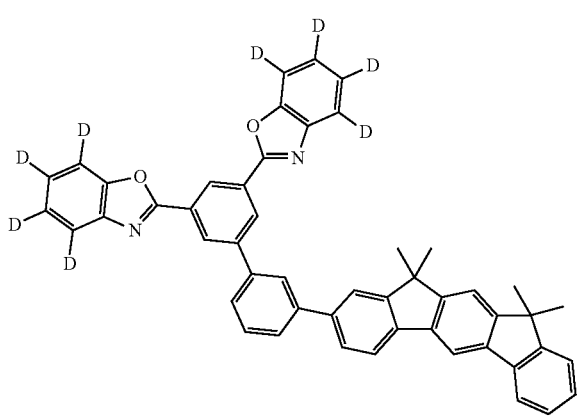
-continued
182
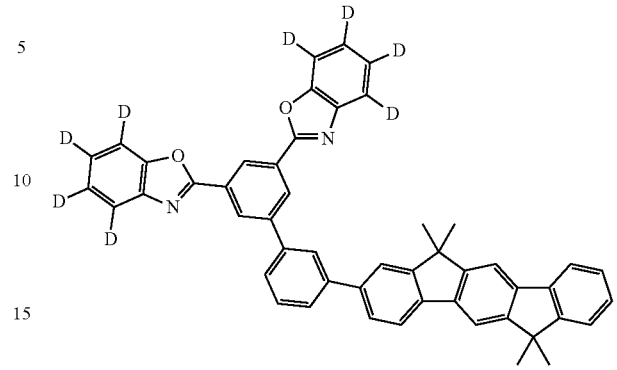
183
184

185
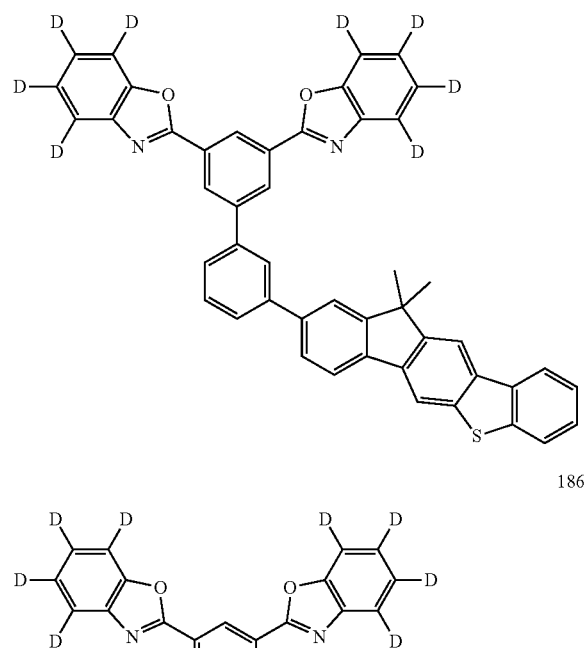
186
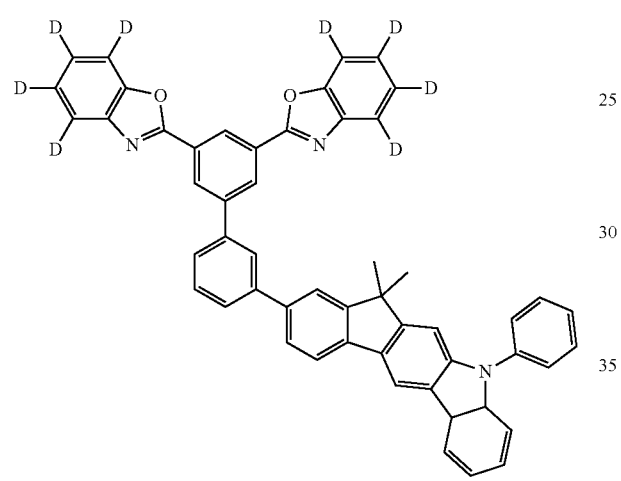
187
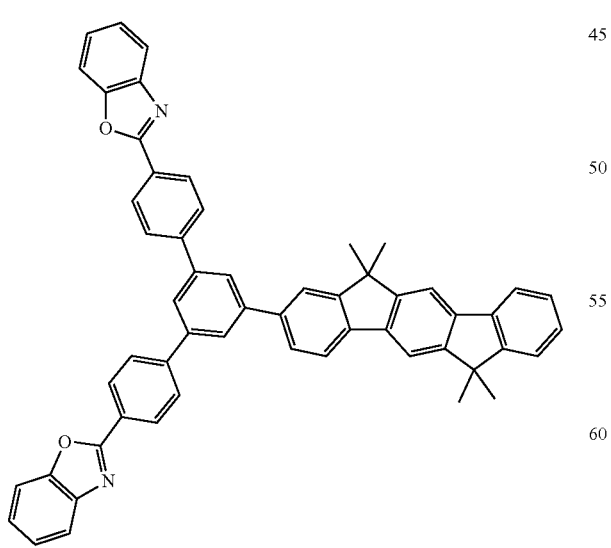
188
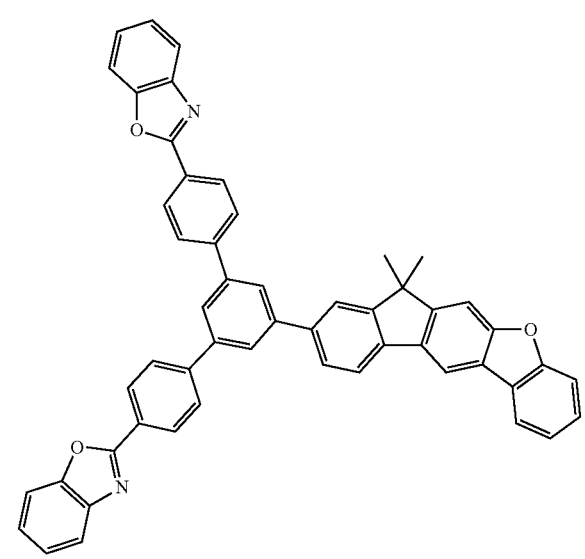
189
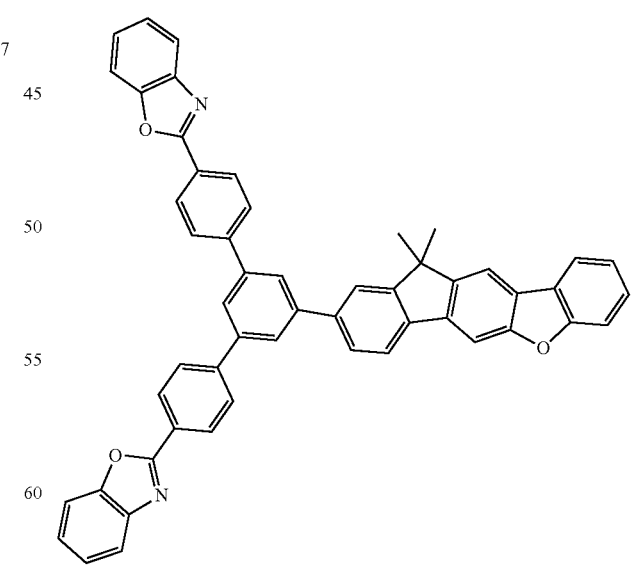

190
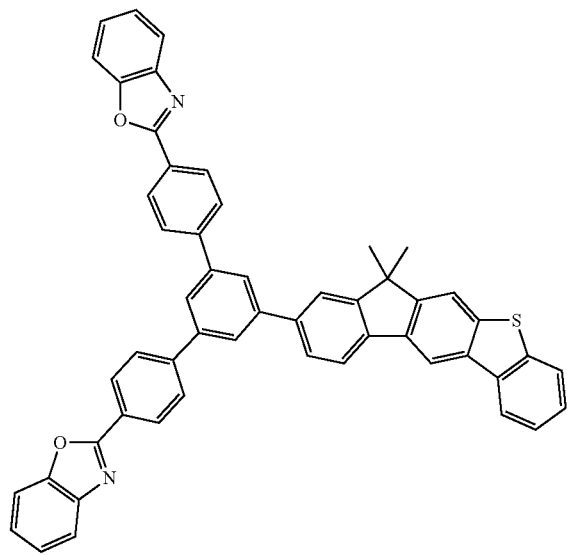
192
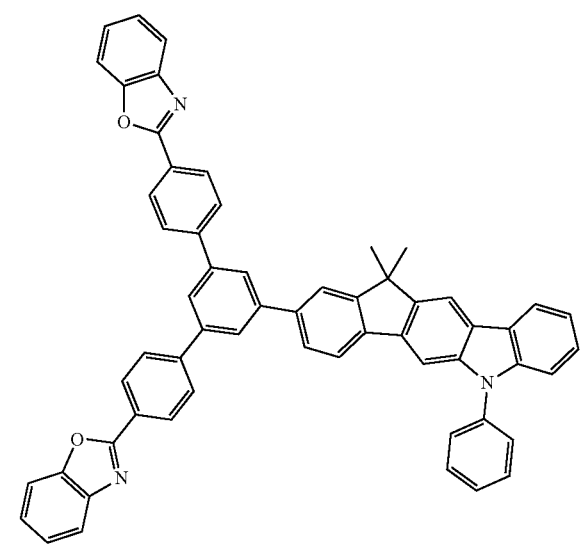
193
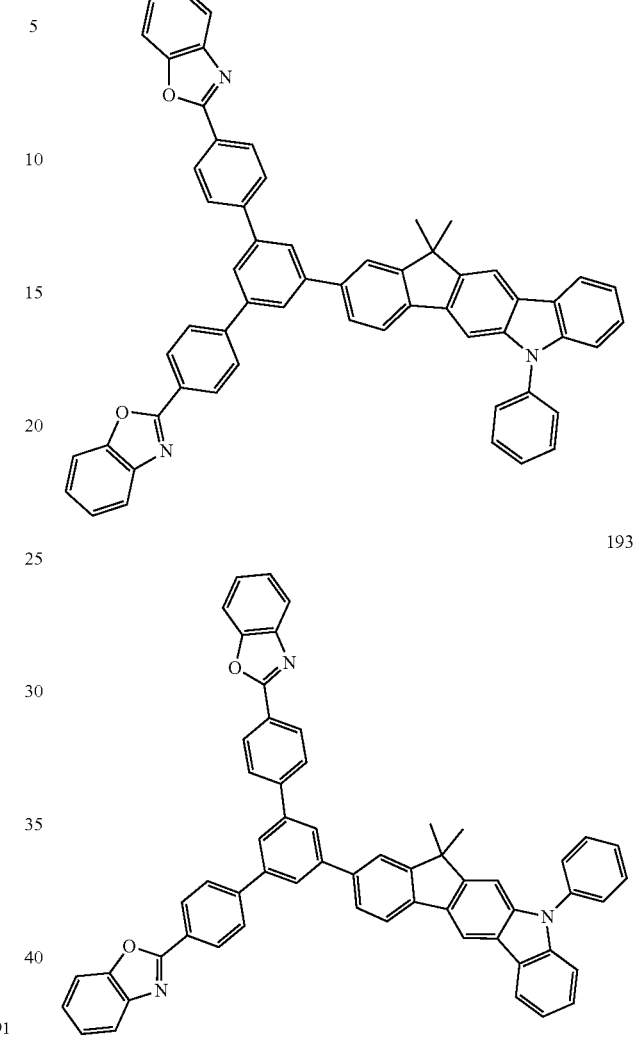
191
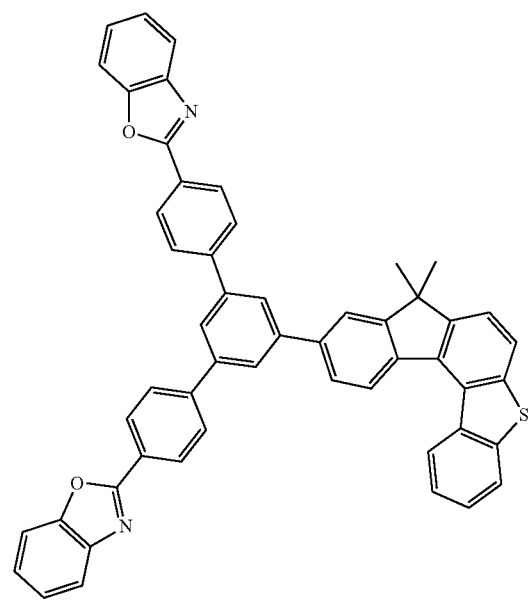
194
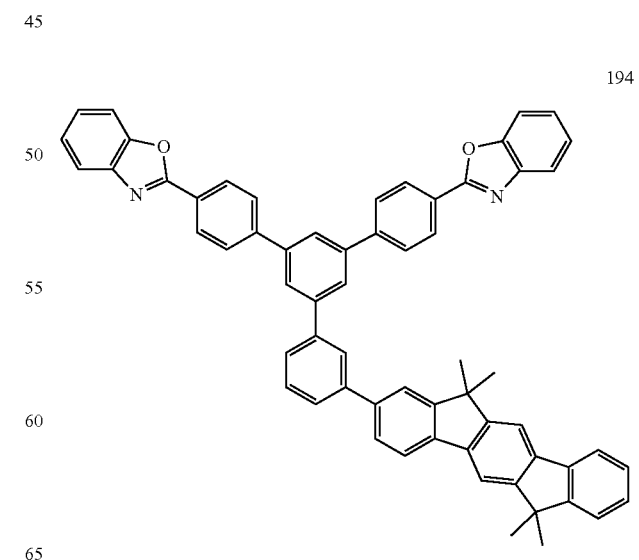

235
-continued
195
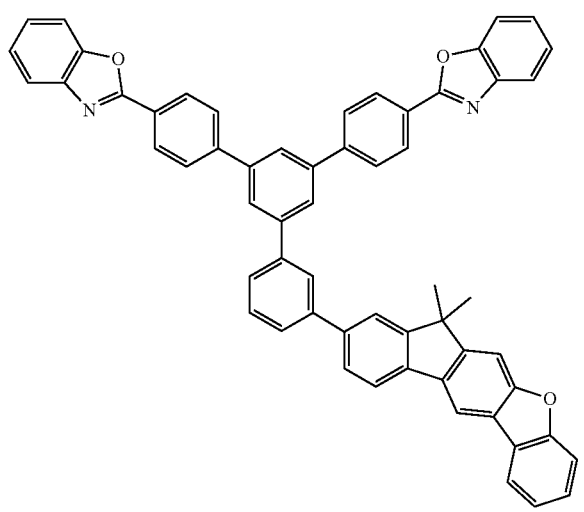
196
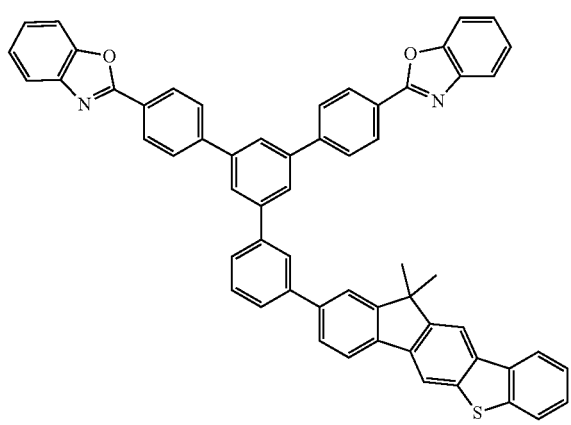
197
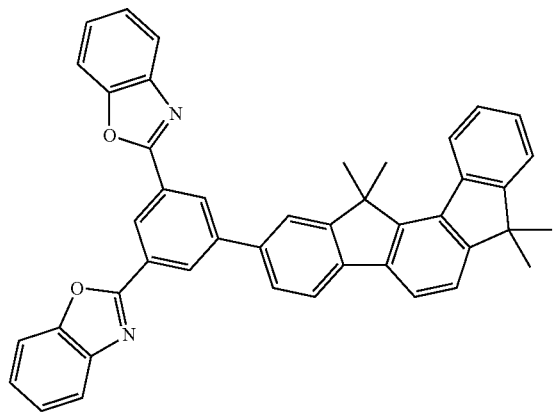
236
-continued
198
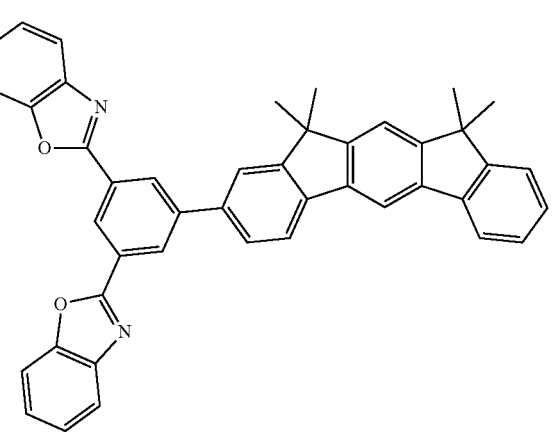
199
200
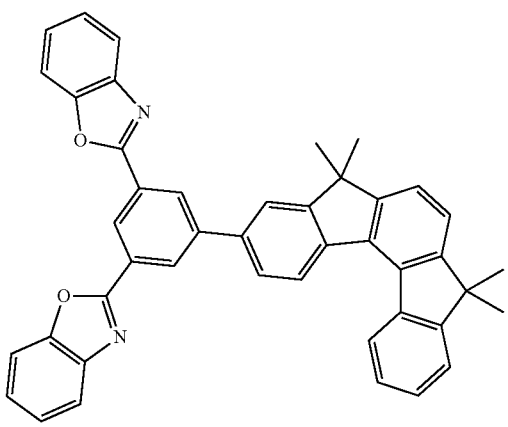

201
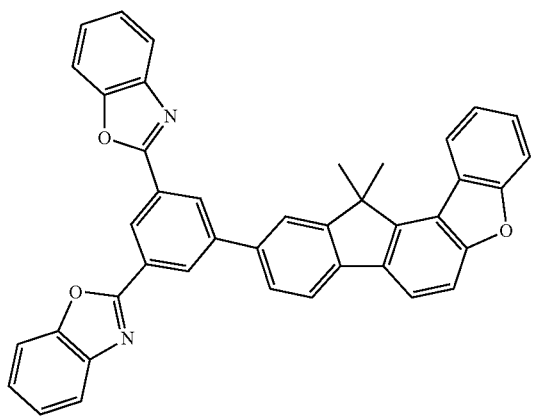
202
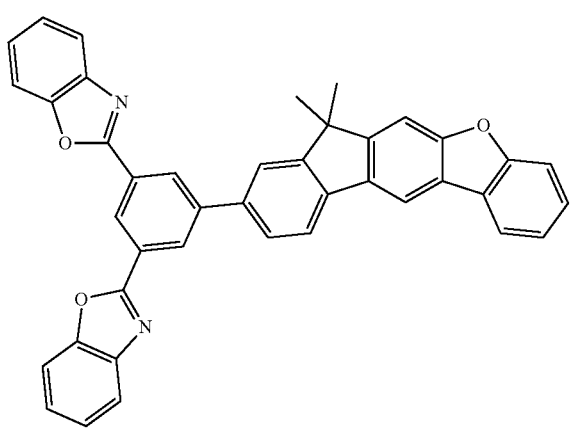
203
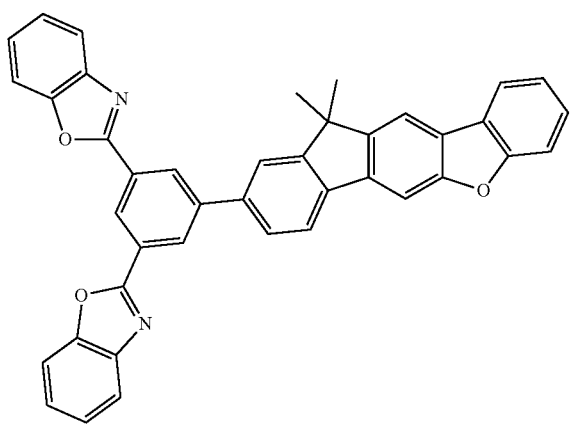
204
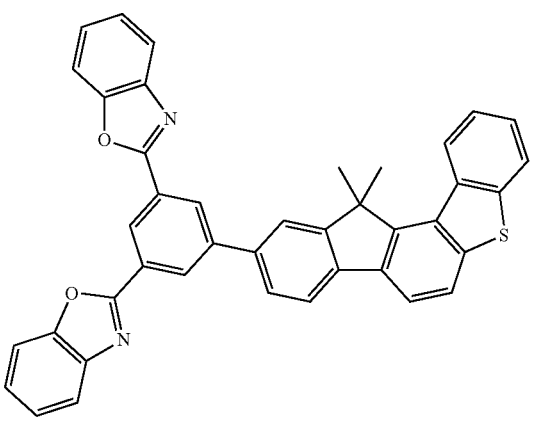
205
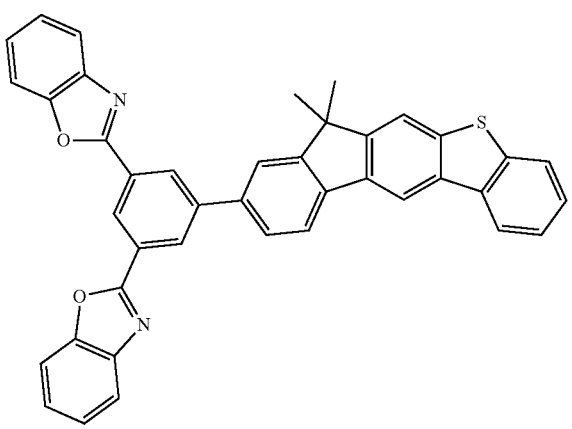
206
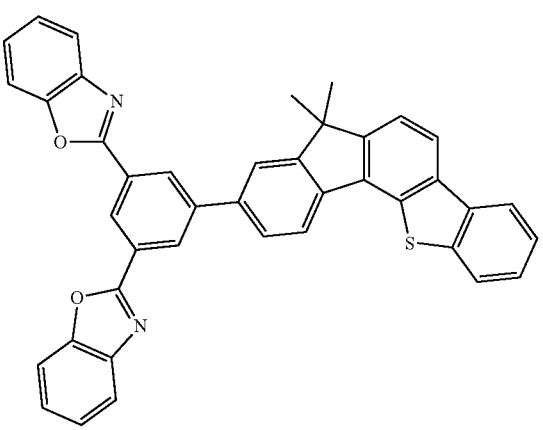

207
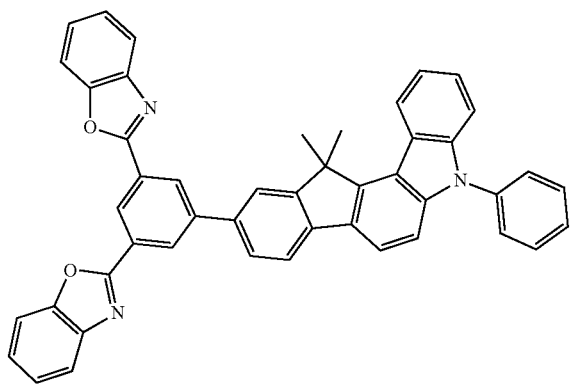
208
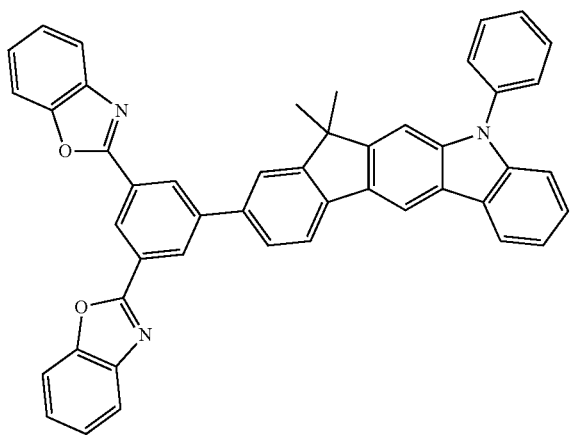
209
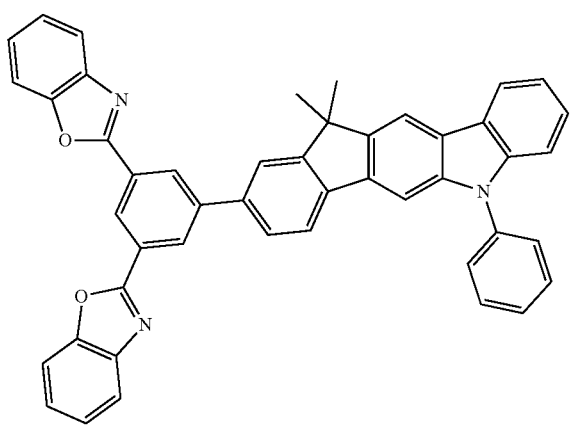
210
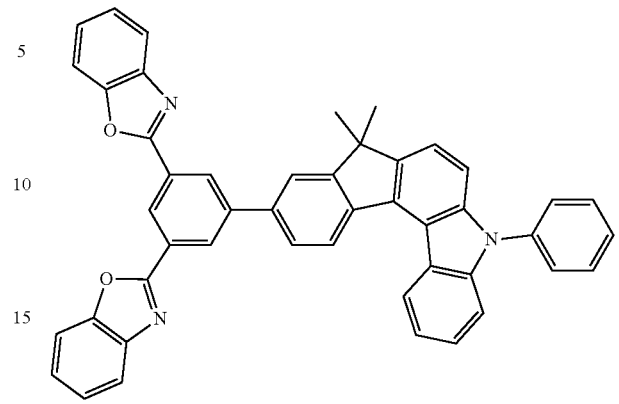
211
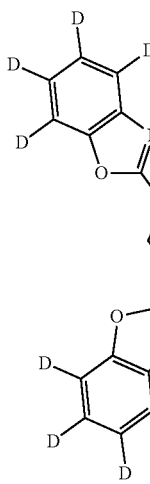
212
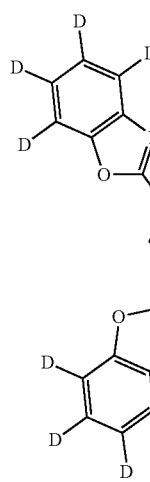

213
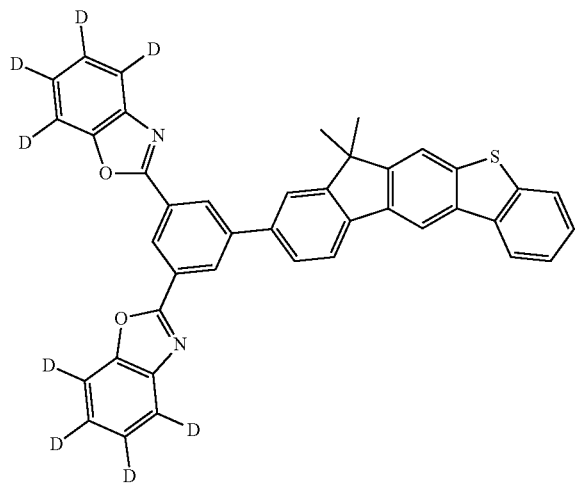
214
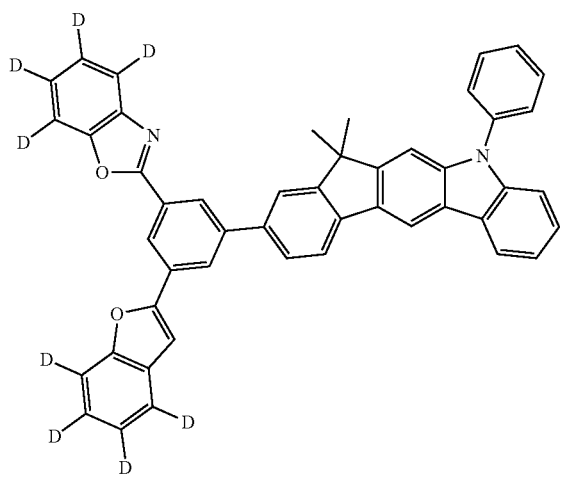
215
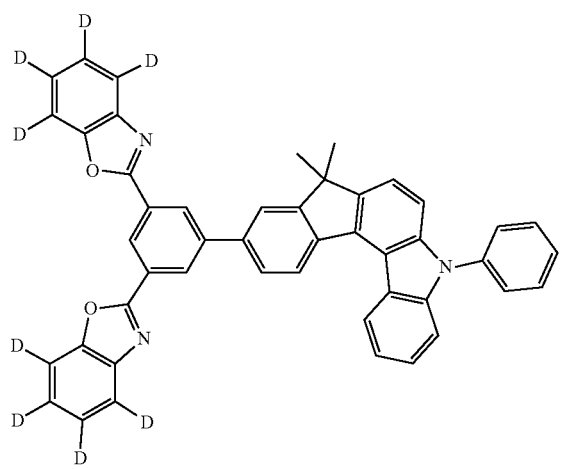
216
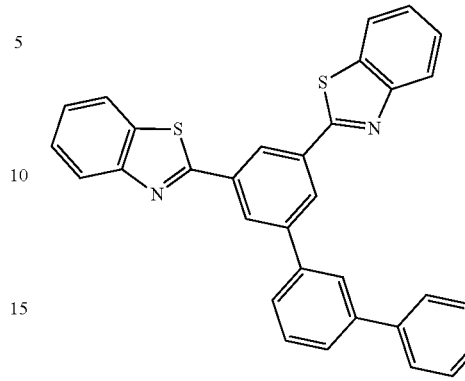
217
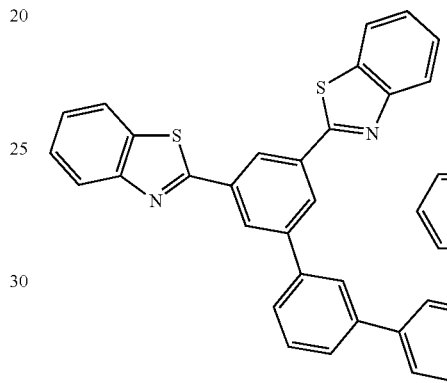
218
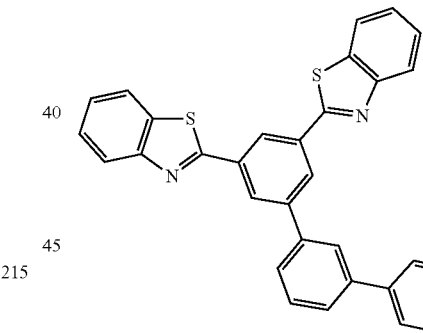
219
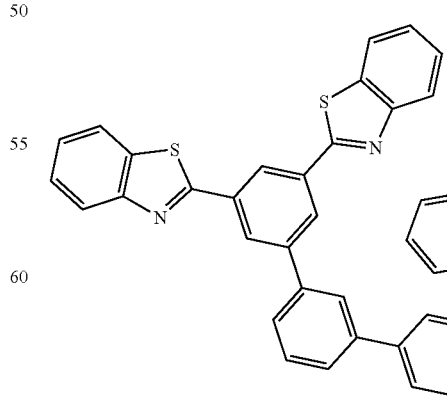

220
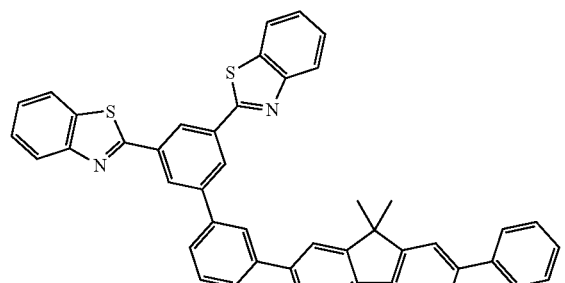
221
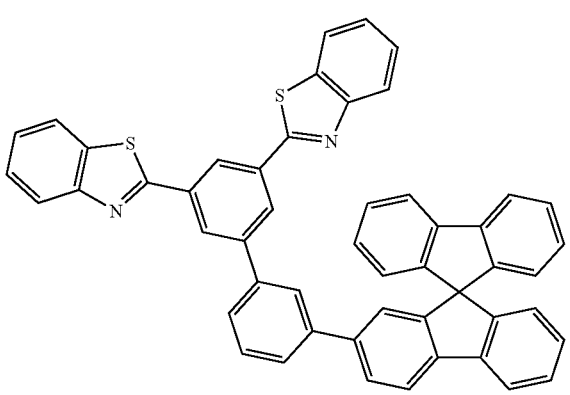
222
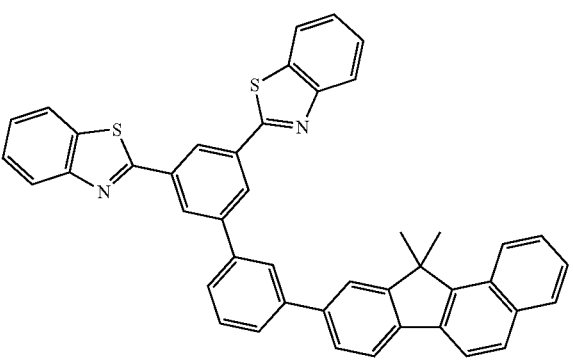
223
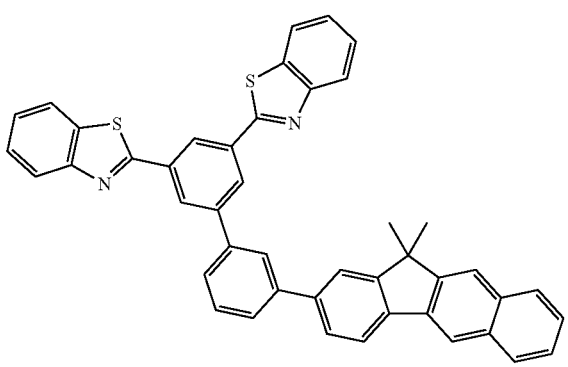
224
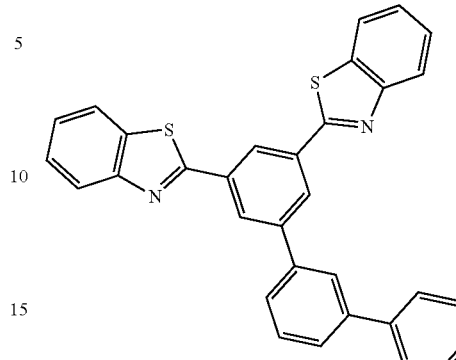
225
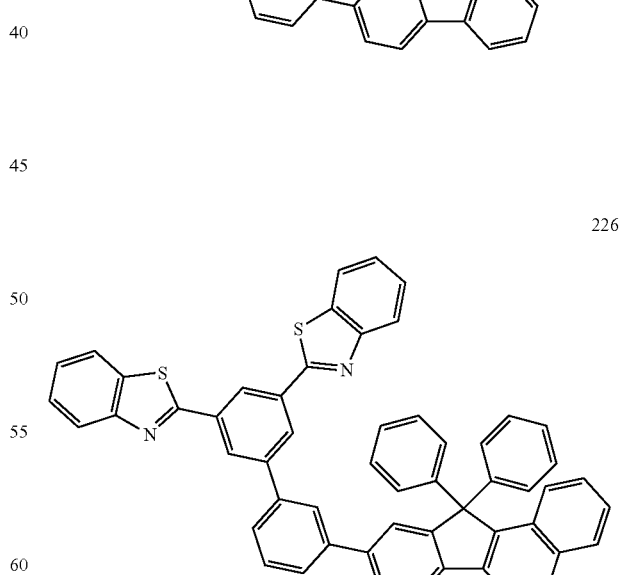
226

-continued
227
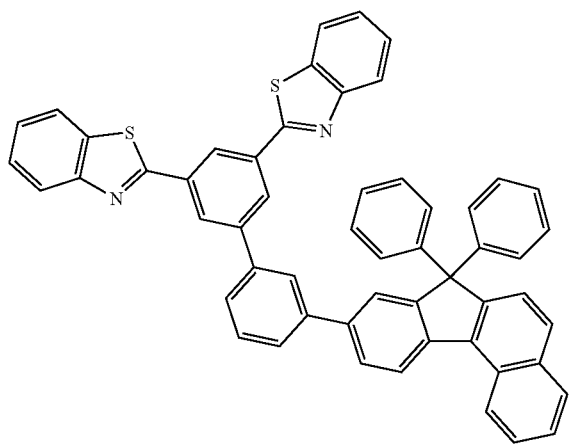
228
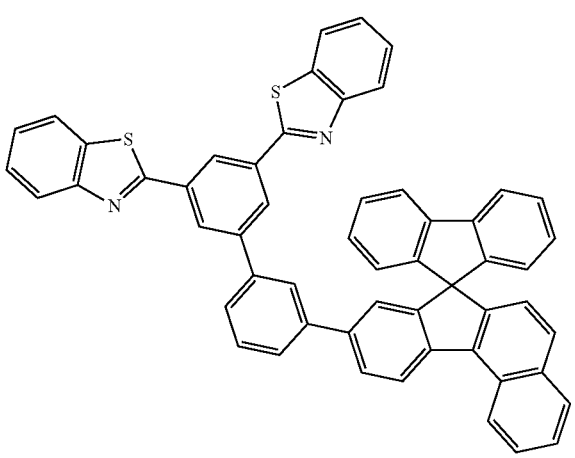
229
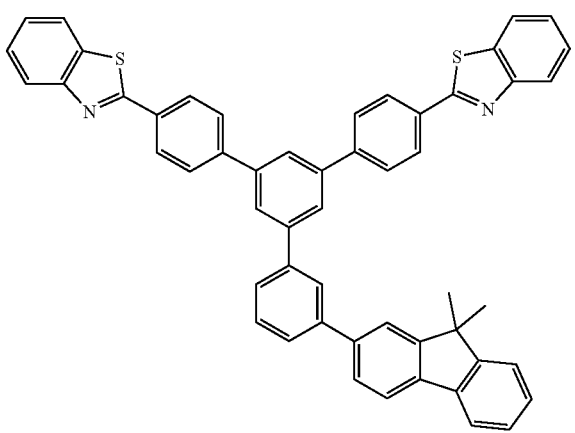
-continued
230
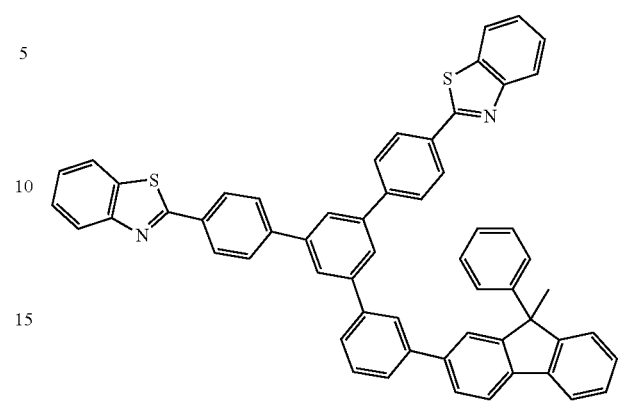
231
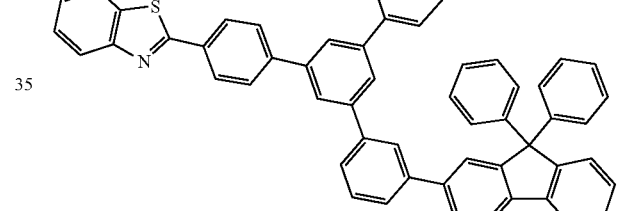
232
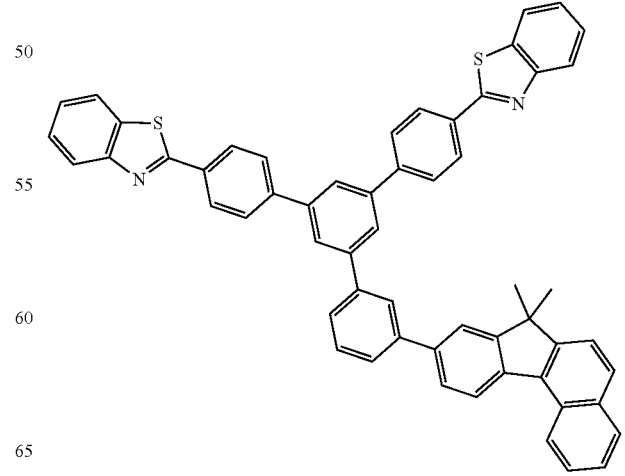

-continued
233
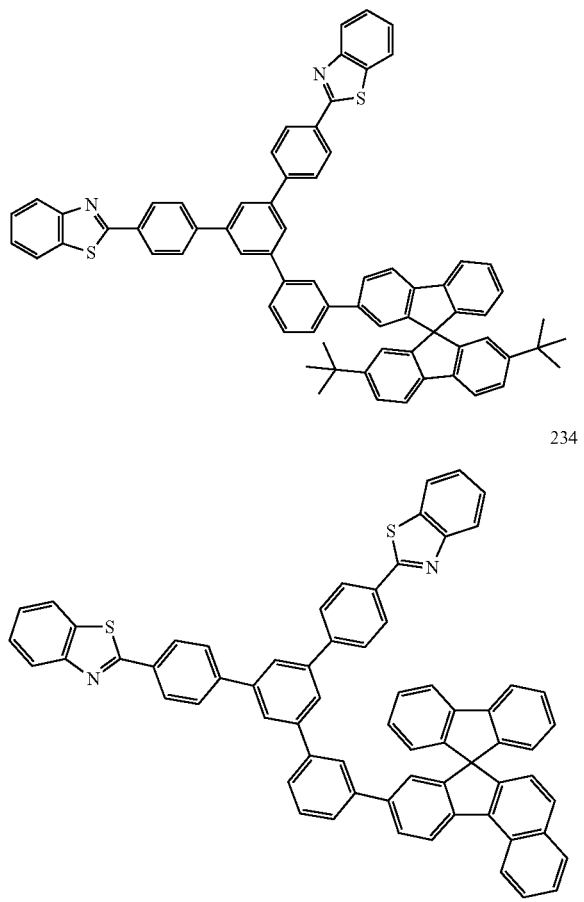
234
235
236
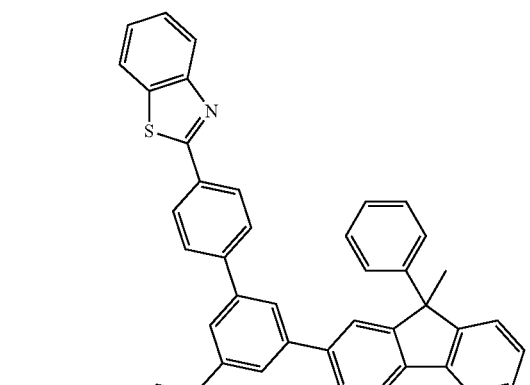
237
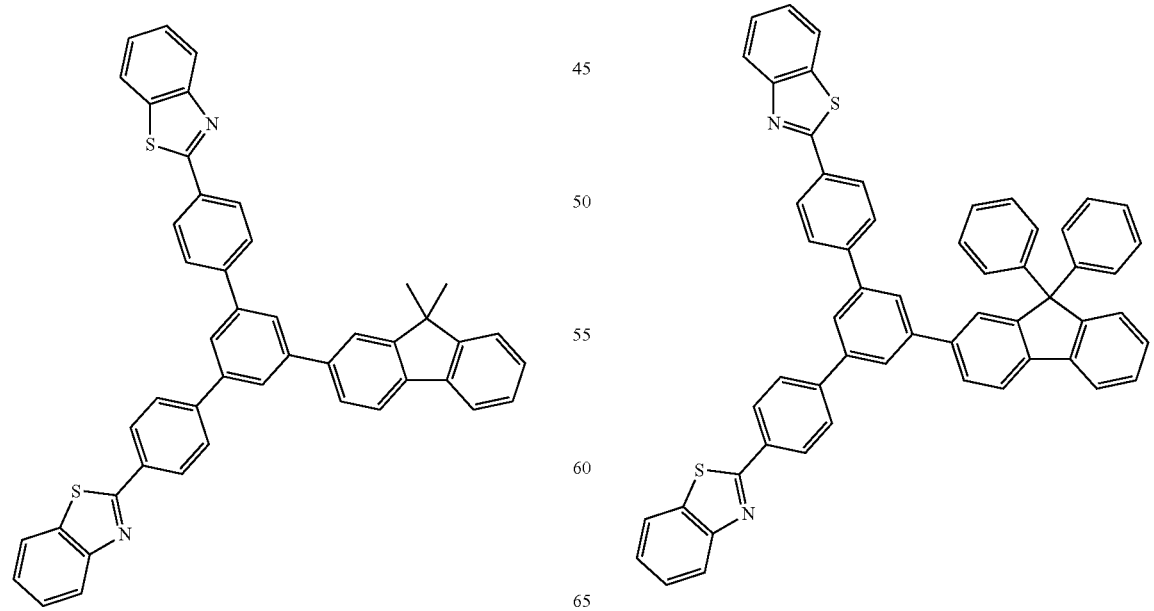

249
-continued
238
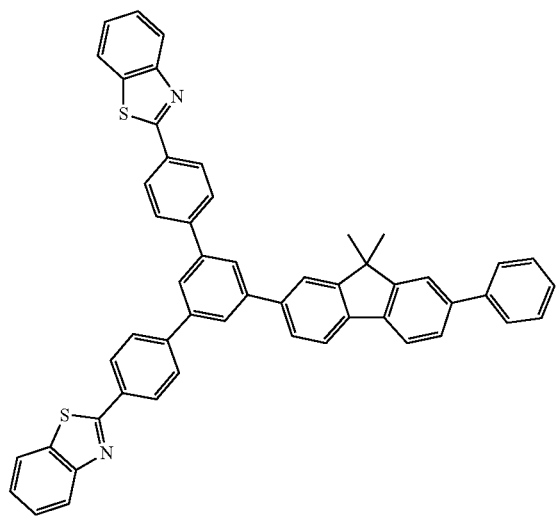
239
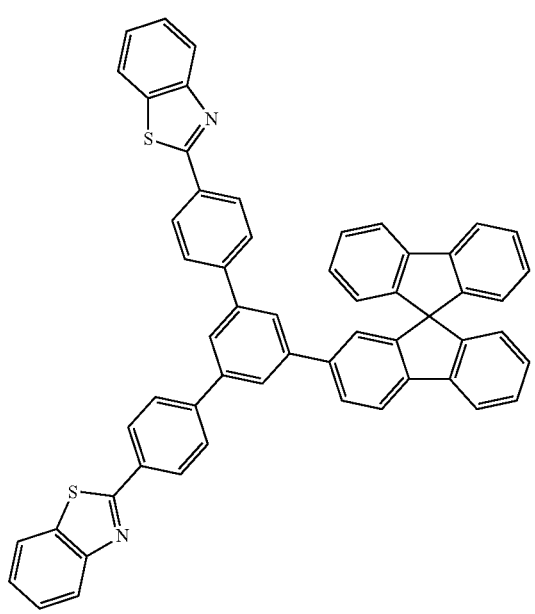
250
-continued
240
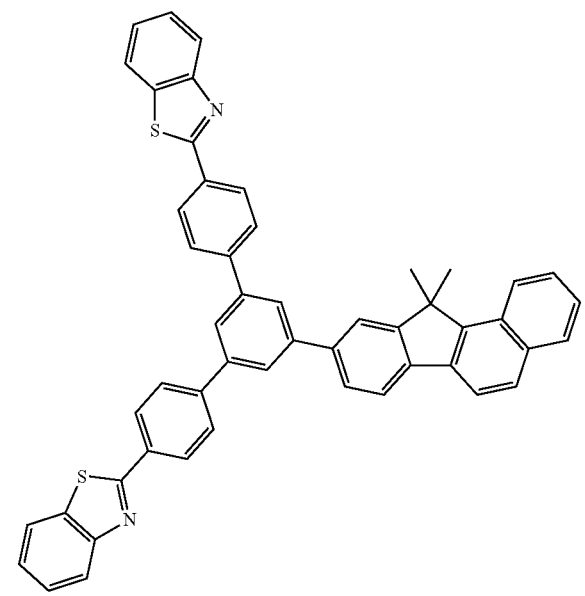
241
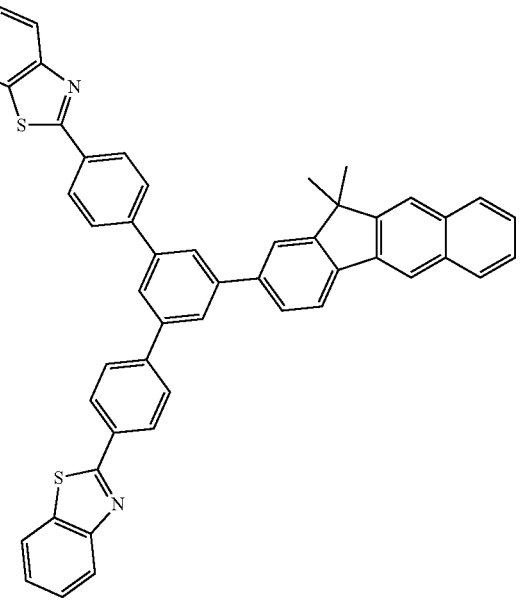

251
-continued
242
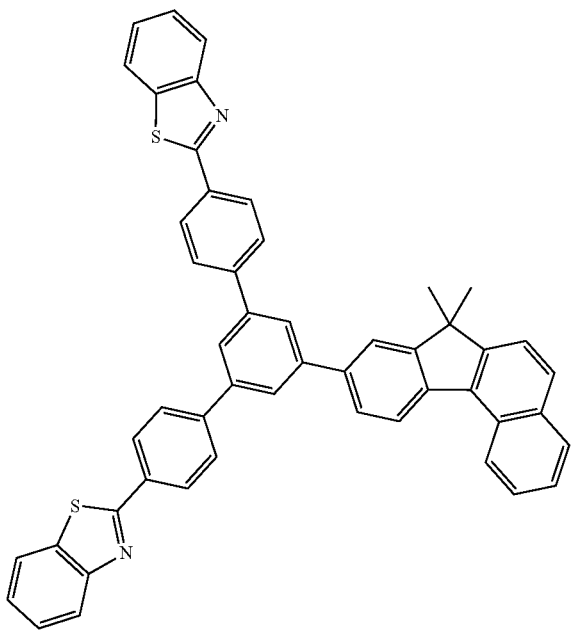
243
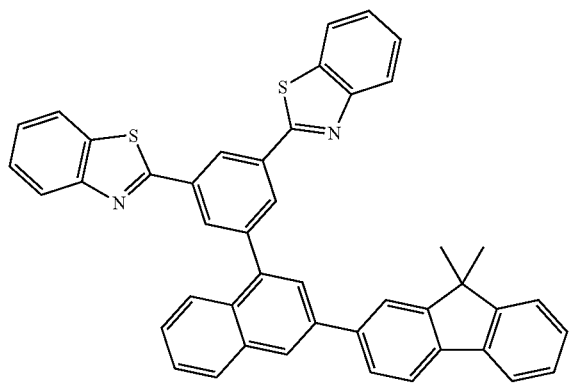
244
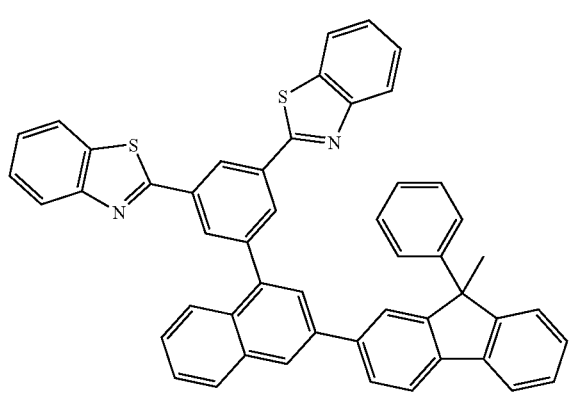
252
-continued
245
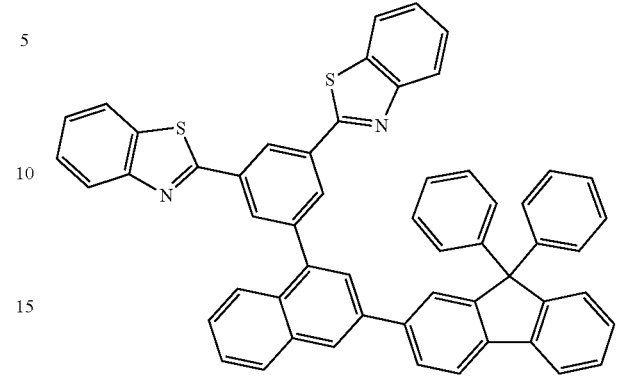
246
247
248
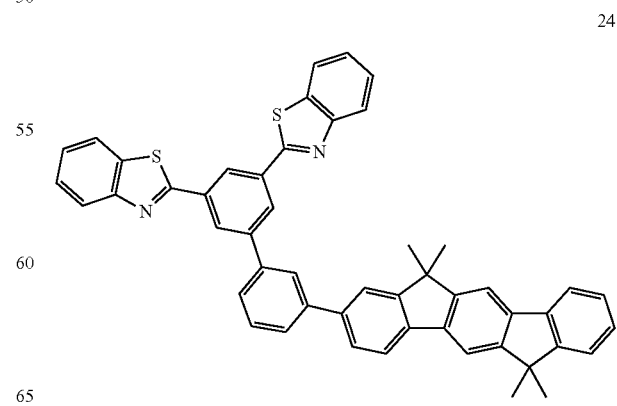

249
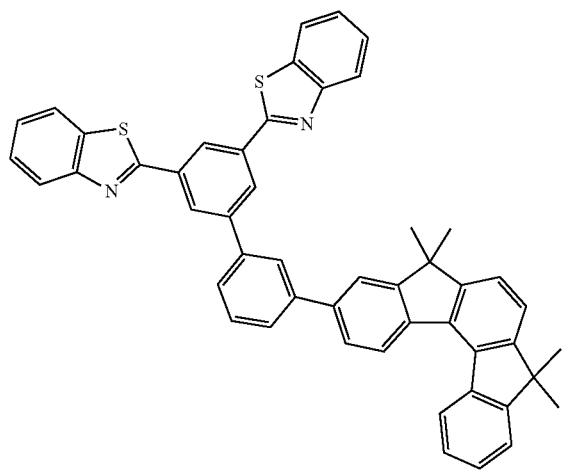
250
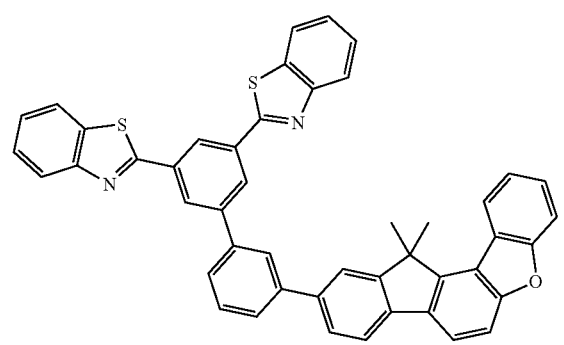
251
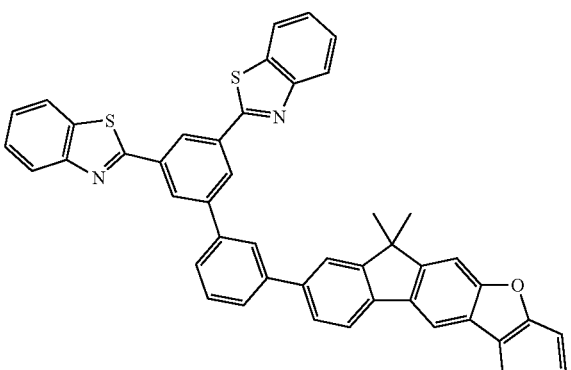
252
253
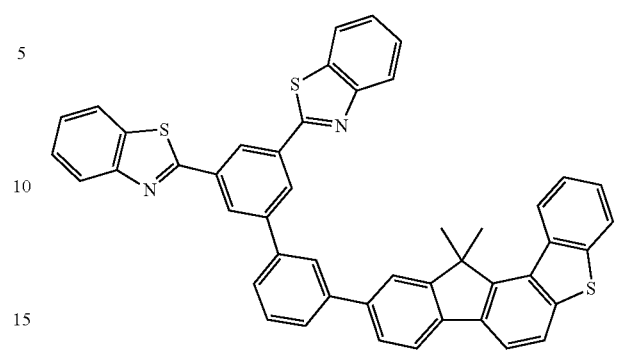
254
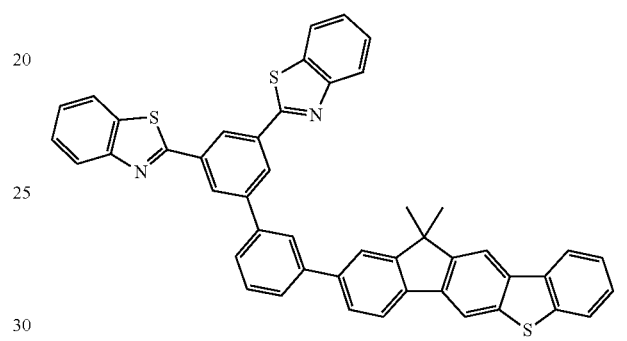
255
256
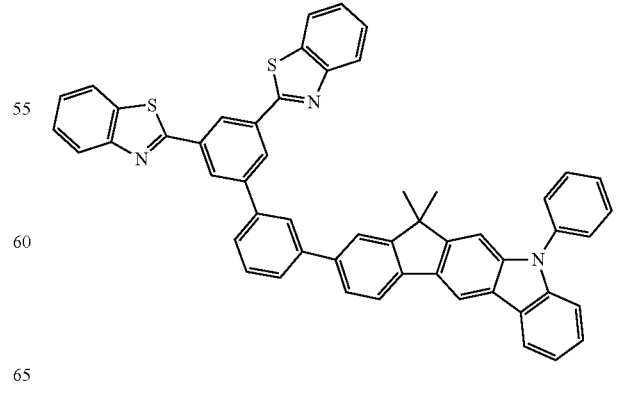

257
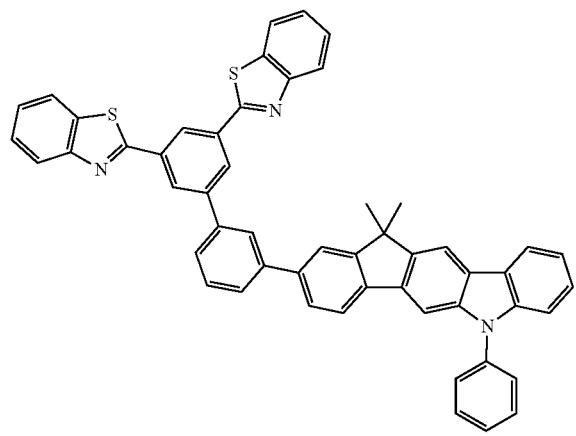
258
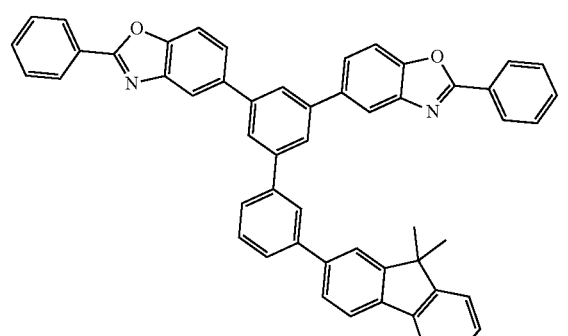
259
261
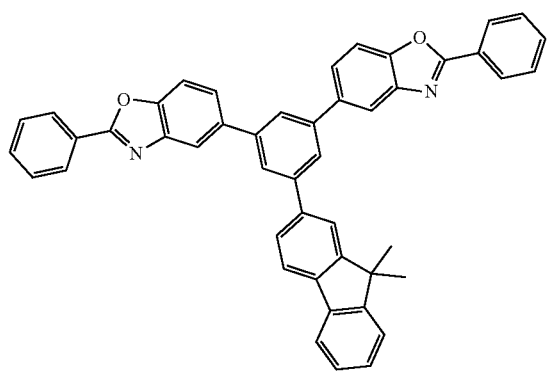
262
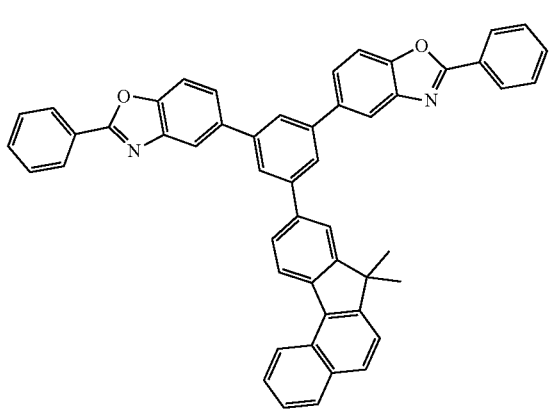
260
263
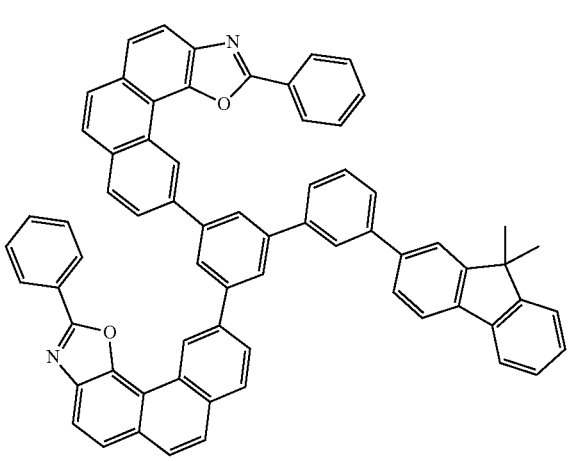

257
-continued
264
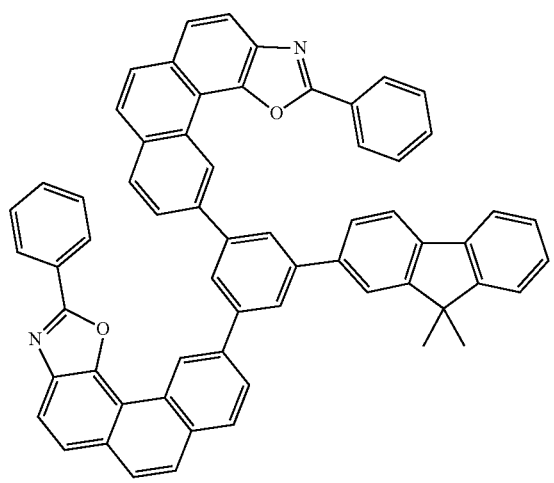
265
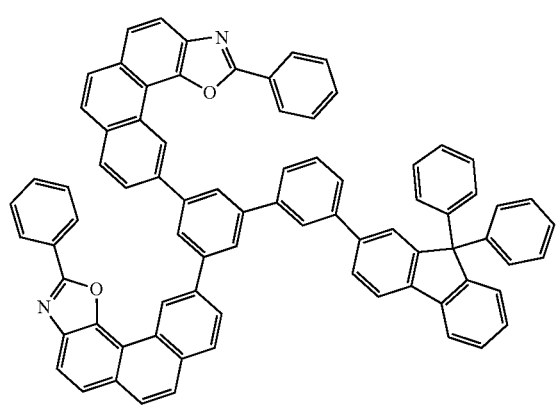
266
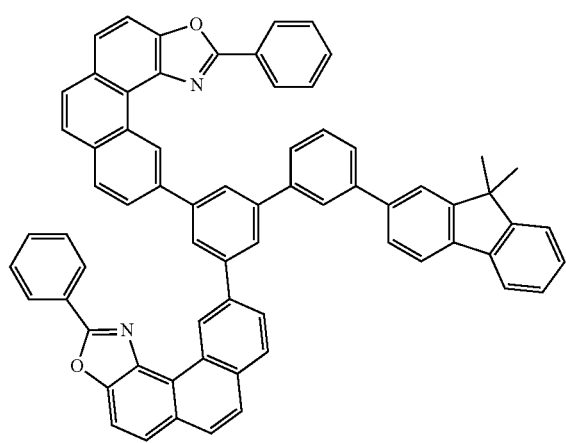
258
-continued
267
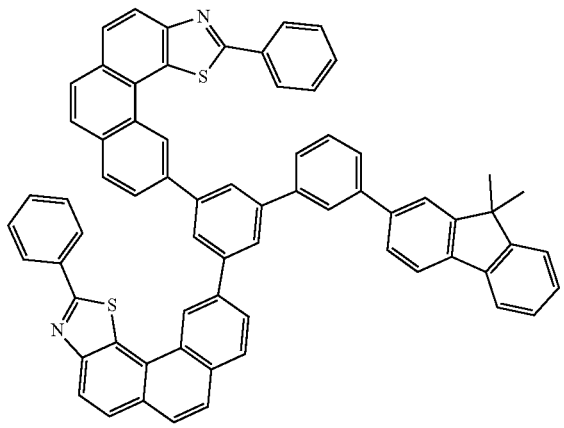
268
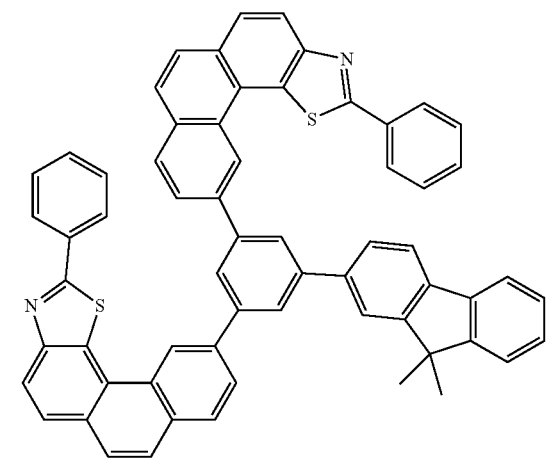
269
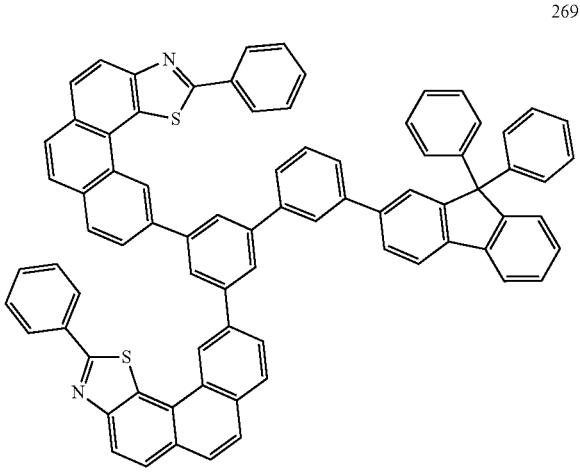

259
-continued
270
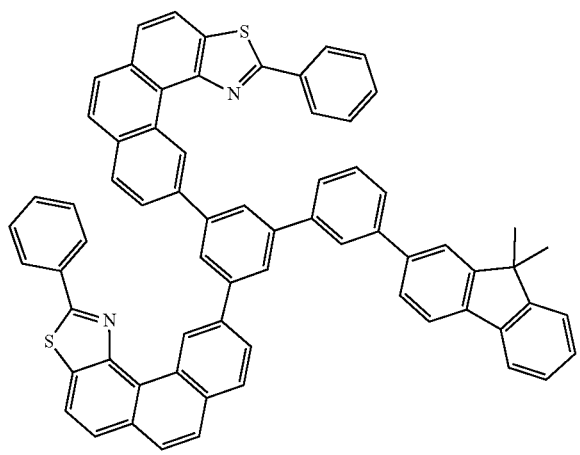
271
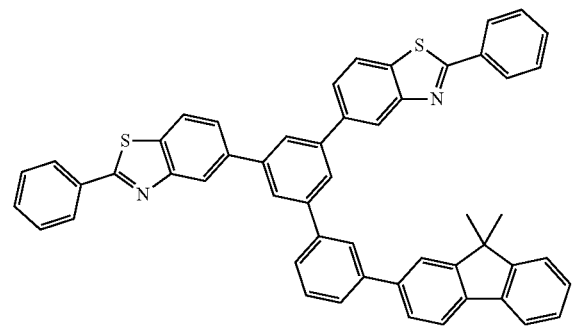
272
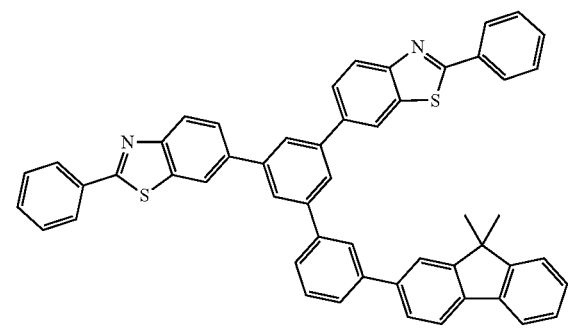
273
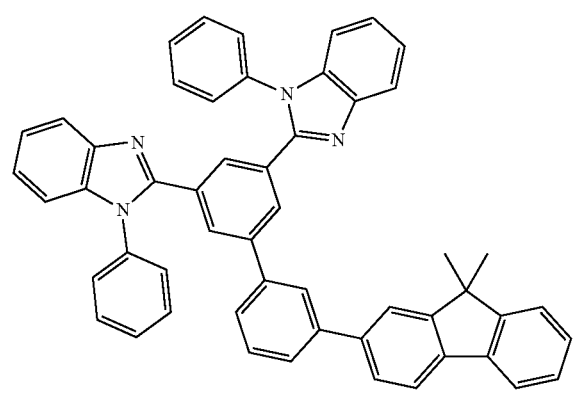
260
-continued
274
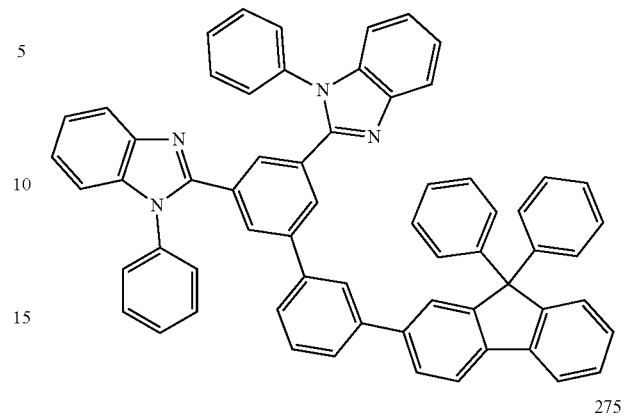
275
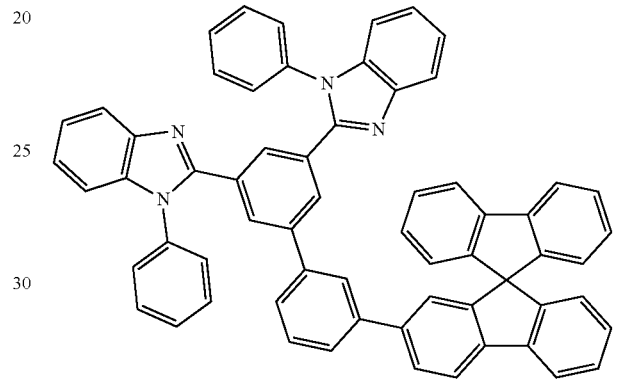
276
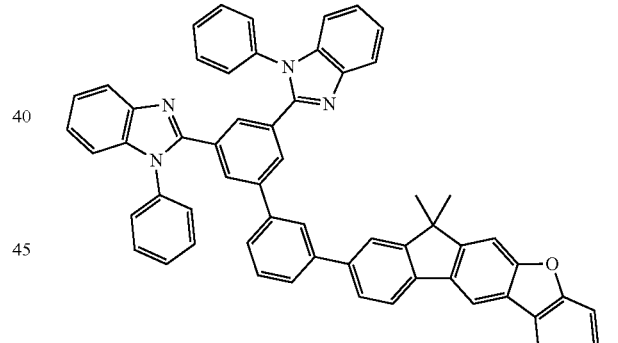
277
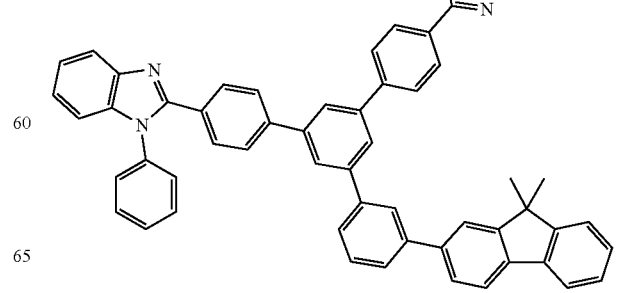

278 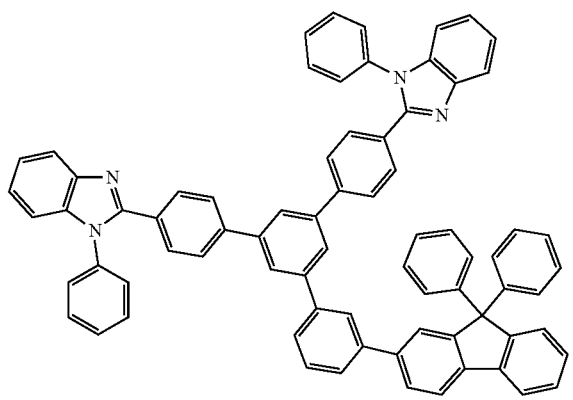
279 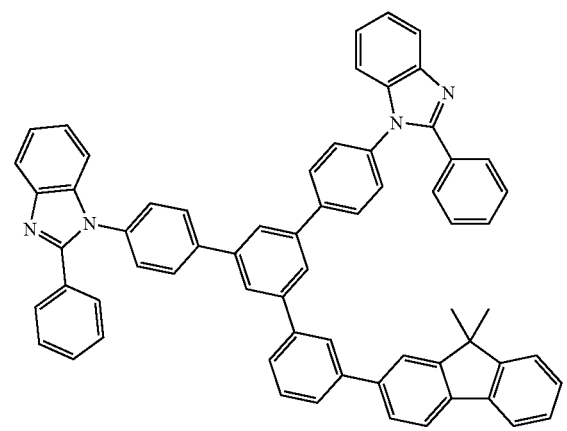
280 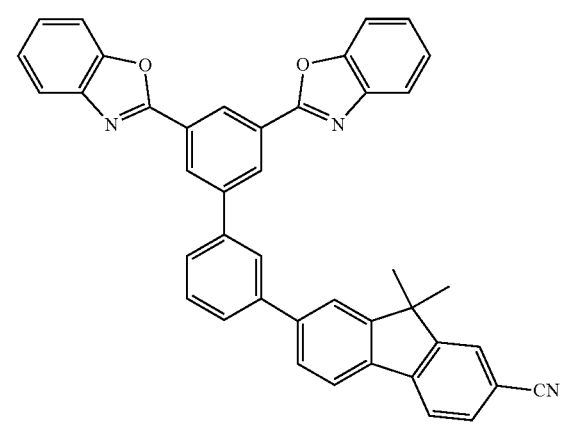
281 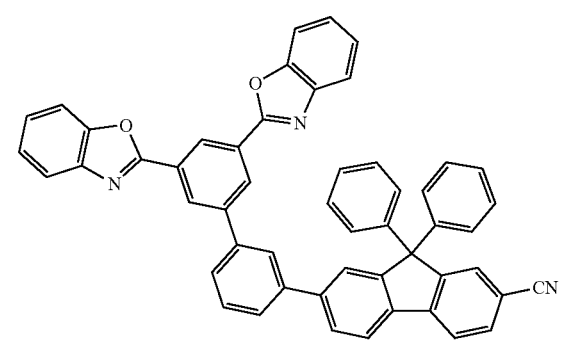
282 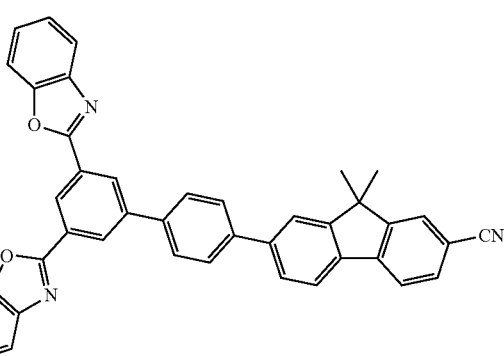
283 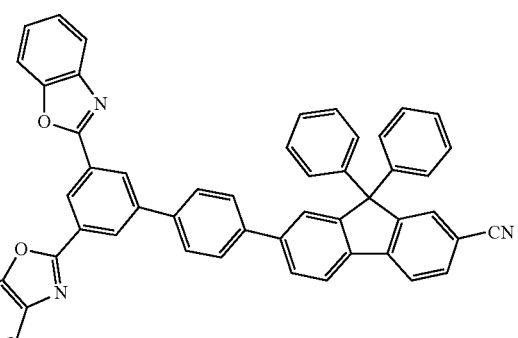
284 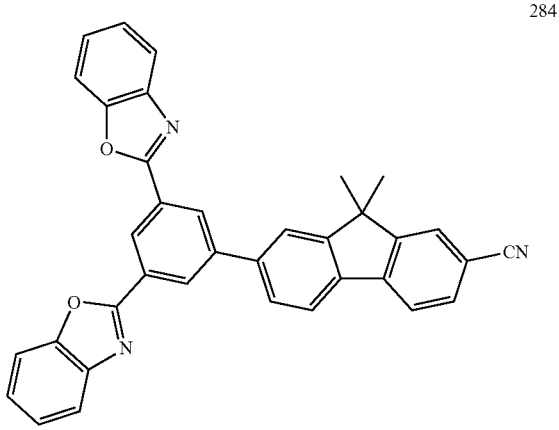
285 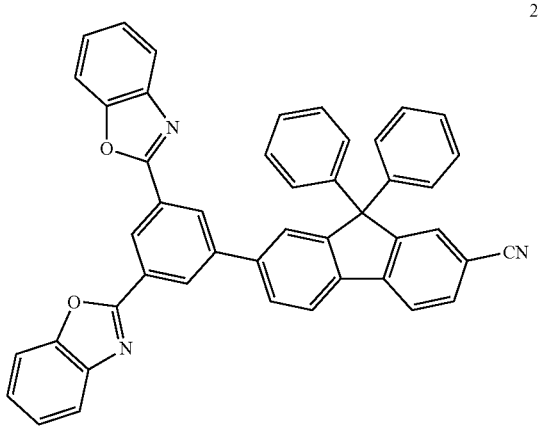

286
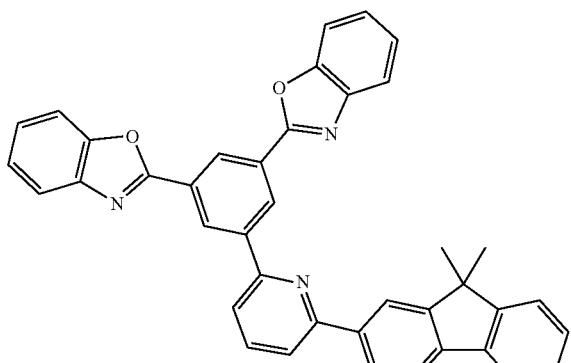
287
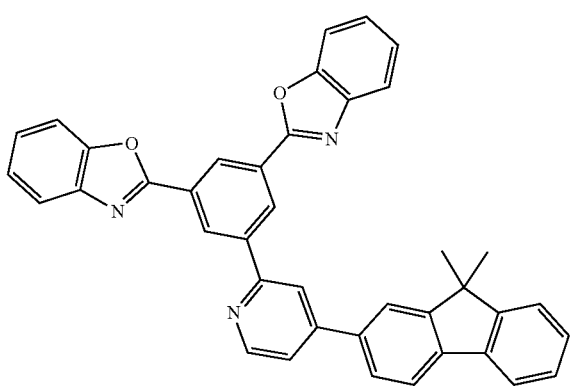
288
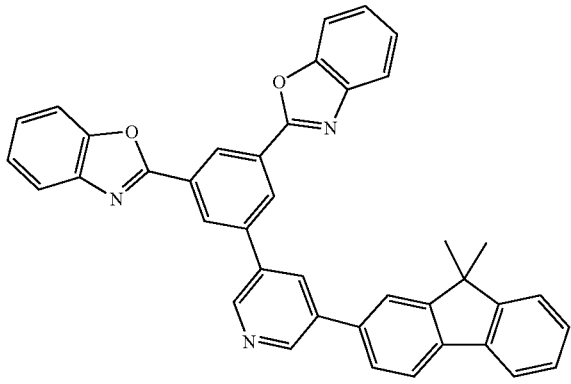
289
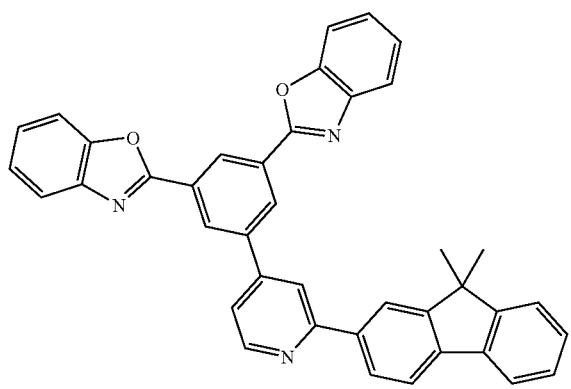
290
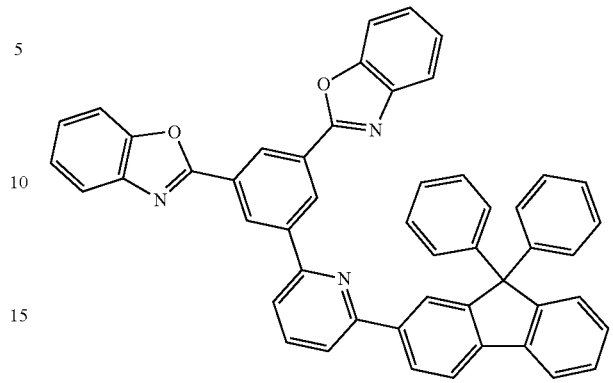
291
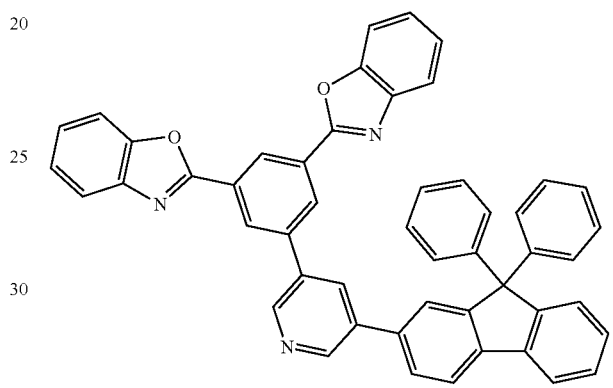
292
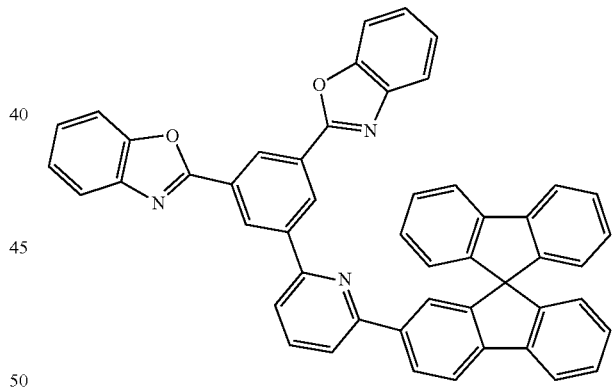
293
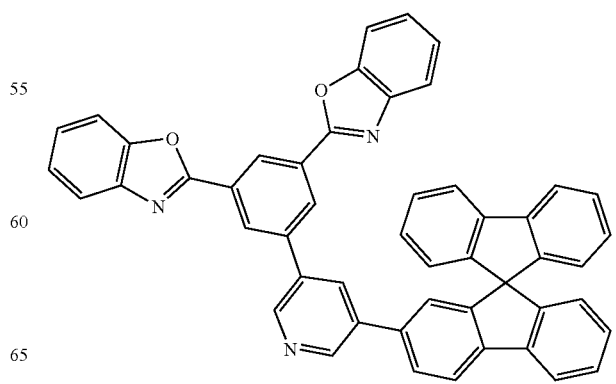

294
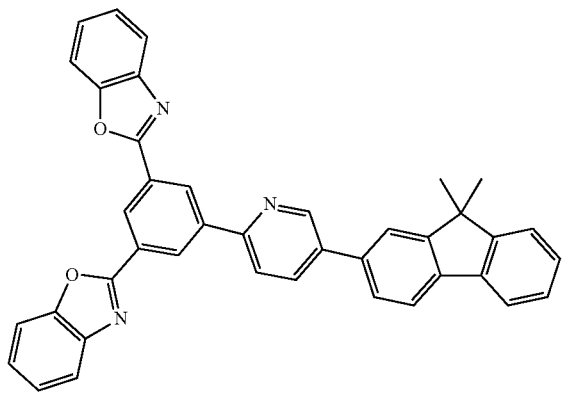
295
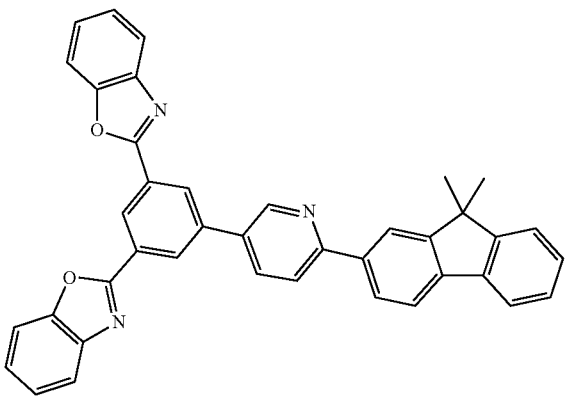
296
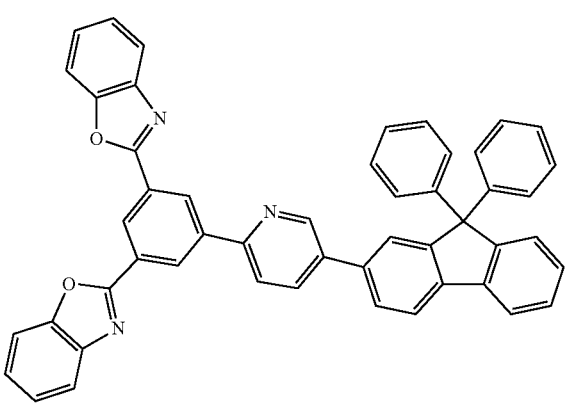
297
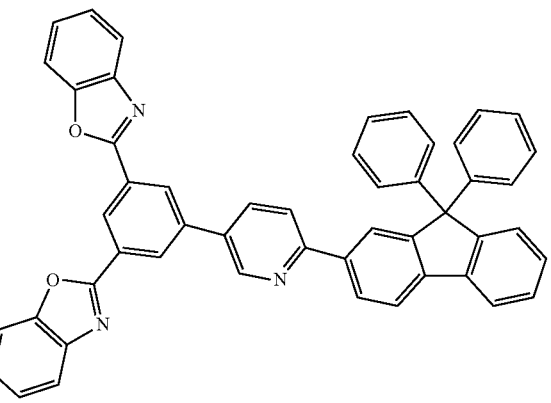
298
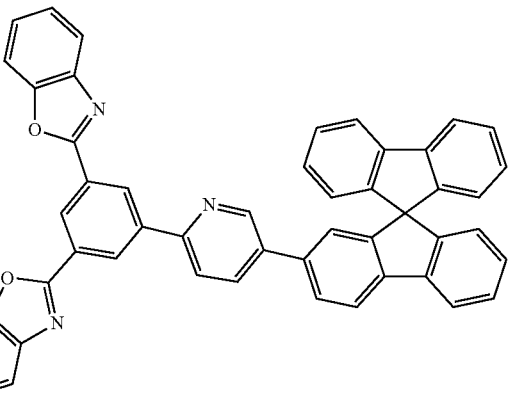
299
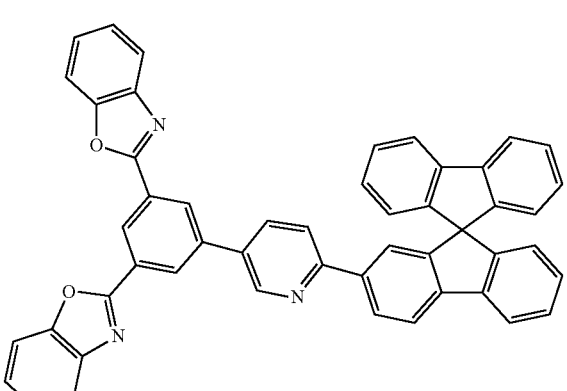

300
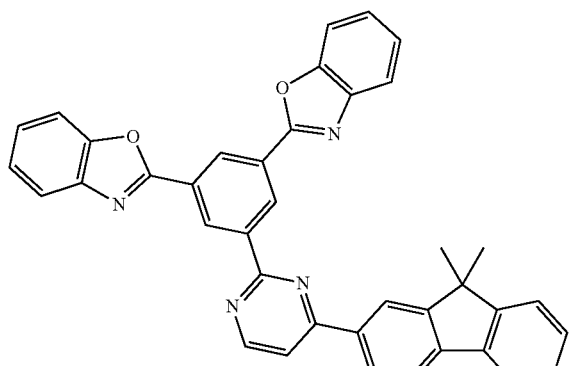
301
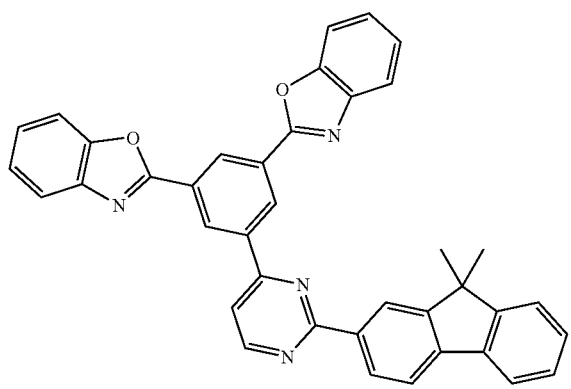
302
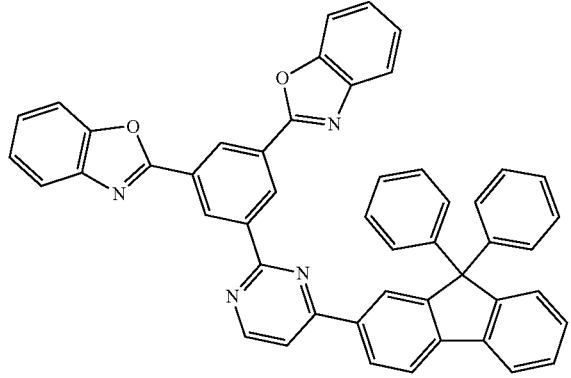
303
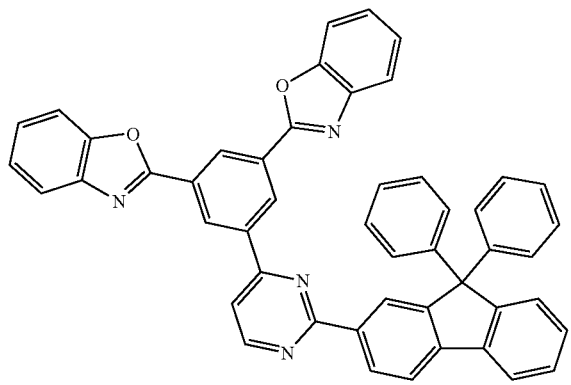
304
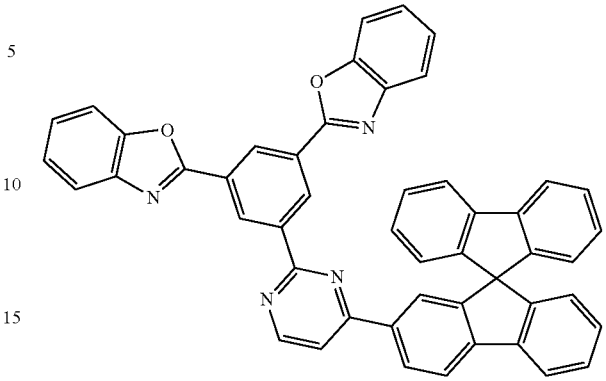
305
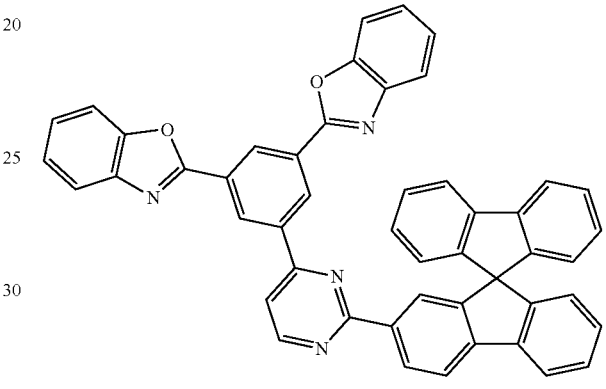
306
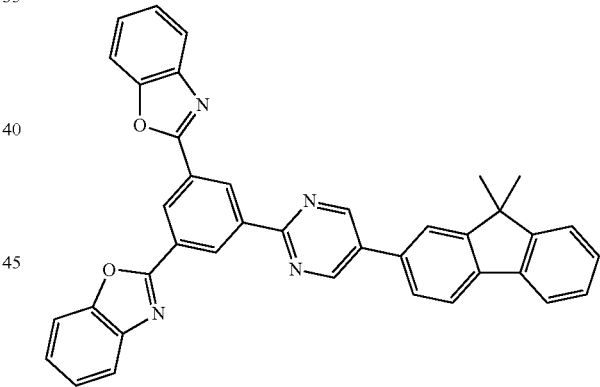
307
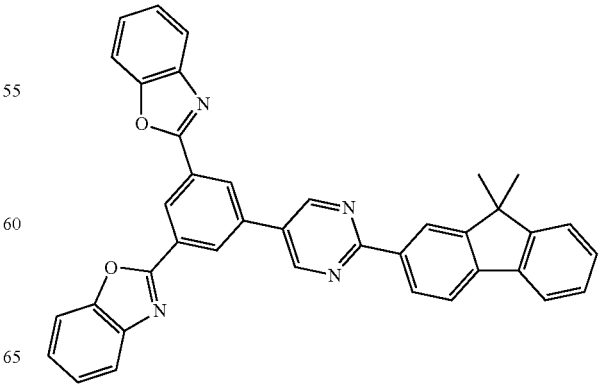

308
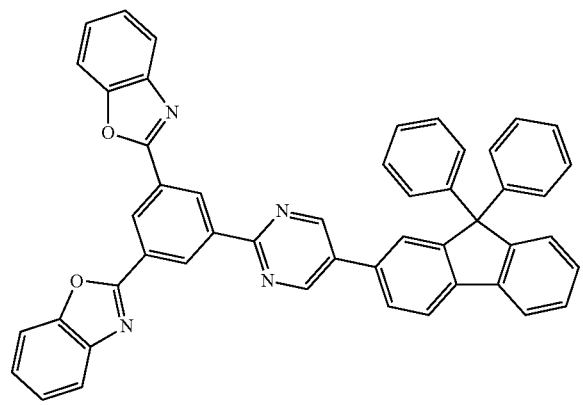
309
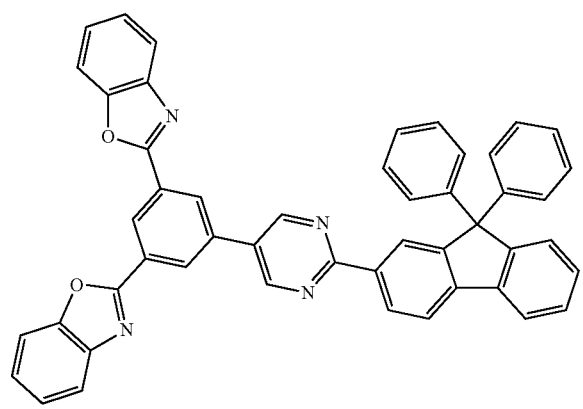
310
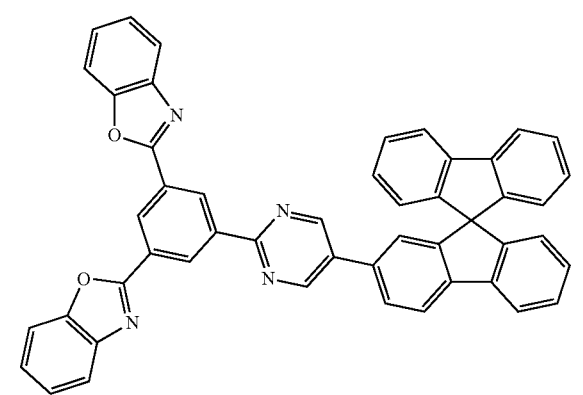
311
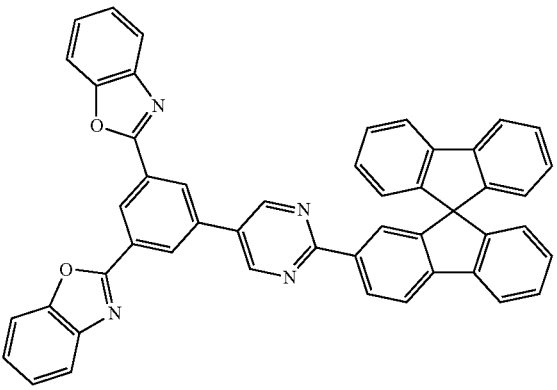
312
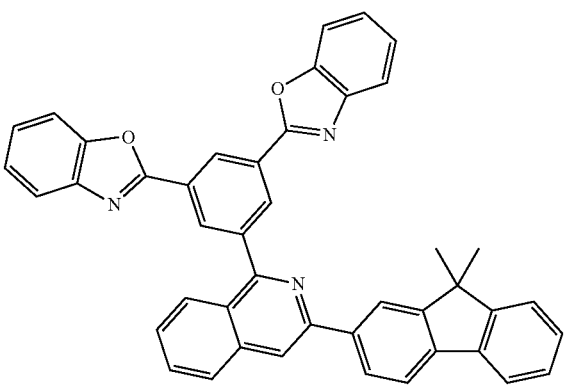
313
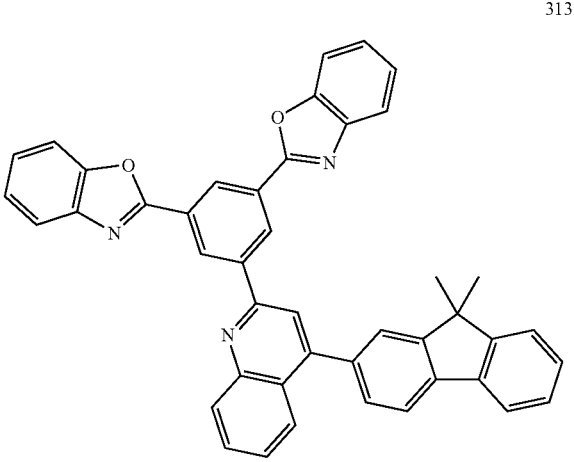

271
-continued
314
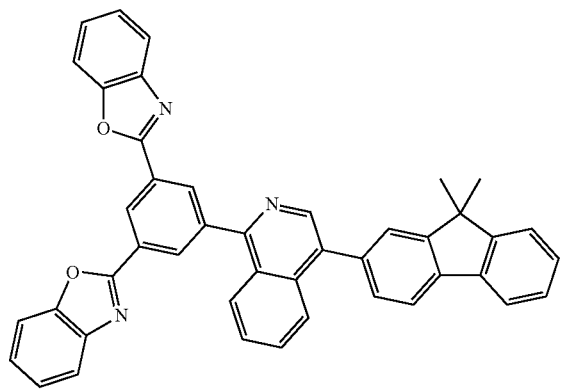
315
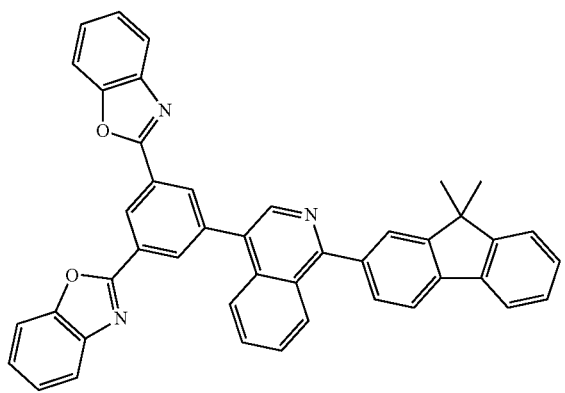
316
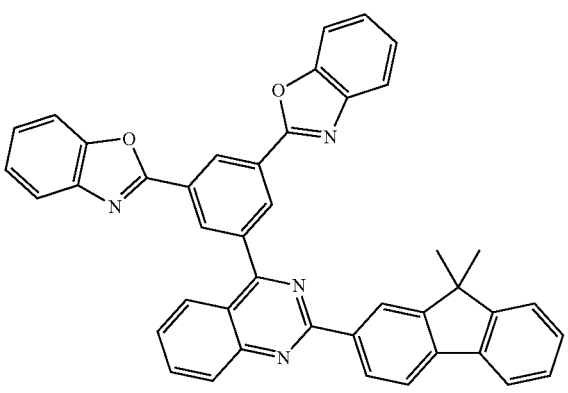
272
-continued
317
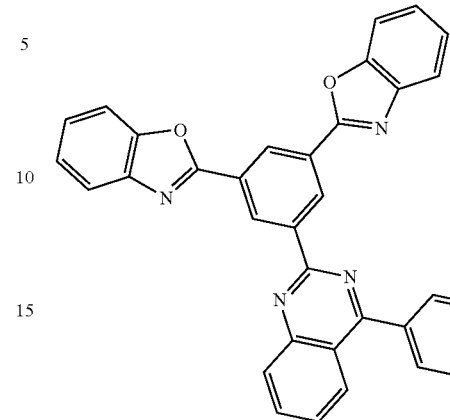
318
319
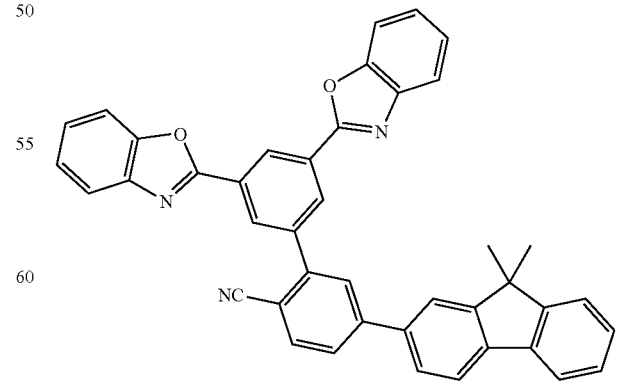

273
-continued
320
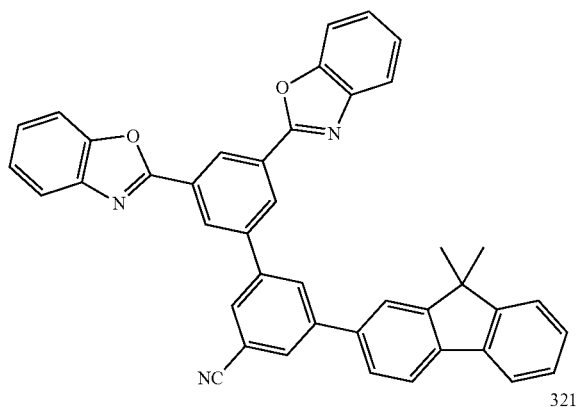
321
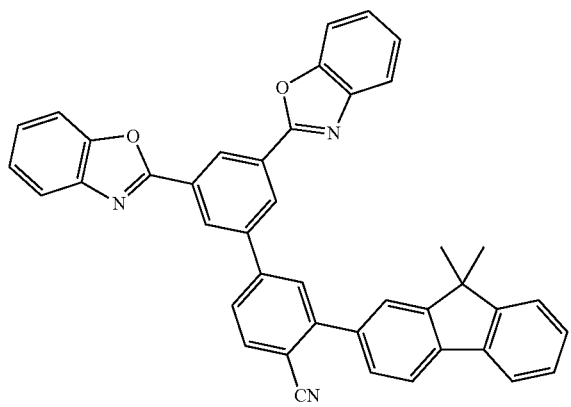
322
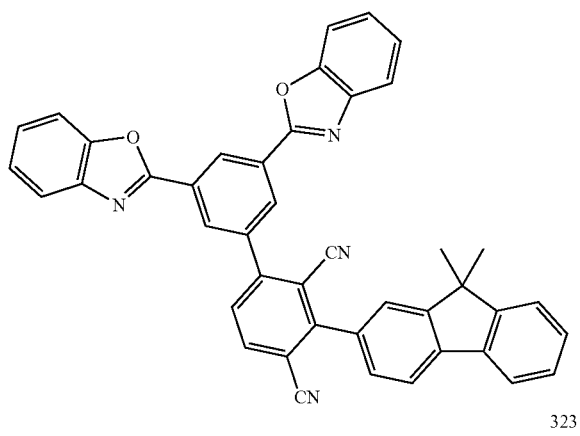
323
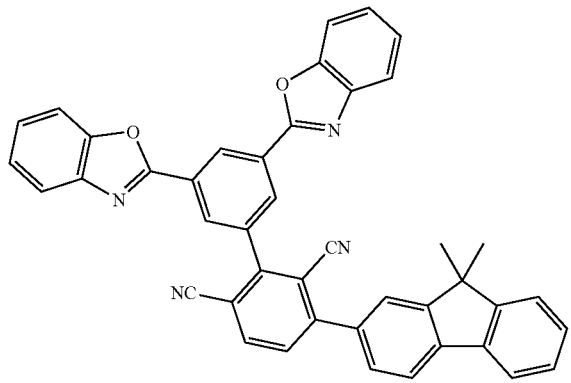
274
-continued
324
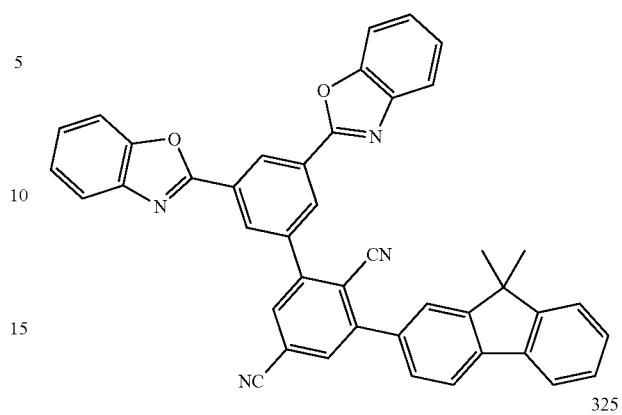
325
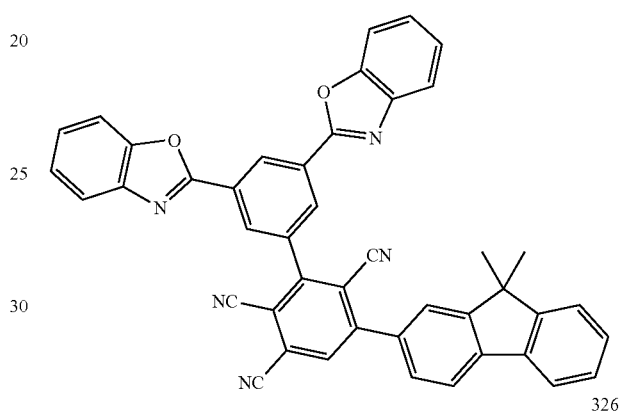
326
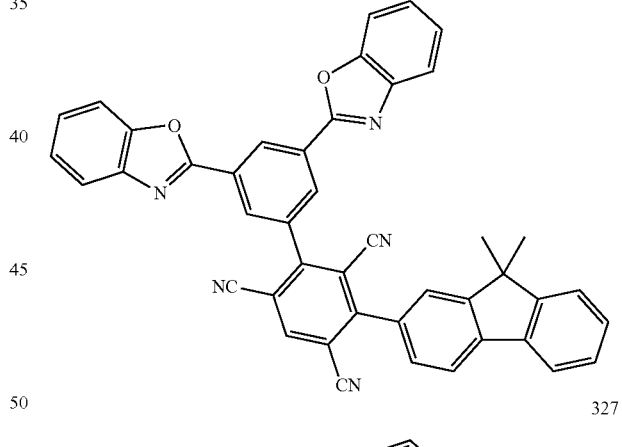
327
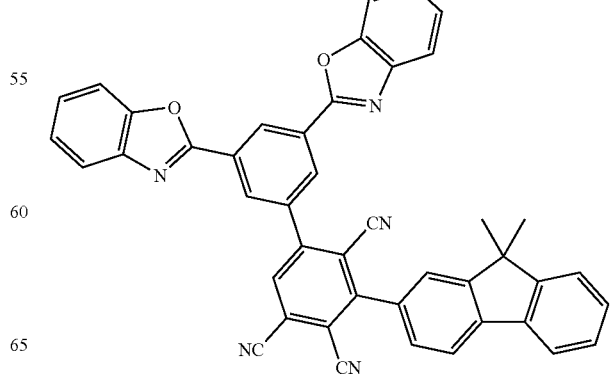

328
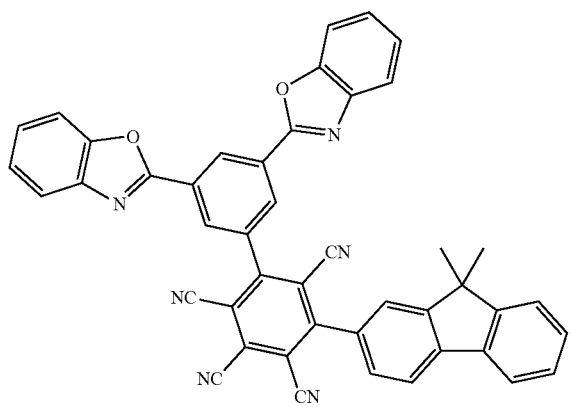
329
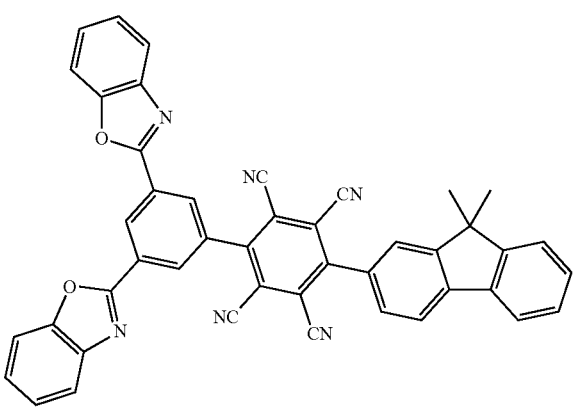
330
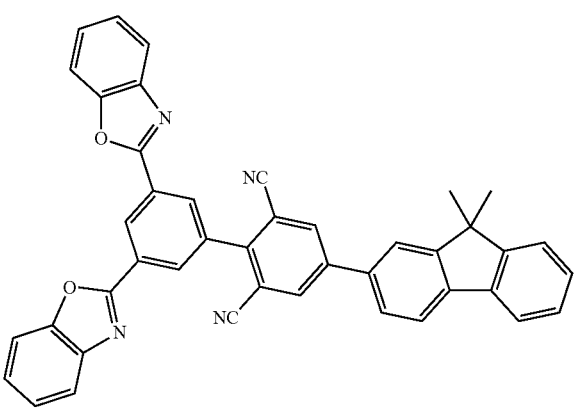
331
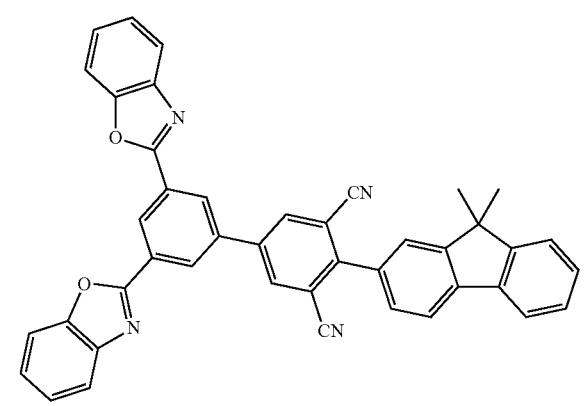
332
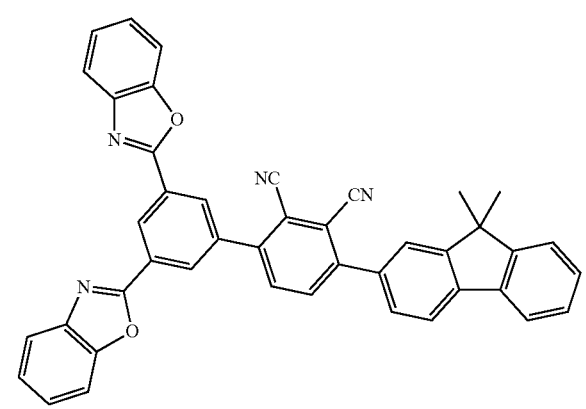
333
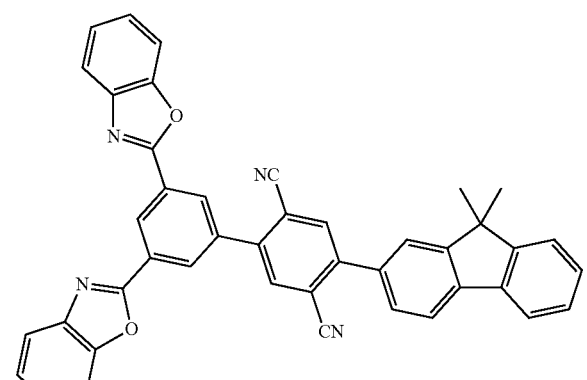

-continued
334
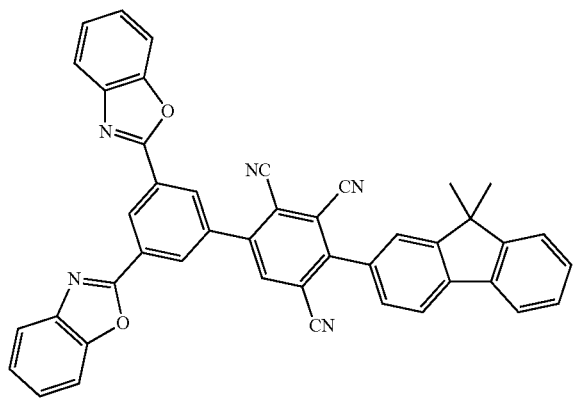
335
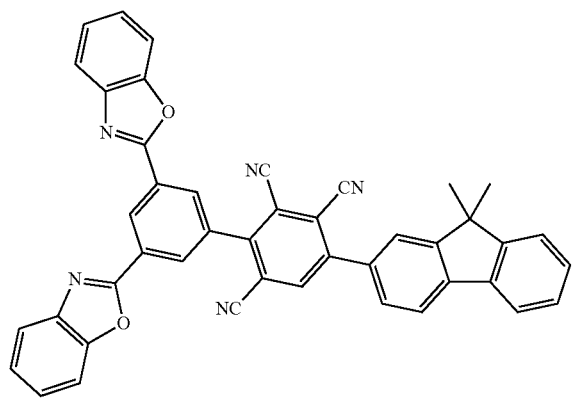
336
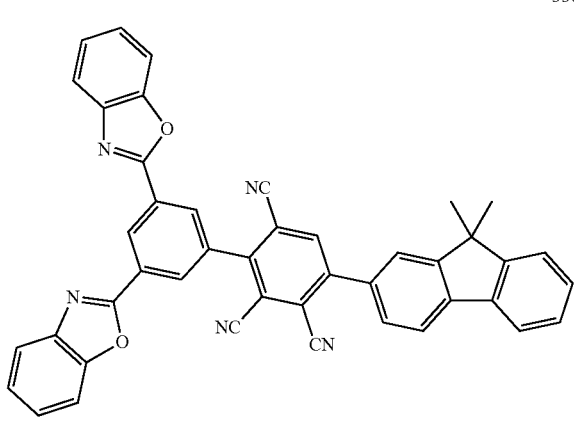
-continued
337
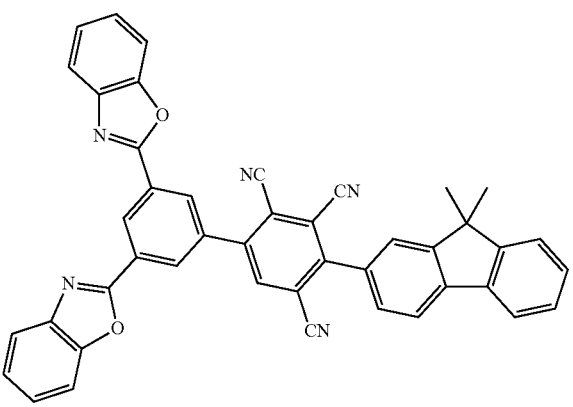
338
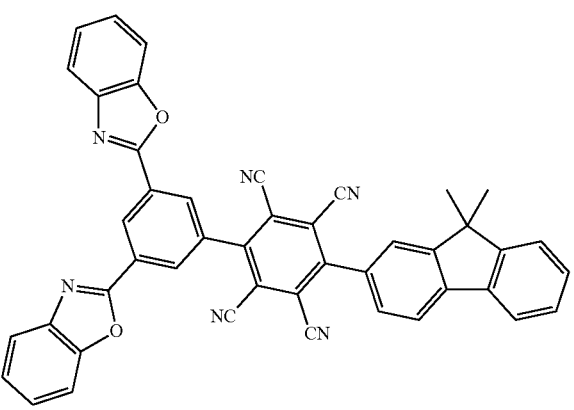
339
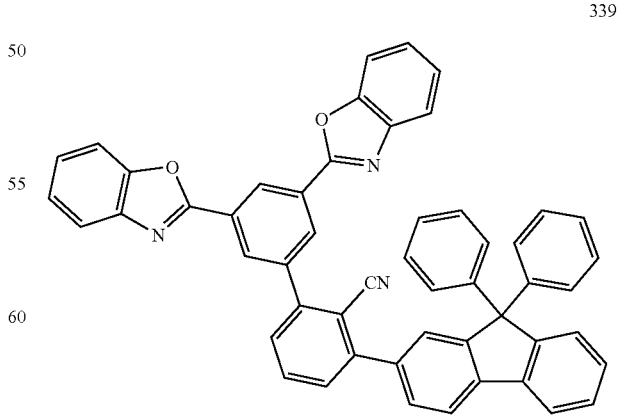

-continued

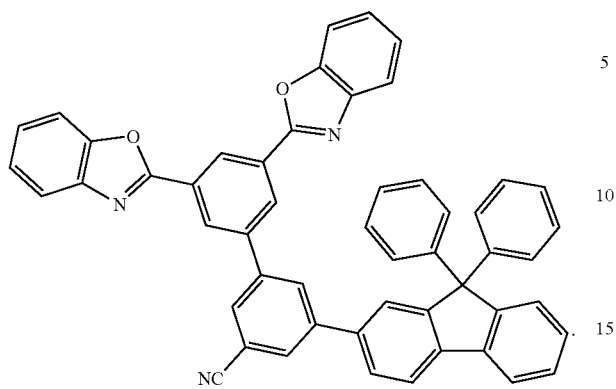

340

6. An organic electroluminescent device, comprising an anode, a cathode, and an organic layer disposed between the anode and the cathode, wherein the organic layer comprises a heterocyclic compound of Formula 1.

7. The organic electroluminescent device according to claim 6, wherein the organic layer comprises a hole blocking layer and an electron transport layer, wherein the electron transport layer or the hole blocking layer comprises the heterocyclic compound as shown in Formula 1.

* * * * *